(12) United States Patent
Plant et al.

(10) Patent No.: US 8,680,290 B2
(45) Date of Patent: Mar. 25, 2014

(54) ISOXAZOLINE DERIVATIVES AND THEIR USE AS HERBICIDES

(75) Inventors: Andrew Plant, Bracknell (GB); Jutta Elisabeth Boehmer, Bracknell (GB); Janice Black, Bracknell (GB); Timothy David Sparks, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 1275 days.

(21) Appl. No.: 11/574,648

(22) PCT Filed: Aug. 17, 2005

(86) PCT No.: PCT/GB2005/003228
§ 371 (c)(1),
(2), (4) Date: Mar. 2, 2007

(87) PCT Pub. No.: WO2006/024820
PCT Pub. Date: Mar. 9, 2006

(65) Prior Publication Data
US 2008/0139390 A1    Jun. 12, 2008

(30) Foreign Application Priority Data

Sep. 3, 2004    (GB) .................................. 0419634.1
Sep. 16, 2004   (GB) .................................. 0420645.4
Feb. 7, 2005    (GB) .................................. 0502486.4

(51) Int. Cl.
C07D 261/10    (2006.01)
A61K 31/421    (2006.01)

(52) U.S. Cl.
USPC ........................................ 548/243; 514/380

(58) Field of Classification Search
None
See application file for complete search history.

(56) References Cited

U.S. PATENT DOCUMENTS 6,841,519 B1 *    1/2005    Nakatani et al. ............. 504/271

FOREIGN PATENT DOCUMENTS

| EP | 1203768 A | | 5/2002 |
|---|---|---|---|
| EP | 1364946 A | | 11/2003 |
| EP | 1405853 A | | 4/2004 |
| JP | 08225548 A | * | 9/1996 |
| JP | 08225548 A | | 1/1997 |
| JP | 09328483 A | | 12/1997 |
| JP | 2005035924 A | | 2/2005 |
| WO | 03010165 A | | 2/2003 |

OTHER PUBLICATIONS

Lyga, John W. N-difluoromethylation of phenylazoles. Journal of Fluorine Chemistry 92 (1998) 141-145.*

* cited by examiner

*Primary Examiner* — Nyeemah A Grazier
(74) *Attorney, Agent, or Firm* — James Cueva

(57) ABSTRACT

Compounds of formula (I) wherein the substituents are as defined in claim 1, are suitable for use as herbicides. Also claimed is a process for the preparation of compounds of the formula I, wherein m is 2 and n is 1, and the other substituents are defined as in claim 1, formula (Ia) by reacting a compound of the formula Ia in a single step or stepwise in succession with compounds of the formula $R^5$—X and/or $R^6$—X, wherein $R^5$ and $R^6$ are as defined in claim 1, and X is a leaving group, and a process for the preparation of compounds of the formula I, wherein $R^6$ is $C_1$-$C_{10}$alkyl or halogen, m is 2 and n is 1, and the other substituents are defined as in claim 1, formula (Ib) by reacting a compound of the formula Ib with a compound of the formula $R^5$—X, wherein $R^5$ is as defined in claim 1, and X is a leaving group, and a process for the preparation of compounds of the formula I, wherein $R^5$ is chlorine, bromine or iodine, m is 1 or 2, and n is 1, and the other substituents are defined as in claim 1, formula (Ic) by reacting a compound of the formula 1e with an N-halosuccinimide and an oxidising agent.

(I)

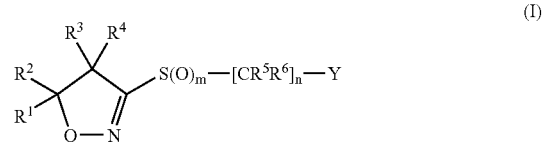

22 Claims, No Drawings

ISOXAZOLINE DERIVATIVES AND THEIR USE AS HERBICIDES

This application is a 371 of International Application No. PCT/GB2005/003228 filed Aug. 17, 2005, which claims priority to GB 0419634.1 filed Sept. 3, 2004, GB 0420645.4 filed Sept. 16, 2004, and GB 0502486.4 filed Feb. 7, 2005, the contents of which are incorporated herein by reference.

The present invention relates to novel, herbicidal isoxazoline compounds, to processes for their preparation, to compositions comprising those compounds, and to their use in controlling weeds, especially in crops of useful plants, or in inhibiting plant growth.

Isoxazoline compounds which display a herbicidal action are described, for example, in WO 01/012613, WO 02/062770, WO 03/000686, WO 04/010165 and JP 2005/035924. The preparation of these compounds is also described in WO 04/013106.

Novel isoxazoline compounds which display herbicidal and growth-inhibiting properties have now been found.

The present invention accordingly relates to compounds of formula I

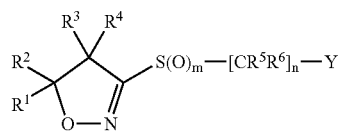

(I)

wherein
$R^1$ and $R^2$ are each independently of the other hydrogen, $C_1$-$C_{10}$alkyl, $C_1$-$C_{10}$haloalkyl, $C_3$-$C_8$cycloalkyl or $C_3$-$C_8$cycloalkyl-$C_1$-$C_3$alkyl, or
$R^1$ and $R^2$ together with the carbon atom to which they are bonded form a $C_3$-$C_7$ring,
$R^3$ and $R^4$ are each independently of the other hydrogen, $C_1$-$C_{10}$alkyl, $C_1$-$C_{10}$haloalkyl, $C_3$-$C_8$cycloalkyl-$C_1$-$C_{10}$alkyl, $C_1$-$C_6$alkoxy-$C_1$-$C_{10}$alkyl or $C_3$-$C_8$cycloalkyl, or
$R^3$ and $R^4$ together with the carbon atom to which they are bonded form a $C_3$-$C_7$ring, or
$R^1$ with $R^3$ or $R^4$ and together with the carbon atoms to which they are bonded form a $C_5$-$C_8$ring, or
$R^2$ with $R^3$ or $R^4$ and together with the carbon atoms to which they are bonded form a $C_5$-$C_8$ring;
$R^5$ and $R^6$ are each independently of the other $C_3$-$C_6$cycloalkyl, $C_1$-$C_6$haloalkyl, $C_1$-$C_6$-hydroxyalkyl, pyrrolyl-$CH_2$—, pyrazolyl-$CH_2$—, 4,5-dihydropyrazolyl-$CH_2$—, triazolyl-$CH_2$—, imidazolyl-$CH_2$—, tetrazolyl-$CH_2$—, indolyl-$CH_2$—, indazolyl-$CH_2$—, benzotriazolyl-$CH_2$—, $C_2$-$C_6$alkenyl, $C_2$-$C_6$alkynyl, $C_2$-$C_6$haloalkenyl, $C_1$-$C_6$alkylcarbonyloxy-$C_2$-$C_6$alkenyl, $C_2$-$C_6$alkenyloxy, $C_2$-$C_6$alkynyloxy, $C_1$-$C_6$alkylcarbonyl, $C_1$-$C_6$haloalkylcarbonyl, $C_3$-$C_6$cycloalkylcarbonyl, $C_1$-$C_6$alkoxy-$C_1$-$C_6$alkylcarbonyl, phenylcarbonyl or phenylcarbonyl substituted by one to three $R^9$, or
$R^5$ and $R^6$ are each independently of the other phenoxycarbonyl or phenoxycarbonyl substituted by one to three $R^9$, or
$R^5$ and $R^6$ are each independently of the other benzyloxycarbonyl or benzyloxycarbonyl substituted by one to three $R^9$, or
$R^5$ and $R^6$ are each independently of the other nitro, formyl, carboxyl, halogen, azido, thiocyanato, tri($C_1$-$C_6$alkyl)silyl, $C_1$-$C_6$alkylcarbonyl-$C_1$-$C_2$alkyl, $C_1$-$C_6$alkoxycarbonyl-$C_1$-$C_2$alkyl, cyano-$C_1$-$C_2$alkyl, $C_1$-$C_6$alkylaminocarbonyl-$C_1$-$C_2$alkyl, di-$C_1$-$C_6$alkyl-aminocarbonyl-$C_1$-$C_2$alkyl, $C_1$-$C_6$alkoxy-$C_1$-$C_2$alkyl, $C_1$-$C_2$alkyl-P(O)(O$C_1$-$C_6$alkyl)$_2$, $C_1$-$C_2$alkyl-NO$_2$, mercapto, phenylthio or phenylthio substituted by one to three $R^9$, or
$R_5$ and $R_6$ are each independently of the other pyridylthio, $C_1$-$C_6$alkylthio, $C_1$-$C_6$haloalkylthio, $C_1$-$C_6$alkylthio-$C_1$-$C_6$alkyl, $C_1$-$C_6$alkylsulfinyl, $C_1$-$C_6$haloalkylsulfinyl, $C_1$-$C_6$alkylsulfinyl-$C_1$-$C_6$alkyl, $C_1$-$C_6$alkylsulfonyl, $C_1$-$C_6$haloalkylsulfonyl, $C_1$-$C_6$alkylsulfonyl-$C_1$-$C_6$alkyl, $C_1$-$C_6$alkylsulfonyloxy-$C_1$-$C_6$alkyl, benzylsulfonyl or benzylsulfonyl substituted by one to three $R^9$, or
$R^5$ and $R^6$ are each independently of the other phenylsulfinyl or phenylsulfinyl substituted by one to three $R^9$, or
$R^5$ and $R^6$ are each independently of the other phenylsulfonyl or phenylsulfonyl substituted by one to three $R^9$, or
$R^5$ and $R^6$ are each independently of the other hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, or
$R^5$ and $R^6$ are each independently of the other benzyl or benzyl substituted by one to three $R^9$, or
$R^5$ and $R^6$ are each independently of the other benzyloxy or benzyloxy substituted by one to three $R^9$, or
$R^5$ and $R^6$ are each independently of the other —CONH—SO$_2$—$C_1$-$C_6$alkyl, —CONH—SO$_2$—$C_1$-$C_6$haloalkyl, —NHCHO, —NHCO—$C_1$-$C_6$alkyl, —NHCO—$C_1$-$C_6$haloalkyl, —NHCOO—$C_1$-$C_6$alkyl, —NHCONH—$C_1$-$C_6$alkyl, —NHCONH—$C_1$-$C_6$haloalkyl, —NHSO$_2$—$C_1$-$C_6$alkyl, —NHSO$_2$—$C_1$-$C_6$haloalkyl, —NHSO$_2$-phenyl or —NHSO$_2$-phenyl substituted by one to three $R^9$, or
$R^5$ and $R^6$ are each independently of the other —OCO—$C_1$-$C_6$alkyl, —OCO—$C_1$-$C_6$haloalkyl, —OCO-phenyl or —OCO-phenyl substituted by one to three $R^9$, or
$R^5$ and $R^6$ are each independently of the other —OCONH—$C_1$-$C_6$alkyl, —OCONH—$C_1$-$C_6$haloalkyl, —OCONH-phenyl or —OCONH-phenyl substituted by one to three $R^9$, or
$R^5$ and $R^6$ are each independently of the other —CONR$^7$R$^8$ wherein $R^7$ and $R^8$ are each independently of the other hydrogen, $C_1$-$C_6$alkyl, $C_3$-$C_6$cycloalkyl, $C_1$-$C_6$haloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, or
$R^5$ and $R^6$ are each independently of the other phenyl or naphthyl, which is optionally substituted by one to three substituents independently selected from $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by one to three $R^9$, nitro, cyano, formyl, carboxyl, halogen, azido, thiocyanato, tri($C_1$-$C_6$alkyl)silyl, mercapto, phenylthio or phenylthio substituted by one to three $R^9$, phenylsulfinyl or phenylsulfinyl substituted by one to three $R^9$, —SF$_5$, $C_1$-$C_6$alkylthio, $C_1$-$C_6$alkylsulfinyl, $C_1$-$C_6$alkylsulfonyl, $C_1$-$C_6$alkyl-SO(NH)—, $C_1$-$C_6$alkyl-SO(NCH$_3$), $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—SO$_2$—$C_1$-$C_6$alkyl, —CONH—SO$_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—

$C_1$-$C_6$alkyl, —OCONH—$C_1$-$C_6$haloalkyl, —OCONH-phenyl or —OCONH-phenyl substituted by one to three $R^9$, or by —CONR$^7$R$^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, or $R^5$ and $R^6$ are each independently of the other a 5- to 10-membered heterocycle containing one to three nitrogen, oxygen or sulfur atoms, which is optionally benzo-fused, and which is optionally substituted by one to three substituents independently selected from $C_1$-$C_6$alkyl, $C_3$-$C_6$cycloalkyl, $C_1$-$C_6$haloalkyl, $C_1$-$C_6$-hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by one to three $R^9$, phenylthio or phenylthio substituted by one to three $R^9$, phenylsulfinyl or phenylsulfinyl substituted by one to three $R^9$, nitro, cyano, formyl, carboxyl, halogen, azido, thiocyanato, tri($C_1$-$C_6$alkyl)silyl, mercapto, —SF$_5$, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—SO$_2$—$C_1$-$C_6$alkyl, —CONH—SO$_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CONR$^7$R$^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups, and $R^6$ may additionally be hydrogen, cyano, $C_1$-$C_6$alkyl or $C_1$-$C_6$alkoxycarbonyl, or $R^5$ and $R^6$ together with the carbon atom to which they are bonded form a 3- to 10-membered ring, which optionally contains one to three nitrogen, oxygen or sulfur atoms, and which is optionally substituted by one to four substituents independently selected from $C_1$-$C_6$alkyl, $C_1$-$C_6$haloalkyl, $C_1$-$C_6$alkoxy, $C_1$-$C_6$alkoxycarbonyl, $C_1$-$C_6$alkylcarbonyl, $C_1$-$C_6$alkylsulfonyl, $C_1$-$C_6$haloalkylsulfonyl, $C_1$-$C_6$haloalkylcarbonyl, $C_1$-$C_6$alkenyl, halogen, cyano, nitro, phenyl or phenyl substituted by $C_1$-$C_6$haloalkyl, nitro, cyano or by halogen, phenylcarbonyl or phenylcarbonyl substituted by $C_1$-$C_6$haloalkyl, nitro, cyano or by halogen, or $R^5$ and $R^6$ together with the carbon atom to which they are bonded form a group of the formula C=CR$^{10}$R$^{11}$ wherein $R^{10}$ and $R^{11}$ are independently selected from hydrogen, $C_1$-$C_6$alkyl, $C_1$-$C_6$alkoxy, —NH($C_1$-$C_6$alkyl), —N($C_1$-$C_6$alkyl)$_2$, $C_1$-$C_6$alkoxy-$C_1$-$C_2$alkyl, $C_1$-$C_6$alkylcarbonyloxy, $C_1$-$C_6$alkylcarbonyloxy-$C_1$-$C_2$alkyl, $C_1$-$C_6$alkoxy-$C_1$-$C_2$alkylcarbonyloxy or $C_1$-$C_6$alkylcarbonyloxy-$C_1$-$C_2$alkylcarbonyloxy;

m is 0, 1 or 2;

n is 1, 2 or 3;

Y is hydrogen, $C_1$-$C_6$alkyl, $C_3$-$C_6$cycloalkyl, $C_1$-$C_6$haloalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, nitro, cyano, formyl, hydroxyl, carboxyl, halogen, azido, thiocyanato, tri($C_1$-$C_6$alkyl)silyl, $C_1$-$C_6$alkylthio, $C_1$-$C_6$alkylsulfinyl, $C_1$-$C_6$alkylsulfonyl, benzylsulfonyl or benzylsulfonyl substituted by one to three $R^9$, or Y is phenylsulfonyl or phenylsulfonyl substituted by one to three $R^9$, or Y is $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by one to three $R^9$, or Y is benzyloxy or benzyloxy substituted by one to three $R^9$, or Y is —CONH—SO$_2$—$C_1$-$C_6$alkyl or —CONH—SO$_2$—$C_1$-$C_6$haloalkyl, or Y is phenyl, naphthyl or tetrahydronaphthyl, which is optionally substituted by one to three substituents independently selected from $C_1$-$C_6$alkyl, $C_3$-$C_6$cycloalkyl, $C_1$-$C_6$haloalkyl, $C_1$-$C_6$hydroxyalkyl, $C_1$-$C_6$alkoxy-$C_1$-$C_6$alkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$alkoxycarbonyl, benzyloxycarbonyl, nitro, cyano, formyl, carboxyl, halogen, azido, thiocyanato, tri($C_1$-$C_6$alkyl)silyl, mercapto, phenylthio, phenylsulfinyl, —SF$_5$, $C_1$-$C_6$alkylthio, $C_1$-$C_6$haloalkylthio, $C_1$-$C_6$haloalkylsulfinyl, $C_1$-$C_6$haloalkylsulfonyl, $C_1$-$C_6$alkylsulfinyl, $C_1$-$C_6$alkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_3$-$C_6$cycloalkyloxy wherein one of the CH$_2$ groups is optionally replaced by an oxygen atom, $C_1$-$C_6$haloalkoxy, $C_2$-$C_6$alkenyloxy, $C_2$-$C_6$alkynyloxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—SO$_2$—$C_1$-$C_6$alkyl, —CONH—SO$_2$—$C_1$-$C_6$haloalkyl, —NH—SO$_2$—$C_1$-$C_6$alkyl, —NH—SO$_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —CONR$^7$R$^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ form a $C_3$-$C_8$alkylene group which optionally contains one oxygen or sulfur atom or one to two amino or $C_1$-$C_6$alkylamino groups, or Y is a 5- to 10-membered heterocycle containing one to three nitrogen, oxygen or sulfur atoms, which is optionally benzo-fused, and which is optionally substituted by one to three substituents independently selected from $C_1$-$C_6$alkyl, $C_3$-$C_6$cycloalkyl, $C_1$-$C_6$haloalkyl, $C_1$-$C_6$hydroxyalkyl, $C_1$-$C_6$alkoxy-$C_1$-$C_6$alkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$alkoxycarbonyl, nitro, cyano, formyl, carboxyl, halogen, azido, thiocyanato, tri($C_1$-$C_6$alkyl)silyl, mercapto, —SF$_5$, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, benzylsulfonyl or benzylsulfonyl substituted by one to three $R^9$, phenylsulfonyl or phenylsulfonyl substituted by one to three $R^9$, hydroxyl, $C_1$-$C_6$alkoxy, $C_3$-$C_6$cycloalkyloxy wherein one of the CH$_2$ groups is optionally replaced by an oxygen atom, $C_1$-$C_6$haloalkoxy, $C_2$-$C_6$alkenyloxy, $C_2$-$C_6$alkynyloxy, $C_1$-$C_6$alkylsulfonyloxy, $C_1$-$C_6$haloalkylsulfonyloxy, phenoxy or phenoxy substituted by one to three $R^9$, benzyloxy or benzyloxy substituted by one to three $R^9$, —CONH—$SO_2$—$C_1$-$C_6$alkyl, —CONH—$SO_2$—$C_1$-$C_6$haloalkyl, —NH—$SO_2$—$C_1$-$C_6$alkyl, —NH—$SO_2$—$C_1$-$C_6$haloalkyl, —NHCO—$C_1$-$C_6$alkyl, —NHCO—$C_1$-$C_6$haloalkyl, —$NHCO_2$—$C_1$-$C_6$alkyl, —$NHCO_2$—$C_1$-$C_6$haloalkyl, —OCO—$C_1$-$C_6$alkyl, —OCO—$C_1$-$C_6$haloalkyl, —OCO-phenyl or —OCO-phenyl substituted by one to three $R^9$, —OCONH—$C_1$-$C_6$alkyl, —OCONH—$C_1$-$C_6$haloalkyl, —OCONH-phenyl or —OCONH-phenyl substituted by one to three $R^9$, or by —$CONR^7R^8$ wherein $R^7$ and $R^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which optionally contains one oxygen or sulfur atom or one to two amino or $C_1$-$C_6$alkylamino groups;

$R^9$ are independently from each other $C_1$-$C_6$haloalkyl, $C_1$-$C_6$alkoxycarbonyl, nitro, cyano, formyl, carboxyl or halogen;

and to N-oxides, salts and optical isomers of compounds of formula I.

The compounds of the invention may contain one or more asymmetric carbon atoms, for example, in the —$CR^5R^6$— group and may exist as enantiomers (or as pairs of diastereoisomers) or as mixtures of such. Further, when m is 1, the compounds of the invention are sulfoxides, which can exists in two enantiomeric forms, and the adjacent carbon can also exists in two enantiomeric forms. Compounds of general formula I can therefore exist as racemates, diastereoisomers, or single enantiomers, and the invention includes all possible isomers or isomer mixtures in all proportions. It is to be expected that for any given compound, one isomer may be more herbicidal than another.

Except where otherwise stated, alkyl groups and alkyl moieties of alkoxy, alkylthio, etc., suitably contain from 1 to 10, typically from 1 to 6, carbon atoms in the form of straight or branched chains. Examples are methyl, ethyl, n- and iso-propyl and n-, sec-, iso- and tert-butyl.

Except where otherwise stated, cycloalkyl groups and cycloalkyl moieties of cycloalkoxy, cycloalkyl-alkoxy, etc., suitably contain from 3 to 8, typically from 3 to 6, carbon atoms. Examples are cyclopropyl, cyclobutyl, cyclopentyl and cyclohexyl. The cycloalkyl radicals may be in bi- or tri-cyclic form.

Except where otherwise stated, haloalkyl groups and haloalkyl moieties of haloalkoxy, haloalkylthio, etc., also suitably contain from 1 to 6, typically from 1 to 4, carbon atoms in the form of straight or branched chains. Examples are difluoromethyl and 2,2,2-trifluoroethyl.

Except where otherwise stated, hydroxyalkyl groups also suitably contain from 1 to 6, typically from 1 to 4, carbon atoms in the form of straight or branched chains. Examples are 1,2-dihydroxyethyl and 3-hydroxypropyl.

Except where otherwise stated, alkenyl and alkynyl moieties also suitably contain from 2 to 6, typically from 2 to 4, carbon atoms in the form of straight or branched chains. Examples are allyl, but-2-enyl, 3-methylbut-2-enyl, ethynyl, propargyl and but-2-ynyl.

Except where otherwise stated, haloalkenyl groups and haloalkynyl groups also suitably contain from 2 to 6, typically from 2 to 4, carbon atoms in the form of straight or branched chains. Examples are trifluoroallyl and 1-chloroprop-1-yn-3-yl.

Halo includes fluoro, chloro, bromo and iodo. Most commonly it is fluoro, chloro or bromo and usually fluoro or chloro.

Except where otherwise stated, alkylene groups suitably contain from 1 to 10, typically from 1 to 6, carbon atoms in the form of straight or branched chains. Examples are methylene, ethylene, n- and iso-propylene and n-, sec-, iso- and tert-butylene.

Except where otherwise stated, heterocyclic groups suitably are 5- to 10-membered rings containing one to three nitrogen, oxygen or sulfur atoms, which may be optionally benzo-fused. Examples are furyl, thienyl, pyrrolyl, pyrazolyl, imidazolyl, 1,2,3-triazolyl, 1,2,4-triazolyl, tetrazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, benzofuryl, isobenzofuryl, benzothiophenyl, isobenzothiophenyl, indolyl, isoindolyl, indazolyl, benzimidazolyl, benztriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,1,3-benzoxadiazolyl, 1,2,3-benzothiadiazolyl, 2,1,3-benzothiadiazolyl, quinolyl, isoquinolyl, cinnolinyl, phthalazinyl, quinazolinyl, quinoxalinyl, naphthyridinyl, benzotriazinyl, purinyl, pteridinyl, indolizinyl, benzo-1,3-dioxolyl, 4H-benzo-1,3-dioxinyl, and 4H-benzo-1,4-dioxinyl groups and, where appropriate, N-oxides and salts thereof.

The 3- to 10-membered rings which may be present as substituents in the compounds according to the invention include both carbocyclic and heterocyclic, aromatic and non-aromatic rings. Such rings may be in the form of single rings or in the form of polycyclic rings. They may carry further substituents and/or be benzo-fused. There may be mentioned by way of example phenyl, naphthyl, anthryl, indenyl and phenanthrenyl, the above-mentioned cycloalkyl radicals, and also rings containing oxygen, sulfur or nitrogen atoms, such as tetrahydrofuranyl, tetrahydropyranyl, 1,3-dioxolanyl, 1,3-dioxanyl, 1,4-dioxanyl, and morpholinyl, also furyl, thienyl, pyrrolyl, pyrazolyl, imidazolyl, 1,2,3-triazolyl, 1,2,4-triazolyl, tetrazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, benzofuryl, isobenzofuryl, benzothiophenyl, isobenzothiophenyl, indolyl, isoindolyl, indazolyl, benzimidazolyl, benztriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,1,3-benzoxadiazolyl, 1,2,3-benzothiadiazolyl, 2,1,3-benzothiadiazolyl, quinolyl, isoquinolyl, cinnolinyl, phthalazinyl, quinazolinyl, quinoxalinyl, naphthyridinyl, benzotriazinyl, purinyl, pteridinyl, indolizinyl, benzo-1,3-dioxolyl, 4H-benzo-1,3-dioxinyl, and 4H-benzo-1,4-dioxinyl.

Where $R^5$ or $R^6$ is independently a heterocycle-methyl group, for example imidazolyl-$CH_2$—, the heterocycle is connected to the methyl group by a nitrogen.

The invention also includes N-oxides of the compounds of formula I.

The invention relates likewise to the salts which the compounds of formula I are able to form with amines, alkali metal and alkaline earth metal bases and quaternary ammonium bases.

Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C^1C^{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines such as, for example, pyridine, quinoline, isoquinoline, morpholine, piperidine, pyrrolidine, indoline, quinuclidine and azepine; primary arylamines such as, for example, anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_aR_bR_cR_d)]OH$ wherein $R_a$, $R_b$, $R_c$ and $R_d$ are each independently of the others $C_1$-$C_4$alkyl. Other suitable tetraalkylammonium bases with other anions can be obtained, for example, by anion exchange reactions.

Furthermore this invention relates to compounds of formula I wherein $R^1$ and $R^2$ are each independently of the other hydrogen, $C_1$-$C_{10}$alkyl, $C_1$-$C_{10}$haloalkyl, $C_3$-$C_8$cycloalkyl or $C_3$-$C_8$cycloalkyl-$C_1$-$C_3$alkyl, or $R^1$ and $R^2$ together with the carbon atom to which they are bonded form a $C_3$-$C_7$ring, $R^3$ and $R^4$ are each independently of the other hydrogen, $C_1$-$C_{10}$alkyl, $C_1$-$C_{10}$haloalkyl, $C_3$-$C_8$cycloalkyl-$C_1$-$C_{10}$alkyl, $C_1$-$C_6$alkoxy-$C_1$-$C_{10}$alkyl or $C_3$-$C_8$cycloalkyl, or $R^3$ and $R^4$ together with the carbon atom to which they are bonded form a $C_3$-$C_7$ring, or $R^1$ with $R^3$ or $R^4$ and together with the carbon atoms to which they are bonded form a $C_5$-$C_8$ring, or $R^2$ with $R^3$ or $R^4$ and together with the carbon atoms to which they are bonded form a $C_5$-$C_8$ring, $R^5$ and $R^6$ are each independently of the other $C_3$-$C_6$cycloalkyl, $C_1$-$C_6$haloalkyl, $C_1$-$C_6$-hydroxyalkyl, pyrrolyl-$CH_2$—, pyrazolyl-$CH_2$—, triazolyl-$CH_2$—, imidazolyl-$CH_2$—, tetrazolyl-$CH_2$—, indolyl-$CH_2$—, indazolyl-$CH_2$—, benzotriazolyl-$CH_2$—, $C_2$-$C_6$alkenyl, $C_2$-$C_6$alkynyl, $C_2$-$C_6$haloalkenyl, $C_2$-$C_6$alkenyloxy, $C_2$-$C_6$alkynyloxy, $C_1$-$C_6$alkylcarbonyl, $C_1$-$C_6$haloalkylcarbonyl, phenylcarbonyl or phenylcarbonyl substituted by $C_1$-$C_6$haloalkyl, $C_1$-$C_6$alkoxycarbonyl, nitro, cyano, formyl, carboxyl or by halogen, or $R^5$ and $R^6$ are each independently of the other phenoxycarbonyl or phenoxycarbonyl substituted by $C_1$-$C_6$haloalkyl, $C_1$-$C_6$alkoxycarbonyl, nitro, cyano, formyl, carboxyl or by halogen, or $R^5$ and $R^6$ are each independently of the other benzyloxycarbonyl or benzyloxycarbonyl substituted by $C_1$-$C_6$haloalkyl, $C_1$-$C_6$alkoxycarbonyl, nitro, cyano, formyl, carboxyl or by halogen, or $R^5$ and $R^6$ are each independently of the other nitro, formyl, carboxyl, halogen, azido, thiocyanato, tri($C_1$-$C_6$alkyl)silyl, $C_1$-$C_6$alkylcarbonyl-$C_1$-$C_2$alkyl, $C_1$-$C_6$alkoxycarbonyl-$C_1$-$C_2$alkyl, cyano-$C_1$-$C_2$alkyl, $C_1$-$C_6$alkylaminocarbonyl-$C_1$-$C_2$alkyl, di-$C_1$-$C_6$alkylaminocarbonyl-$C_1$-$C_2$alkyl, $C_1$-$C_6$alkoxy-$C_1$-$C_2$alkyl, $C_1$-$C_2$alkyl-P(O)(O$C_1$-$C_6$alkyl)$_2$, $C_1$-$C_2$alkyl-$NO_2$, mercapto, phenylthio or phenylthio substituted by $C_1$-$C_6$haloalkyl, $C_1$-$C_6$alkoxycarbonyl, nitro, cyano, formyl, carboxyl or by halogen, or $R_5$ and $R_6$ are each independently of the other pyridylthio, $C_1$-$C_6$alkylthio, $C_1$-$C_6$haloalkylthio, $C_1$-$C_6$alkylthio-$C_1$-$C_6$alkyl, $C_1$-$C_6$alkylsulfinyl, $C_1$-$C_6$haloalkylsulfinyl, $C_1$-$C_6$alkylsulfinyl-$C_1$-$C_6$alkyl, $C_1$-$C_6$alkylsulfonyl, $C_1$-$C_6$haloalkylsulfonyl, $C_1$-$C_6$alkylsulfonyl-$C_1$-$C_6$alkyl, benzylsulfonyl or benzylsulfonyl substituted by $C_1$-$C_6$haloalkyl, $C_1$-$C_6$alkoxycarbonyl, nitro, cyano, formyl, carboxyl or by halogen, or $R^5$ and $R^6$ are each independently of the other phenylsulfinyl or phenylsulfinyl substituted by $C_1$-$C_6$haloalkyl, $C_1$-$C_6$alkoxycarbonyl, nitro, cyano, formyl, carboxyl or by halogen, or $R^5$ and $R^6$ are each independently of the other phenylsulfonyl or phenylsulfonyl substituted by $C_1$-$C_6$haloalkyl, $C_1$-$C_6$alkoxycarbonyl, nitro, cyano, formyl, carboxyl or by halogen, or $R^5$ and $R^6$ are each independently of the other hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by $C_1$-$C_6$haloalkyl, $C_1$-$C_6$alkoxycarbonyl, nitro, cyano, formyl, carboxyl or by halogen, or $R^5$ and $R^6$ are each independently of the other benzyl or benzyl substituted by $C_1$-$C_6$haloalkyl, $C_1$-$C_6$alkoxycarbonyl, nitro, cyano, formyl, carboxyl or by halogen, or $R^5$ and $R^6$ are each independently of the other benzyloxy or benzyloxy substituted by $C_1$-$C_6$haloalkyl, $C_1$-$C_6$alkoxycarbonyl, nitro, cyano, formyl, carboxyl or by halogen, or $R^5$ and $R^6$ are each independently of the other —CONH—$SO_2$—$C_1$-$C_6$alkyl, —CONH—$SO_2$—$C_1$-$C_6$haloalkyl, —NHCHO, —NHCO—$C_1$-$C_6$alkyl, —NHCO—$C_1$-$C_6$haloalkyl, —NHCOO—$C_1$-$C_6$alkyl, —NHCONH—$C_1$-$C_6$alkyl, —NHCONH—$C_1$-$C_6$haloalkyl, —NHSO$_2$—$C_1$-$C_6$alkyl, —NHSO$_2$—$C_1$-$C_6$haloalkyl, —NHSO$_2$-phenyl, —OCO—$C_1$-$C_6$alkyl, —OCO—$C_1$-$C_6$haloalkyl, —OCO-phenyl or —OCO-phenyl substituted by $C_1$-$C_6$haloalkyl, $C_1$-$C_6$alkoxycarbonyl, nitro, cyano, formyl, carboxyl or by halogen, or $R^5$ and $R^6$ are each independently of the other —OCONH—$C_1$-$C_6$alkyl, —OCONH—$C_1$-$C_6$haloalkyl, —OCONH-phenyl or —OCONH-phenyl substituted by $C_1$-$C_6$haloalkyl, $C_1$-$C_6$alkoxycarbonyl, carboxyl, nitro, cyano or by halogen, or $R^5$ and $R^6$ are each independently of the other —CONR$^7$R$^8$ wherein R$^7$ and R$^8$ are each independently of the other hydrogen, $C_1$-$C_6$alkyl, $C_3$-$C_6$cycloalkyl, $C_1$-$C_6$haloalkyl, phenyl or phenyl substituted by $C_1$-$C_6$haloalkyl, nitro, cyano or by halogen, or $R^7$ and $R^8$ together form a $C_3$-$C_8$alkylene group which may contain one or more oxygen or sulfur atoms or one or more amino or alkylamino groups, or $R^5$ and $R^6$ are each independently of the other phenyl or naphthyl, which rings may be substituted by $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl or benzyloxycarbonyl substituted by $C_1$-$C_6$haloalkyl, $C_1$-$C_6$alkoxycarbonyl, nitro, cyano, formyl, carboxyl or by halogen, nitro, cyano, formyl, carboxyl, halogen, azido, thiocyanato, tri($C_1$-$C_6$alkyl)silyl, mercapto, phenylthio or phenylthio substituted by $C_1$-$C_6$haloalkyl, $C_1$-$C_6$alkoxycarbonyl, nitro, cyano, formyl, carboxyl or by halogen, phenylsulfinyl or phenylsulfinyl substituted by $C_1$-$C_6$haloalkyl, $C_1$-$C_6$alkoxycarbonyl, nitro, cyano, formyl, carboxyl or by halogen, —$SF_5$, $C_1$-$C_6$alkylthio, $C_1$-$C_6$alkylsulfinyl, $C_1$-$C_6$alkylsulfonyl, $C_1$-$C_6$alkyl-SO(NH)—, $C_1$-$C_6$alkyl-SO(NCH$_3$), $C_1$-$C_6$haloalkylthio, $C_1$-$C_6$haloalkylsulfinyl, $C_1$-$C_6$haloalkylsulfonyl, benzylsulfonyl or benzylsulfonyl substituted by $C_1$-$C_6$haloalkyl, $C_1$-$C_6$alkoxycarbonyl, nitro, cyano, formyl, carboxyl or by halogen, phenylsulfonyl or phenylsulfonyl substituted by $C_1$-$C_6$haloalkyl, $C_1$-$C_6$alkoxycarbonyl, nitro, cyano, formyl, carboxyl or by halogen, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by $C_1$-$C_6$haloalkyl, $C_1$-$C_6$alkoxycarbonyl, nitro, cyano, formyl, carboxyl or by halogen, benzyloxy or benzyloxy substituted by $C_1$-$C_6$haloalkyl, $C_1$-$C_6$alkoxycarbonyl, nitro, cyano, formyl, carboxyl or by halogen, —CONH—SO$_2$—$C_1$-$C_6$alkyl, —CONH—SO$_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by $C_1$-$C_6$haloalkyl, $C_1$-$C_6$alkoxycarbonyl, nitro, cyano, formyl, carboxyl or by halogen, —OCONH—$C_1$-$C_6$alkyl, —OCONH—$C_1$-$C_6$haloalkyl, —OCONH-phenyl or —OCONH-phenyl substituted by $C_1$-$C_6$haloalkyl, $C_1$-$C_6$alkoxycarbonyl, carboxyl, nitro, cyano or by halogen, or by —CONR$^7$R$^8$ wherein R$^7$ and R$^8$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or $R^7$ and $R^8$ together form a $C_3$-$C_8$alkylene group which may contain one or more oxygen or sulfur atoms or one or more amino or alkylamino groups, or $R^5$ and $R^6$ are each independently of the other a 5- to 10-membered heterocycle containing one or more nitrogen, oxygen or sulfur atoms, which heterocycle may be benzo-fused, and which heterocycle may be substituted by $C_1$-$C_6$alkyl, $C_3$-$C_6$cycloalkyl, $C_1$-$C_6$haloalkyl, $C_1$-$C_6$-hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, benzyloxycarbonyl, benzyloxycarbonyl substituted by $C_1$-$C_6$haloalkyl, $C_1$-$C_6$alkoxycarbonyl, nitro, cyano, formyl, carboxyl or by halogen, phenylthio, phenylthio substituted by $C_1$-$C_6$haloalkyl, $C_1$-$C_6$alkoxycarbonyl, nitro, cyano, formyl, carboxyl or by halogen, phenylsulfinyl, phenylsulfinyl substituted by $C_1$-$C_6$haloalkyl, $C_1$-$C_6$alkoxycarbonyl, nitro, cyano, formyl, carboxyl or by halogen, nitro, cyano, formyl, carboxyl, halogen, azido, thiocyanato, tri($C_1$-$C_6$alkyl)silyl, mercapto, —$SF_5$, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, benzylsulfonyl or benzylsulfonyl substituted by $C_1$-$C_6$haloalkyl, $C_1$-$C_6$alkoxycarbonyl, nitro, cyano, formyl, carboxyl or by halogen, phenylsulfonyl or phenylsulfonyl substituted by $C_1$-$C_6$haloalkyl, $C_1$-$C_6$alkoxycarbonyl, nitro, cyano, formyl, carboxyl or by halogen, hydroxyl, $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by $C_1$-$C_6$haloalkyl, $C_1$-$C_6$alkoxycarbonyl, nitro, cyano, formyl, carboxyl or by halogen, benzyloxy or benzyloxy substituted by $C_1$-$C_6$haloalkyl, $C_1$-$C_6$alkoxycarbonyl, nitro, cyano, formyl, carboxyl or by halogen, —CONH—SO$_2$—$C_1$-$C_6$alkyl, —CONH—SO$_2$—$C_1$-$C_6$haloalkyl, —NHCO—$C_1$-$C_6$alkyl, —NHCO—$C_1$-$C_6$haloalkyl, —NHCO$_2$—$C_1$-$C_6$alkyl, —NHCO$_2$—$C_1$-$C_6$haloalkyl, —OCO—$C_1$-$C_6$alkyl, —OCO—$C_1$-$C_6$haloalkyl, —OCO-phenyl or —OCO-phenyl substituted by $C_1$-$C_6$haloalkyl, $C_1$-$C_6$alkoxycarbonyl, nitro, cyano, formyl, carboxyl or by halogen, —OCONH—$C_1$-$C_6$alkyl, —OCONH—$C_1$-$C_6$haloalkyl, —OCONH-phenyl or —OCONH-phenyl substituted by $C_1$-$C_6$haloalkyl, $C_1$-$C_6$alkoxycarbonyl, carboxyl, nitro, cyano or by halogen, or by —CONR$^7$R$^8$ wherein R$^7$ and R$^9$ are each independently of the other hydrogen, $C_1$-$C_6$alkyl, $C_1$-$C_6$haloalkyl, $C_3$-$C_6$cycloalkyl, phenyl or phenyl substituted by $C_1$-$C_6$haloalkyl, nitro, cyano or by halogen, or R$^7$ and R$^8$ together form a $C_3$-$C_8$alkylene group which may contain one or more oxygen or sulfur atoms or one or more amino or alkylamino groups, and $R^6$ may additionally be hydrogen, cyano, $C_1$-$C_6$alkyl or $C_1$-$C_6$alkoxycarbonyl, or $R^5$ and $R^6$ together with the carbon atom to which they are bonded form a 3- to 10-membered ring which may contain one or more nitrogen, oxygen or sulfur atoms and which may be substituted by $C_1$-$C_6$alkyl, $C_1$-$C_6$haloalkyl, $C_1$-$C_6$alkoxy, $C_1$-$C_6$alkoxycarbonyl, $C_1$-$C_6$alkylcarbonyl, $C_1$-$C_6$alkylsulfonyl, $C_1$-$C_6$haloalkylsulfonyl, $C_1$-$C_6$haloalkylcarbonyl, $C_1$-$C_6$alkenyl, halogen, cyano, nitro, phenyl or phenyl substituted by $C_1$-$C_6$haloalkyl, nitro, cyano or by halogen, phenylcarbonyl or phenylcarbonyl substituted by $C_1$-$C_6$haloalkyl, nitro, cyano or by halogen, or $R^5$ and $R^6$ together with the carbon atom to which they are bonded form a group of the formula C=CH$_2$, C=CH—$C_1$-$C_6$alkyl, C=CH—N($C_1$-$C_6$alkyl)$_2$, C=CH—NH($C_1$-$C_6$alkyl) or C=CH—$C_1$-$C_6$alkoxy, m is 0, 1 or 2, n is 1, 2 or 3, Y is hydrogen, $C_1$-$C_6$alkyl, $C_3$-$C_6$cycloalkyl, $C_1$-$C_6$haloalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$alkoxycarbonyl, nitro, cyano, formyl, hydroxyl, carboxyl, halogen, azido, thiocyanato, tri($C_1$-$C_6$alkyl)silyl, $C_1$-$C_6$alkylthio, $C_1$-$C_6$alkylsulfinyl, $C_1$-$C_6$alkylsulfonyl, benzylsulfonyl or benzylsulfonyl substituted by $C_1$-$C_6$haloalkyl, $C_1$-$C_6$alkoxycarbonyl, carboxyl, nitro, cyano or by halogen, or Y is phenylsulfonyl or phenylsulfonyl substituted by $C_1$-$C_6$haloalkyl, $C_1$-$C_6$alkoxycarbonyl, carboxyl, nitro, cyano or by halogen, or Y is $C_1$-$C_6$alkoxy, $C_1$-$C_6$haloalkoxy, $C_1$-$C_6$alkylsulfonyloxy, $C_1$-$C_6$haloalkylsulfonyloxy, phenoxy or phenoxy substituted by $C_1$-$C_6$haloalkyl, $C_1$-$C_6$alkoxycarbonyl, carboxyl, nitro, cyano or by halogen, or Y is benzyloxy or benzyloxy substituted by $C_1$-$C_6$haloalkyl, $C_1$-$C_6$alkoxycarbonyl, carboxyl, nitro, cyano or by halogen, or Y is —CONH—SO$_2$—$C_1$-$C_6$alkyl or —CONH—SO$_2$—$C_1$-$C_6$haloalkyl, or Y is phenyl, naphthyl or tetrahydronaphthyl, which rings may be substituted by $C_1$-$C_6$alkyl, $C_3$-$C_6$cycloalkyl, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$alkoxycarbonyl, benzyloxycarbonyl, nitro, cyano, formyl, carboxyl, halogen, azido, thiocyanato, tri($C_1$-$C_6$alkyl)silyl, mercapto, phenylthio, phenylsulfinyl, —SF$_5$, C$_1$-C$_6$alkylthio, C$_1$-C$_6$haloalkylthio, C$_1$-C$_6$haloalkylsulfinyl, C$_1$-C$_6$haloalkylsulfonyl, C$_1$-C$_6$alkylsulfinyl, C$_1$-C$_6$alkylsulfonyl, benzylsulfonyl or benzylsulfonyl substituted by C$_1$-C$_6$haloalkyl, C$_1$-C$_6$alkoxycarbonyl, nitro, cyano, formyl, carboxyl or by halogen, phenylsulfonyl or phenylsulfonyl substituted by C$_1$-C$_6$haloalkyl, C$_1$-C$_6$alkoxycarbonyl, nitro, cyano, formyl, carboxyl or by halogen, hydroxyl, C$_1$-C$_6$alkoxy, C$_1$-C$_6$haloalkoxy, C$_1$-C$_6$alkylsulfonyloxy, C$_1$-C$_6$haloalkylsulfonyloxy, phenoxy or phenoxy substituted by C$_1$-C$_6$haloalkyl, C$_1$-C$_6$alkoxycarbonyl, nitro, cyano, formyl, carboxyl or by halogen, benzyloxy or benzyloxy substituted by C$_1$-C$_6$haloalkyl, C$_1$-C$_6$alkoxycarbonyl, nitro, cyano, formyl, carboxyl or by halogen, —CONH—SO$_2$—C$_1$-C$_6$alkyl, —CONH—SO$_2$—C$_1$-C$_6$haloalkyl, —NHCO—C$_1$-C$_6$alkyl, —NHCO—C$_1$-C$_6$haloalkyl, —NHCO$_2$—C$_1$-C$_6$alkyl, —NHCO$_2$—C$_1$-C$_6$haloalkyl, —OCO—C$_1$-C$_6$alkyl, —OCO—C$_1$-C$_6$haloalkyl, —OCO-phenyl or —OCO-phenyl substituted by C$_1$-C$_6$haloalkyl, C$_1$-C$_6$alkoxycarbonyl, nitro, cyano, formyl, carboxyl or by halogen, —OCONH—C$_1$-C$_6$alkyl, —OCONH—C$_1$-C$_6$haloalkyl, —OCONH-phenyl or —OCONH-phenyl substituted by C$_1$-C$_6$haloalkyl, C$_1$-C$_6$alkoxycarbonyl, carboxyl, nitro, cyano or by halogen, or by —CONR$^7$R$^8$ wherein R$^7$ and R$^8$ are each independently of the other hydrogen, C$_1$-C$_6$alkyl, C$_1$-C$_6$haloalkyl, C$_3$-C$_6$cycloalkyl, phenyl or phenyl substituted by C$_1$-C$_6$haloalkyl, nitro, cyano or by halogen, or R$^7$ and R$^8$ form a C$_3$-C$_8$alkylene group which may contain one or more oxygen or sulfur atoms or one or more amino or alkylamino groups, or Y is a 5- to 10-membered heterocycle containing one or more nitrogen, oxygen or sulfur atoms, which heterocycle may be benzo-fused, and which heterocycle may be substituted by C$_1$-C$_6$alkyl, C$_3$-C$_6$cycloalkyl, C$_1$-C$_6$haloalkyl, C$_1$-C$_6$hydroxyalkyl, C$_2$-C$_6$alkenyl, C$_2$-C$_6$alkynyl, C$_2$-C$_6$haloalkenyl, C$_1$-C$_6$alkylcarbonyl, C$_1$-C$_6$haloalkylcarbonyl, C$_1$-C$_6$alkoxycarbonyl, nitro, cyano, formyl, carboxyl, halogen, azido, thiocyanato, tri(C$_1$-C$_6$alkyl)silyl, mercapto, —SF$_5$, C$_1$-C$_6$alkylthio, C$_1$-C$_6$alkylsulfinyl, C$_1$-C$_6$alkylsulfonyl, C$_1$-C$_6$haloalkylthio, C$_1$-C$_6$haloalkylsulfinyl, C$_1$-C$_6$haloalkylsulfonyl, benzylsulfonyl or benzylsulfonyl substituted by C$_1$-C$_6$haloalkyl, C$_1$-C$_6$alkoxycarbonyl, nitro, cyano, formyl, carboxyl or by halogen, phenylsulfonyl or phenylsulfonyl substituted by C$_1$-C$_6$haloalkyl, C$_1$-C$_6$alkoxycarbonyl, nitro, cyano, formyl, carboxyl or by halogen, hydroxyl, C$_1$-C$_6$alkoxy, C$_1$-C$_6$haloalkoxy, C$_1$-C$_6$alkylsulfonyloxy, C$_1$-C$_6$haloalkylsulfonyloxy, phenoxy or phenoxy substituted by C$_1$-C$_6$haloalkyl, C$_1$-C$_6$alkoxycarbonyl, nitro, cyano, formyl, carboxyl or by halogen, benzyloxy or benzyloxy substituted by C$_1$-C$_6$haloalkyl, C$_1$-C$_6$alkoxycarbonyl, nitro, cyano, formyl, carboxyl or by halogen, —CONH—SO$_2$—C$_1$-C$_6$alkyl, —CONH—SO$_2$—C$_1$-C$_6$haloalkyl, —NHCO—C$_1$-C$_6$alkyl, —NHCO—C$_1$-C$_6$haloalkyl, —NHCO$_2$—C$_1$-C$_6$alkyl, —NHCO$_2$—C$_1$-C$_6$haloalkyl, —OCO—C$_1$-C$_6$alkyl, —OCO—C$_1$-C$_6$haloalkyl, —OCO-phenyl or —OCO-phenyl substituted by C$_1$-C$_6$haloalkyl, C$_1$-C$_6$alkoxycarbonyl, nitro, cyano, formyl, carboxyl or by halogen, —OCONH—C$_1$-C$_6$alkyl, —OCONH—C$_1$-C$_6$haloalkyl, —OCONH-phenyl or —OCONH-phenyl substituted by C$_1$-C$_6$haloalkyl, C$_1$-C$_6$alkoxycarbonyl, carboxyl, nitro, cyano or by halogen, or by —CONR$^7$R$^8$ wherein R$^7$ and R$^8$ are each independently of the other hydrogen, C$_1$-C$_6$alkyl, C$_1$-C$_6$haloalkyl, C$_3$-C$_6$cycloalkyl, phenyl or phenyl substituted by C$_1$-C$_6$haloalkyl, nitro, cyano or by halogen, or R$^7$ and R$^8$ together form a C$_3$-C$_8$alkylene group which may contain one or more oxygen or sulfur atoms or one or more amino or alkylamino groups, and to N-oxides, salts and optical isomers of compounds of formula I.

Alkyl and alkoxy radicals appearing in the substituent definitions are, for example, methyl, methoxy, ethyl, ethoxy, propyl, propoxy, butyl, butoxy, hexyl, hexyloxy, nonyl, nonyloxy and decyl and decyloxy and also branched isomers thereof. Suitable alkenyl and alkynyl radicals are derived from the mentioned alkyl radicals. Cycloalkyl radicals are generally cyclopropyl, cyclobutyl, cyclopentyl, cyclohexyl, cycloheptyl and cyclooctyl. The cycloalkyl radicals may be in bi- or tri-cyclic form. Phenyl radicals may be in substituted form. For example, Y may be a phenyl radical which can be substituted, for example, by alkoxy or by alkoxy substituted by halogen etc. The 3- to 10-membered rings which may be present as substituents in the compounds according to the invention include both carbocyclic and heterocyclic, aromatic and non-aromatic rings. Such rings may be in the form of single rings or in the form of polycyclic rings. They may carry further substituents and/or be benzo-fused. There may be mentioned by way of example phenyl, naphthyl, anthryl, indenyl and phenanthrenyl, the above-mentioned cycloalkyl radicals, and also rings containing oxygen, sulfur or nitrogen atoms, such as 1,3-dioxalanyl, dihydro-1,3-dioxolyl, tetrahydrofuranyl and morpholinyl, also furyl, thienyl, pyrrolyl, pyrazolyl, imidazolyl, 1,2,3-triazolyl, 1,2,4-triazolyl, oxazolyl, isoxazolyl, isothiazolyl, 1,2,3-oxadiazolyl, 1,2,4-oxadiazolyl, 1,3,4-oxadiazolyl, 1,2,5-oxadiazolyl, dihydroisoxazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, tetrazolyl, tetrazinyl, benzofuryl, benzisofuryl, benzothienyl, benzisothienyl, indolyl, benzimidazolyl, 2,1,3-benzoxadiazolyl, quinolyl, isoquinolyl, cinnolinyl, phthalazinyl, quinazolinyl, quinoxalinyl, naphthyridinyl, benzotriazinyl, purinyl, pteridinyl and indolizinyl.

The invention also includes N-oxides of the compounds of formula I.

The invention also includes the optical isomers of the compounds of formula I, especially those which have a chiral carbon atom in the —CR$^5$R$^6$— group.

TABLE 1

Compounds of formula I.1.

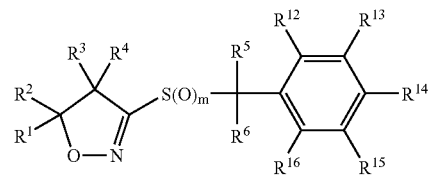

| R$^1$ | R$^2$ | R$^3$ | R$^4$ | m | R$^5$ | R$^6$ | R$^{12}$ | R$^{13}$ | R$^{14}$ | R$^{15}$ | R$^{16}$ |
|---|---|---|---|---|---|---|---|---|---|---|---|
| CH$_2$Cl | Me | H | H | 0 | CF$_3$ | H | NO$_2$ | H | H | Cl | H |
| Me | Me | H | H | 1 | Br | H | NO$_2$ | H | H | Cl | H |

TABLE 1-continued

Compounds of formula I.1.

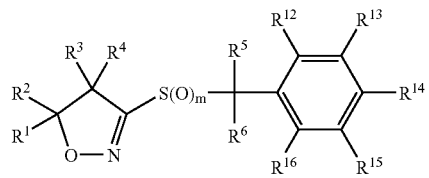

| R¹ | R² | R³ | R⁴ | m | R⁵ | R⁶ | R¹² | R¹³ | R¹⁴ | R¹⁵ | R¹⁶ |
|---|---|---|---|---|---|---|---|---|---|---|---|
| CH₂Cl | Me | H | H | 2 | I | H | F | H | H | H | F |
| Me | Me | H | H | 1 | CF₃ | H | F | H | H | H | Cl |
| CH₂Cl | Me | H | H | 1 | Cl | H | NO₂ | H | H | Cl | H |
| CH₂Cl | Me | H | H | 1 | Br | H | NO₂ | H | H | Cl | H |
| CH₂Cl | Me | H | H | 1 | I | H | H | Me | H | H | H |
| CH₂Cl | Me | H | H | 2 | CF₃ | H | NO₂ | H | H | Cl | H |
| Me | Me | H | H | 1 | I | H | NO₂ | H | H | Cl | H |
| CH₂Cl | Me | H | H | 1 | I | H | NO₂ | H | H | Cl | H |
| CH₂Cl | Me | H | H | 0 | Cl | H | NO₂ | H | H | Cl | H |
| Me | Me | H | H | 2 | F | H | F | H | H | H | F |
| CH₂Cl | Me | H | H | 1 | F | H | H | Me | H | H | H |
| CH₂Cl | Me | H | H | 1 | CF₃ | H | F | H | H | H | F |
| CH₂Cl | Me | H | H | 0 | CF₃ | H | F | H | H | H | Cl |
| Me | Me | H | H | 0 | I | H | F | H | H | H | Cl |
| Me | Me | H | H | 2 | Cl | H | NO₂ | H | H | Cl | H |
| Me | Me | H | H | 1 | Br | H | NO₂ | H | H | Cl | H |
| CH₂Cl | Me | H | H | 0 | CF₃ | H | H | Me | H | H | H |
| CH₂Cl | Me | H | H | 1 | I | H | NO₂ | H | H | Cl | H |
| Me | Me | H | H | 1 | Cl | H | NO₂ | H | H | Cl | H |
| CH₂Cl | Me | H | H | 1 | I | H | F | H | H | H | F |
| Me | Me | H | H | 1 | F | H | H | Me | H | H | H |
| Me | Me | H | H | 0 | F | H | H | Me | H | H | H |
| Me | Me | H | H | 2 | CF₃ | H | F | H | H | H | F |
| Me | Me | H | H | 2 | I | H | NO₂ | H | H | Cl | H |
| Me | Me | H | H | 1 | Br | H | H | Me | H | H | H |
| CH₂Cl | Me | H | H | 1 | Cl | H | F | H | H | H | F |
| Me | Me | H | H | 1 | F | H | NO₂ | H | H | Cl | H |
| Me | Me | H | H | 0 | Br | H | H | Me | H | H | H |
| Me | Me | H | H | 1 | I | H | NO₂ | H | H | Cl | H |
| CH₂Cl | Me | H | H | 1 | Cl | H | NO₂ | H | H | Cl | H |
| CH₂Cl | Me | H | H | 1 | Cl | H | H | Me | H | H | H |
| CH₂Cl | Me | H | H | 2 | Cl | H | F | H | H | H | Cl |
| CH₂Cl | Me | H | H | 0 | I | H | NO₂ | H | H | Cl | H |
| CH₂Cl | Me | H | H | 2 | Cl | H | H | Me | H | H | H |
| CH₂Cl | Me | H | H | 1 | CF₃ | H | F | H | H | H | Cl |
| CH₂Cl | Me | H | H | 0 | Cl | H | H | Me | H | H | H |
| Me | Me | H | H | 1 | CF₃ | H | H | Me | H | H | H |
| CH₂Cl | Me | H | H | 0 | Br | H | F | H | H | H | F |
| Me | Me | H | H | 0 | Br | H | F | H | H | H | F |
| CH₂Cl | Me | H | H | 1 | Br | H | F | H | H | H | F |
| Me | Me | H | H | 0 | I | H | NO₂ | H | H | Cl | H |
| CH₂Cl | Me | H | H | 1 | CF₃ | H | NO₂ | H | H | Cl | H |
| CH₂Cl | Me | H | H | 0 | F | H | F | H | H | H | F |
| CH₂Cl | Me | H | H | 1 | I | H | F | H | H | H | Cl |
| Me | Me | H | H | 2 | Br | H | H | Me | H | H | H |
| CH₂Cl | Me | H | H | 0 | Cl | H | NO₂ | H | H | Cl | H |
| Me | Me | H | H | 2 | CF₃ | H | F | H | H | H | Cl |
| Me | Me | H | H | 1 | Br | H | F | H | H | H | F |
| Me | Me | H | H | 1 | I | H | H | Me | H | H | H |
| Me | Me | H | H | 2 | F | H | NO₂ | H | H | Cl | H |
| Me | Me | H | H | 1 | F | H | H | Me | H | H | H |
| CH₂Cl | Me | H | H | 1 | F | H | F | H | H | H | Cl |
| Me | Me | H | H | 2 | Br | H | F | H | H | H | F |
| Me | Me | H | H | 2 | I | H | F | H | H | H | F |
| CH₂Cl | Me | H | H | 2 | I | H | H | Me | H | H | H |
| CH₂Cl | Me | H | H | 0 | Br | H | H | Me | H | H | H |
| Me | Me | H | H | 0 | Br | H | NO₂ | H | H | Cl | H |
| Me | Me | H | H | 0 | Br | H | NO₂ | H | H | Cl | H |
| Me | Me | H | H | 0 | F | H | F | H | H | H | Cl |
| CH₂Cl | Me | H | H | 1 | F | H | F | H | H | H | F |
| CH₂Cl | Me | H | H | 2 | Br | H | NO₂ | H | H | Cl | H |
| CH₂Cl | Me | H | H | 2 | I | H | NO₂ | H | H | Cl | H |
| Me | Me | H | H | 2 | CF₃ | H | NO₂ | H | H | Cl | H |
| Me | Me | H | H | 2 | Cl | H | F | H | H | H | F |
| CH₂Cl | Me | H | H | 0 | I | H | NO₂ | H | H | Cl | H |
| CH₂Cl | Me | H | H | 2 | CF₃ | H | F | H | H | H | Cl |
| CH₂Cl | Me | H | H | 0 | Cl | H | F | H | H | H | F |

TABLE 1-continued

Compounds of formula I.1.

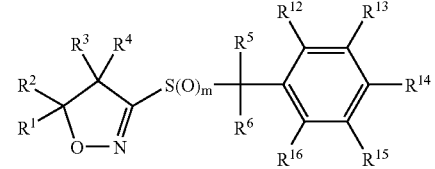

| R¹ | R² | R³ | R⁴ | m | R⁵ | R⁶ | R¹² | R¹³ | R¹⁴ | R¹⁵ | R¹⁶ |
|---|---|---|---|---|---|---|---|---|---|---|---|
| CH₂Cl | Me | H | H | 2 | I | H | NO₂ | H | H | Cl | H |
| Me | Me | H | H | 1 | Br | H | F | H | H | H | Cl |
| CH₂Cl | Me | H | H | 2 | I | H | F | H | H | H | Cl |
| CH₂Cl | Me | H | H | 2 | Cl | H | H | Me | H | H | H |
| Me | Me | H | H | 1 | CF₃ | H | F | H | H | H | F |
| Me | Me | H | H | 0 | Cl | H | NO₂ | H | H | Cl | H |
| Me | Me | H | H | 2 | F | H | H | Me | H | H | H |
| Me | Me | H | H | 2 | I | H | H | Me | H | H | H |
| CH₂Cl | Me | H | H | 2 | Br | H | H | Me | H | H | H |
| CH₂Cl | Me | H | H | 1 | F | H | NO₂ | H | H | Cl | H |
| CH₂Cl | Me | H | H | 1 | Br | H | NO₂ | H | H | Cl | H |
| Me | Me | H | H | 2 | Br | H | NO₂ | H | H | Cl | H |
| Me | Me | H | H | 2 | CF₃ | H | NO₂ | H | H | Cl | H |
| CH₂Cl | Me | H | H | 0 | F | H | H | Me | H | H | H |
| Me | Me | H | H | 0 | I | H | F | H | H | H | F |
| CH₂Cl | Me | H | H | 2 | CF₃ | H | H | Me | H | H | H |
| CH₂Cl | Me | H | H | 0 | Br | H | NO₂ | H | H | Cl | H |
| CH₂Cl | Me | H | H | 0 | Br | H | NO₂ | H | H | Cl | H |
| Me | Me | H | H | 1 | Cl | H | F | H | H | H | F |
| Me | Me | H | H | 0 | CF₃ | H | F | H | H | H | F |
| Me | Me | H | H | 0 | F | H | H | Me | H | H | H |
| CH₂Cl | Me | H | H | 0 | I | H | F | H | H | H | F |
| Me | Me | H | H | 2 | Cl | H | H | Me | H | H | H |
| CH₂Cl | Me | H | H | 2 | I | H | H | Me | H | H | H |
| CH₂Cl | Me | H | H | 1 | Cl | H | H | Me | H | H | H |
| Me | Me | H | H | 0 | Cl | H | H | Me | H | H | H |
| CH₂Cl | Me | H | H | 2 | F | H | F | H | H | H | Cl |
| CH₂Cl | Me | H | H | 0 | Br | H | F | H | H | H | Cl |
| Me | Me | H | H | 0 | I | H | H | Me | H | H | H |
| CH₂Cl | Me | H | H | 2 | CF₃ | H | F | H | H | H | F |
| Me | Me | H | H | 1 | F | H | NO₂ | H | H | Cl | H |
| CH₂Cl | Me | H | H | 2 | Br | H | NO₂ | H | H | Cl | H |
| CH₂Cl | Me | H | H | 2 | CF₃ | H | H | Me | H | H | H |
| CH₂Cl | Me | H | H | 0 | Cl | H | H | Me | H | H | H |
| Me | Me | H | H | 1 | Cl | H | NO₂ | H | H | Cl | H |
| Me | Me | H | H | 2 | I | H | F | H | H | H | Cl |
| CH₂Cl | Me | H | H | 2 | CF₃ | H | NO₂ | H | H | Cl | H |
| CH₂Cl | Me | H | H | 2 | Cl | H | F | H | H | H | F |
| Me | Me | H | H | 0 | Br | H | F | H | H | H | Cl |
| Me | Me | H | H | 0 | CF₃ | H | NO₂ | H | H | Cl | H |
| Me | Me | H | H | 0 | Br | H | H | Me | H | H | H |
| Me | Me | H | H | 0 | F | H | NO₂ | H | H | Cl | H |
| CH₂Cl | Me | H | H | 1 | F | H | NO₂ | H | H | Cl | H |
| Me | Me | H | H | 2 | I | H | H | Me | H | H | H |
| CH₂Cl | Me | H | H | 2 | Cl | H | NO₂ | H | H | Cl | H |
| Me | Me | H | H | 2 | Br | H | NO₂ | H | H | Cl | H |
| CH₂Cl | Me | H | H | 0 | CF₃ | H | H | Me | H | H | H |
| Me | Me | H | H | 2 | Cl | H | NO₂ | H | H | Cl | H |
| CH₂Cl | Me | H | H | 2 | Br | H | H | Me | H | H | H |
| CH₂Cl | Me | H | H | 0 | Cl | H | F | H | H | H | Cl |
| Me | Me | H | H | 1 | CF₃ | H | H | Me | H | H | H |
| CH₂Cl | Me | H | H | 1 | Br | H | H | Me | H | H | H |
| Me | Me | H | H | 2 | F | H | F | H | H | H | Cl |
| CH₂Cl | Me | H | H | 1 | Cl | H | F | H | H | H | Cl |
| CH₂Cl | Me | H | H | 2 | F | H | NO₂ | H | H | Cl | H |
| Me | Me | H | H | 0 | Cl | H | F | H | H | H | F |
| Me | Me | H | H | 0 | Cl | H | F | H | H | H | Cl |
| CH₂Cl | Me | H | H | 2 | F | H | H | Me | H | H | H |
| CH₂Cl | Me | H | H | 0 | F | H | NO₂ | H | H | Cl | H |
| Me | Me | H | H | 0 | F | H | F | H | H | H | F |
| CH₂Cl | Me | H | H | 2 | F | H | F | H | H | H | F |
| CH₂Cl | Me | H | H | 0 | Br | H | H | Me | H | H | H |
| Me | Me | H | H | 1 | I | H | F | H | H | H | F |
| CH₂Cl | Me | H | H | 2 | Cl | H | NO₂ | H | H | Cl | H |
| Me | Me | H | H | 2 | Cl | H | F | H | H | H | Cl |
| Me | Me | H | H | 1 | F | H | F | H | H | H | Cl |
| CH₂Cl | Me | H | H | 0 | F | H | F | H | H | H | Cl |

TABLE 1-continued

Compounds of formula I.1.

| $R^1$ | $R^2$ | $R^3$ | $R^4$ | m | $R^5$ | $R^6$ | $R^{12}$ | $R^{13}$ | $R^{14}$ | $R^{15}$ | $R^{16}$ |
|---|---|---|---|---|---|---|---|---|---|---|---|
| Me | Me | H | H | 0 | $CF_3$ | H | F | H | H | H | Cl |
| Me | Me | H | H | 1 | Cl | H | H | Me | H | H | H |
| $CH_2Cl$ | Me | H | H | 1 | $CF_3$ | H | $NO_2$ | H | H | Cl | H |
| Me | Me | H | H | 2 | Br | H | F | H | H | H | Cl |
| Me | Me | H | H | 1 | Cl | H | H | Me | H | H | H |
| $CH_2Cl$ | Me | H | H | 2 | F | H | H | Me | H | H | H |
| $CH_2Cl$ | Me | H | H | 2 | Br | H | F | H | H | H | F |
| $CH_2Cl$ | Me | H | H | 1 | $CF_3$ | H | H | Me | H | H | H |
| Me | Me | H | H | 1 | Cl | H | F | H | H | H | Cl |
| $CH_2Cl$ | Me | H | H | 2 | F | H | $NO_2$ | H | H | Cl | H |
| Me | Me | H | H | 0 | $CF_3$ | H | $NO_2$ | H | H | Cl | H |
| $CH_2Cl$ | Me | H | H | 1 | F | H | H | Me | H | H | H |
| Me | Me | H | H | 2 | F | H | $NO_2$ | H | H | Cl | H |
| $CH_2Cl$ | Me | H | H | 0 | I | H | H | Me | H | H | H |
| Me | Me | H | H | 2 | $CF_3$ | H | H | Me | H | H | H |
| Me | Me | H | H | 1 | I | H | H | Me | H | H | H |
| $CH_2Cl$ | Me | H | H | 0 | $CF_3$ | H | $NO_2$ | H | H | Cl | H |
| Me | Me | H | H | 2 | F | H | H | Me | H | H | H |
| Me | Me | H | H | 0 | F | H | $NO_2$ | H | H | Cl | H |
| Me | Me | H | H | 1 | I | H | F | H | H | H | Cl |
| $CH_2Cl$ | Me | H | H | 0 | F | H | $NO_2$ | H | H | Cl | H |
| Me | Me | H | H | 1 | $CF_3$ | H | $NO_2$ | H | H | Cl | H |
| Me | Me | H | H | 0 | I | H | H | Me | H | H | H |
| $CH_2Cl$ | Me | H | H | 1 | Br | H | H | Me | H | H | H |
| Me | Me | H | H | 0 | Cl | H | $NO_2$ | H | H | Cl | H |
| Me | Me | H | H | 2 | I | H | $NO_2$ | H | H | Cl | H |
| Me | Me | H | H | 0 | $CF_3$ | H | H | Me | H | H | H |
| $CH_2Cl$ | Me | H | H | 0 | I | H | H | Me | H | H | H |
| Me | Me | H | H | 1 | $CF_3$ | H | $NO_2$ | H | H | Cl | H |
| $CH_2Cl$ | Me | H | H | 1 | $CF_3$ | H | H | Me | H | H | H |
| $CH_2Cl$ | Me | H | H | 1 | Br | H | F | H | H | H | Cl |
| Me | Me | H | H | 1 | Br | H | H | Me | H | H | H |
| $CH_2Cl$ | Me | H | H | 2 | Br | H | F | H | H | H | Cl |
| Me | Me | H | H | 0 | $CF_3$ | H | H | Me | H | H | H |
| Me | Me | H | H | 0 | Cl | H | H | Me | H | H | H |
| $CH_2Cl$ | Me | H | H | 0 | F | H | H | Me | H | H | H |
| Me | Me | H | H | 1 | F | H | F | H | H | H | F |
| Me | Me | H | H | 2 | Br | H | H | Me | H | H | H |
| Me | Me | H | H | 0 | I | H | $NO_2$ | H | H | Cl | H |
| Me | Me | H | H | 2 | $CF_3$ | H | H | Me | H | H | H |
| Me | Me | H | H | 2 | Cl | H | H | Me | H | H | H |
| $CH_2Cl$ | Me | H | H | 0 | $CF_3$ | H | F | H | H | H | F |
| $CH_2Cl$ | Me | H | H | 0 | I | H | F | H | H | H | Cl |
| $CH_2Cl$ | Me | H | H | 1 | I | H | H | Me | H | H | H |

TABLE 2

Compounds of formula I.1.

| $R^1$ | $R^2$ | $R^3$ | $R^4$ | m | $R^5$ | $R^6$ | $R^{12}$ | $R^{13}$ | $R^{14}$ | $R^{15}$ | $R^{16}$ |
|---|---|---|---|---|---|---|---|---|---|---|---|
| $CH_2Cl$ | Me | H | H | 1 | I | Br | F | H | H | H | Cl |
| Me | Me | H | H | 2 | I | Br | F | H | H | H | F |
| Me | Me | H | H | 2 | F | Br | F | H | H | H | F |
| $CH_2Cl$ | Me | H | H | 2 | I | Br | $NO_2$ | H | H | Cl | H |

TABLE 2-continued

Compounds of formula I.1.

| R¹ | R² | R³ | R⁴ | m | R⁵ | R⁶ | R¹² | R¹³ | R¹⁴ | R¹⁵ | R¹⁶ |
|---|---|---|---|---|---|---|---|---|---|---|---|
| CH₂Cl | Me | H | H | 1 | F | Br | H | Me | H | H | H |
| Me | Me | H | H | 0 | I | Br | H | Me | H | H | H |
| CH₂Cl | Me | H | H | 2 | CF₃ | Br | NO₂ | H | H | Cl | H |
| CH₂Cl | Me | H | H | 2 | Cl | Br | F | H | H | H | Cl |
| Me | Me | H | H | 0 | Br | Br | NO₂ | H | H | Cl | H |
| CH₂Cl | Me | H | H | 2 | Br | Br | NO₂ | H | H | Cl | H |
| Me | Me | H | H | 2 | Br | Br | NO₂ | H | H | Cl | H |
| CH₂Cl | Me | H | H | 1 | CF₃ | Br | NO₂ | H | H | Cl | H |
| CH₂Cl | Me | H | H | 0 | Br | Br | F | H | H | H | Cl |
| CH₂Cl | Me | H | H | 0 | Br | Br | H | Me | H | H | H |
| CH₂Cl | Me | H | H | 1 | Cl | Br | F | H | H | H | Cl |
| CH₂Cl | Me | H | H | 1 | I | Br | H | Me | H | H | H |
| CH₂Cl | Me | H | H | 0 | Br | Br | F | H | H | H | F |
| Me | Me | H | H | 1 | F | Br | H | Me | H | H | H |
| Me | Me | H | H | 2 | Br | Br | F | H | H | H | F |
| Me | Me | H | H | 1 | I | Br | NO₂ | H | H | Cl | H |
| Me | Me | H | H | 0 | Cl | Br | NO₂ | H | H | Cl | H |
| Me | Me | H | H | 1 | I | Br | H | Me | H | H | H |
| Me | Me | H | H | 2 | I | Br | H | Me | H | H | H |
| Me | Me | H | H | 0 | Br | Br | H | Me | H | H | H |
| Me | Me | H | H | 1 | Br | Br | NO₂ | H | H | Cl | H |
| Me | Me | H | H | 2 | CF₃ | Br | H | Me | H | H | H |
| CH₂Cl | Me | H | H | 1 | Cl | Br | H | Me | H | H | H |
| CH₂Cl | Me | H | H | 0 | F | Br | H | Me | H | H | H |
| Me | Me | H | H | 1 | Br | Br | F | H | H | H | Cl |
| Me | Me | H | H | 1 | CF₃ | Br | H | Me | H | H | H |
| Me | Me | H | H | 0 | F | Br | F | H | H | H | Cl |
| Me | Me | H | H | 0 | CF₃ | Br | NO₂ | H | H | Cl | H |
| Me | Me | H | H | 1 | CF₃ | Br | NO₂ | H | H | Cl | H |
| CH₂Cl | Me | H | H | 1 | Cl | Br | NO₂ | H | H | Cl | H |
| Me | Me | H | H | 0 | CF₃ | Br | H | Me | H | H | H |
| CH₂Cl | Me | H | H | 2 | CF₃ | Br | H | Me | H | H | H |
| CH₂Cl | Me | H | H | 2 | Cl | Br | H | Me | H | H | H |
| Me | Me | H | H | 0 | F | Br | H | Me | H | H | H |
| CH₂Cl | Me | H | H | 2 | CF₃ | Br | NO₂ | H | H | Cl | H |
| CH₂Cl | Me | H | H | 1 | I | Br | F | H | H | H | F |
| Me | Me | H | H | 1 | F | Br | F | H | H | H | Cl |
| Me | Me | H | H | 2 | F | Br | F | H | H | H | Cl |
| Me | Me | H | H | 2 | I | Br | F | H | H | H | Cl |
| CH₂Cl | Me | H | H | 1 | F | Br | F | H | H | H | Cl |
| CH₂Cl | Me | H | H | 0 | I | Br | H | Me | H | H | H |
| CH₂Cl | Me | H | H | 0 | Cl | Br | H | Me | H | H | H |
| Me | Me | H | H | 1 | Br | Br | H | Me | H | H | H |
| Me | Me | H | H | 1 | Br | Br | H | Me | H | H | H |
| CH₂Cl | Me | H | H | 2 | F | Br | F | H | H | H | F |
| CH₂Cl | Me | H | H | 0 | F | Br | F | H | H | H | F |
| Me | Me | H | H | 0 | I | Br | H | Me | H | H | H |
| Me | Me | H | H | 2 | F | Br | H | Me | H | H | H |
| CH₂Cl | Me | H | H | 2 | Br | Br | H | Me | H | H | H |
| Me | Me | H | H | 2 | Cl | Br | NO₂ | H | H | Cl | H |
| Me | Me | H | H | 2 | CF₃ | Br | NO₂ | H | H | Cl | H |
| Me | Me | H | H | 0 | CF₃ | Br | F | H | H | H | F |
| Me | Me | H | H | 2 | Br | Br | F | H | H | H | Cl |
| Me | Me | H | H | 1 | Cl | Br | H | Me | H | H | H |
| Me | Me | H | H | 1 | Cl | Br | NO₂ | H | H | Cl | H |
| Me | Me | H | H | 0 | F | Br | H | Me | H | H | H |
| Me | Me | H | H | 1 | CF₃ | Br | F | H | H | H | F |
| CH₂Cl | Me | H | H | 1 | Cl | Br | NO₂ | H | H | Cl | H |
| CH₂Cl | Me | H | H | 0 | F | Br | H | Me | H | H | H |
| Me | Me | H | H | 2 | CF₃ | Br | H | Me | H | H | H |
| CH₂Cl | Me | H | H | 0 | Br | Br | NO₂ | H | H | Cl | H |
| Me | Me | H | H | 2 | Cl | Br | H | Me | H | H | H |
| Me | Me | H | H | 1 | Cl | Br | F | H | H | H | F |
| CH₂Cl | Me | H | H | 2 | I | Br | H | Me | H | H | H |
| CH₂Cl | Me | H | H | 2 | CF₃ | Br | F | H | H | H | Cl |
| Me | Me | H | H | 1 | I | Br | H | Me | H | H | H |
| CH₂Cl | Me | H | H | 0 | F | Br | F | H | H | H | Cl |

TABLE 2-continued

Compounds of formula I.1.

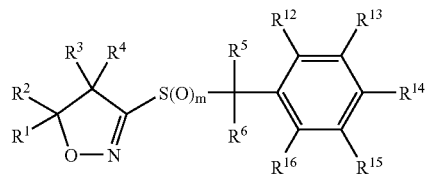

| R¹ | R² | R³ | R⁴ | m | R⁵ | R⁶ | R¹² | R¹³ | R¹⁴ | R¹⁵ | R¹⁶ |
|---|---|---|---|---|---|---|---|---|---|---|---|
| Me | Me | H | H | 0 | CF₃ | Br | H | Me | H | H | H |
| Me | Me | H | H | 2 | F | Br | NO₂ | H | H | Cl | H |
| CH₂Cl | Me | H | H | 2 | Cl | Br | NO₂ | H | H | Cl | H |
| CH₂Cl | Me | H | H | 2 | F | Br | H | Me | H | H | H |
| CH₂Cl | Me | H | H | 2 | F | Br | NO₂ | H | H | Cl | H |
| Me | Me | H | H | 1 | CF₃ | Br | NO₂ | H | H | Cl | H |
| Me | Me | H | H | 0 | I | Br | F | H | H | H | Cl |
| CH₂Cl | Me | H | H | 0 | Cl | Br | NO₂ | H | H | Cl | H |
| CH₂Cl | Me | H | H | 2 | Br | Br | F | H | H | H | Cl |
| Me | Me | H | H | 2 | Cl | Br | H | Me | H | H | H |
| Me | Me | H | H | 0 | Br | Br | F | H | H | H | Cl |
| CH₂Cl | Me | H | H | 0 | Cl | Br | H | Me | H | H | H |
| CH₂Cl | Me | H | H | 0 | I | Br | NO₂ | H | H | Cl | H |
| Me | Me | H | H | 0 | CF₃ | Br | NO₂ | H | H | Cl | H |
| Me | Me | H | H | 2 | Cl | Br | F | H | H | H | F |
| Me | Me | H | H | 2 | CF₃ | Br | F | H | H | H | Cl |
| CH₂Cl | Me | H | H | 1 | Cl | Br | H | Me | H | H | H |
| Me | Me | H | H | 0 | Cl | Br | F | H | H | H | Cl |
| CH₂Cl | Me | H | H | 0 | I | Br | H | Me | H | H | H |
| Me | Me | H | H | 1 | CF₃ | Br | H | Me | H | H | H |
| CH₂Cl | Me | H | H | 2 | Br | Br | H | Me | H | H | H |
| Me | Me | H | H | 2 | I | Br | NO₂ | H | H | Cl | H |
| Me | Me | H | H | 1 | F | Br | F | H | H | H | F |
| CH₂Cl | Me | H | H | 0 | CF₃ | Br | H | Me | H | H | H |
| Me | Me | H | H | 1 | Cl | Br | H | Me | H | H | H |
| Me | Me | H | H | 1 | I | Br | NO₂ | H | H | Cl | H |
| Me | Me | H | H | 1 | F | Br | NO₂ | H | H | Cl | H |
| CH₂Cl | Me | H | H | 1 | I | Br | H | Me | H | H | H |
| CH₂Cl | Me | H | H | 2 | F | Br | F | H | H | H | Cl |
| Me | Me | H | H | 2 | F | Br | H | Me | H | H | H |
| CH₂Cl | Me | H | H | 2 | I | Br | F | H | H | H | F |
| Me | Me | H | H | 1 | Cl | Br | F | H | H | H | Cl |
| CH₂Cl | Me | H | H | 0 | Cl | Br | F | H | H | H | F |
| Me | Me | H | H | 0 | I | Br | NO₂ | H | H | Cl | H |
| Me | Me | H | H | 2 | Br | Br | H | Me | H | H | H |
| CH₂Cl | Me | H | H | 1 | Br | Br | NO₂ | H | H | Cl | H |
| Me | Me | H | H | 1 | Br | Br | F | H | H | H | F |
| Me | Me | H | H | 1 | F | Br | NO₂ | H | H | Cl | H |
| Me | Me | H | H | 0 | Cl | Br | F | H | H | H | F |
| Me | Me | H | H | 1 | Br | Br | NO₂ | H | H | Cl | H |
| CH₂Cl | Me | H | H | 2 | F | Br | NO₂ | H | H | Cl | H |
| CH₂Cl | Me | H | H | 2 | Cl | Br | F | H | H | H | F |
| CH₂Cl | Me | H | H | 0 | CF₃ | Br | NO₂ | H | H | Cl | H |
| Me | Me | H | H | 1 | Cl | Br | NO₂ | H | H | Cl | H |
| Me | Me | H | H | 2 | F | Br | NO₂ | H | H | Cl | H |
| Me | Me | H | H | 0 | Cl | Br | H | Me | H | H | H |
| Me | Me | H | H | 2 | Cl | Br | NO₂ | H | H | Cl | H |
| CH₂Cl | Me | H | H | 0 | CF₃ | Br | F | H | H | H | F |
| Me | Me | H | H | 0 | F | Br | NO₂ | H | H | Cl | H |
| Me | Me | H | H | 1 | F | Br | H | Me | H | H | H |
| Me | Me | H | H | 0 | Br | Br | F | H | H | H | F |
| Me | Me | H | H | 1 | I | Br | F | H | H | H | F |
| CH₂Cl | Me | H | H | 1 | CF₃ | Br | F | H | H | H | F |
| CH₂Cl | Me | H | H | 0 | I | Br | F | H | H | H | F |
| Me | Me | H | H | 2 | CF₃ | Br | F | H | H | H | F |
| CH₂Cl | Me | H | H | 0 | Cl | Br | F | H | H | H | Cl |
| CH₂Cl | Me | H | H | 2 | I | Br | F | H | H | H | Cl |
| CH₂Cl | Me | H | H | 2 | CF₃ | Br | H | Me | H | H | H |
| CH₂Cl | Me | H | H | 2 | F | Br | H | Me | H | H | H |
| Me | Me | H | H | 0 | Br | Br | NO₂ | H | H | Cl | H |
| CH₂Cl | Me | H | H | 2 | Cl | Br | NO₂ | H | H | Cl | H |
| CH₂Cl | Me | H | H | 0 | I | Br | NO₂ | H | H | Cl | H |
| CH₂Cl | Me | H | H | 2 | CF₃ | Br | F | H | H | H | F |
| CH₂Cl | Me | H | H | 1 | CF₃ | Br | NO₂ | H | H | Cl | H |
| CH₂Cl | Me | H | H | 2 | Br | Br | F | H | H | H | F |
| Me | Me | H | H | 2 | I | Br | H | Me | H | H | H |
| CH₂Cl | Me | H | H | 1 | Br | Br | NO₂ | H | H | Cl | H |

TABLE 2-continued

Compounds of formula I.1.

| R¹ | R² | R³ | R⁴ | m | R⁵ | R⁶ | R¹² | R¹³ | R¹⁴ | R¹⁵ | R¹⁶ |
|---|---|---|---|---|---|---|---|---|---|---|---|
| CH₂Cl | Me | H | H | 1 | F | Br | F | H | H | H | F |
| CH₂Cl | Me | H | H | 0 | Br | Br | NO₂ | H | H | Cl | H |
| CH₂Cl | Me | H | H | 1 | CF₃ | Br | H | Me | H | H | H |
| CH₂Cl | Me | H | H | 1 | F | Br | H | Me | H | H | H |
| CH₂Cl | Me | H | H | 1 | Br | Br | H | Me | H | H | H |
| Me | Me | H | H | 1 | CF₃ | Br | F | H | H | H | Cl |
| Me | Me | H | H | 0 | I | Br | F | H | H | H | F |
| Me | Me | H | H | 1 | I | Br | F | H | H | H | Cl |
| CH₂Cl | Me | H | H | 1 | CF₃ | Br | F | H | H | H | Cl |
| CH₂Cl | Me | H | H | 1 | Br | Br | F | H | H | H | F |
| CH₂Cl | Me | H | H | 1 | Br | Br | F | H | H | H | Cl |
| CH₂Cl | Me | H | H | 1 | I | Br | NO₂ | H | H | Cl | H |
| CH₂Cl | Me | H | H | 2 | I | Br | NO₂ | H | H | Cl | H |
| Me | Me | H | H | 0 | F | Br | NO₂ | H | H | Cl | H |
| CH₂Cl | Me | H | H | 0 | CF₃ | Br | NO₂ | H | H | Cl | H |
| CH₂Cl | Me | H | H | 0 | F | Br | NO₂ | H | H | Cl | H |
| CH₂Cl | Me | H | H | 1 | I | Br | NO₂ | H | H | Cl | H |
| CH₂Cl | Me | H | H | 1 | Cl | Br | F | H | H | H | F |
| CH₂Cl | Me | H | H | 0 | I | Br | F | H | H | H | Cl |
| Me | Me | H | H | 0 | Cl | Br | NO₂ | H | H | Cl | H |
| Me | Me | H | H | 0 | F | Br | F | H | H | H | F |
| CH₂Cl | Me | H | H | 0 | Br | Br | H | Me | H | H | H |
| Me | Me | H | H | 0 | CF₃ | Br | F | H | H | H | Cl |
| CH₂Cl | Me | H | H | 1 | CF₃ | Br | H | Me | H | H | H |
| Me | Me | H | H | 0 | I | Br | NO₂ | H | H | Cl | H |
| CH₂Cl | Me | H | H | 2 | I | Br | H | Me | H | H | H |
| CH₂Cl | Me | H | H | 1 | Br | Br | H | Me | H | H | H |
| CH₂Cl | Me | H | H | 2 | Br | Br | NO₂ | H | H | Cl | H |
| Me | Me | H | H | 2 | Cl | Br | F | H | H | H | Cl |
| CH₂Cl | Me | H | H | 1 | F | Br | NO₂ | H | H | Cl | H |
| Me | Me | H | H | 2 | CF₃ | Br | NO₂ | H | H | Cl | H |
| CH₂Cl | Me | H | H | 0 | CF₃ | Br | H | Me | H | H | H |
| Me | Me | H | H | 0 | Cl | Br | H | Me | H | H | H |
| Me | Me | H | H | 2 | Br | Br | H | Me | H | H | H |
| Me | Me | H | H | 0 | Br | Br | NO₂ | H | H | Cl | H |
| Me | Me | H | H | 0 | Br | Br | H | Me | H | H | H |
| CH₂Cl | Me | H | H | 0 | Cl | Br | NO₂ | H | H | Cl | H |
| CH₂Cl | Me | H | H | 0 | CF₃ | Br | F | H | H | H | Cl |
| Me | Me | H | H | 2 | I | Br | NO₂ | H | H | Cl | H |
| CH₂Cl | Me | H | H | 1 | F | Br | NO₂ | H | H | Cl | H |
| CH₂Cl | Me | H | H | 0 | F | Br | NO₂ | H | H | Cl | H |
| CH₂Cl | Me | H | H | 2 | Cl | Br | H | Me | H | H | H |

TABLE 3

Compounds of formula I.1.

| R¹ | R² | R³ | R⁴ | m | R⁵ |
|---|---|---|---|---|---|
| Me | Me | H | H | 0 | CF₃ |
| Me | Me | H | H | 2 | CF₃ |
| Me | Me | H | H | 1 | I |
| CH₂Cl | Me | H | H | 1 | F |
| CH₂Cl | Me | H | H | 2 | CF₃ |
| CH₂Cl | Me | H | H | 0 | F |
| CH₂Cl | Me | H | H | 0 | I |
| Me | Me | H | H | 1 | F |
| CH₂Cl | Me | H | H | 1 | Cl |
| CH₂Cl | Me | H | H | 0 | CF₃ |
| Me | Me | H | H | 2 | Cl |
| CH₂Cl | Me | H | H | 1 | CF₃ |
| Me | Me | H | H | 2 | Cl |
| CH₂Cl | Me | H | H | 0 | Cl |

TABLE 3-continued

Compounds of formula I.1.

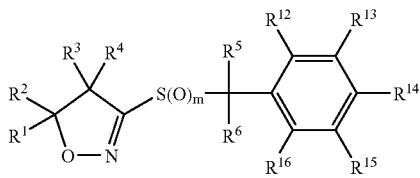
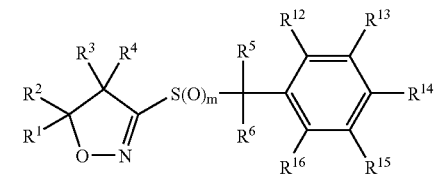

| R1 | R2 | R3 | R4 | m | R14 |
|---|---|---|---|---|---|
| CH2Cl | Me | H | H | 2 | I |
| CH2Cl | Me | H | H | 1 | F |
| CH2Cl | Me | H | H | 0 | I |
| CH2Cl | Me | H | H | 0 | Cl |
| Me | Me | H | H | 1 | Cl |
| CH2Cl | Me | H | H | 1 | CF3 |
| Me | Me | H | H | 2 | I |
| Me | Me | H | H | 0 | CF3 |
| CH2Cl | Me | H | H | 2 | F |
| Me | Me | H | H | 1 | I |
| CH2Cl | Me | H | H | 2 | I |
| Me | Me | H | H | 0 | Cl |
| CH2Cl | Me | H | H | 2 | I |
| Me | Me | H | H | 0 | F |
| CH2Cl | Me | H | H | 1 | I |
| Me | Me | H | H | 0 | F |
| CH2Cl | Me | H | H | 0 | CF3 |
| CH2Cl | Me | H | H | 1 | CF3 |
| Me | Me | H | H | 1 | CF3 |
| Me | Me | H | H | 0 | CF3 |
| CH2Cl | Me | H | H | 1 | F |
| CH2Cl | Me | H | H | 1 | Cl |
| CH2Cl | Me | H | H | 0 | CF3 |
| Me | Me | H | H | 2 | I |
| CH2Cl | Me | H | H | 2 | Cl |
| Me | Me | H | H | 1 | CF3 |
| Me | Me | H | H | 0 | Cl |
| CH2Cl | Me | H | H | 2 | Cl |
| Me | Me | H | H | 2 | F |
| CH2Cl | Me | H | H | 0 | F |
| Me | Me | H | H | 2 | CF3 |
| Me | Me | H | H | 1 | I |
| Me | Me | H | H | 0 | I |
| Me | Me | H | H | 0 | F |
| Me | Me | H | H | 2 | Cl |
| CH2Cl | Me | H | H | 2 | CF3 |
| Me | Me | H | H | 0 | Cl |
| CH2Cl | Me | H | H | 1 | Cl |
| CH2Cl | Me | H | H | 1 | Cl |
| CH2Cl | Me | H | H | 1 | Cl |
| Me | Me | H | H | 2 | Cl |
| Me | Me | H | H | 0 | I |
| Me | Me | H | H | 1 | CF3 |
| Me | Me | H | H | 2 | I |
| Me | Me | H | H | 1 | I |
| Me | Me | H | H | 1 | F |
| CH2Cl | Me | H | H | 0 | I |
| CH2Cl | Me | H | H | 0 | F |
| CH2Cl | Me | H | H | 1 | I |
| CH2Cl | Me | H | H | 0 | F |
| CH2Cl | Me | H | H | 0 | CF3 |
| CH2Cl | Me | H | H | 2 | I |
| CH2Cl | Me | H | H | 2 | CF3 |
| CH2Cl | Me | H | H | 2 | F |
| Me | Me | H | H | 1 | CF3 |
| CH2Cl | Me | H | H | 1 | CF3 |
| Me | Me | H | H | 2 | CF3 |
| Me | Me | H | H | 2 | I |
| CH2Cl | Me | H | H | 2 | F |
| Me | Me | H | H | 0 | I |
| CH2Cl | Me | H | H | 0 | Cl |
| Me | Me | H | H | 2 | CF3 |
| Me | Me | H | H | 2 | F |
| Me | Me | H | H | 1 | CF3 |
| Me | Me | H | H | 2 | F |
| Me | Me | H | H | 0 | Cl |
| CH2Cl | Me | H | H | 1 | CF3 |
| Me | Me | H | H | 1 | F |
| Me | Me | H | H | 1 | F |
| CH2Cl | Me | H | H | 0 | I |
| CH2Cl | Me | H | H | 0 | Cl |
| CH2Cl | Me | H | H | 2 | F |
| CH2Cl | Me | H | H | 1 | I |
| CH2Cl | Me | H | H | 1 | CF3 |
| CH2Cl | Me | H | H | 0 | Cl |
| CH2Cl | Me | H | H | 1 | F |
| Me | Me | H | H | 1 | Cl |
| Me | Me | H | H | 1 | I |
| Me | Me | H | H | 0 | I |
| CH2Cl | Me | H | H | 2 | Cl |
| Me | Me | H | H | 0 | CF3 |
| Me | Me | H | H | 2 | Cl |
| CH2Cl | Me | H | H | 2 | Cl |
| CH2Cl | Me | H | H | 2 | I |
| Me | Me | H | H | 1 | Cl |
| Me | Me | H | H | 0 | I |
| Me | Me | H | H | 2 | Cl |
| CH2Cl | Me | H | H | 2 | F |
| Me | Me | H | H | 0 | Cl |
| Me | Me | H | H | 2 | F |
| Me | Me | H | H | 0 | CF3 |
| CH2Cl | Me | H | H | 1 | I |
| CH2Cl | Me | H | H | 1 | F |
| Me | Me | H | H | 1 | Cl |
| Me | Me | H | H | 2 | CF3 |
| Me | Me | H | H | 0 | CF3 |
| Me | Me | H | H | 1 | I |
| CH2Cl | Me | H | H | 0 | Cl |
| CH2Cl | Me | H | H | 0 | F |
| CH2Cl | Me | H | H | 0 | I |
| Me | Me | H | H | 2 | F |
| CH2Cl | Me | H | H | 2 | Cl |
| CH2Cl | Me | H | H | 0 | CF3 |
| Me | Me | H | H | 0 | Cl |
| CH2Cl | Me | H | H | 2 | CF3 |
| CH2Cl | Me | H | H | 1 | Cl |
| Me | Me | H | H | 2 | CF3 |
| CH2Cl | Me | H | H | 0 | CF3 |
| Me | Me | H | H | 2 | I |
| Me | Me | H | H | 1 | Cl |
| CH2Cl | Me | H | H | 1 | I |
| Me | Me | H | H | 0 | I |
| Me | Me | H | H | 0 | F |
| CH2Cl | Me | H | H | 2 | CF3 |
| CH2Cl | Me | H | H | 0 | F |
| Me | Me | H | H | 1 | F |
| Me | Me | H | H | 1 | Cl |
| CH2Cl | Me | H | H | 2 | Cl |
| CH2Cl | Me | H | H | 2 | F |
| CH2Cl | Me | H | H | 1 | I |
| CH2Cl | Me | H | H | 0 | I |
| Me | Me | H | H | 1 | CF3 |
| Me | Me | H | H | 0 | F |
| Me | Me | H | H | 1 | F |
| Me | Me | H | H | 1 | Cl |
| Me | Me | H | H | 0 | F |
| CH2Cl | Me | H | H | 1 | F |
| Me | Me | H | H | 2 | F |
| Me | Me | H | H | 2 | I |
| CH2Cl | Me | H | H | 2 | I |
| CH2Cl | Me | H | H | 2 | CF3 |

| R6 | R12 | R13 | R14 | R15 | R16 |
|---|---|---|---|---|---|
| Cl | F | H | H | H | Cl |
| Cl | F | H | H | H | Cl |
| Cl | H | Me | H | H | H |
| Cl | H | Me | H | H | H |
| Cl | H | Me | H | H | H |

TABLE 3-continued

Compounds of formula I.1.

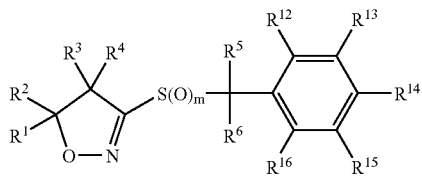
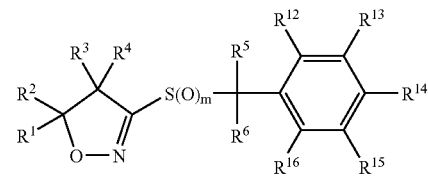

| $R^1$ | $R^2$ | $R^3$ | $R^4$ | $R^{12}$/$R^{13}$/$R^{14}$/$R^{15}$/$R^{16}$ | |
|---|---|---|---|---|---|
| Cl | F | H | H | H | Cl |
| Cl | H | Me | H | H | H |
| Cl | F | H | H | H | Cl |
| Cl | NO$_2$ | H | H | Cl | H |
| Cl | H | Me | H | H | H |
| Cl | F | H | H | H | F |
| Cl | H | Me | H | H | H |
| Cl | H | Me | H | H | H |
| Cl | NO$_2$ | H | H | Cl | H |
| Cl | H | Me | H | H | H |
| Cl | NO$_2$ | H | H | Cl | H |
| Cl | F | H | H | H | F |
| Cl | F | H | H | H | Cl |
| Cl | NO$_2$ | H | H | Cl | H |
| Cl | NO$_2$ | H | H | Cl | H |
| Cl | H | Me | H | H | H |
| Cl | H | Me | H | H | H |
| Cl | NO$_2$ | H | H | Cl | H |
| Cl | F | H | H | H | F |
| Cl | NO$_2$ | H | H | Cl | H |
| Cl | F | H | H | H | F |
| Cl | H | Me | H | H | H |
| Cl | NO$_2$ | H | H | Cl | H |
| Cl | NO$_2$ | H | H | Cl | H |
| Cl | NO$_2$ | H | H | Cl | H |
| Cl | H | Me | H | H | H |
| Cl | H | Me | H | H | H |
| Cl | F | H | H | H | Cl |
| Cl | NO$_2$ | H | H | Cl | H |
| Cl | F | H | H | H | F |
| Cl | F | H | H | H | Cl |
| Cl | NO$_2$ | H | H | Cl | H |
| Cl | F | H | H | H | F |
| Cl | H | Me | H | H | H |
| Cl | F | H | H | H | F |
| Cl | H | Me | H | H | H |
| Cl | NO$_2$ | H | H | Cl | H |
| Cl | F | H | H | H | F |
| Cl | H | Me | H | H | H |
| Cl | NO$_2$ | H | H | Cl | H |
| Cl | NO$_2$ | H | H | Cl | H |
| Cl | F | H | H | H | Cl |
| Cl | F | H | H | H | F |
| Cl | H | Me | H | H | H |
| Cl | NO$_2$ | H | H | Cl | H |
| Cl | NO$_2$ | H | H | Cl | H |
| Cl | H | Me | H | H | H |
| Cl | NO$_2$ | H | H | Cl | H |
| Cl | F | H | H | H | F |
| Cl | NO$_2$ | H | H | Cl | H |
| Cl | NO$_2$ | H | H | Cl | H |
| Cl | H | Me | H | H | H |
| Cl | NO$_2$ | H | H | Cl | H |
| Cl | NO$_2$ | H | H | Cl | H |
| Cl | NO$_2$ | H | H | Cl | H |
| Cl | NO$_2$ | H | H | Cl | H |
| Cl | H | Me | H | H | H |
| Cl | F | H | H | H | F |
| Cl | NO$_2$ | H | H | Cl | H |
| Cl | F | H | H | H | F |
| Cl | F | H | H | H | Cl |
| Cl | NO$_2$ | H | H | Cl | H |
| Cl | NO$_2$ | H | H | Cl | H |
| Cl | H | Me | H | H | H |
| Cl | F | H | H | H | Cl |
| Cl | F | H | H | H | F |
| Cl | H | Me | H | H | H |
| Cl | H | Me | H | H | H |
| Cl | F | H | H | H | F |
| Cl | NO$_2$ | H | H | Cl | H |
| Cl | H | Me | H | H | H |
| Cl | F | H | H | H | Cl |
| Cl | NO$_2$ | H | H | Cl | H |
| Cl | NO$_2$ | H | H | Cl | H |
| Cl | NO$_2$ | H | H | Cl | H |
| Cl | H | Me | H | H | H |
| Cl | H | Me | H | H | H |
| Cl | NO$_2$ | H | H | Cl | H |
| Cl | H | Me | H | H | H |
| Cl | F | H | H | H | Cl |
| Cl | H | Me | H | H | H |
| Cl | NO$_2$ | H | H | Cl | H |
| Cl | NO$_2$ | H | H | Cl | H |
| Cl | F | H | H | H | Cl |
| Cl | H | Me | H | H | H |
| Cl | NO$_2$ | H | H | Cl | H |
| Cl | H | Me | H | H | H |
| Cl | F | H | H | H | Cl |
| Cl | H | Me | H | H | H |
| Cl | H | Me | H | H | H |
| Cl | H | Me | H | H | H |
| Cl | F | H | H | H | F |
| Cl | NO$_2$ | H | H | Cl | H |
| Cl | H | Me | H | H | H |
| Cl | NO$_2$ | H | H | Cl | H |
| Cl | H | Me | H | H | H |
| Cl | F | H | H | H | Cl |
| Cl | F | H | H | H | Cl |
| Cl | F | H | H | H | Cl |
| Cl | H | Me | H | H | H |
| Cl | NO$_2$ | H | H | Cl | H |
| Cl | NO$_2$ | H | H | Cl | H |
| Cl | NO$_2$ | H | H | Cl | H |
| Cl | F | H | H | H | F |
| Cl | H | Me | H | H | H |
| Cl | H | Me | H | H | H |
| Cl | H | Me | H | H | H |
| Cl | F | H | H | H | F |
| Cl | F | H | H | H | F |
| Cl | H | Me | H | H | H |
| Cl | F | H | H | H | Cl |
| Cl | F | H | H | H | F |
| Cl | F | H | H | H | Cl |
| Cl | F | H | H | H | Cl |
| Cl | NO$_2$ | H | H | Cl | H |
| Cl | H | Me | H | H | H |
| Cl | NO$_2$ | H | H | Cl | H |
| Cl | F | H | H | H | Cl |
| Cl | F | H | H | H | Cl |
| Cl | H | Me | H | H | H |
| Cl | F | H | H | H | Cl |

TABLE 3-continued

Compounds of formula I.1.

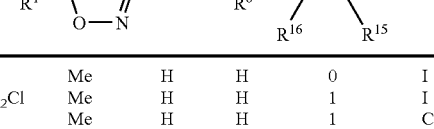

| | | | | | |
|---|---|---|---|---|---|
| Cl | NO₂ | H | H | Cl | H |
| Cl | F | H | H | H | F |

TABLE 4

Compounds of formula I.1.

| R¹ | R² | R³ | R⁴ | m | R⁵ |
|---|---|---|---|---|---|
| CH₂Cl | Me | H | H | 0 | F |
| CH₂Cl | Me | H | H | 1 | CF₃ |
| CH₂Cl | Me | H | H | 1 | CF₃ |
| CH₂Cl | Me | H | H | 0 | CF₃ |
| CH₂Cl | Me | H | H | 2 | CF₃ |
| CH₂Cl | Me | H | H | 2 | I |
| CH₂Cl | Me | H | H | 0 | CF₃ |
| CH₂Cl | Me | H | H | 0 | F |
| Me | Me | H | H | 2 | I |
| Me | Me | H | H | 0 | I |
| CH₂Cl | Me | H | H | 2 | F |
| Me | Me | H | H | 1 | F |
| Me | Me | H | H | 2 | I |
| Me | Me | H | H | 2 | I |
| Me | Me | H | H | 2 | CF₃ |
| CH₂Cl | Me | H | H | 1 | F |
| Me | Me | H | H | 0 | F |
| Me | Me | H | H | 1 | CF₃ |
| Me | Me | H | H | 2 | CF₃ |
| Me | Me | H | H | 1 | I |
| Me | Me | H | H | 2 | I |
| CH₂Cl | Me | H | H | 0 | CF₃ |
| Me | Me | H | H | 2 | I |
| Me | Me | H | H | 1 | F |
| CH₂Cl | Me | H | H | 2 | F |
| Me | Me | H | H | 1 | F |
| Me | Me | H | H | 0 | F |
| CH₂Cl | Me | H | H | 2 | F |
| Me | Me | H | H | 0 | CF₃ |
| CH₂Cl | Me | H | H | 1 | F |
| CH₂Cl | Me | H | H | 0 | F |
| Me | Me | H | H | 2 | F |
| Me | Me | H | H | 0 | CF₃ |
| CH₂Cl | Me | H | H | 1 | CF₃ |
| CH₂Cl | Me | H | H | 1 | CF₃ |
| CH₂Cl | Me | H | H | 1 | F |
| CH₂Cl | Me | H | H | 2 | F |
| CH₂Cl | Me | H | H | 2 | CF₃ |
| CH₂Cl | Me | H | H | 1 | I |
| Me | Me | H | H | 0 | CF₃ |
| CH₂Cl | Me | H | H | 0 | F |
| Me | Me | H | H | 2 | F |
| CH₂Cl | Me | H | H | 0 | I |
| CH₂Cl | Me | H | H | 0 | F |
| CH₂Cl | Me | H | H | 2 | F |
| CH₂Cl | Me | H | H | 1 | F |
| Me | Me | H | H | 1 | I |
| Me | Me | H | H | 0 | F |
| Me | Me | H | H | 0 | I |
| CH₂Cl | Me | H | H | 1 | I |
| Me | Me | H | H | 1 | CF₃ |
| CH₂Cl | Me | H | H | 1 | I |
| CH₂Cl | Me | H | H | 0 | F |
| Me | Me | H | H | 0 | I |
| Me | Me | H | H | 0 | F |
| Me | Me | H | H | 2 | I |
| Me | Me | H | H | 2 | F |
| CH₂Cl | Me | H | H | 1 | CF₃ |
| CH₂Cl | Me | H | H | 0 | I |
| Me | Me | H | H | 0 | I |
| Me | Me | H | H | 1 | I |
| Me | Me | H | H | 0 | CF₃ |
| Me | Me | H | H | 1 | F |
| Me | Me | H | H | 1 | CF₃ |
| CH₂Cl | Me | H | H | 0 | I |
| CH₂Cl | Me | H | H | 0 | I |
| CH₂Cl | Me | H | H | 2 | CF₃ |
| CH₂Cl | Me | H | H | 2 | CF₃ |
| CH₂Cl | Me | H | H | 0 | I |
| Me | Me | H | H | 2 | CF₃ |
| Me | Me | H | H | 0 | CF₃ |
| Me | Me | H | H | 0 | F |
| Me | Me | H | H | 1 | CF₃ |
| CH₂Cl | Me | H | H | 2 | I |
| Me | Me | H | H | 0 | I |
| CH₂Cl | Me | H | H | 2 | I |
| CH₂Cl | Me | H | H | 2 | F |
| Me | Me | H | H | 1 | F |
| Me | Me | H | H | 2 | CF₃ |
| Me | Me | H | H | 0 | F |
| CH₂Cl | Me | H | H | 1 | I |
| CH₂Cl | Me | H | H | 2 | CF₃ |
| Me | Me | H | H | 2 | F |
| Me | Me | H | H | 2 | F |
| Me | Me | H | H | 2 | CF₃ |
| CH₂Cl | Me | H | H | 2 | CF₃ |
| CH₂Cl | Me | H | H | 0 | CF₃ |
| CH₂Cl | Me | H | H | 1 | CF₃ |
| Me | Me | H | H | 2 | F |
| Me | Me | H | H | 0 | CF₃ |
| CH₂Cl | Me | H | H | 0 | CF₃ |
| CH₂Cl | Me | H | H | 1 | I |
| CH₂Cl | Me | H | H | 0 | CF₃ |
| Me | Me | H | H | 1 | CF₃ |
| Me | Me | H | H | 1 | I |
| CH₂Cl | Me | H | H | 0 | I |
| CH₂Cl | Me | H | H | 1 | F |
| CH₂Cl | Me | H | H | 2 | I |
| Me | Me | H | H | 1 | I |
| CH₂Cl | Me | H | H | 1 | F |
| CH₂Cl | Me | H | H | 1 | I |
| Me | Me | H | H | 2 | CF₃ |
| Me | Me | H | H | 0 | I |
| Me | Me | H | H | 1 | F |
| Me | Me | H | H | 1 | I |
| Me | Me | H | H | 2 | CF₃ |
| Me | Me | H | H | 1 | CF₃ |
| CH₂Cl | Me | H | H | 2 | I |
| CH₂Cl | Me | H | H | 2 | I |

| R⁶ | R¹² | R¹³ | R¹⁴ | R¹⁵ | R¹⁶ |
|---|---|---|---|---|---|
| F | H | Me | H | H | H |
| F | NO₂ | H | H | Cl | H |
| F | NO₂ | H | H | Cl | H |
| F | F | H | H | H | Cl |
| F | H | Me | H | H | H |
| F | F | H | H | H | Cl |

TABLE 4-continued

Compounds of formula I.1.

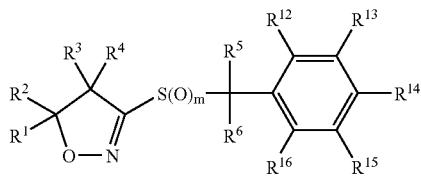

| R12 | R13 | R14 | R15 | R16 |
|---|---|---|---|---|
| F | F | H | H | H | F |
| F | F | H | H | H | Cl |
| F | NO$_2$ | H | H | Cl | H |
| F | F | H | H | H | F |
| F | NO$_2$ | H | H | Cl | H |
| F | F | H | H | H | F |
| F | H | Me | H | H | H |
| F | H | Me | H | H | H |
| F | NO$_2$ | H | H | Cl | H |
| F | F | H | H | H | Cl |
| F | F | H | H | H | Cl |
| F | F | H | H | H | F |
| F | H | Me | H | H | H |
| F | H | Me | H | H | H |
| F | NO$_2$ | H | H | Cl | H |
| F | H | Me | H | H | H |
| F | F | H | H | H | F |
| F | H | Me | H | H | H |
| F | F | H | H | H | Cl |
| F | F | H | H | H | Cl |
| F | NO$_2$ | H | H | Cl | H |
| F | H | Me | H | H | H |
| F | NO$_2$ | H | H | Cl | H |
| F | NO$_2$ | H | H | Cl | H |
| F | NO$_2$ | H | H | Cl | H |
| F | H | Me | H | H | H |
| F | F | H | H | H | F |
| F | H | Me | H | H | H |
| F | F | H | H | H | F |
| F | H | Me | H | H | H |
| F | F | H | H | H | F |
| F | F | H | H | H | F |
| F | H | Me | H | H | H |
| F | H | Me | H | H | H |
| F | H | Me | H | H | H |
| F | F | H | H | H | Cl |
| F | F | H | H | H | Cl |
| F | NO$_2$ | H | H | Cl | H |
| F | H | Me | H | H | H |
| F | NO$_2$ | H | H | Cl | H |
| F | NO$_2$ | H | H | Cl | H |
| F | F | H | H | H | F |
| F | NO$_2$ | H | H | Cl | H |
| F | F | H | H | H | Cl |
| F | NO$_2$ | H | H | Cl | H |
| F | F | H | H | H | F |
| F | H | Me | H | H | H |
| F | H | Me | H | H | H |
| F | F | H | H | H | Cl |
| F | NO$_2$ | H | H | Cl | H |
| F | F | H | H | H | Cl |
| F | F | H | H | H | F |
| F | NO$_2$ | H | H | Cl | H |
| F | F | H | H | H | F |
| F | H | Me | H | H | H |
| F | H | Me | H | H | H |
| F | H | Me | H | H | H |
| F | H | Me | H | H | H |
| F | NO$_2$ | H | H | Cl | H |
| F | NO$_2$ | H | H | Cl | H |
| F | NO$_2$ | H | H | Cl | H |
| F | H | Me | H | H | H |
| F | F | H | H | H | Cl |
| F | NO$_2$ | H | H | Cl | H |
| F | H | Me | H | H | H |
| F | NO$_2$ | H | H | Cl | H |
| F | H | Me | H | H | H |
| F | NO$_2$ | H | H | Cl | H |

TABLE 4-continued

Compounds of formula I.1.

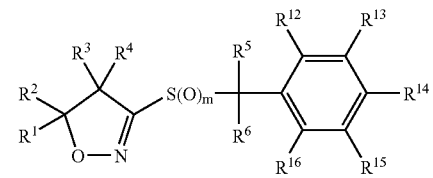

| R12 | R13 | R14 | R15 | R16 |
|---|---|---|---|---|
| F | NO$_2$ | H | H | Cl | H |
| F | NO$_2$ | H | H | Cl | H |
| F | NO$_2$ | H | H | Cl | H |
| F | H | Me | H | H | H |
| F | NO$_2$ | H | H | Cl | H |
| F | F | H | H | H | Cl |
| F | H | Me | H | H | H |
| F | F | H | H | H | F |
| F | NO$_2$ | H | H | Cl | H |
| F | F | H | H | H | Cl |
| F | H | Me | H | H | H |
| F | H | Me | H | H | H |
| F | F | H | H | H | Cl |
| F | NO$_2$ | H | H | Cl | H |
| F | F | H | H | H | F |
| F | NO$_2$ | H | H | Cl | H |
| F | H | Me | H | H | H |
| F | F | H | H | H | Cl |
| F | NO$_2$ | H | H | Cl | H |
| F | F | H | H | H | F |
| F | H | Me | H | H | H |
| F | H | Me | H | H | H |
| F | H | Me | H | H | H |
| F | NO$_2$ | H | H | Cl | H |
| F | F | H | H | H | Cl |
| F | NO$_2$ | H | H | Cl | H |
| F | NO$_2$ | H | H | Cl | H |
| F | F | H | H | H | F |
| F | NO$_2$ | H | H | Cl | H |
| F | NO$_2$ | H | H | Cl | H |
| F | F | H | H | H | F |

TABLE 5

Compounds of formula I.1.

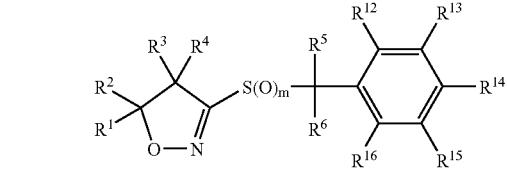

| R$^1$ | R$^2$ | R$^3$ | R$^4$ | m | R$^5$ |
|---|---|---|---|---|---|
| CH$_2$Cl | Me | H | H | 2 | CF$_3$ |
| CH$_2$Cl | Me | H | H | 2 | CF$_3$ |
| CH$_2$Cl | Me | H | H | 2 | CF$_3$ |
| CH$_2$Cl | Me | H | H | 1 | CF$_3$ |
| Me | Me | H | H | 0 | CF$_3$ |
| Me | Me | H | H | 0 | CF$_3$ |
| Me | Me | H | H | 1 | CF$_3$ |
| Me | Me | H | H | 1 | I |
| Me | Me | H | H | 2 | CF$_3$ |
| CH$_2$Cl | Me | H | H | 2 | I |
| Me | Me | H | H | 1 | I |
| CH$_2$Cl | Me | H | H | 2 | CF$_3$ |
| Me | Me | H | H | 0 | CF$_3$ |
| Me | Me | H | H | 1 | I |
| Me | Me | H | H | 1 | I |
| CH$_2$Cl | Me | H | H | 0 | CF$_3$ |
| Me | Me | H | H | 1 | I |

TABLE 5-continued

Compounds of formula I.1.

| R¹ | R² | R³ | R⁴ | m | R⁶ |
|---|---|---|---|---|---|
| CH₂Cl | Me | H | H | 0 | I |
| Me | Me | H | H | 2 | I |
| CH₂Cl | Me | H | H | 1 | CF₃ |
| CH₂Cl | Me | H | H | 2 | I |
| CH₂Cl | Me | H | H | 1 | I |
| Me | Me | H | H | 0 | CF₃ |
| CH₂Cl | Me | H | H | 0 | CF₃ |
| CH₂Cl | Me | H | H | 0 | I |
| Me | Me | H | H | 0 | I |
| Me | Me | H | H | 2 | CF₃ |
| Me | Me | H | H | 0 | I |
| Me | Me | H | H | 1 | I |
| Me | Me | H | H | 1 | CF₃ |
| CH₂Cl | Me | H | H | 0 | I |
| Me | Me | H | H | 2 | CF₃ |
| Me | Me | H | H | 2 | I |
| CH₂Cl | Me | H | H | 1 | CF₃ |
| CH₂Cl | Me | H | H | 1 | I |
| Me | Me | H | H | 2 | I |
| CH₂Cl | Me | H | H | 0 | CF₃ |
| CH₂Cl | Me | H | H | 1 | I |
| CH₂Cl | Me | H | H | 2 | I |
| Me | Me | H | H | 0 | CF₃ |
| Me | Me | H | H | 2 | I |
| Me | Me | H | H | 0 | CF₃ |
| CH₂Cl | Me | H | H | 2 | I |
| Me | Me | H | H | 0 | I |
| CH₂Cl | Me | H | H | 1 | CF₃ |
| Me | Me | H | H | 2 | CF₃ |
| Me | Me | H | H | 0 | I |
| CH₂Cl | Me | H | H | 1 | CF₃ |
| Me | Me | H | H | 0 | I |
| CH₂Cl | Me | H | H | 2 | CF₃ |
| Me | Me | H | H | 1 | CF₃ |
| CH₂Cl | Me | H | H | 0 | CF₃ |
| CH₂Cl | Me | H | H | 0 | CF₃ |
| CH₂Cl | Me | H | H | 0 | I |
| CH₂Cl | Me | H | H | 2 | CF₃ |
| CH₂Cl | Me | H | H | 1 | CF₃ |
| Me | Me | H | H | 0 | I |
| Me | Me | H | H | 1 | CF₃ |
| Me | Me | H | H | 2 | CF₃ |
| CH₂Cl | Me | H | H | 2 | I |
| Me | Me | H | H | 2 | CF₃ |
| CH₂Cl | Me | H | H | 1 | I |
| CH₂Cl | Me | H | H | 1 | I |
| CH₂Cl | Me | H | H | 0 | I |
| Me | Me | H | H | 2 | I |
| Me | Me | H | H | 1 | CF₃ |
| CH₂Cl | Me | H | H | 2 | I |
| Me | Me | H | H | 2 | I |
| CH₂Cl | Me | H | H | 1 | I |
| Me | Me | H | H | 1 | CF₃ |
| CH₂Cl | Me | H | H | 0 | I |

| R⁶ | R¹² | R¹³ | R¹⁴ | R¹⁵ | R¹⁶ |
|---|---|---|---|---|---|
| I | H | Me | H | H | H |
| I | NO₂ | H | H | Cl | H |
| I | NO₂ | H | H | Cl | H |
| I | F | H | H | H | Cl |
| I | NO₂ | H | H | Cl | H |
| I | F | H | H | H | Cl |
| I | NO₂ | H | H | Cl | H |
| I | NO₂ | H | H | Cl | H |
| I | H | Me | H | H | H |
| I | H | Me | H | H | H |
| I | F | H | H | H | F |
| I | F | H | H | H | Cl |
| I | F | H | H | H | F |
| I | H | Me | H | H | H |
| I | F | H | H | H | Cl |
| I | NO₂ | H | H | Cl | H |
| I | H | Me | H | H | H |
| I | F | H | H | H | F |
| I | NO₂ | H | H | Cl | H |
| I | H | Me | H | H | H |
| I | F | H | H | H | Cl |
| I | F | H | H | H | Cl |
| I | NO₂ | H | H | Cl | H |
| I | F | H | H | H | Cl |
| I | F | H | H | H | Cl |
| I | F | H | H | H | F |
| I | F | H | H | H | F |
| I | H | Me | H | H | H |
| I | NO₂ | H | H | Cl | H |
| I | H | Me | H | H | H |
| I | H | Me | H | H | H |
| I | NO₂ | H | H | Cl | H |
| I | H | Me | H | H | H |
| I | F | H | H | H | F |
| I | NO₂ | H | H | Cl | H |
| I | NO₂ | H | H | Cl | H |
| I | F | H | H | H | F |
| I | NO₂ | H | H | Cl | H |
| I | H | Me | H | H | H |
| I | H | Me | H | H | H |
| I | H | Me | H | H | H |
| I | F | H | H | H | F |
| I | NO₂ | H | H | Cl | H |
| I | H | Me | H | H | H |
| I | NO₂ | H | H | Cl | H |
| I | H | Me | H | H | H |
| I | NO₂ | H | H | Cl | H |
| I | F | H | H | H | Cl |
| I | F | H | H | H | F |
| I | F | H | H | H | F |
| I | H | Me | H | H | H |
| I | H | Me | H | H | H |
| I | NO₂ | H | H | Cl | H |
| I | NO₂ | H | H | Cl | H |
| I | H | Me | H | H | H |
| I | NO₂ | H | H | Cl | H |
| I | NO₂ | H | H | Cl | H |
| I | NO₂ | H | H | Cl | H |
| I | H | Me | H | H | H |
| I | NO₂ | H | H | Cl | H |
| I | F | H | H | H | Cl |
| I | F | H | H | H | F |
| I | H | Me | H | H | H |
| I | NO₂ | H | H | Cl | H |
| I | F | H | H | H | F |
| I | H | Me | H | H | H |
| I | NO₂ | H | H | Cl | H |
| I | F | H | H | H | Cl |
| I | H | Me | H | H | H |
| I | F | H | H | H | Cl |
| I | H | Me | H | H | H |

TABLE 6

Compounds of formula I.1.

| $R^1$ | $R^2$ | $R^3$ | $R^4$ | m | $R^5$ |
|---|---|---|---|---|---|
| Me | Me | H | H | 2 | $CF_3$ |
| $CH_2Cl$ | Me | H | H | 1 | $CF_3$ |
| Me | Me | H | H | 0 | $CF_3$ |
| $CH_2Cl$ | Me | H | H | 0 | $CF_3$ |
| $CH_2Cl$ | Me | H | H | 2 | $CF_3$ |
| Me | Me | H | H | 2 | $CF_3$ |
| Me | Me | H | H | 1 | $CF_3$ |
| $CH_2Cl$ | Me | H | H | 0 | $CF_3$ |
| $CH_2Cl$ | Me | H | H | 1 | $CF_3$ |
| Me | Me | H | H | 1 | $CF_3$ |
| Me | Me | H | H | 0 | $CF_3$ |
| $CH_2Cl$ | Me | H | H | 2 | $CF_3$ |
| $CH_2Cl$ | Me | H | H | 0 | $CF_3$ |
| Me | Me | H | H | 2 | $CF_3$ |
| $CH_2Cl$ | Me | H | H | 1 | $CF_3$ |
| Me | Me | H | H | 0 | $CF_3$ |
| Me | Me | H | H | 1 | $CF_3$ |
| Me | Me | H | H | 0 | $CF_3$ |
| Me | Me | H | H | 1 | $CF_3$ |
| $CH_2Cl$ | Me | H | H | 2 | $CF_3$ |
| $CH_2Cl$ | Me | H | H | 1 | $CF_3$ |
| Me | Me | H | H | 1 | $CF_3$ |
| $CH_2Cl$ | Me | H | H | 0 | $CF_3$ |
| $CH_2Cl$ | Me | H | H | 2 | $CF_3$ |
| $CH_2Cl$ | Me | H | H | 1 | $CF_3$ |
| $CH_2Cl$ | Me | H | H | 0 | $CF_3$ |
| Me | Me | H | H | 2 | $CF_3$ |
| Me | Me | H | H | 0 | $CF_3$ |
| $CH_2Cl$ | Me | H | H | 2 | $CF_3$ |
| Me | Me | H | H | 2 | $CF_3$ |
| Me | Me | H | H | 1 | $CF_3$ |
| $CH_2Cl$ | Me | H | H | 2 | $CF_3$ |
| $CH_2Cl$ | Me | H | H | 1 | $CF_3$ |
| Me | Me | H | H | 0 | $CF_3$ |
| $CH_2Cl$ | Me | H | H | 0 | $CF_3$ |
| Me | Me | H | H | 2 | $CF_3$ |

| $R^6$ | $R^{12}$ | $R^{13}$ | $R^{14}$ | $R^{15}$ | $R^{16}$ |
|---|---|---|---|---|---|
| $CF_3$ | $NO_2$ | H | H | Cl | H |
| $CF_3$ | H | Me | H | H | H |
| $CF_3$ | $NO_2$ | H | H | Cl | H |
| $CF_3$ | H | Me | H | H | H |
| $CF_3$ | $NO_2$ | H | H | Cl | H |
| $CF_3$ | F | H | H | H | F |
| $CF_3$ | $NO_2$ | H | H | Cl | H |
| $CF_3$ | H | Me | H | H | H |
| $CF_3$ | F | H | H | H | F |
| $CF_3$ | $NO_2$ | H | H | Cl | H |
| $CF_3$ | F | H | H | H | F |
| $CF_3$ | F | H | H | H | Cl |
| $CF_3$ | F | H | H | H | Cl |
| $CF_3$ | F | H | H | H | Cl |
| $CF_3$ | F | H | H | H | Cl |
| $CF_3$ | $NO_2$ | H | H | Cl | H |
| $CF_3$ | F | H | H | H | F |
| $CF_3$ | H | Me | H | H | H |
| $CF_3$ | H | Me | H | H | H |
| $CF_3$ | F | H | H | H | F |
| $CF_3$ | H | Me | H | H | H |
| $CF_3$ | F | H | H | H | Cl |
| $CF_3$ | $NO_2$ | H | H | Cl | H |
| $CF_3$ | H | Me | H | H | H |
| $CF_3$ | $NO_2$ | H | H | Cl | H |
| $CF_3$ | $NO_2$ | H | H | Cl | H |
| $CF_3$ | H | Me | H | H | H |
| $CF_3$ | H | Me | H | H | H |
| $CF_3$ | H | Me | H | H | H |
| $CF_3$ | $NO_2$ | H | H | Cl | H |
| $CF_3$ | H | Me | H | H | H |
| $CF_3$ | $NO_2$ | H | H | Cl | H |
| $CF_3$ | $NO_2$ | H | H | Cl | H |
| $CF_3$ | F | H | H | H | Cl |
| $CF_3$ | F | H | H | H | F |
| $CF_3$ | H | Me | H | H | H |

TABLE 7

Compounds of formula I.2.

| $R^1$ | $R^2$ | $R^3$ | $R^4$ | m | $R^5$ | $R^6$ | $R^{17}$ | $R^{18}$ | $R^{19}$ |
|---|---|---|---|---|---|---|---|---|---|
| $CH_2Cl$ | Me | H | H | 2 | Br | H | Me | $CF_3$ | Cl |
| $CH_2Cl$ | Me | H | H | 1 | Br | H | Me | $CHF_3$ | $OCH_2F$ |
| $CH_2Cl$ | Me | H | H | 1 | Br | H | Me | $CHF_2$ | $OCF_3$ |
| Me | Me | H | H | 1 | Br | H | Et | $OCF_3$ | $CHF_3$ |
| Me | Me | H | H | 2 | Br | H | Me | $CF_3$ | Cl |
| $CH_2Cl$ | Me | H | H | 2 | Br | H | Et | $CHF_2$ | Cl |
| Me | Me | H | H | 1 | Br | H | Me | $OCH_2CF_3$ | $CF_3$ |
| Me | Me | H | H | 2 | Br | H | Et | $CHF_2$ | $OCF_3$ |
| Me | Me | H | H | 1 | Br | H | Et | $CH_2F$ | $OCH_2CF_3$ |
| $CH_2Cl$ | Me | H | H | 1 | Br | H | Et | $CF_3$ | Cl |
| Me | Me | H | H | 1 | Br | H | Me | Cl | $CF_3$ |
| Me | Me | H | H | 2 | Br | H | Me | $OCH_2CF_3$ | $CHF_2$ |
| Me | Me | H | H | 1 | Br | H | Me | $OCHF_2$ | $CH_2F$ |
| Me | Me | H | H | 2 | Br | H | Me | $CHF_2$ | $OCHF_2$ |
| Me | Me | H | H | 1 | Br | H | Me | $OCHF_2$ | $CHF_2$ |
| $CH_2Cl$ | Me | H | H | 2 | Br | H | Et | $CF_3$ | $OCHF_2$ |
| Me | Me | H | H | 1 | Br | H | Me | $OCF_3$ | $CF_3$ |
| $CH_2Cl$ | Me | H | H | 2 | Br | H | Me | $CH_2F$ | $OCHF_2$ |
| Me | Me | H | H | 1 | Br | H | Me | $CHF_2$ | Cl |
| Me | Me | H | H | 2 | Br | H | Et | $CHF_2$ | $OCH_2CF_3$ |
| Me | Me | H | H | 1 | Br | H | Me | $CF_3$ | $OCF_3$ |
| Me | Me | H | H | 1 | Br | H | Me | $CF_3$ | $OCH_2CF_3$ |
| $CH_2Cl$ | Me | H | H | 1 | Br | H | Me | $OCF_3$ | $CF_3$ |
| Me | Me | H | H | 2 | Br | H | Me | $OCH_2CF_3$ | $CF_3$ |
| Me | Me | H | H | 1 | Br | H | Et | $OCHF_2$ | $CF_3$ |
| $CH_2Cl$ | Me | H | H | 2 | Br | H | Me | $OCH_2CF_3$ | $CHF_2$ |
| Me | Me | H | H | 2 | Br | H | Et | $CH_2F$ | $OCF_3$ |
| $CH_2Cl$ | Me | H | H | 1 | Br | H | Et | $OCH_2F$ | $CHF_2$ |
| $CH_2Cl$ | Me | H | H | 1 | Br | H | Me | $CHF_2$ | Cl |
| $CH_2Cl$ | Me | H | H | 2 | Br | H | Et | $OCH_2CF_3$ | $CF_3$ |
| $CH_2Cl$ | Me | H | H | 1 | Br | H | Et | $OCH_2F$ | $CH_2F$ |
| Me | Me | H | H | 1 | Br | H | Et | $CF_3$ | $OCH_2CF_3$ |
| $CH_2Cl$ | Me | H | H | 1 | Br | H | Et | Cl | $CHF_2$ |
| $CH_2Cl$ | Me | H | H | 2 | Br | H | Me | Cl | $CF_3$ |
| Me | Me | H | H | 1 | Br | H | Et | $OCF_3$ | $CH_2F$ |
| Me | Me | H | H | 2 | Br | H | Me | $OCF_3$ | $CHF_3$ |
| $CH_2Cl$ | Me | H | H | 2 | Br | H | Et | $CHF_2$ | $OCH_2F$ |
| $CH_2Cl$ | Me | H | H | 1 | Br | H | Et | $CHF_2$ | $OCH_2F$ |
| $CH_2Cl$ | Me | H | H | 2 | Br | H | Et | $CH_2F$ | $OCF_3$ |
| $CH_2Cl$ | Me | H | H | 2 | Br | H | Me | $CF_3$ | $OCHF_2$ |
| $CH_2Cl$ | Me | H | H | 1 | Br | H | Me | $OCH_2F$ | $CHF_2$ |

TABLE 6-continued

Compounds of formula I.1.

| $CF_3$ | H | Me | H | H | H |
|---|---|---|---|---|---|
| $CF_3$ | $NO_2$ | H | H | Cl | H |
| $CF_3$ | H | Me | H | H | H |
| $CF_3$ | $NO_2$ | H | H | Cl | H |
| $CF_3$ | $NO_2$ | H | H | Cl | H |
| $CF_3$ | F | H | H | H | Cl |
| $CF_3$ | F | H | H | H | F |
| $CF_3$ | H | Me | H | H | H |

TABLE 7-continued

Compounds of formula I.2.

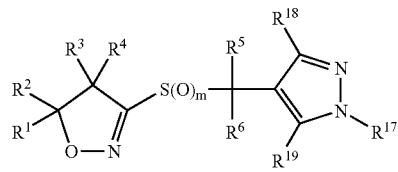

| R¹ | R² | R³ | R⁴ | m | R⁵ | R⁶ | R¹⁷ | R¹⁸ | R¹⁹ |
|---|---|---|---|---|---|---|---|---|---|
| CH₂Cl | Me | H | H | 1 | Br | H | Et | OCHF₂ | CHF₂ |
| CH₂Cl | Me | H | H | 2 | Br | H | Me | CHF₂ | OCH₂F |
| CH₂Cl | Me | H | H | 1 | Br | H | Et | OCF₃ | CH₂F |
| Me | Me | H | H | 1 | Br | H | Me | OCH₂F | CHF₂ |
| CH₂Cl | Me | H | H | 2 | Br | H | Me | OCH₂F | OCH₂F |
| Me | Me | H | H | 2 | Br | H | Me | OCHF₂ | CH₂F |
| Me | Me | H | H | 2 | Br | H | Et | OCH₂F | CH₂F |
| CH₂Cl | Me | H | H | 1 | Br | H | Me | CHF₂ | Cl |
| Me | Me | H | H | 1 | Br | H | Me | CH₂F | OCH₃ |
| CH₂Cl | Me | H | H | 1 | Br | H | Et | OCH₂CF₃ | CH₂F |
| CH₂Cl | Me | H | H | 2 | Br | H | Me | OCF₃ | CF₃ |
| CH₂Cl | Me | H | H | 1 | Br | H | Me | OCHF₂ | CHF₂ |
| Me | Me | H | H | 2 | Br | H | Me | CH₂F | OCH₂F |
| Me | Me | H | H | 2 | Br | H | Me | CHF₂ | OCF₃ |
| Me | Me | H | H | 2 | Br | H | Et | CH₂F | Cl |
| Me | Me | H | H | 2 | Br | H | Et | CHF₂ | Cl |
| Me | Me | H | H | 1 | Br | H | Et | CH₂F | Cl |
| CH₂Cl | Me | H | H | 1 | Br | H | Et | CH₂F | OCH₂CF₃ |
| CH₂Cl | Me | H | H | 1 | Br | H | Me | CHF₂ | OCHF₂ |
| CH₂Cl | Me | H | H | 2 | Br | H | Et | CH₂F | Cl |
| CH₂Cl | Me | H | H | 1 | Br | H | Et | CF₃ | OCH₂CF₃ |
| Me | Me | H | H | 2 | Br | H | Et | OCH₂CF₃ | CH₂F |
| CH₂Cl | Me | H | H | 2 | Br | H | Me | CH₂F | OCF₃ |
| CH₂Cl | Me | H | H | 1 | Br | H | Et | CHF₂ | OCF₃ |
| CH₂Cl | Me | H | H | 2 | Br | H | Et | CHF₂ | OCF₃ |
| Me | Me | H | H | 2 | Br | H | Et | CHF₂ | OCHF₂ |
| CH₂Cl | Me | H | H | 2 | Br | H | Et | OCH₂CF₃ | CHF₂ |
| CH₂Cl | Me | H | H | 1 | Br | H | Et | OCHF₂ | CF₃ |
| Me | Me | H | H | 2 | Br | H | Me | Cl | CHF₂ |
| CH₂Cl | Me | H | H | 2 | Br | H | Me | CF₃ | OCH₂F |
| Me | Me | H | H | 2 | Br | H | Et | Cl | CF₃ |
| CH₂Cl | Me | H | H | 1 | Br | H | Et | CH₂F | OCHF₂ |
| Me | Me | H | H | 1 | Br | H | Me | Cl | CH₂F |
| Me | Me | H | H | 2 | Br | H | Me | CHF₂ | OCH₂F |
| Me | Me | H | H | 2 | Br | H | Me | Cl | CHF₂ |
| CH₂Cl | Me | H | H | 2 | Br | H | Me | OCH₂CF₃ | CF₃ |
| CH₂Cl | Me | H | H | 1 | Br | H | Me | CF₃ | OCF₃ |
| CH₂Cl | Me | H | H | 1 | Br | H | Et | OCH₂CF₃ | CHF₂ |
| CH₂Cl | Me | H | H | 1 | Br | H | Me | CH₂F | OCH₂CF₃ |
| CH₂Cl | Me | H | H | 2 | Br | H | Et | OCH₂CF₃ | CH₂F |
| CH₂Cl | Me | H | H | 2 | Br | H | Me | CF₃ | OCF₃ |
| Me | Me | H | H | 1 | Br | H | Et | CF₃ | OCF₃ |
| CH₂Cl | Me | H | H | 2 | Br | H | Me | CH₂F | Cl |
| Me | Me | H | H | 2 | Br | H | Et | CH₂F | OCH₂CF₃ |
| Me | Me | H | H | 2 | Br | H | Et | CF₃ | OCH₂F |
| Me | Me | H | H | 2 | Br | H | Et | CHF₂ | OCH₂F |
| CH₂Cl | Me | H | H | 1 | Br | H | Et | OCH₂F | CF₃ |
| Me | Me | H | H | 1 | Br | H | Me | CH₂F | OCHF₂ |
| Me | Me | H | H | 2 | Br | H | Et | OCH₂CF₃ | CF₃ |
| CH₂Cl | Me | H | H | 2 | Br | H | Me | CHF₂ | OCF₃ |
| CH₂Cl | Me | H | H | 1 | Br | H | Et | CF₃ | OCHF₂ |
| Me | Me | H | H | 1 | Br | H | Et | Cl | CHF₂ |
| Me | Me | H | H | 2 | Br | H | Me | OCH₂F | CF₃ |
| CH₂Cl | Me | H | H | 2 | Br | H | Et | CF₃ | OCF₃ |
| Me | Me | H | H | 1 | Br | H | Me | OCHF₂ | CF₃ |
| CH₂Cl | Me | H | H | 1 | Br | H | Et | Cl | CH₂F |
| Me | Me | H | H | 1 | Br | H | Et | CF₃ | OCHF₂ |
| CH₂Cl | Me | H | H | 1 | Br | H | Et | OCH₂CF₃ | CF₃ |
| Me | Me | H | H | 2 | Br | H | Me | CH₂F | OCHF₂ |
| Me | Me | H | H | 2 | Br | H | Et | CH₂F | OCHF₂ |
| Me | Me | H | H | 2 | Br | H | Me | OCH₂F | CF₃ |
| Me | Me | H | H | 1 | Br | H | Et | CH₂F | OCHF₂ |
| Me | Me | H | H | 2 | Br | H | Et | Cl | CH₂F |
| Me | Me | H | H | 2 | Br | H | Me | CH₂F | OCH₂CF₃ |
| Me | Me | H | H | 1 | Br | H | Et | CH₂F | OCF₃ |
| Me | Me | H | H | 1 | Br | H | Et | OCH₂F | CH₂F |
| Me | Me | H | H | 2 | Br | H | Me | CH₂F | OCH₂F |
| Me | Me | H | H | 1 | Br | H | Me | CF₃ | OCH₂F |
| CH₂Cl | Me | H | H | 2 | Br | H | Me | OCHF₂ | CHF₂ |
| Me | Me | H | H | 2 | Br | H | Et | OCH₂F | CHF₂ |
| Me | Me | H | H | 2 | Br | H | Me | CHF₂ | OCH₂CF₃ |
| CH₂Cl | Me | H | H | 2 | Br | H | Me | OCH₂F | CH₂F |
| CH₂Cl | Me | H | H | 2 | Br | H | Et | CF₃ | Cl |
| CH₂Cl | Me | H | H | 1 | Br | H | Me | CH₂F | OCH₂F |
| CH₂Cl | Me | H | H | 1 | Br | H | Me | OCH₂F | CF₃ |
| Me | Me | H | H | 1 | Br | H | Et | OCH₂CF₃ | CH₂F |
| Me | Me | H | H | 1 | Br | H | Et | CF₃ | OCH₂F |
| Me | Me | H | H | 2 | Br | H | Me | OCF₃ | CF₃ |
| Me | Me | H | H | 1 | Br | H | Et | Cl | CH₂F |
| Me | Me | H | H | 1 | Br | H | Et | OCH₂F | CHF₂ |
| CH₂Cl | Me | H | H | 1 | Br | H | Me | Cl | CH₂F |
| CH₂Cl | Me | H | H | 2 | Br | H | Et | CF₃ | OCF₃ |
| CH₂Cl | Me | H | H | 2 | Br | H | Et | OCH₂F | CHF₂ |
| CH₂Cl | Me | H | H | 1 | Br | H | Me | OCF₃ | CHF₂ |
| CH₂Cl | Me | H | H | 1 | Br | H | Me | CHF₂ | OCH₂CF₃ |
| CH₂Cl | Me | H | H | 2 | Br | H | Et | CF₃ | OCH₂CF₃ |
| Me | Me | H | H | 1 | Br | H | Me | CF₃ | Cl |
| Me | Me | H | H | 1 | Br | H | Me | OCF₃ | CH₂F |
| CH₂Cl | Me | H | H | 2 | Br | H | Me | CH₂F | OCH₂CF₃ |
| Me | Me | H | H | 1 | Br | H | Et | CF₃ | OCH₂F |
| Me | Me | H | H | 1 | Br | H | Me | Cl | CHF₂ |
| Me | Me | H | H | 1 | Br | H | Me | CHF₂ | OCF₃ |
| Me | Me | H | H | 1 | Br | H | Et | OCF₃ | CF₃ |
| Me | Me | H | H | 2 | Br | H | Et | CF₃ | OCHF₂ |
| CH₂Cl | Me | H | H | 1 | Br | H | Me | CH₂F | Cl |
| Me | Me | H | H | 1 | Br | H | Et | CF₃ | Cl |
| Me | Me | H | H | 1 | Br | H | Me | CH₂F | OCH₂CF₃ |
| CH₂Cl | Me | H | H | 1 | Br | H | Et | OCHF₂ | CH₂F |
| CH₂Cl | Me | H | H | 1 | Br | H | Et | CH₂F | Cl |
| Me | Me | H | H | 1 | Br | H | Me | OCH₂F | CH₂F |
| Me | Me | H | H | 2 | Br | H | Et | OCF₃ | CHF₂ |
| Me | Me | H | H | 2 | Br | H | Et | OCHF₂ | CF₃ |
| CH₂Cl | Me | H | H | 1 | Br | H | Me | OCH₂CF₃ | CH₂F |
| Me | Me | H | H | 1 | Br | H | Et | CH₂F | OCH₂F |
| CH₂Cl | Me | H | H | 2 | Br | H | Me | OCHF₂ | CH₂F |
| Me | Me | H | H | 2 | Br | H | Me | CF₃ | OCH₂CF₃ |
| Me | Me | H | H | 1 | Br | H | Et | CHF₂ | OCHF₂ |
| Me | Me | H | H | 1 | Br | H | Et | OCHF₂ | CHF₂ |
| CH₂Cl | Me | H | H | 2 | Br | H | Me | OCF₃ | CH₂F |
| CH₂Cl | Me | H | H | 2 | Br | H | Et | CF₃ | OCHF₂ |
| Me | Me | H | H | 2 | Br | H | Et | OCH₂CF₃ | CHF₂ |
| CH₂Cl | Me | H | H | 2 | Br | H | Et | OCF₃ | CF₃ |

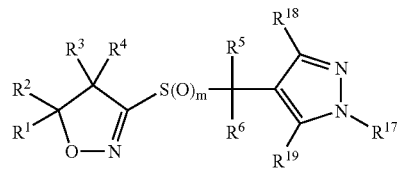

TABLE 7-continued

Compounds of formula I.2.

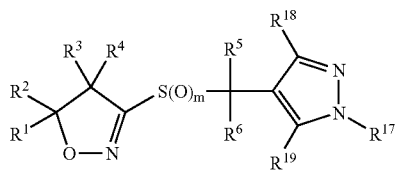

| $R^1$ | $R^2$ | $R^3$ | $R^4$ | m | $R^5$ | $R^6$ | $R^{17}$ | $R^{18}$ | $R^{19}$ |
|---|---|---|---|---|---|---|---|---|---|
| $CH_2Cl$ | Me | H | H | 1 | Br | H | Et | $OCF_3$ | $CF_3$ |
| Me | Me | H | H | 2 | Br | H | Et | $CF_3$ | Cl |
| Me | Me | H | H | 2 | Br | H | Me | $OCH_2F$ | $CHF_2$ |
| $CH_2Cl$ | Me | H | H | 2 | Br | H | Me | $OCHF_2$ | $CH_2F$ |
| Me | Me | H | H | 1 | Br | H | Et | $OCH_2CF_3$ | $CF_3$ |
| Me | Me | H | H | 1 | Br | H | Me | Cl | $CH_2F$ |
| $CH_2Cl$ | Me | H | H | 2 | Br | H | Me | $OCF_3$ | $CH_2F$ |
| $CH_2Cl$ | Me | H | H | 2 | Br | H | Et | $OCF_3$ | $CH_2F$ |
| Me | Me | H | H | 1 | Br | H | Et | $CHF_2$ | Cl |
| $CH_2Cl$ | Me | H | H | 2 | Br | H | Me | $OCH_2F$ | $CHF_2$ |
| Me | Me | H | H | 1 | Br | H | Me | $CHF_2$ | $OCH_2F$ |
| $CH_2Cl$ | Me | H | H | 2 | Br | H | Et | Cl | $CH_2F$ |
| $CH_2Cl$ | Me | H | H | 1 | Br | H | Me | $OCH_2CF_3$ | $CHF_2$ |
| $CH_2Cl$ | Me | H | H | 2 | Br | H | Et | $OCH_2F$ | $CF_3$ |
| $CH_2Cl$ | Me | H | H | 2 | Br | H | Me | $CF_3$ | $OCH_2CF_3$ |
| $CH_2Cl$ | Me | H | H | 1 | Br | H | Et | $CHF_2$ | Cl |
| $CH_2Cl$ | Me | H | H | 1 | Br | H | Et | $CF_3$ | $OCF_3$ |
| $CH_2Cl$ | Me | H | H | 1 | Br | H | Me | $CF_3$ | $OCH_2CF_3$ |
| Me | Me | H | H | 2 | Br | H | Me | $CF_3$ | $OCF_3$ |
| $CH_2Cl$ | Me | H | H | 1 | Br | H | Et | $CHF_2$ | $OCHF_2$ |
| Me | Me | H | H | 2 | Br | H | Me | $OCH_2F$ | $CH_2F$ |
| $CH_2Cl$ | Me | H | H | 2 | Br | H | Et | $CHF_2$ | $OCHF_2$ |
| $CH_2Cl$ | Me | H | H | 2 | Br | H | Me | Cl | $CH_2F$ |
| Me | Me | H | H | 1 | Br | H | Et | $OCH_2CF_3$ | $CHF_2$ |
| $CH_2Cl$ | Me | H | H | 1 | Br | H | Et | $CH_2F$ | $OCHF_2$ |
| Me | Me | H | H | 2 | Br | H | Me | $OCHF_2$ | $CF_3$ |
| $CH_2Cl$ | Me | H | H | 1 | Br | H | Et | $CHF_2$ | $OCH_2CF_3$ |
| Me | Me | H | H | 1 | Br | H | Et | Cl | $CF_3$ |
| Me | Me | H | H | 1 | Br | H | Me | $OCF_3$ | $CHF_2$ |
| $CH_2Cl$ | Me | H | H | 2 | Br | H | Et | $CH_2F$ | $OCH_2F$ |
| $CH_2Cl$ | Me | H | H | 1 | Br | H | Me | $OCHF_2$ | $CF_3$ |
| Me | Me | H | H | 1 | Br | H | Me | $CH_2F$ | Cl |
| $CH_2Cl$ | Me | H | H | 1 | Br | H | Me | $CF_3$ | $OCHF_2$ |
| Me | Me | H | H | 1 | Br | H | Me | $CHF_2$ | $OCHF_2$ |
| Me | Me | H | H | 1 | Br | H | Et | $CHF_2$ | $OCH_2CF_3$ |
| Me | Me | H | H | 2 | Br | H | Me | $CH_2F$ | $OCF_3$ |
| Me | Me | H | H | 2 | Br | H | Et | $CF_3$ | $OCH_2CF_3$ |
| $CH_2Cl$ | Me | H | H | 1 | Br | H | Et | Cl | $CF_3$ |
| Me | Me | H | H | 2 | Br | H | Et | $OCHF_2$ | $CHF_2$ |
| $CH_2Cl$ | Me | H | H | 1 | Br | H | Me | Cl | $CHF_2$ |
| Me | Me | H | H | 2 | Br | H | Et | $OCF_3$ | $CHF_2$ |
| $CH_2Cl$ | Me | H | H | 1 | Br | H | Me | $OCHF_2$ | $CH_2F$ |
| Me | Me | H | H | 2 | Br | H | Me | $CHF_2$ | Cl |
| Me | Me | H | H | 2 | Br | H | Me | $CF_3$ | $OCHF_2$ |
| Me | Me | H | H | 2 | Br | H | Me | $OCF_3$ | $CH_2F$ |
| $CH_2Cl$ | Me | H | H | 2 | Br | H | Me | Cl | $CHF_2$ |
| Me | Me | H | H | 1 | Br | H | Et | $CHF_2$ | $OCH_2F$ |
| $CH_2Cl$ | Me | H | H | 2 | Br | H | Et | Cl | $CHF_2$ |
| Me | Me | H | H | 2 | Br | H | Et | $CH_2F$ | Cl |
| $CH_2Cl$ | Me | H | H | 2 | Br | H | Et | $OCHF_2$ | $CHF_2$ |
| $CH_2Cl$ | Me | H | H | 1 | Br | H | Me | $OCH_2CF_3$ | $CF_3$ |
| $CH_2Cl$ | Me | H | H | 1 | Br | H | Me | $CF_3$ | Cl |
| $CH_2Cl$ | Me | H | H | 2 | Br | H | Et | $CHF_2$ | $OCH_2CF_3$ |
| $CH_2Cl$ | Me | H | H | 1 | Br | H | Me | $CH_2F$ | $OCF_3$ |
| $CH_2Cl$ | Me | H | H | 2 | Br | H | Me | $CH_2F$ | $OCHF_2$ |
| $CH_2Cl$ | Me | H | H | 2 | Br | H | Me | $OCF_3$ | $CHF_2$ |
| $CH_2Cl$ | Me | H | H | 2 | Br | H | Me | $CHF_2$ | $OCHF_2$ |
| $CH_2Cl$ | Me | H | H | 2 | Br | H | Et | $OCHF_2$ | $CF_3$ |
| $CH_2Cl$ | Me | H | H | 1 | Br | H | Me | $CF_3$ | $OCHF_2$ |
| Me | Me | H | H | 2 | Br | H | Et | $OCHF_2$ | $CH_2F$ |
| Me | Me | H | H | 2 | Br | H | Et | $OCF_3$ | $CH_2F$ |
| $CH_2Cl$ | Me | H | H | 1 | Br | H | Et | $OCF_3$ | $CHF_2$ |
| Me | Me | H | H | 1 | Br | H | Et | $CHF_2$ | $OCF_3$ |

Table 8:

Table 8 consists of 240 compounds of the general formula I.2, where $R^5$ is chloro, and $R^1$, $R^2$, $R^3$, $R^4$, m, $R^6$, $R^{17}$, $R^{18}$ and $R^{19}$ have the values listed in Table 7. Thus compound 1 of Table 8 is the same as compound 1 of Table 7 except that in compound 1 of Table 8 $R^5$ is chloro instead of bromo. Similarly, compounds 2 to 240 of Table 8 are the same as compounds 2 to 240 of Table 7, respectively, except that in the compounds of Table 8 $R^5$ is chloro instead of bromo.

Table 9:

Table 9 consists of 240 compounds of the general formula I.2, where $R^1$ is fluoro, and $R^1$, $R^2$, $R^3$, $R^4$, m, $R^6$, $R^{17}$, $R^{18}$ and $R^{19}$ have the values listed in Table 7. Thus compound 1 of Table 9 is the same as compound 1 of Table 7 except that in compound 1 of Table 9 $R^1$ is fluoro instead of bromo. Similarly, compounds 2 to 240 of Table 9 are the same as compounds 2 to 240 of Table 7, respectively, except that in the compounds of Table 9 $R^5$ is fluoro instead of bromo.

Table 10:

Table 10 consists of 240 compounds of the general formula I.2, where $R^5$ is iodo, and $R^1$, $R^2$, $R^3$, $R^4$, m, $R^6$, $R^{17}$, $R^{18}$ and $R^{19}$ have the values listed in Table 7. Thus compound 1 of Table 10 is the same as compound 1 of Table 7 except that in compound 1 of Table 10 $R^5$ is iodo instead of bromo. Similarly, compounds 2 to 240 of Table 10 are the same as compounds 2 to 240 of Table 7, respectively, except that in the compounds of Table 10 $R^5$ is iodo instead of bromo.

Table 11:

Table 11 consists of 240 compounds of the general formula I.2, where $R^1$ is trifluoromethyl, and $R^1$, $R^2$, $R^3$, $R^4$, m, $R^6$, $R^{17}$, $R^{18}$ and $R^{19}$ have the values listed in Table 7. Thus compound 1 of Table 11 is the same as compound 1 of Table 7 except that in compound 1 of Table 11 $R^5$ is trifluoromethyl instead of bromo. Similarly, compounds 2 to 240 of Table 11 are the same as compounds 2 to 240 of Table 7, respectively, except that in the compounds of Table 11 $R^5$ is trifluoromethyl instead of bromo.

Table 12:

Table 12 consists of 240 compounds of the general formula I.2, where $R^6$ is fluoro, and $R^1$, $R^2$, $R^3$, $R^4$, m, $R^5$, $R^{17}$, $R^{18}$ and $R^{19}$ have the values listed in Table 7. Thus compound 1 of Table 12 is the same as compound 1 of Table 7 except that in compound 1 of Table 12 $R^6$ is fluoro instead of hydrogen. Similarly, compounds 2 to 240 of Table 12 are the same as compounds 2 to 240 of Table 7, respectively, except that in the compounds of Table 12 $R^6$ is fluoro instead of hydrogen.

Table 13:

Table 13 consists of 240 compounds of the general formula I.2, where $R^5$ is chloro and
$R^6$ is fluoro, and $R^1$, $R^2$, $R^3$, $R^4$, m, $R^{17}$, $R^{18}$ and $R^{19}$ have the values listed in Table 7. Thus compound 1 of Table 13 is the same as compound 1 of Table 12 except that in compound 1 of Table 13 $R^5$ is chloro instead of bromo. Similarly, compounds 2 to 240 of Table 13 are the same as compounds 2 to 240 of Table 12, respectively, except that in the compounds of Table 13 $R^5$ is chloro instead of bromo.

Table 14:

Table 14 consists of 240 compounds of the general formula I.2, where $R^5$ and $R^6$ are fluoro, and $R^1$, $R^2$, $R^3$, $R^4$, m, $R^{17}$, $R^{18}$ and $R^{19}$ have the values listed in Table 7. Thus compound 1 of Table 14 is the same as compound 1 of Table 12 except that in compound 1 of Table 14 $R^5$ is fluoro instead of bromo. Similarly, compounds 2 to 240 of Table 14 are the same as compounds 2 to 240 of Table 12, respectively, except that in the compounds of Table 14 $R^5$ is fluoro instead of bromo.

Table 15:

Table 15 consists of 240 compounds of the general formula I.2, where $R^5$ is iodo and $R^6$ is fluoro, and $R^1$, $R^2$, $R^3$, $R^4$, m, $R^{17}$, $R^{18}$ and $R^{19}$ have the values listed in Table 7. Thus compound 1 of Table 15 is the same as compound 1 of Table 12 except that in compound 1 of Table 15 $R^5$ is iodo instead of bromo. Similarly, compounds 2 to 240 of Table 15 are the same as compounds 2 to 240 of Table 12, respectively, except that in the compounds of Table 15 $R^5$ is iodo instead of bromo.

Table 16:

Table 16 consists of 240 compounds of the general formula I.2, where $R^5$ is trifluoromethyl and $R^6$ is fluoro, and $R^1$, $R^2$, $R^3$, $R^4$, m, $R^{17}$, $R^{18}$ and $R^{19}$ have the values listed in Table 7. Thus compound 1 of Table 16 is the same as compound 1 of Table 12 except that in compound 1 of Table 16 $R^5$ is trifluoromethyl instead of bromo. Similarly, compounds 2 to 240 of Table 16 are the same as compounds 2 to 240 of Table 12, respectively, except that in the compounds of Table 16 $R^5$ is trifluoromethyl instead of bromo.

Table 17:

Table 17 consists of 240 compounds of the general formula I.2, where $R^6$ is bromo, and $R^1$, $R^2$, $R^3$, $R^4$, m, $R^5$, $R^{17}$, $R^{18}$ and $R^{19}$ have the values listed in Table 7. Thus compound 1 of Table 17 is the same as compound 1 of Table 7 except that in compound 1 of Table 17 $R^6$ is bromo instead of hydrogen. Similarly, compounds 2 to 240 of Table 17 are the same as compounds 2 to 240 of Table 7, respectively, except that in the compounds of Table 17 $R^6$ is bromo instead of hydrogen.

Table 18:

Table 18 consists of 240 compounds of the general formula I.2, where $R^5$ is chloro and $R^6$ is bromo, and $R^1$, $R^2$, $R^3$, $R^4$, m, $R^{17}$, $R^{18}$ and $R^{19}$ have the values listed in Table 7. Thus compound 1 of Table 18 is the same as compound 1 of Table 17 except that in compound 1 of Table 18 $R^5$ is chloro instead of bromo. Similarly, compounds 2 to 240 of Table 18 are the same as compounds 2 to 240 of Table 17, respectively, except that in the compounds of Table 18 $R^5$ is chloro instead of bromo.

Table 19:

Table 19 consists of 240 compounds of the general formula I.2, where $R^5$ is iodo and $R^6$ is bromo, and $R^1$, $R^2$, $R^3$, $R^4$, m, $R^{17}$, $R^{18}$ and $R^{19}$ have the values listed in Table 7. Thus compound 1 of Table 19 is the same as compound 1 of Table 17 except that in compound 1 of Table 19 $R^5$ is iodo instead of bromo. Similarly, compounds 2 to 240 of Table 19 are the same as compounds 2 to 240 of Table 17, respectively, except that in the compounds of Table 19 $R^5$ is iodo instead of bromo.

Table 20:

Table 20 consists of 240 compounds of the general formula I.2, where $R^5$ is trifluoromethyl and $R^6$ is bromo, and $R^1$, $R^2$, $R^3$, $R^4$, m, $R^{17}$, $R^{18}$ and $R^{19}$ have the values listed in Table 7. Thus compound 1 of Table 20 is the same as compound 1 of Table 17 except that in compound 1 of Table 20 $R^5$ is trifluoromethyl instead of bromo. Similarly, compounds 2 to 240 of Table 20 are the same as compounds 2 to 240 of Table 17, respectively, except that in the compounds of Table 20 $R^5$ is trifluoromethyl instead of bromo.

Table 21:

Table 21 consists of 240 compounds of the general formula I.2, where $R^5$ and $R^6$ are chloro, and $R^1$, $R^2$, $R^3$, $R^4$, m, $R^{17}$, $R^{18}$ and $R^{19}$ have the values listed in Table 7. Thus compound 1 of Table 21 is the same as compound 1 of Table 7 except that in compound 1 of Table 21 $R^5$ is chloro instead of bromo and $R^6$ is chloro instead of hydrogen. Similarly, compounds 2 to 240 of Table 21 are the same as compounds 2 to 240 of Table 7, respectively, except that in the compounds of Table 21 $R^5$ is chloro instead of bromo and $R^6$ is chloro instead of hydrogen.

Table 22:

Table 22 consists of 240 compounds of the general formula I.2, where $R^5$ is iodo and $R^6$ is chloro, and $R^1$, $R^2$, $R^3$, $R^4$, m, $R^{17}$, $R^{18}$ and $R^{19}$ have the values listed in Table 7. Thus compound 1 of Table 22 is the same as compound 1 of Table 21 except that in compound 1 of Table 22 $R^5$ is iodo instead of chloro. Similarly, compounds 2 to 240 of Table 22 are the same as compounds 2 to 240 of Table 21, respectively, except that in the compounds of Table 22 $R^5$ is iodo instead of chloro.

Table 23:

Table 23 consists of 240 compounds of the general formula I.2, where $R^5$ is trifluoromethyl and $R^6$ is chloro, and $R^1$, $R^2$, $R^3$, $R^4$, m, $R^{17}$, $R^{18}$ and $R^{19}$ have the values listed in Table 7. Thus compound 1 of Table 23 is the same as compound 1 of Table 21 except that in compound 1 of Table 23 $R^5$ is trifluoromethyl instead of chloro. Similarly, compounds 2 to 240 of Table 23 are the same as compounds 2 to 240 of Table 21, respectively, except that in the compounds of Table 23 $R^5$ is trifluoromethyl instead of chloro.

Table 24:

Table 24 consists of 240 compounds of the general formula I.2, where $R^5$ and $R^6$ are iodo, and $R^1$, $R^2$, $R^3$, $R^4$, m, $R^{17}$, $R^{18}$ and $R^{19}$ have the values listed in Table 7. Thus compound 1 of Table 24 is the same as compound 1 of Table 7 except that in compound 1 of Table 24 $R^5$ is iodo instead of bromo and $R^6$ is iodo instead of hydrogen. Similarly, compounds 2 to 240 of Table 24 are the same as compounds 2 to 240 of Table 7, respectively, except that in the compounds of Table 24 $R^5$ is iodo instead of bromo and $R^6$ is iodo instead of hydrogen.

Table 25:

Table 25 consists of 240 compounds of the general formula I.2, where $R^5$ is trifluoromethyl and $R^6$ is iodo, and $R^1$, $R^2$, $R^3$, $R^4$, m, $R^{17}$, $R^{18}$ and $R^{19}$ have the values listed in Table 7. Thus compound 1 of Table 25 is the same as compound 1 of Table 24 except that in compound 1 of Table 25 $R^5$ is trifluoromethyl instead of iodo. Similarly, compounds 2 to 240 of Table 25 are the same as compounds 2 to 240 of Table 24, respectively, except that in the compounds of Table 25 $R^5$ is trifluoromethyl instead of iodo.

Table 26:

Table 26 consists of 240 compounds of the general formula I.2, where $R^5$ and $R^6$ are trifluoromethyl, and $R^1$, $R^2$, $R^3$, $R^4$, m, $R^{17}$, $R^{18}$ and $R^{19}$ have the values listed in Table 7. Thus compound 1 of Table 26 is the same as compound 1 of Table 7 except that in compound 1 of Table 26 $R^5$ is trifluoromethyl instead of bromo and $R^6$ is trifluoromethyl instead of hydrogen. Similarly, compounds 2 to 240 of Table 26 are the same as compounds 2 to 240 of Table 7, respectively, except that in the compounds of Table 26 $R^5$ is trifluoromethyl instead of bromo and $R^6$ is trifluoromethyl instead of hydrogen.

A group of preferred compounds of formula I comprises those wherein $R^1$ and $R^2$ are both $C_1$-$C_{10}$alkyl;

$R^3$ and $R^4$ are both hydrogen;

$R^5$ and $R^6$ are each independently of the other $C_1$-$C_6$haloalkyl, $C_1$-$C_6$hydroxyalkyl, pyrazolyl-$CH_2$—, 4,5-dihydropyrazolyl-$CH_2$—, triazolyl-$CH_2$—, imidazolyl-$CH_2$—, indazolyl-$CH_2$—, $C_2$-$C_6$alkenyl, $C_2$-$C_6$alkynyl, $C_2$-$C_6$haloalkenyl, $C_1$-$C_6$alkylcarbonyloxy-$C_2$-$C_6$alkenyl, $C_1$-$C_6$alkylcarbonyl, $C_1$-$C_6$haloalkylcarbonyl, $C_3$-$C_6$cycloalkylcarbonyl, or $C_1$-$C_6$alkoxy$C_1$-$C_6$alkylcarbonyl, or $R^5$ and $R^6$ are each independently of the other halogen, $C_1$-$C_6$alkylcarbonyl-$C_1$-$C_2$alkyl, $C_1$-$C_6$alkoxycarbonyl-$C_1$-$C_2$alkyl, $C_1$-$C_6$alkylaminocarbonyl-$C_1$-$C_2$alkyl, di-$C_1$-$C_6$alkylaminocarbonyl-$C_1$-$C_2$alkyl, $C_1$-$C_6$alkoxy-$C_1$-$C_2$alkyl, $C_1$-$C_2$alkyl-$P(O)(OC_1$-$C_6$alkyl$)_2$, or $R_5$ and $R_6$ are each independently of the other $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkylsulfonyl-$C_1$-$C_6$alkyl, $C_1$-$C_6$alkylsulfonyloxy-$C_1$-$C_6$alkyl, benzylsulfonyl or benzylsulfonyl substituted by one to three halogen, or $R^5$ and $R^6$ are each independently of the other benzyl or benzyl substituted by one to three halogen, or $R^5$ and $R^6$ are each independently of the other —$CONR^7R^8$ wherein $R^7$ and $R^8$ are each independently of the other hydrogen, $C_1$-$C_6$alkyl, $C_3$-$C_6$cycloalkyl, $C_1$-$C_6$haloalkyl, phenyl or phenyl substituted by $C_1$-$C_6$haloalkyl, nitro, cyano or by halogen, and $R^6$ may additionally be hydrogen, cyano, $C_1$-$C_6$alkyl or $C_1$-$C_6$alkoxycarbonyl, or $R^5$ and $R^6$ together with the carbon atom to which they are bonded form a 3- to 10-membered ring which is optionally substituted by one to four substituents independently selected from $C_1$-$C_6$alkyl, $C_2$-$C_6$alkenyl, $C_1$-$C_6$alkoxycarbonyl, halogen, nitro, or phenylcarbonyl, or $R^5$ and $R^6$ together with the carbon atom to which they are bonded form a group of the formula $C=CR^{10}R^{11}$ wherein $R^{10}$ and $R^{11}$ are independently selected from hydrogen, $C_1$-$C_6$alkyl, —$NH(C_1$-$C_6$alkyl), —$N(C_1$-$C_6$alkyl)$_2$, $C_1$-$C_6$alkoxy-$C_1$-$C_2$alkyl, $C_1$-$C_6$alkylcarbonyloxy, $C_1$-$C_6$alkylcarbonyloxy-$C_1$-$C_2$alkyl, $C_1$-$C_6$alkoxy-$C_1$-$C_2$alkylcarbonyloxy or $C_1$-$C_6$alkylcarbonyloxy-$C_1$-$C_2$alkylcarbonyloxy;

m is 1 or 2;

n is 1;

Y is phenyl, which is optionally substituted by one to three substituents independently selected from $C_1$-$C_6$alkyl, $C_1$-$C_6$haloalkyl, $C_1$-$C_6$alkoxycarbonyl, nitro, cyano, halogen, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $C_1$-$C_6$alkoxy, $C_1$-$C_6$haloalkoxy, $C_2$-$C_6$alkenyloxy, $C_2$-$C_6$alkynyloxy, $C_1$-$C_6$alkylsulfonyloxy, $C_1$-$C_6$haloalkylsulfonyloxy, phenyl or phenyl substituted by $C_1$-$C_6$haloalkyl, nitro, cyano or by halogen, or Y is a 5- to 10-membered heterocycle containing one to three nitrogen, oxygen or sulfur atoms, which is optionally substituted by one to three substituents independently selected from $C_1$-$C_6$alkyl, $C_3$-$C_6$cycloalkyl, $C_1$-$C_6$haloalkyl, $C_1$-$C_6$alkoxy-$C_1$-$C_6$alkyl, cyano, halogen, $C_1$-$C_6$alkylsulfonyl, $C_1$-$C_6$haloalkylsulfonyl, $C_1$-$C_6$alkoxy, $C_3$-$C_6$cycloalkyloxy wherein one of the $CH_2$ groups is optionally replaced by an oxygen atom, or $C_1$-$C_6$haloalkoxy;

and to N-oxides, salts and optical isomers of compounds of formula I.

A group of especially preferred compounds of formula I comprises those wherein $R^1$ and $R^2$ are both $C_1$-$C_{10}$alkyl;

$R^3$ and $R^4$ are both hydrogen;

$R^5$ and $R^6$ are each independently of the other $C_1$-$C_6$haloalkyl, triazolyl-$CH_2$—, imidazolyl-$CH_2$—, $C_2$-$C_6$alkenyl, $C_2$-$C_6$alkynyl, $C_2$-$C_6$haloalkenyl, $C_1$-$C_6$alkylcarbonyloxy-$C_2$-$C_6$alkenyl, $C_1$-$C_6$alkylcarbonyl, $C_1$-$C_6$haloalkylcarbonyl, $C_3$-$C_6$cycloalkylcarbonyl, or $C_1$-$C_6$alkoxy-$C_1$-$C_6$alkylcarbonyl, or $R^5$ and $R^6$ are each independently of the other halogen, $C_1$-$C_6$alkoxycarbonyl-$C_1$-$C_2$alkyl, or $C_1$-$C_6$alkoxy-$C_1$-$C_2$alkyl, or $R_5$ and $R_6$ are each independently of the other benzylsulfonyl, or $R^5$ and $R^6$ are each independently of the other —$CONH_2$, and $R^6$ may additionally be hydrogen, $C_1$-$C_6$alkyl or $C_1$-$C_6$alkoxycarbonyl, or $R^5$ and $R^6$ together with the carbon atom to which they are bonded form a 3- to 10-membered ring which is optionally substituted by one to four substituents independently selected from $C_1$-$C_6$alkyl, $C_2$-$C_6$alkenyl, halogen, or nitro, or $R^5$ and $R^6$ together with the carbon atom to which they are bonded form a group of the formula $C=CR^{10}R^{11}$ wherein $R^{10}$ and $R^{11}$ are independently selected from hydrogen, $C_1$-$C_6$alkyl, or $C_1$-$C_6$alkylcarbonyloxy;

m is 1 or 2;

n is 1;

Y is phenyl, which is optionally substituted by one to three substituents independently selected from $C_1$-$C_6$alkyl, $C_1$-$C_6$haloalkyl, $C_1$-$C_6$alkoxycarbonyl, cyano, halogen, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkoxy, $C_1$-$C_6$haloalkoxy, $C_1$-$C_6$alkylsulfonyloxy, or phenyl, or Y is a 5- to 10-membered heterocycle containing one to three nitrogen, oxygen or sulfur atoms, which is optionally substituted by one to three substituents independently selected from $C_1$-$C_6$alkyl, $C_3$-$C_6$cycloalkyl, $C_1$-$C_6$haloalkyl, cyano, halogen, $C_1$-$C_6$alkoxy, or $C_1$-$C_6$haloalkoxy;

and to N-oxides, salts and optical isomers of compounds of formula I.

A group of preferred compounds of formula I comprises those wherein $R^1$ and $R^2$ are each independently of the other hydrogen, methyl, ethyl, cyclopropyl, cyclobutyl, fluoromethyl, chloromethyl, difluoromethyl or trifluoromethyl, or $R^1$ and $R^2$ together with the carbon atom to which they are bonded form a $C_3$- or $C_4$-ring, $R^3$ and $R^4$ are each independently of the other hydrogen, methyl, ethyl, cyclopropyl, cyclobutyl, fluoromethyl, chloromethyl, difluoromethyl or trifluoromethyl, or $R^3$ and $R^4$ together with the carbon atom to which they are bonded form a $C_3$- or $C_4$-ring, or $R^1$ with $R^3$ or $R^4$ and together with the carbon atoms to which they are bonded form a $C_5$- or $C_6$-ring, or $R^2$ with $R^3$ or $R^4$ and together with the carbon atoms to which they are bonded form a $C_5$- or $C_6$-ring.

A group of especially preferred compounds of formula I comprises those wherein $R^1$, $R^2$, $R^3$ and $R^4$ are each independently of the others hydrogen, methyl, fluoromethyl, chloromethyl, difluoromethyl or trifluoromethyl.

A further group of especially preferred compounds of formula I comprises those wherein $R^1$ and $R^2$ are both $C_1$-$C_{10}$alkyl.

A further group of especially preferred compounds of formula I comprises those wherein $R^1$ and $R^2$ are both methyl.

Another group of especially preferred compounds of formula I comprises those wherein $R^3$ and $R^4$ are both hydrogen.

A further group of especially preferred compounds of formula I comprises those wherein m is 1 or 2.

A further group of very especially preferred compounds of formula I comprises those wherein m is 2.

A group of preferred compounds of formula I comprises those wherein $R^5$ and $R^6$ are each independently of the other fluoro, chloro, bromo, iodo, acetyl, 1-acetyloxy-ethen-1-yl, benzylsulfonyl, carbamoyl, chloroacetyl, N-cyclopropyl-carbamoyl, cyclopropylcarbonyl, N,N-diethyl-carbamoyl, 2-diethylphosphonato-eth-1-yl, difluoroacetyl, N-(2,2-difluoro-ethyl)-carbamoyl, 1,1-difluoroprop-1-en-3-yl, 4,5-dihydropyrazol-1-ylmethyl, 2-(N,N-dimethyl-carbamoyl)-eth-1-yl, 2-ethoxycarbonyl-eth-1-yl, 4-fluoroanilinocarbonyl, 4-fluorobenzyl, 1-hydroxy-but-1-yl, 1-hydroxy-prop-1-yl, imidazol-1-ylmethyl, indazol-1-ylmethyl, methoxyacetyl, 2-methoxy-eth-1-yl, methoxymethyl, methylsulfonyl, 2-methylsulfonyl-eth-1-yl, methylsulfonylmethyl, 1-methylsulfonyloxy-but-1-yl, propargyl, 2-propionoyl-eth-1-yl, pyrazol-1-ylmethyl, 1,2,4-triazol-1-ylmethyl, trifluoromethyl, or trifluoromethylthio, and $R^6$ is additionally hydrogen, ethoxycarbonyl, ethyl, methoxycarbonyl or methyl, or $R^5$ and $R^6$ together with the carbon they are bonded to form 1-chloro-1-methoxycarbonyl-cyclopropyl, cyclopropyl, 1,1-dichlorocyclopropyl, nitro-cyclopropyl, phenylcarbonyl-cyclopropyl, propen-2-yl-cyclopropyl, or vinyl-cyclopropyl, or $R^5$ and $R^6$ together with the carbon they are bonded to form 3-acetyloxy-2-acetyloxyacetyloxy-propylidene, 2-acetyloxy-propylidene, butylidene, N,N-dimethylaminoethylidene, or 3-methoxy-2-methoxyacetyloxy-propylidene.

A group of especially preferred compounds of formula I comprises those wherein $R^5$ and $R^6$ are each independently of the other fluoro, chloro, bromo, iodo, acetyl, 1-acetyloxy-ethen-1-yl, benzylsulfonyl, carbamoyl, chloroacetyl, cyclopropylcarbonyl, difluoroacetyl, 1,1-difluoroprop-1-en-3-yl, imidazol-1-ylmethyl, methoxymethyl, 2-methoxy-eth-1-yl, methoxymethyl, propargyl, 1,2,4-triazol-1-ylmethyl, or trifluoromethyl, and $R^6$ is additionally hydrogen, ethyl, methoxycarbonyl or methyl, or $R^5$ and $R^6$ together with the carbon they are bonded to form cyclopropyl, 1,1-dichlorocyclopropyl, nitro-cyclopropyl, or vinyl-cyclopropyl, or $R^5$ and $R^6$ together with the carbon they are bonded to form 2-acetyloxy-propylidene.

A group of preferred compounds of formula I comprises those wherein $R^5$ and $R^6$ are each independently of the other fluoro, chloro, bromo, iodo, acetyl, 1-acetyloxy-ethen-1-yl, benzylsulfonyl, carbamoyl, chloroacetyl, N-cyclopropyl-carbamoyl, cyclopropylcarbonyl, N,N-diethyl-carbamoyl, 2-diethylphosphonato-eth-1-yl, difluoroacetyl, N-(2,2-difluoroethyl)-carbamoyl, 1,1-difluoroprop-1-en-3-yl, 4,5-dihydropyrazol-1-ylmethyl, 2-(N,N-dimethyl-carbamoyl)-eth-1-yl, 2-ethoxycarbonyl-eth-1-yl, 4-fluoroanilinocarbonyl, 4-fluorobenzyl, 1-hydroxy-but-1-yl, 1-hydroxy-prop-1-yl, imidazol-1-ylmethyl, indazol-1-ylmethyl, methoxyacetyl, 2-methoxy-eth-1-yl, methoxymethyl, methylsulfonyl, 2-methylsulfonyl-eth-1-yl, methylsulfonylmethyl, 1-methylsulfonyloxy-but-1-yl, propargyl, 2-propionoyl-eth-1-yl, pyrazol-1-ylmethyl, 1,2,4-triazol-1-ylmethyl, trifluoromethyl, or trifluoromethylthio, and $R^6$ is additionally hydrogen, ethoxycarbonyl, ethyl, methoxycarbonyl or methyl.

A group of especially preferred compounds of formula I comprises those wherein $R^5$ and $R^6$ are each independently of the other fluoro, chloro, bromo, iodo, acetyl, 1-acetyloxy-ethen-1-yl, benzylsulfonyl, carbamoyl, chloroacetyl, cyclopropylcarbonyl, difluoroacetyl, 1,1-difluoroprop-1-en-3-yl, imidazol-1-ylmethyl, methoxymethyl, 2-methoxy-eth-1-yl, methoxymethyl, propargyl, 1,2,4-triazol-1-ylmethyl, or trifluoromethyl, and $R^6$ is additionally hydrogen, ethyl, methoxycarbonyl or methyl.

A group of preferred compounds of formula I comprises those wherein $R^5$ and $R^6$ together with the carbon they are bonded to form 1-chloro-1-methoxycarbonyl-cyclopropyl, cyclopropyl, 1,1-dichlorocyclopropyl, nitro-cyclopropyl, phenylcarbonyl-cyclopropyl, propen-2-yl-cyclopropyl, or vinyl-cyclopropyl.

A group of especially preferred compounds of formula I comprises those wherein $R^5$ and $R^6$ together with the carbon they are bonded to form cyclopropyl, 1,1-dichlorocyclopropyl, nitro-cyclopropyl, or vinyl-cyclopropyl.

A group of preferred compounds of formula I comprises those wherein $R^5$ and $R^6$ together with the carbon they are bonded to form 3-acetyloxy-2-acetyloxyacetyloxy-propylidene, 2-acetyloxy-propylidene, butylidene, N,N-dimethylaminoethylidene, or 3-methoxy-2-methoxyacetyloxy-propylidene.

A group of especially preferred compounds of formula I comprises those wherein $R^5$ and $R^6$ together with the carbon they are bonded to form 2-acetyloxy-propylidene.

A group of especially preferred compounds of formula I comprises those wherein $R^5$ and $R^6$ are each independently of the other cyclopropyl, difluoromethyl, trifluoromethyl, trifluoroethyl, hydroxymethyl, methoxymethyl, methylthiomethyl, methylsulfinylmethyl, methylsulfonylmethyl, vinyl, difluorovinyl, dichlorovinyl, ethynyl, propargyl, acetyl, trifluoroacetyl, methoxycarbonylethyl, nitro, formyl, bromine, chlorine, fluorine, iodine, azido, trimethylsilyl, methoxycarbonylmethyl, ethoxycarbonylmethyl, cyanomethyl, cyanoethyl, —CH$_2$CH$_2$CON(CH$_3$)$_2$, —CH$_2$CH$_2$P(O)(OCH$_3$)$_2$, —CH$_2$CH$_2$P(O)(OC$_2$H$_5$)$_2$, —CH$_2$CH$_2$COCH$_3$, —CH$_2$CH$_2$COCH$_2$CH$_3$, —CH$_2$CH$_2$CO$_2$CH$_3$, —CH$_2$CH$_2$CO$_2$CH$_2$H$_3$, —CH$_2$CH$_2$SO$_2$CH$_3$, —CH$_2$CH$_2$NO$_2$, mercapto, phenylthio, methylthio, methylsulfinyl, methylsulfonyl, benzylsulfonyl, phenylsulfinyl, phenylsulfonyl, trifluoromethylthio, trifluoromethylsulfinyl, trifluoromethylsulfonyl, hydroxyl, methoxy, ethoxy, trifluoromethoxy, trifluoroethoxy, methanesulfonyloxy, trifluoromethanesulfonyloxy, phenoxy, benzyloxy, —CONH—SO$_2$—CH$_3$, —CONH—SO$_2$—CF$_3$, —NHCO—CH$_3$, —NHCO—CF$_3$, —OCO—CH$_3$, —OCO—CF$_3$, —OCO-phenyl, —OCONH—CH$_3$, —OCONH—CH$_2$CF$_3$, —OCONH-phenyl, —CONH$_2$, —CONHCH$_3$ or —CON(CH$_3$)$_2$, and $R^6$ may additionally be hydrogen, cyano, methyl, ethyl, isopropyl, methoxycarbonyl, ethoxycarbonyl or benzyloxycarbonyl.

A further group of especially preferred compounds of formula I comprises those wherein $R^5$ and $R^6$ are each independently of the other phenyl or naphthyl, which rings may be substituted by fluorine, chlorine, bromine, iodine, trifluoromethyl, cyclopropyl, methyl, methylthio, methylsulfinyl, methylsulfonyl, trifluoromethylthio, trifluoromethylsulfinyl, trifluoromethylsulfonyl, methoxy, ethoxy, trifluoromethoxy, difluoromethoxy, cyano, nitro, methoxycarbonyl, —CONH$_2$ or by carboxyl, and $R^6$ may additionally be hydrogen, cyano, methyl, ethyl, isopropyl, methoxycarbonyl, ethoxycarbonyl or benzyloxycarbonyl or halogen or trifluoromethyl.

A further group of especially preferred compounds of formula I comprises those wherein $R^5$ and $R^6$ are each independently of the other 1,3-dioxalanyl, tetrahydrofuranyl, morpholinyl, furyl, thienyl, pyrrolyl, pyrazolyl, imidazolyl, 1,2,3-triazolyl, 1,2,4-triazolyl, oxazolyl, thiazolyl, isoxazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, tetrazolyl, tetrazinyl, benzofuryl, benzisofuryl, benzothienyl, benzisothienyl, indolyl, benzimidazolyl, 2,1,3-benzoxadiazolyl, quinolyl, isoquinolyl, cinnolinyl, phthalazinyl, quinazolinyl, quinoxalinyl, naphthyridinyl, benzotriazinyl, purinyl, pteridinyl and indolizinyl, which heterocycles may be substituted by fluorine, chlorine, bromine, iodine, trifluoromethyl, cyclopropyl, methyl, methylthio, methylsulfinyl, methylsulfonyl, trifluoromethylthio, trifluoromethylsulfinyl, trifluoromethylsulfonyl, methoxy, ethoxy, trifluoromethoxy, difluoromethoxy, cyano, nitro, methoxycarbonyl, —CONH$_2$ or by carboxyl, and $R^6$ may additionally be hydrogen, cyano, methyl, ethyl, isopropyl, methoxycarbonyl, ethoxycarbonyl or benzyloxycarbonyl or halogen or trifluoromethyl.

A further group of especially preferred compounds of formula I comprises those wherein $R^5$ and $R^6$ are each independently of the other 1,3-dioxalanyl, tetrahydrofuranyl, morpholinyl, furyl, thienyl, pyrrolyl, pyrazolyl, imidazolyl, 1,2,3-triazolyl, 1,2,4-triazolyl, oxazolyl, isoxazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, tetrazolyl, tetrazinyl, benzofuryl, benzisofuryl, benzothienyl, benzisothienyl, indolyl, benzimidazolyl, 2,1,3-benzoxadiazolyl, quinolyl, isoquinolyl, cinnolinyl, phthalazinyl, quinazolinyl, quinoxalinyl, naphthyridinyl, benzotriazinyl, purinyl, pteridinyl and indolizinyl, which heterocycles may be substituted by fluorine, chlorine, bromine, iodine, trifluoromethyl, cyclopropyl, methyl, methylthio, methylsulfinyl, methylsulfonyl, trifluoromethylthio, trifluoromethylsulfinyl, trifluoromethylsulfonyl, methoxy, ethoxy, trifluoromethoxy, difluoromethoxy, cyano, nitro, methoxycarbonyl, —$CONH_2$ or by carboxyl, and $R^6$ may additionally be hydrogen, cyano, methyl, ethyl, isopropyl, methoxycarbonyl, ethoxycarbonyl or benzyloxycarbonyl or halogen or trifluoromethyl.

A further group of especially preferred compounds of formula I comprises those wherein $R^5$ and $R^6$ together with the carbon atom to which they are bonded form a cyclopropyl ring which may be substituted by methyl, trifluoromethyl, methoxycarbonyl, ethoxycarbonyl, nitro, vinyl, 2-propenyl, acetyl, phenylcarbonyl, phenyl, trifluoroacetyl, methylsulfonyl, cyano, chlorine, fluorine, bromine or by methoxy.

A further group of especially preferred compounds of formula I comprises those wherein $R^5$ and $R^6$ together with the carbon atom to which they are bonded form a 3- to 6-membered heterocycle containing a nitrogen, oxygen or sulfur atom, which heterocycle may be substituted by methyl, trifluoromethyl, methoxycarbonyl, ethoxycarbonyl, trifluoroacetyl, trifluoromethylsulfonyl, methylsulfonyl, acetyl, phenyl, cyano, chlorine, fluorine, bromine or by methoxy.

A further group of especially preferred compounds of formula I comprises those wherein $R^5$ and $R^6$ together with the carbon atom to which they are bonded form a radical of formula C=$CH_2$, C=CH—$CH_3$, C=CH—$N(CH_3)_2$, C=CH—$NH(CH_3)$, C=CH—$OCH_3$ or C=CH—$OC_2H_5$.

A further group of especially preferred compounds of formula I comprises those wherein $R^1$, $R^2$, $R^3$, $R^4$, m, n and Y are as defined above and $R^5$ and $R^6$ together with the carbon atom to which they are bonded form a 3- to 10-membered ring which may contain one or more nitrogen, oxygen or sulfur atoms, especially a 3- to 6-membered carbocyclic ring, more especially cyclopropyl, and which may be substituted by alkyl, haloalkyl, alkoxy, alkoxycarbonyl, halogen, nitro or by cyano.

A further group of very especially preferred compounds of formula I comprises those wherein $R^5$ and $R^6$ are each independently of the other cyclopropyl, difluoromethyl, trifluoromethyl, trifluoroethyl, vinyl, difluorovinyl, dichlorovinyl, ethynyl, propargyl, acetyl, trifluoroacetyl, benzyloxycarbonyl, nitro, formyl, bromine, chlorine, fluorine, iodine, azido, trimethylsilyl, methoxycarbonylmethyl, ethoxycarbonylmethyl, cyanomethyl, mercapto, phenylthio, methylthio, methylsulfinyl, methylsulfonyl, benzylsulfonyl, phenylsulfinyl, phenylsulfonyl, trifluoromethylthio, trifluoromethylsulfinyl, trifluoromethylsulfonyl, hydroxyl, methoxy, ethoxy, trifluoromethoxy, trifluoroethoxy, methylthiomethyl, methylsulfinylmethyl, methylsulfonylmethyl, methylsulfonyloxy, trifluoromethylsulfonyloxy, phenoxy, benzyloxy, —CONH—$SO_2$—$CH_3$, —CONH—$SO_2$—$CF_3$, —NHCO—$CH_3$, —NHCO—$CF_3$, —OCO—$CH_3$, —OCO—$CF_3$, —OCO-phenyl, —OCONH—$CH_3$, —OCONH—$CH_2CF_3$ or —OCONH-phenyl, and $R^6$ may additionally be hydrogen, cyano, methyl, ethyl, methoxycarbonyl or ethoxycarbonyl or halogen or trifluoromethyl.

A further group of very especially preferred compounds of formula I comprises those wherein $R^5$ and $R^6$ are each independently of the other phenyl or naphthyl, which rings may be substituted by fluorine, chlorine, trifluoromethyl, methylsulfonyl, methoxy, trifluoromethoxy, cyano, nitro or by methoxycarbonyl and $R_6$ may additionally be hydrogen, cyano, methyl, ethyl, methoxycarbonyl or ethoxycarbonyl or halogen or trifluoromethyl.

A further group of very especially preferred compounds of formula I comprises those wherein $R^5$ and $R^6$ are each independently of the other isothiazolyl, isoxazolyl, pyrazolyl, thiadiazolyl, oxadiazolyl, dihydroisoxazolyl or a radical of formula

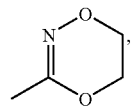

which rings may be substituted by methyl or methoxy and $R^6$ may additionally be hydrogen, cyano, methyl, ethyl, methoxycarbonyl or ethoxycarbonyl or halogen or trifluoromethyl.

A further group of very especially preferred compounds of formula I comprises those wherein $R^5$ and $R^6$ together with the carbon atom to which they are bonded form a cyclopropyl ring which may be substituted by methoxycarbonyl, ethoxycarbonyl, cyano, trifluoromethyl, methoxy, nitro, vinyl, bromine, fluorine or by chlorine.

A further group of especially preferred compounds of formula I comprises those wherein $R^1$, $R^2$, $R^3$, $R^4$, $R^6$, m, n and Y are as defined above and $R^5$ is halogen.

A further group of especially preferred compounds of formula I comprises those wherein $R^1$, $R^2$, $R^3$, $R^4$, m, n and Y are as defined above and $R^5$ and $R^6$ are both halogen.

A further group of especially preferred compounds of formula I comprises those wherein $R^1$, $R^2$, $R^3$, $R^4$, $R^6$, m, n and Y are as defined above and $R^5$ is fluorine.

A further group of especially preferred compounds of formula I comprises those wherein $R^1$, $R^2$, $R^3$, $R^4$, m, n and Y are as defined above and $R^5$ and $R^6$ are both fluorine.

A further group of especially preferred compounds of formula I comprises those wherein $R^1$, $R^2$, $R^3$, $R^4$, $R^6$, m, n and Y are as defined above and $R^5$ is chlorine.

A further group of especially preferred compounds of formula I comprises those wherein $R^1$, $R^2$, $R^3$, $R^4$, m, n and Y are as defined above and $R^5$ and $R^6$ are both chlorine.

A further group of especially preferred compounds of formula I comprises those wherein $R^1$, $R^2$, $R^3$, $R^4$, m, n and Y are as defined above and $R^5$ is fluorine and $R^6$ is chlorine.

A further group of especially preferred compounds of formula I comprises those wherein $R^1$, $R^2$, $R^3$, $R^4$, $R^6$, m, n and Y are as defined above and $R^5$ is $C_1$-$C_6$haloalkyl, especially trifluoromethyl.

A further group of especially preferred compounds of formula I comprises those wherein n is 1 or 2.

A further group of very especially preferred compounds of formula I comprises those wherein n is 1.

A further group of especially preferred compounds of formula I comprises those wherein Y is hydrogen, methyl, ethyl, propyl, butyl, cyclopropyl, trifluoromethyl, trifluoroethyl, vinyl, ethynyl, difluorovinyl, propargyl, acetyl, methoxycarbonyl, ethoxycarbonyl, nitro, cyano, formyl, hydroxyl, carboxyl, halogen, azido, thiocyanato, trimethylsilyl, methylthio, methylsulfonyl, ethylsulfonyl, benzylsulfonyl, phenylsulfonyl, methoxy, ethoxy, propoxy, butoxy, difluoromethoxy, trifluoromethoxy, trifluoroethoxy, methylsulfonyloxy, trifluoromethylsulfonyloxy, phenoxy, benzyloxy, —CONH—SO$_2$—CH$_3$ or —CONH—SO$_2$—CF$_3$.

A group of preferred compounds of formula I comprises those wherein Y is phenyl which is optionally substituted by one to three substituents independently selected from fluoro, chloro, cyano, difluoromethoxy, ethoxycarbonyl, methoxy, methoxycarbonyl, methyl, methylsulfonyloxy, nitro, phenyl, propargyloxy, trifluoromethoxy, trifluoromethyl, trifluoromethylthio or trifluoromethylsulfinyl.

A group of especially preferred compounds of formula I comprises those wherein Y is phenyl which is optionally substituted by one to three substituents independently selected from fluoro, chloro, cyano, difluoromethoxy, ethoxycarbonyl, methoxy, methoxycarbonyl, methyl, methylsulfonyloxy, phenyl, trifluoromethoxy, trifluoromethyl, trifluoromethylthio or trifluoromethylsulfinyl.

A further group of especially preferred compounds of formula I comprises those wherein Y is phenyl.

A further group of especially preferred compounds of formula I comprises those wherein Y is 2-biphenyl.

A further group of especially preferred compounds of formula I comprises those wherein Y is 6-chloro-2-fluorophenyl.

A further group of especially preferred compounds of formula I comprises those wherein Y is 2-cyanophenyl.

A further group of especially preferred compounds of formula I comprises those wherein Y is 2-difluoromethoxyphenyl.

A further group of especially preferred compounds of formula I comprises those wherein Y is 2,3-difluorophenyl.

A further group of especially preferred compounds of formula I comprises those wherein Y is 2,4-difluorophenyl.

A further group of especially preferred compounds of formula I comprises those wherein Y is 2,5-difluorophenyl.

A further group of especially preferred compounds of formula I comprises those wherein Y is 2,6-difluorophenyl.

A further group of especially preferred compounds of formula I comprises those wherein Y is 3,5-difluorophenyl.

A further group of especially preferred compounds of formula I comprises those wherein Y is 2,6-difluoro-3-tolyl.

A further group of especially preferred compounds of formula I comprises those wherein Y is 3,5-dimethoxyphenyl.

A further group of especially preferred compounds of formula I comprises those wherein Y is 2-fluorophenyl.

A further group of especially preferred compounds of formula I comprises those wherein Y is 2-fluoro-4-ethoxycarbonylphenyl.

A further group of especially preferred compounds of formula I comprises those wherein Y is 2-fluoro-4-methoxycarbonylphenyl.

A further group of especially preferred compounds of formula I comprises those wherein Y is 2-fluoro-6-trifluoromethylphenyl.

A further group of especially preferred compounds of formula I comprises those wherein Y is 2-methoxyphenyl.

A further group of especially preferred compounds of formula I comprises those wherein Y is 2-methylsulfonyloxyphenyl.

A further group of especially preferred compounds of formula I comprises those wherein Y is 2-tolyl.

A further group of especially preferred compounds of formula I comprises those wherein Y is 3-tolyl.

A further group of especially preferred compounds of formula I comprises those wherein Y is 2-trifluoromethoxyphenyl.

A further group of especially preferred compounds of formula I comprises those wherein Y is 2-trifluoromethylphenyl.

A further group of especially preferred compounds of formula I comprises those wherein Y is 2-trifluoromethylsulfinylphenyl.

A further group of especially preferred compounds of formula I comprises those wherein Y is 2-trifluoromethylthiophenyl.

A group of preferred compounds of formula I comprises those wherein Y is pyrazolyl which is optionally substituted by one to three substituents independently selected from chloro, 2,2-difluoroethoxy, difluoromethoxy, ethoxy, methoxy, methyl, oxetan-3-yloxy, iso-propylsulfonyl, 2,2,2-trifluoroethoxy or trifluoromethyl.

A group of especially preferred compounds of formula I comprises those wherein
Y is pyrazol-3-yl, most preferably 1-methyl-4-trifluoromethyl-pyrazol-3-yl.

A group of especially preferred compounds of formula I comprises those wherein
Y is pyrazol-4-yl.

A further group of especially preferred compounds of formula I comprises those wherein Y is 5-chloro-1-methyl-3-trifluoromethyl-pyrazol-4-yl. A further group of especially preferred compounds of formula I comprises those wherein Y is 3-difluoromethoxy-1-methyl-5-trifluoromethyl-pyrazol-4-yl.

A further group of especially preferred compounds of formula I comprises those wherein Y is 5-difluoromethoxy-1-methyl-3-trifluoromethyl-pyrazol-4-yl.

A further group of especially preferred compounds of formula I comprises those wherein Y is 1,3-dimethyl-5-(2,2,2-trifluoroethoxy)-pyrazol-4-yl.

A further group of especially preferred compounds of formula I comprises those wherein Y is 5-ethoxy-1-methyl-3-trifluoromethyl-pyrazol-4-yl.

A group of especially preferred compounds of formula I comprises those wherein Y is pyrazol-5-yl.

A group of especially preferred compounds of formula I comprises those wherein Y is 1-methyl-5-(2,2-difluoroethoxy)-3-trifluoromethyl-pyrazol-4-yl.

A group of especially preferred compounds of formula I comprises those wherein Y is 1-methyl-5-methoxy-3-trifluoromethyl-pyrazol-4-yl.

A group of especially preferred compounds of formula I comprises those wherein Y is 1-methyl-5-(oxetan-3-yloxy)-3-trifluoromethyl-pyrazol-4-yl.

A group of especially preferred compounds of formula I comprises those wherein Y is 1-methyl-5-iso-propylsulfonyl-3-trifluoromethyl-pyrazol-4-yl.

A group of especially preferred compounds of formula I comprises those wherein Y is 1-methyl-5-(2,2,2-trifluoroethoxy)-3-trifluoromethyl-pyrazol-4-yl.

A group of especially preferred compounds of formula I comprises those wherein Y is 1-methyl-3-trifluoromethyl-pyrazol-4-yl.

A group of preferred compounds of formula I comprises those wherein Y is imidazolyl which is optionally substituted by one to three substituents independently selected from methyl.

A group of especially preferred compounds of formula I comprises those wherein Y is imidazol-2-yl, most preferably 1-methylimidazol-2-yl.

A group of preferred compounds of formula I comprises those wherein Y is isoxazolyl which is optionally substituted by one or two substituents independently selected from bromo, cyclopropyl, methoxy or methyl.

A group of especially preferred compounds of formula I comprises those wherein Y is isoxazol-3-yl, most preferably 5-methylisoxazol-3-yl.

A group of especially preferred compounds of formula I comprises those wherein Y is isoxazol-4-yl, most preferably 3,5-dimethylisoxazol-4-yl, 3-cyclopropyl-5-methylisoxazol-4-yl or 5-cyclopropyl-3-methylisoxazol-4-yl.

A group of especially preferred compounds of formula I comprises those wherein Y is isoxazol-5-yl, most preferably 3-methoxyisoxazol-5-yl or 3-bromo-4-methylisoxazol-5-yl.

A group of preferred compounds of formula I comprises those wherein Y is isothiazolyl which is optionally substituted by one or two substituents independently selected from cyano or methyl.

A group of especially preferred compounds of formula I comprises those wherein Y is isothiazol-4-yl, most preferably 5-cyano-3-methylisothiazol-4-yl.

A group of preferred compounds of formula I comprises those wherein Y is thiazolyl which is optionally substituted by one or two substituents independently selected from ethoxy, ethyl, methoxymethyl and trifluoromethyl.

A group of especially preferred compounds of formula I comprises those wherein Y is thiazol-5-yl, most preferably 4-ethoxy-2-trifluoromethylthiazol-5-yl or 2-ethyl-4-methoxymethylthiazol-5-yl.

A group of preferred compounds of formula I comprises those wherein Y is pyridyl which is optionally substituted by one to three substituents independently selected from chloro, methyl, or trifluoromethyl.

A group of especially preferred compounds of formula I comprises those wherein Y is pyrid-3-yl, most preferably 2-chloropyrid-3-yl or 2-methyl-6-trifluoromethyl-pyrid-3-yl.

A group of preferred compounds of formula I comprises those wherein Y is 4H-benzo-1,3-dioxinyl which is optionally substituted by one or two fluorine atoms.

A group of especially preferred compounds of formula I comprises those wherein Y is 4H-benzo-1,3-dioxin-8-yl, most preferably 6-fluoro-4H-benzo-1,3-dioxin-8-yl.

A group of preferred compounds of formula I comprises those wherein Y is benzo-1,3-dioxolyl which is optionally substituted by one or two fluorine atoms.

A group of especially preferred compounds of formula I comprises those wherein Y is benzo-1,3-dioxol-5-yl, most preferably 2,2-difluoro-benzo-1,3-dioxol-5-yl.

A further group of especially preferred compounds of formula I comprises those wherein Y is phenyl, naphthyl, tetrahydronaphthyl, 1,3-dioxalanyl, tetrahydrofuranyl, morpholinyl, furyl, thienyl, pyrrolyl, pyrazolyl, imidazolyl, 1,2,3-triazolyl, 1,2,4-triazolyl, oxazolyl, thiazolyl, isoxazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, tetrazolyl, tetrazinyl, 4H-benzo-1,3-dioxinyl, benzo-1,3-dioxolyl, benzofuryl, benzisofuryl, benzothienyl, benzisothienyl, indolyl, benzimidazolyl, 2,1,3-benzoxadiazolyl, quinolyl, isoquinolyl, cinnolinyl, phthalazinyl, quinazolinyl, quinoxalinyl, naphthyridinyl, benzotriazinyl, purinyl, pteridinyl or indolizinyl, which rings may be substituted by fluorine, chlorine, bromine, iodine, trifluoromethyl, cyclopropyl, methyl, methylthio, methylsulfinyl, methylsulfonyl, trifluoromethylthio, trifluoromethylsulfinyl, trifluoromethylsulfonyl, methoxy, ethoxy, trifluoromethoxy, difluoromethoxy, cyano, nitro, methoxycarbonyl, —CONH$_2$ or by carboxyl.

A further group of especially preferred compounds of formula I comprises those wherein Y is phenyl, naphthyl, tetrahydronaphthyl, 1,3-dioxalanyl, tetrahydrofuranyl, morpholinyl, furyl, thienyl, pyrrolyl, pyrazolyl, imidazolyl, 1,2,3-triazolyl, 1,2,4-triazolyl, oxazolyl, isoxazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, tetrazolyl, tetrazinyl, benzofuryl, benzisofuryl, benzothienyl, benzisothienyl, indolyl, benzimidazolyl, 2,1,3-benzoxadiazolyl, quinolyl, isoquinolyl, cinnolinyl, phthalazinyl, quinazolinyl, quinoxalinyl, naphthyridinyl, benzotriazinyl, purinyl, pteridinyl or indolizinyl, which rings may be substituted by fluorine, chlorine, bromine, iodine, trifluoromethyl, cyclopropyl, methyl, methylthio, methylsulfinyl, methylsulfonyl, trifluoromethylthio, trifluoromethylsulfinyl, trifluoromethylsulfonyl, methoxy, ethoxy, trifluoromethoxy, difluoromethoxy, cyano, nitro, methoxycarbonyl, —CONH$_2$ or by carboxyl.

A further group of very especially preferred compounds of formula I comprises those wherein Y is phenyl, pyrimidin-5-yl, pyridin-3-yl, thiazol-2-yl, thiazol-5-yl, isothiazol-4-yl, isoxazol-3-yl, isoxazol-4-yl, isoxazol-5-yl, imidazol-2-yl, pyrazol-4-yl, pyrazol-5-yl, thiophen-3-yl, 4H-benzo-1,3-dioxin-8-yl or benzo-1,3-dioxol-5-yl, where all of these heterocycles can be further substituted, preferably by the substituents shown in Tables 1 to 26.

A further group of very especially preferred compounds of formula I comprises those wherein Y is phenyl, pyrimidin-5-yl, pyridin-3-yl, isothiazol-4-yl, isoxazol-4-yl, pyrazol-4-yl, pyrazol-5-yl or thiophen-3-yl, where all of these heterocycles can be further substituted, preferably by the substituents shown in Tables 1 to 26.

The compounds of formula I wherein $R^1$, $R^2$, $R^3$, $R^4$, $R^5$, $R^6$ and Y are as defined above, m is 2, and n is 1, can be prepared by processes known per se, by reacting e.g. the compounds of formula Ia

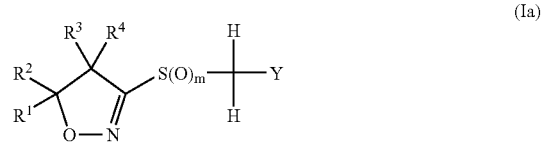
(Ia)

wherein $R^1$, $R^2$, $R^3$, $R^4$ and Y are as defined above, and m is 2,
a) in a single step or stepwise in succession with compounds of the formula $R^5$—X and/or $R^6$—X, wherein $R^5$ and $R^6$ are as defined above and X is a suitable leaving group such as e.g. halogen, such as bromide, a carboxylate, such as acetate, an alkyl- or aryl-sulfonate, such as p-toluene-sulfonate, an imide, such as succinimide, a sulfonimide, such as bis(phenylsulfonyl)imide, or a haloalkylsulfonate, such as trifluoromethylsulfonate, in the presence of a base, optionally in the presence of a diluent, preferably an inert solvent, and optionally in the presence of a complexing agent in a temperature range of from −120° C. to 100° C., preferably from −80° C. to 50° C. Such processes are known in the literature and are described, for example, in J. Med. Chem., 2003 (46) 3021-

3032; J. Org. Chem., 2003 (68) 1443-1446; J. Org. Chem., 2002 (67) 5216-5225 and J. Org. Chem., 2002 (67) 3065-3071.

The compounds of formula Ia, wherein $R^1$, $R^2$, $R^3$, $R^4$ and Y are as defined above, and m is 2, can also be reacted b) with compounds of formula

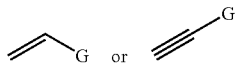

wherein G is an electron-withdrawing group, such as cyano, nitro, $P(O)(O\text{—}C_1\text{-}C_6\text{alkyl})_2$, $CON(C_1\text{-}C_6\text{alkyl})_2$, $CONH(C_1\text{-}C_6\text{alkyl})$, $C_1\text{-}C_6\text{alkoxycarbonyl}$, $C_1\text{-}C_4\text{alkylsulfonyl}$ or $C_1\text{-}C_4\text{alkylcarbonyl}$, optionally in the presence of a base, optionally in the presence of a diluent and optionally in the presence of a complexing agent in a temperature range of from −120° C. to 100° C., preferably from −80° C. to 50° C. Such processes are known in the literature and are described, for example, in J. Org. Chem., 2002 (67) 5216-5225 and Heterocycles, 2002 (57) 2267-2278.

The compounds of formula Ia, wherein $R^1$, $R^2$, $R^3$, $R^4$ and Y are as defined above, and m is 2, can also be reacted c) with compounds of formula

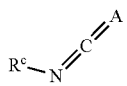

wherein A may be O or S and $R^C$ is $C_1\text{-}C_6\text{alkyl}$, $C_1\text{-}C_6\text{haloalkyl}$, phenyl (unsubstituted or substituted on the phenyl ring by $C_1\text{-}C_6\text{haloalkyl}$, nitro, cyano, halogen), benzyl (unsubstituted or substituted by $C_1\text{-}C_6\text{haloalkyl}$, nitro, cyano, halogen), tri-$C_1\text{-}C_4\text{alkylsilyl}$, $C_1\text{-}C_6\text{alkylcarbonyl}$, $C_1\text{-}C_6\text{haloalkylcarbonyl}$, benzylcarbonyl (unsubstituted or substituted by $C_1\text{-}C_6\text{haloalkyl}$, nitro, cyano, halogen), phenylcarbonyl (unsubstituted or substituted by $C_1\text{-}C_6\text{haloalkyl}$, nitro, cyano, halogen), $C_1\text{-}C_6\text{alkylsulfonyl}$, $C_1\text{-}C_6\text{haloalkylsulfonyl}$, $C_1\text{-}C_6\text{benzylsulfonyl}$ (unsubstituted or substituted by $C_1\text{-}C_6\text{haloalkyl}$, nitro, cyano, halogen), $C_1\text{-}C_6\text{phenylsulfonyl}$ (unsubstituted or substituted by $C_1\text{-}C_6\text{haloalkyl}$, nitro, cyano, halogen), optionally in the presence of a base, optionally in the presence of a diluent and optionally in the presence of a complexing agent in a temperature range of from −120° C. to 100° C., preferably from −80° C. to 50° C. Such processes are known in the literature and are described, for example, in Eur. J. Org. Chem., 2000 (16) 2851-2860; J. Org. Chem., 1996 (61) 5004-5012 and Tetrahedron, 1995 (51) 2763-2776.

The compounds of formula Ia, wherein $R^1$, $R^2$, $R^3$, $R^4$ and Y are as defined above, and m is 2, can also be reacted d) with compounds of formula

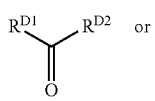  i)

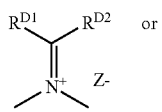  ii)

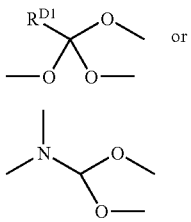

wherein $R^{D1}$ and $R^{D2}$ are hydrogen or $C_1\text{-}C_6\text{alkyl}$ and Z is a suitable counter-ion, e.g. halogen, optionally in the presence of a base, optionally in the presence of a diluent, optionally in the presence of a complexing agent and optionally in the presence of a Lewis acid in a temperature range of from −120° C. to 100° C., preferably from −80° C. to 50° C. Some of those processes are known in the literature and are described, for example, in J. Org. Chem., 2002 (67) 5216-5225; Chem. Europ. J., 1999 (5) 1355-1363; J. Amer. Chem. Soc., 1974 (96) 2275-2276 and Synthesis, 1984 (12) 1045-1047. Reagent ii) can be generated in situ from N,N,N',N'-tetramethyldiaminomethane in the presence of acetic anhydride as described in Tetrahedron Lett., 2004 (45) 3345-3348.

The compounds of formula Ia, wherein $R^1$, $R^2$, $R^3$, $R^4$ and Y are as defined above, and m is 2, can also be reacted e) with compounds of formula

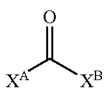

in which $X^A$ and $X^B$ are each independently of the other a suitable leaving group, such as Cl, $OCCl_3$ or 1-imidazolyl, and compounds of formula $HNR^7R^8$, wherein $R^7$ and $R^8$ are as defined above, in the presence of a base, optionally in the presence of a diluent and optionally in the presence of a complexing agent in a temperature range of from −120° C. to 100° C., preferably from −80° C. to 50° C.

As diluents in the said processes there may be used inert solvents such as e.g. hydrocarbons, ethers, such as THF or 1,2-dimethoxyethane, N,N-dimethylformamide or halogenated hydrocarbons, such as dichloromethane, or optionally mixtures thereof. The base can be, for example, an alkyl-lithium compound, such as methyl-lithium, n-butyl-lithium and tert-butyl-lithium, a lithium dialkylamide, such as lithium diisopropylamide, a metal hydride, preferably an alkali metal hydride, such as sodium hydride, or an alkali metal amide, such as sodium amide, a metal bis(tri($C_1$-$C_6$alkyl)silyl)amide, such as lithium bis(trimethylsilyl)amide, a metal alkoxide, such as potassium tert-butoxide, or a phosphazene base, such as N'-tert-butyl-N,N,N',N',N'',N''-hexamethylphosphorimidic triamide ($P_1$-$^t$Bu), 1-ethyl-2,2,4,4,4-pentakis(dimethylamino)-2-lambda$^5$-5,4-lambda$^5$-5-catenadi(phosphazene) ($P_2$-Et), 1-tert-butyl-2,2,4,4,4-pentakis(dimethylamino)-2-lambda$^5$-5,4-lambda$^5$-5-catenadi(phosphazene) ($P_2$-$^t$Bu), 2-tert-butylimino-2-diethylamino-1,3-dimethyl-perhydro-1,3,2-diazaphosphorine (BEMP) or 2,8,9-triisobutyl-2,5,8,9-tetraaza-1-phosphabicyclo[3.3.3]undecane (Verkade's base). The complexing agent can be, for example, 1,3-dimethyl-3,4,5,6-tetrahydro-2(1H)-pyrimidinone (DMPU), hexamethylphosphoramide (HMPA) and tetramethylethylenediamine (TMEDA). The Lewis acid can be, for example, $SnCl_4$, $AlCl_3$ and $ZnCl_2$.

Process steps a), b), c) and e) can be carried out independently, repeatedly or in combination with each other.

Compounds of formula Ia are known e.g. from WO 01/012613, WO 02/062770, WO 03/000686, WO 04/010165 and WO 04/013106.

In particular, process a) is useful for the preparation of a compound of formula I wherein $R^1$, $R^2$, $R^3$, $R^4$ and Y are as defined above, $R^5$ is halogen, $R^6$ is hydrogen or halogen, m is 2, and n is 1, by halogenation of a compound of formula Ia (see above), wherein $R^1$, $R^2$, $R^3$, $R^4$ and Y are defined as above, and m is 2, in a single step or stepwise in succession with compounds of formula $R^5$—X and/or $R^6$—X, wherein $R^5$ and/or $R^6$ are halogen, e.g. fluorine, chlorine, bromine and iodine, and X is a suitable leaving group as described above. Preferred reagents are N-fluorobenzenesulfonimide (NFSI) or 1-(chloromethyl)-4-fluoro-1,4-diazoniabicyclo[2.2.2]octane bis(tetrafluoroborate) (SELECTFLUOR) for the fluorination, N-chlorosuccinimide (NCS) or hexachloroethane for the chlorination, N-bromosuccinimide (NBS) or phenyl trimethylamino tribromide (PTT) for the bromination, and N-iodosuccinimide (NIS) for the iodination. The halogenations are conveniently carried out in an inert solvent, preferably an ether, e.g. THF, and in the presence of a base, preferably phosphazene bases, e.g. 1-tert-butyl-2,2,4,4,4-pentakis(dimethylamino)-2-lambda$^5$-5,4-lambda$^5$-5-catenadi(phosphazene) ($P_2$-$^t$Bu) or 1-ethyl-2,2,4,4,4-pentakis(dimethylamino)-2-lambda$^5$-5,4 lambda$^5$-5-catenadi(phosphazene) ($P_2$-Et), or 2,8,9-triisobutyl-2,5,8,9-tetraaza-1-phosphabicyclo[3.3.3]undecane (Verkade's base), in a temperature range from 0° C. to 50° C., preferably from 0° C. to 30° C. Alternatively, the halogenations are carried out in the presence of alkoxide bases, e.g. potassium tert-butoxide, in the presence of a diluent, preferably an ether, e.g. THF, in a temperature range from –100° C. to 50° C., preferably from –80° C. to 0° C. Alternatively, the halogenations are carried out in the presence of an alkyl-lithium compound, e.g. n-butyl lithium, in the presence of a complexing agent, e.g. 1,3-dimethyl-3,4,5,6-tetrahydro-2(1H)-pyrimidinone (DMPU), in the presence of a diluent, preferably an ether, e.g. THF, in a temperature range from –100° C. to 50° C., preferably from –80° C. to 0° C. Alternatively, the halogenations are carried out in the presence of a metal bis(tri($C_1$-$C_6$alkyl)silyl)amide, e.g. sodium bis(trimethylsilyl)amide, in the presence of a diluent, preferably an ether, e.g. THF, in a temperature range from –100° C. to 50° C., preferably from –80° C. to 0° C.

Furthermore, process a) is useful for the preparation of a compound of formula I wherein $R^1$, $R^2$, $R^3$, $R^4$, $R^5$ and Y are as defined above, $R^6$ is $C_1$-$C_{10}$alkyl or halogen, m is 2, and n is 1, by reaction of a compound of formula Ib,

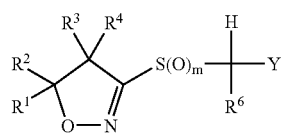

(Ib)

wherein $R^1$, $R^2$, $R^3$, $R^4$ and Y are defined as above, m is 2, and $R^6$ is $C_1$-$C_{10}$alkyl, e.g. methyl, or halogen, e.g. chlorine or fluorine, with a compound of formula $R^5$—X, wherein $R^5$ is as defined above, and X is a suitable leaving group as described above, in the presence of a base, optionally in the presence of a diluent, preferably an inert solvent, and optionally in the presence of a complexing agent in a temperature range of from –120° C. to 100° C., preferably from –80° C. to 50° C.

In particular, process a) is useful for the preparation of a compound of formula I wherein $R^1$, $R^2$, $R^3$, $R^4$ and Y are as defined above, $R^5$ is halogen, $R^6$ is $C_1$-$C_{10}$alkyl or halogen, m is 2, and n is 1, by halogenation of a compound of formula Ib,

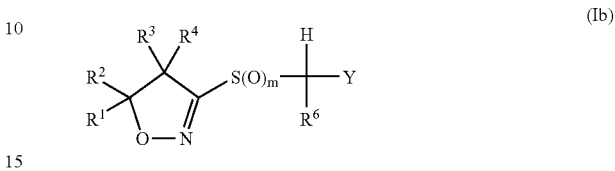

(Ib)

wherein $R^1$, $R^2$, $R^3$, $R^4$ and Y are defined as above, m is 2, and $R^6$ is $C_1$-$C_{10}$alkyl, e.g. methyl, or halogen, e.g. chlorine or fluorine, with a compound of formula $R^5$—X, wherein $R^5$ is halogen, e.g. fluorine, chlorine, bromine and iodine, and X is a suitable leaving group as described above. Preferred reagents are N-fluorobenzenesulfonimide (NFSI) or 1-(chloromethyl)-4-fluoro-1,4-diazoniabicyclo[2.2.2]octane bis(tetrafluoroborate) (SELECTFLUOR) for the fluorination, N-chlorosuccinimide (NCS) or hexachloroethane for the chlorination, N-bromosuccinimide (NBS) or phenyl trimethylamino tribromide (PTT) for the bromination and N-iodosuccinimide (NIS) for the iodination. The halogenations are conveniently carried out in an inert solvent, preferably an ether, e.g. THF, and in the presence of a base, preferably phosphazene bases, e.g. 1-tert-butyl-2,2,4,4,4-pentakis(dimethylamino)-2-lambda$^5$-5,4-lambda$^5$-5-catenadi(phosphazene) ($P_2$-$^t$Bu) or 1-ethyl-2,2,4,4,4-pentakis(dimethylamino)-2-lambda$^5$-5,4-lambda$^5$-5-catenadi(phosphazene) ($P_2$-Et), or 2,8,9-triisobutyl-2,5,8,9-tetraaza-1-phosphabicyclo[3.3.3]undecane (Verkade's base), in a temperature range from 0° C. to 50° C., preferably from 0° C. to 30° C. Alternatively, the halogenations are carried out in the presence of alkoxide bases, e.g. potassium tert-butoxide, in the presence of a diluent, preferably an ether, e.g. THF, in a temperature range from –100° C. to 50° C., preferably from –80° C. to 0° C. Alternatively, the halogenations are carried out in the presence of an alkyl-lithium compound, e.g. n-butyl lithium, in the presence of a complexing agent, e.g. 1,3-dimethyl-3,4,5,6-tetrahydro-2(1H)-pyrimidinone (DMPU), in the presence of a diluent, preferably an ether, e.g. THF, in a temperature range from –100° C. to 50° C., preferably from –80° C. to 0° C. Alternatively, the halogenations are carried out in the presence of a metal bis(tri($C_1$-$C_6$alkyl)silyl)amide, e.g. sodium bis(trimethylsilyl)amide, in the presence of a diluent, preferably an ether, e.g. THF, in a temperature range from –100° C. to 50° C., preferably from –80° C. to 0° C.

The compounds of formula I wherein $R^1$, $R^2$, $R^3$, $R^4$, $R^5$ and Y are as defined above, $R^6$ is hydrogen, m is 2, and n is 1, can, furthermore, be prepared starting from compounds of formula II

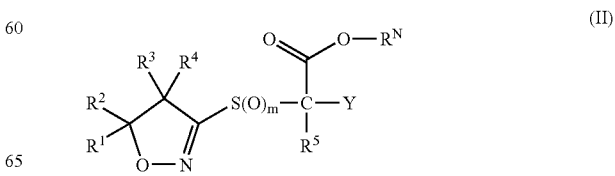

(II)

wherein $R^1$, $R^2$, $R^3$, $R^4$, $R^5$ and Y are as defined above, $R^N$ is $C_1$-$C_6$alkyl or allyl, and m is 2, by decarboxylating those compounds. Such reactions are known in the literature and can be carried out optionally in the presence of a base, e.g. an alkali metal hydroxide, such as NaOH or LiOH (J. Org. Chem., 1998 (63) 220-221), optionally in the presence of a mineral acid or organic acid such as e.g. HCl, $H_2SO_4$ or acetic acid (Synthesis, 1997 (6) 691-695), or optionally under neutral conditions (Tetrahedron 1995 (51) 8573-8584; J. Chem. Soc. Perkin Trans. 1, 1985, 1541-1546). As diluents there are usually used ethers, such as THF or dioxane, alcohols, such as methanol or ethanol, DMSO or water, or mixtures thereof, and the reaction is usually carried out in a temperature range of from −20° C. to 200° C., preferably from 25° C. to 160° C.

The compounds of formula II wherein $R^1$, $R^2$, $R^3$, $R^4$, $R^5$ and Y are as defined above, $R^N$ is $C_1$-$C_6$alkyl or allyl, and m is 2, can be prepared, for example, starting from compounds of formula II wherein $R^1$, $R^2$, $R^3$, $R^4$ and Y are as defined above, $R^5$ is hydrogen, $R^N$ is $C_1$-$C_6$alkyl or allyl, and m is 2, by processes described under a) to c), or e), as the case may be.

The compounds of formula II wherein $R^1$, $R^2$, $R^3$, $R^4$ and Y are as defined above, $R^5$ is hydrogen, $R^N$ is $C_1$-$C_6$alkyl or allyl, and m is 2, can be prepared, for example, starting from compounds of formula Ia (see above) wherein $R^1$, $R_2$, $R^3$, $R^4$ and Y are as defined above, and m is 2, by processes described under a) using the reagent $R^N$—$O_2CX^A$ wherein $R^N$ is $C_1$-$C_6$alkyl or allyl and $X^A$ is a suitable leaving group as described above.

Alternatively, compounds of formula II wherein $R^1$, $R^2$, $R^3$, $R^4$ and Y are as defined above, $R^5$ is hydrogen, $R^N$ is $C_1$-$C_6$alkyl or allyl, and m is 2, are obtainable from compounds of formula III

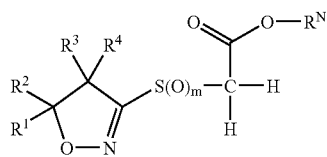

(III)

wherein $R^1$, $R^2$, $R^3$ and $R^4$ are as defined above, $R^N$ is $C_1$-$C_6$alkyl or allyl, and m is 2, by reacting with compounds of formula Y—$X^C$ wherein Y is an activated, electron-poor aromatic or heteroaromatic group and $X^C$ is a suitable leaving group such as e.g. halogen, nitro, alkyl- or aryl-sulfonate, such as methylsulfonate or phenylsulfonate, haloalkylsulfonate, such as trifluoromethylsulfonate, optionally in the presence of a base, e.g. a lithium dialkylamide, such as lithium diisopropylamide, a metal hydride, preferably an alkali metal hydride, such as sodium hydride, a metal bis(tri($C_1$-$C_6$alkyl)silyl)amide, such as lithium bis(trimethylsilyl) amide, a metal alkoxide, such as potassium tert-butoxide, or phosphazene base, such as N'-tert-butyl-N,N,N',N',N'',N''-hexamethylphosphorimidic triamide ($P_1$-$^t$Bu), 1-ethyl-2,2,4,4-pentakis(dimethylamino)-2-lambda$^5$-5,4-lambda$^5$-5-catenadi(phosphazene) ($P_2$-Et), 1-tert-butyl-2,2,4,4,4-pentakis(dimethylamino)-2-lambda$^5$-5,4-lambda$^5$-5-catenadi(phosphazene) ($P_2$-$^t$Bu), 2-tert-butylimino-2-diethylamino-1,3-dimethyl-perhydro-1,3,2-diazaphosphorine (BEMP) or 2,8,9-triisobutyl-2,5,8,9-tetraaza-1-phosphabicyclo[3.3.3]undecane (Verkade's base), optionally in the presence of a diluent such as e.g. THF, DMF or dioxane in a temperature range of from −120° C. to 150° C., preferably from −20° C. to 120° C. Such processes are known in the literature and are described e.g. in Synthesis 1997 (6) 691-695 and Chem. Heterocycl. Compd. (Engl. Trans) 1984 (20) 676-680.

Compounds of formula III wherein $R^1$, $R^2$, $R^3$ and $R^4$ are as defined above, $R^N$ is $C_1$-$C_6$alkyl or allyl, and m is 1 or 2, can be obtained, e.g. by oxidation of compounds of formula III wherein $R^1$, $R^2$, $R^3$ and $R^4$ are as defined above, $R^N$ is $C_1$-$C_6$alkyl or allyl, and m is 0, by reaction with suitable organic or inorganic oxidising agents, e.g. a peroxy acid, such as 3-chloroperoxybenzoic acid, peracetic acid, hydrogen peroxide, an alkoxyperoxide or a periodate, such as sodium periodate, optionally in the presence of a diluent, such as a halogenated hydrocarbon, e.g. dichloromethane, 1,2-dichloroethane, an alcohol, e.g. methanol, N,N-dimethylformamide, water or acetic acid or a mixture thereof. The reactions are usually carried out in a temperature range of from −80° C. to 120° C., preferably from −20° C. to 50° C. Such processes are known in the literature and are described e.g. in J. Org. Chem., 2003 (68) 3849-3859; J. Med. Chem., 2003 (46) 3021-3032; J. Org. Chem., 2003 (68) 500-511 and Bioorg. Med. Chem., 1999 (9) 1837-1844. One equivalent of oxidizing agent is required to convert a sulfide, were m is 0, to the corresponding sulfoxide, where m is 1, or to convert a sulfoxide, where m is 1, to the corresponding sulfone, where m is 2. Two equivalents of oxidizing agent are required to convert a sulfide, where m is 0, to the corresponding sulfone, where m is 2.

Compounds of formula III wherein the substituents $R^1$, $R^2$, $R^3$ and $R^4$ are as defined above, $R^N$ is $C_1$-$C_6$alkyl or allyl, and m is 0, can be prepared, for example, starting from compounds of formula IV

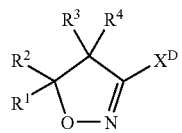

(IV)

wherein $R^1$, $R^2$, $R^3$ and $R^4$ are as defined above and $X^D$ is a suitable leaving group such as halogen, e.g. chloride, an alkyl- or aryl-sulfonyl group, e.g. methylsulfonyl or phenylsulfonyl, a haloalkylsulfonyl group, e.g. trifluoromethylsulfonyl, or nitro, by reaction with compounds of formula V

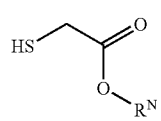

(V)

wherein $R^N$ is $C_1$-$C_6$alkyl or allyl, optionally in the presence of a base, an alkali metal hydride, e.g. sodium hydride, an alkali metal carbonate, such as potassium or sodium carbonate, a basic amine, e.g. triethylamine or pyridine, optionally in the presence of a diluent, e.g. DMF, acetone or an ether, such as THF, in a temperature range of from −20° C. to 120° C., preferably from −0° C. to 80° C.

Compounds of formula IV are known e.g. from WO 01/12613, WO 02/062770 and WO 03/000686; compounds of formula V are commercially available.

The compounds of formula VI are examples of compounds of formula I wherein $R^5$ and $R^6$ together with the carbon atom to which they are bonded form a cyclopropyl ring which is optionally substituted by one to four substituents independently selected from $C_1$-$C_6$alkyl, $C_1$-$C_6$alkoxycarbonyl, $C_1$-$C_6$alkylcarbonyl, nitro or phenylcarbonyl, m is 2, and n is 1. The compounds of formula VI

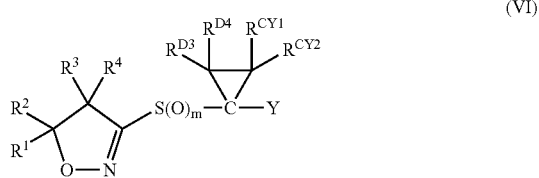
(VI)

wherein $R^1$, $R^2$, $R^3$, $R^4$ and Y are as defined above, m is 2, $R^{D3}$ and $R^{D4}$ are hydrogen or $C_1$-$C_6$alkyl, and $R^{CY1}$ and $R^{CY2}$ are hydrogen, halogen, $C_1$-$C_6$alkoxycarbonyl, $C_1$-$C_6$alkylcarbonyl, phenylcarbonyl or nitro, can be prepared by processes known per se, starting from compounds of formula VII

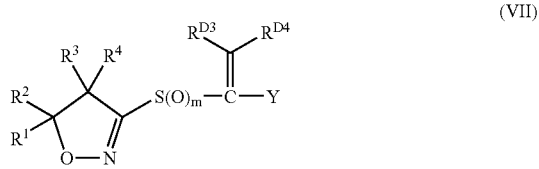
(VII)

wherein $R^1$, $R^2$, $R^3$, $R^4$ and Y are as defined above, m is 2, and $R^{D3}$ and $R^{D4}$ are hydrogen or $C_1$-$C_6$alkyl, which can in turn be prepared as described under process d), for example, by reaction with a tri($C_1$-$C_6$alkyl)sulfonium halide, such as trimethylsulfonium iodide, or a tri($C_1$-$C_6$)alkylsulfoxonium halide, such as trimethylsulfoxonium iodide, in the presence of a base, e.g. an alkali metal hydride, such as NaH or an alkali metal hydroxide, such as NaOH, KOH, in the presence of a diluent, such as DMSO, DMF, water, dichloromethane or a mixture thereof, usually in a temperature range of from 0° C. to 50° C. (Indian. J. Chem. Sect. B; 1982 (21) 1092-1094; J. Chem. Soc., Perkin Trans. 1, 1997 (20) 3035-3042), or by reaction with diazomethane, in the presence of a diluent, e.g. an ether, such as diethyl ether, usually in a temperature range of from –25° C. to 0° C. (Heterocycles, 1995 (40) 191-204) or by reaction with a compound of formula,

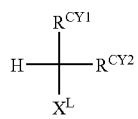

wherein $R^{CY1}$ and $R^{CY2}$ are halogen, $C_1$-$C_6$alkoxycarbonyl, $C_1$-$C_6$alkylcarbonyl, phenylcarbonyl or nitro, $R^{CY1}$ can additionally be hydrogen, and XL is a suitable leaving group, such as halogen, in the presence of a base, such as an alkali metal hydroxide, e.g. NaOH, or an alkyl-lithium compound, e.g. n-butyl-lithium, or a lithium dialkylamide, such as lithium diisopropylamide, or a metal hydride, preferably an alkali metal hydride, such as sodium hydride, or a metal bis(tri($C_1$-$C_6$alkyl)silyl)amide, such as lithium bis(trimethylsilyl) amide, or a alkali metal carbonate, such as potassium carbonate, in the presence of a diluent, e.g. tetrahydrofuran (THF), acetonitrile, water or a halogenated hydrocarbon, such as chloroform, or a mixture. of these solvents, for example water and chloroform, optionally in the presence of a phase transfer catalyst, e.g. triethylbenzylammonium chloride, usually in a temperature range of from –80° C. to 20° C. (Indian. J. Chem. Sect. B; 1997 (36) 608-611; Synth. Commun., 1986 (16) 1255-1259, Tetrahedron, 2001 (57) 9423-9427).

The compounds of formula I wherein $R^1$, $R^2$, $R^3$, $R^4$, $R^5$ and Y are as defined above, $R^6$ is hydrogen, m is 2, and n is 1, can also be prepared by processes known per se, by reacting e.g. the compound of formula VII (see above) wherein $R^1$, $R^2$, $R^3$, $R^4$ and Y are as defined above, $R^{D3}$ and $R^{D4}$ are hydrogen or $C_1$-$C_6$alkyl, m is 1 or 2, as a Michael acceptor with nucleophiles of the formula $R^{D5}$-M or $R^{D5}$—H, wherein $R^{D5}$-M is a suitable salt or an organometal compound in which M is e.g. Li, MgBr, Na, K or tetraalkylammonium and $R^{D5}$ is a nucleophile, such as $C_1$-$C_6$alkyl, $C_1$-$C_6$alkoxy, $C_1$-$C_6$alkylthio, $C_1$-$C_6$alkylsulfinyl, $C_1$-$C_6$alkylsulfonyl, cyano, nitro-$C_1$-$C_6$-alkyl-, imidazolyl, triazolyl, indazolyl, or pyrazolyl. The compounds $R^{D5}$-M can either be preformed or generated in situ. The reactions can also be carried out by using $R^{D5}$—H wherein $R^{D5}$ is, for example, imidazolyl, triazolyl, indazolyl, or pyrazolyl under neutral conditions. As solvents can be used ethers such as THF, halogenated solvent, such as dichloromethane, alcohols such as methanol, acetonitrile or acetone in a temperature range of from –120° C. to 100° C., preferably from –80° C. to 50° C. Such processes are known in the literature and are described, for example, in Tetrahedron Letters (2002), 43(17), 3175-3179; Tetrahedron Letters (1992), 33(1), 131-4; Journal of Organic Chemistry (1991), 56(13), 4098-112; Tetrahedron (1989), 45(18), 5805-5814.

The compounds of formula I wherein $R^1$, $R^2$, $R^3$, $R^4$, $R^5$, $R^6$, Y and n are as defined above, and m is 1 or 2, can, furthermore, be prepared by processes known per se by starting from compounds of formula I wherein $R^1$, $R^2$, $R^3$, $R^4$, $R^5$, $R^6$, Y and n are as defined above, and m is 0 or 1, respectively, and reacting those compounds with suitable organic or inorganic oxidising agents, e.g. a peroxy acid, such as 3-chloroperoxybenzoic acid, peracetic acid, hydrogen peroxide, an alkoxyperoxide or a periodate, such as sodium periodate, optionally in the presence of a diluent, such as a halogenated hydrocarbon, e.g. dichloromethane, 1,2-dichloroethane, an alcohol, e.g. methanol, N,N-dimethylformamide, water or acetic acid or a mixture thereof. The reactions are usually carried out in a temperature range of from –80° C. to 150° C., preferably from –20° C. to 120° C. Such processes are known in the literature and are described e.g. in J. Org. Chem., 2003 (68) 3849-3859; J. Med. Chem., 2003 (46) 3021-3032; J. Org. Chem., 2003 (68) 500-511; Bioorg. Med. Chem., 1999 (9) 1837-1844. One equivalent of oxidizing agent is required to convert a sulfide, were m is 0, to the corresponding sulfoxide, where m is 1, or to convert a sulfoxide, where m is 1, to the corresponding sulfone, where m is 2. Two equivalents of oxidizing agent are required to convert a sulfide, where m is 0, to the corresponding sulfone, where m is 2.

The compounds of formula I wherein $R^1$, $R^2$, $R^3$, $R^4$, $R^5$, $R^6$ and Y are as defined above, m is 0, and n is 1, can be prepared, for example, by starting from compounds of formula I, wherein $R^1$, $R^2$, $R^3$, $R^4$ and Y are as defined above, $R^5$, $R^6$ are hydrogen, m is 0, and n is 1', or compounds of formula I, wherein $R^1$, $R^2$, $R^3$, $R^4$, $R^5$ and Y are as defined above, $R^6$ is hydrogen, m is 0, and n is 1,

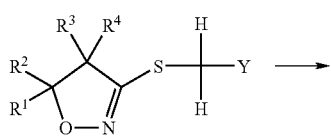

(I) wherein m = 0, n = 1,
and $R^5 = R^6 = H$

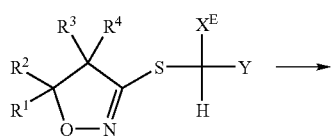

(I) wherein m = 0, n = 1,
and $R^5 = X^E$, and $R^6 = H$

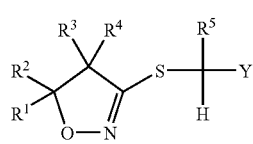

(I) wherein m = 0, n = 1,
and $R^6 = H$

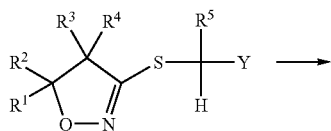

(I) wherein m = 0, n = 1,
and $R^6 = H$

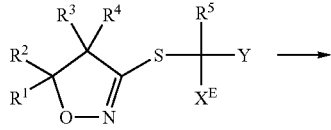

(I) wherein m = 0, n = 1,
and $R^6 = X^E$

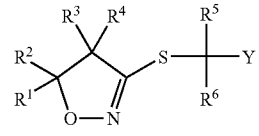

(I) wherein m = 0, n = 1 by reacting those compounds with a halogenating agent, e.g. bromine or an N-halosuccinimide, such as N-chlorosuccinimide or N-bromosuccinimide, to form compounds of formula I wherein $R^1$, $R^2$, $R^3$, $R^4$ and Y are as defined above, $R^5$ is $X^E$, and $X^E$ in turn is halogen, $R^6$ is hydrogen, m is 0, and n is 1, or compounds of formula I wherein $R^1$, $R^2$, $R^3$, $R^4$, $R^5$ and Y are as defined above, $R^6$ is $X^E$, and $X^E$ in turn is halogen, m is 0, and n is 1, respectively, optionally in the presence of a diluent, e.g. acetic acid or a halogenated hydrocarbon, such as $CCl_4$ or dichloromethane, in a temperature range of from −80° C. to 120° C., preferably from −20° C. to 60° C.

The compounds of formula I wherein $R^1$, $R^2$, $R^3$, $R^4$ and Y are as defined above, $R^5$ is $X^E$, and $X^E$ in turn is halogen, $R^6$ is hydrogen, m is 0, and n is 1, or the compounds of formula I wherein $R^1$, $R^2$, $R^3$, $R^4$, $R^5$ and Y are as defined above, $R^6$ is $X^E$, and $X^E$ in turn is halogen, m is 0, and n is 1, can then be oxidised directly as described above, or optionally in a second or third step reacted with compounds of formula $M\text{-}R^5$ and/or $M\text{-}R^6$, wherein $R^5$ and $R^6$ are as defined and $M\text{-}R^5$ and $M\text{-}R^6$ is a suitable salt or an organometal compound in which M is e.g. Li, MgBr, Na, K or tetraalkylammonium, optionally in the presence of a Lewis acid, e.g. $SnCl_4$, optionally in the presence of a complexing agent, e.g. hexamethylphosphoramide (HMPA) or 1,3-dimethyl-3,4,5,6-tetrahydro-2(1H)-pyrimidinone (DMPU), and optionally in the presence of a diluent, e.g. acetonitrile, dichloromethane, ether or THF, in a temperature range of from −120° C. to 100° C., preferably from −80° C. to 80° C. Such processes are known in the literature and are described, for example, in J. Org. Chem., 1998 (63) 3706-3716; J. Chem. Soc. Perkin Trans., 1995 (22) 2845-2848; Synthesis 1982 (2), 131-132; Liebigs Annalen, 1993, 49-54 and Synth. Commun., 1990 (20) 1943-1948.

Compounds of formula I wherein $R^1$, $R^2$, $R^3$, $R^1$, $R^6$ and Y are as defined above, $R^5$ is chlorine, bromine or iodine, m is 1 or 2, and n is 1, can be prepared by reaction of a compound of formula Ic

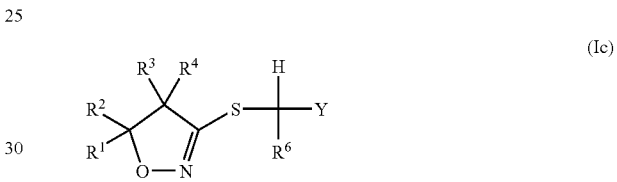

(Ic)

wherein $R^1$, $R^2$, $R^3$, $R^4$, $R^6$ and Y are as defined above, in an inert solvent first with an N-halosuccinimide and then with one of the above-mentioned oxidising agents.

Alternatively, compounds of formula I wherein $R^1$, $R^2$, $R^3$, $R^4$, $R^5$, $R^6$ and Y are as defined above, m is 0, and n is 1, can be prepared by reacting a compound of formula VIII wherein $R^5$, $R^6$ and Y are defined as above, and $X^F$ is a leaving group such as halogen e.g. bromide or chloride, or alkylsulfonate, e.g. methylsulfonate, or arylsulfonate, e.g. tosylate, with thiourea, optionally in the presence of a diluent e.g. an alcohol, e.g. ethanol, optionally in the presence of an alkali iodide, e.g. sodium iodide, potassium iodide, in a temperature range of from −30° C. to 100° C., preferably from 0° C. to 80° C., to give an isothiourea intermediate of formula XI, which is reacted with a compound of formula IV

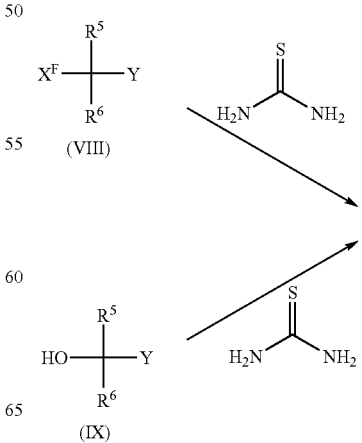

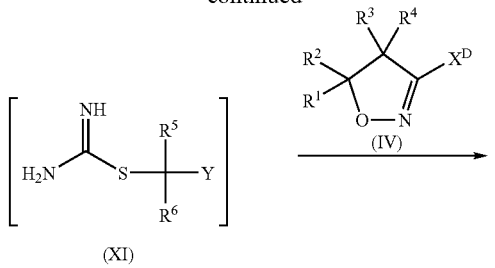

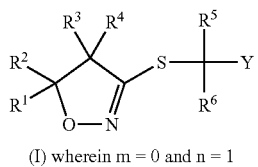

(I) wherein m = 0 and n = 1 wherein $R^1$, $R^2$, $R^3$ and $R^4$ are defined as above, and XD is a suitable leaving group such as halogen, e.g. chloride, an alkyl- or aryl-sulfonyl group, e.g. methylsulfonyl or phenylsulfonyl, a haloalkylsulfonyl group, e.g. trifluoromethylsulfonyl, or nitro, in the presence of a base, such as a carbonate, e.g. potassium carbonate, sodium carbonate or potassium bicarbonate, or a hydroxide, e.g. potassium hydroxide, or an alkoxide, e.g. sodium alkoxide, optionally in the presence of a diluent, such as an alcohol, e.g. ethanol, an ether, e.g. 1,4-dioxane, THF, a polar solvent, e.g. water, DMF, or a mixture of solvents, e.g. a mixture of 1,4-dioxane and water, in a temperature range of from 20° C. to 200° C., preferably from 50° C. to 150° C., optionally in the presence of an inert gas e.g. nitrogen, and optionally under microwave irradiation. Such processes are known in the literature and are described, for example, in WO 04/0131106.

A further method of preparing intermediates of formula XI, wherein $R^5$, $R^6$ and Y are as defined above, is to react a compound of the formula IX, wherein $R^5$, $R^6$ and Y are defined as above, with thiourea in the presence of an acid, for example a mineral acid such as hydrochloric acid or hydrobromic acid, or sulfuric acid, or an organic acid such as trifluoroacetic acid, and optionally in the presence of a diluent, such as an ether, e.g. 1,4-dioxane, THF, a polar solvent, e.g. water, DMF, or a mixture of solvents, e.g. a mixture of 1,4-dioxane and water, in a temperature range of from 20° C. to 270° C., preferably from 20° C. to 150° C., optionally under microwave irradiation. Such processes are known in the literature and are described, for example, in Buchwald and Neilsen, JACS, 110(10), 3171-3175 (1988); Frank and Smith, JACS, 68, 2103-2104 (1946); Vetter, Syn. Comm., 28, 3219-3233 (1998).

A further method of preparing compounds of formula I wherein $R^1$, $R^2$, $R^3$, $R^4$, $R^5$, $R^6$ and Y are as defined above, m is 0, and n is 1, is to react compound of the formula XII wherein $R^5$, $R^6$ and Y are as defined above,

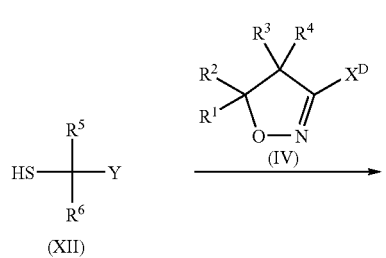

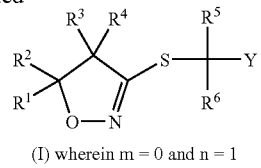

(I) wherein m = 0 and n = 1 with a compound of formula IV wherein $R^1$, $R^2$, $R^3$ and $R^4$ are defined as above, and XD is a suitable leaving group such as halogen, e.g. chloride, an alkyl- or aryl-sulfonyl group, e.g. methylsulfonyl or phenylsulfonyl, a haloalkylsulfonyl group, e.g. trifluoromethylsulfonyl, or nitro, in the presence of a base, e.g. potassium carbonate, optionally in the presence of a diluent e.g. DMF in a temperature range of from 0° C. to 100° C., preferably from 20° C. to 50° C. and optionally under an inert atmosphere, e.g. nitrogen. Such processes are known in the literature and are described, for example in WO 01/012613, WO 02/062770 and WO 04/010165.

In the particular case that $R^5$ is $C_1$-$C_6$haloalkyl, in particular perfluoroalkyl, for example trifluoromethyl, compounds of the formula I wherein $R^1$, $R^2$, $R^3$, $R^4$ and Y are as defined above, $R^6$ is hydrogen, $C_1$-$C_6$alkyl or $C_1$-$C_6$haloalkyl, m is 0, and n is 1, can be conveniently prepared by reacting carbonyl compounds of the formula XIII

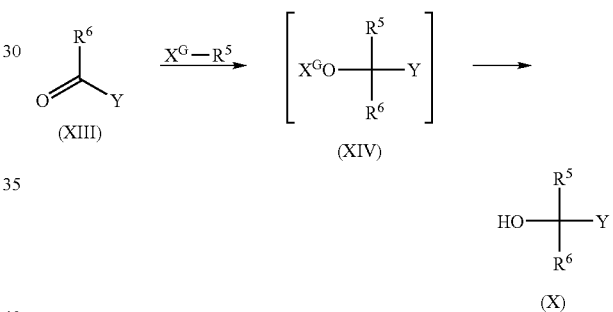

wherein Y is as defined above, and $R^6$ is hydrogen, $C_1$-$C_6$alkyl or $C_1$-$C_6$haloalkyl, with a reagent $R^5$—$X^G$, wherein $X^G$ is a trialkylsilyl group, e.g. trimethylsilyl, in the presence of an initiator, such as a fluoride salt, e.g. caesium fluoride, tetrabutylammonium fluoride, potassium fluoride, or an alkoxide salt, and an optional diluent, such as an ether, e.g. THF, 1,4-dioxane, in a temperature range of from 0° C. to 100° C., preferably from 20° C. to 30° C., to form the silylated intermediate of the formula XIV. Typically the silylated intermediate of formula XIV is desilylated without isolation or purification in the presence of an acid, e.g. hydrochloric acid, hydrobromic acid, or acetic acid, and optionally in the presence of an additional diluent, such as an ether, e.g. THF, 1,4-dioxane, a polar solvent, e.g. water, DMF, or a mixture of solvents, in a temperature range of from 0° C. to 100° C., preferably from 20° C. to 30° C., to form the alcohol of formula X. Such processes are known in the literature and are described, for example, in Chem. Rev., 1997, 97, 757-786; J. Am. Chem. Soc. 1989, 111, 393; J. Med. Chem. 1992, 35, 641; J. Org. Chem. 1992, 57, 1124.

The alcohols obtained in such fashion can be derivatised as described in e.g. WO 01/012613 and WO 02/062770, e.g. first by replacing the alcohol with a more suitable leaving group, such as a halogen, for example bromide, or alkylsulfonate, for example methylsulfonate, or arylsulfonate, for example tosylate, and then by reacting with compounds of the formula IV (see above) wherein $R^1$, $R^2$, $R^3$ and $R^4$ are as defined above and XD is a suitable leaving group e.g. halogen, such as chloride, an alkylsulfonyl group, such as methylsulfonyl, or an aryl-sulfonyl group, such as phenylsulfonyl, in the presence of a base, e.g. potassium carbonate, sodium hydrosulfide hydrate or Rongalit salt (hydroxy methanesulfinic acid sodium salt and hydrate), optionally in the presence of a diluent, e.g. DMF, in a temperature range of from −20° C. to 150° C., preferably from 0° C. to 40° C., optionally in the presence of an inert gas, for example nitrogen. Such processes are known in the literature and are described, for example, in WO 01/012613, WO 02/062770 and WO 04/010165.

Additionally, compounds of formula IX wherein $R^5$ and $R^6$ are hydrogen can be prepared from compounds of formula XV by reacting with reagent XVI

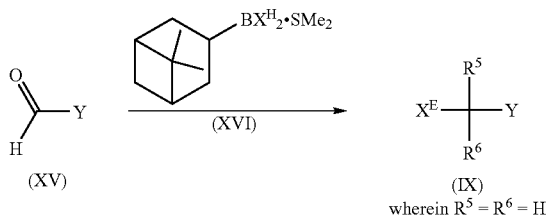

wherein $X^H$ is a halogen atom such as bromine or chlorine in the presence of a diluent such as a halogenated hydrocarbon such as dichloromethane, a hydrocarbon such as hexane, an alcohol such as ethanol, N—N-dimethylformamide, tetrahydrofuran (THF) or a mixture thereof. The preparation of aromatic benzyl halides is described in Tetrahedron Letts. 2000 (41) 5161-5164. The preparation of the reagent XVI is described in J. Org. Chem. 1980 (45) 384-389.

The compounds of formula I according to the invention can be used as herbicides in unmodified form, as obtained in the synthesis, but they are generally formulated into herbicidal compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, micro-emulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilisers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula I and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula I may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula I according to the invention are generally applied at a rate of from 10 to 2000 g/ha, especially from 50 to 1000 g/ha.

Preferred formulations have especially the following compositions (%=percent by weight):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |

| Wettable powders: | |
|---|---|
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

The following Examples further illustrate, but do not limit, the invention.

FORMULATION EXAMPLES FOR HERBICIDES OF FORMULA I

%=% by Weight

| F1. Emulsifiable concentrates | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention relates also to a method for the selective control of grasses and weeds in crops of useful plants, wherein the useful plants or the area of cultivation or locus thereof is treated with the compounds of formula I.

Useful plant crops in which the composition according to the invention can be used include especially maize, soybeans, cotton, cereals, e.g. wheat and barley, rice, sugar cane, sugar beet, sunflowers and rape. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, for example *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate. Crops are also to be understood as being those which are obtained by conventional methods of breeding or genetic engineering and contain so-called output traits (e.g. improved storage stability, higher nutritional value and improved flavour).

Areas under cultivation include land on which the crop plants are already growing and land intended for cultivation with those crop plants.

The compounds of formula I according to the invention can also be used in combination with one or more other herbicides. In particular, the following mixtures of the compound of formula I are important:
compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenzmethyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuronethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester.

The mixing partners of the compound of formula I may also be in the form of esters or salts, as mentioned e.g. in The Pesticide Manual, 12th Edition (BCPC), 2000.

The mixing ratio of the compound of formula I to the mixing partner is preferably from 1:100 to 1000:1.

The mixtures can advantageously be used in the abovementioned formulations (in which case "active ingredient" relates to the respective mixture of compound of formula I with the mixing partner).

Preferred mixtures of a compound of formula I with one or more further herbicides include:

Mixtures of a compound of the formula I with a triazine (e.g. compound of formula I+ametryn, compound of formula I+atrazine, compound of formula I+cyanazine, compound of formula I+dimethametryn, compound of formula I+metribuzin, compound of formula I+prometon, compound of formula I+prometryn, compound of formula I+propazine, compound of formula I+simazine, compound of formula I+simetryn, compound of formula I+terbumeton, compound of formula I+terbuthylazine, compound of formula I+terbutryn, compound of formula I+trietazine). Particularly preferred are mixtures of a compound of formula I with atrazine, metribuzin, prometryn or with terbuthylazine (i.e. compound of formula I+atrazine, compound of formula I+metribuzin, compound of formula I+prometryn, and compound of formula I+terbuthylazine).

Mixtures of a compound of formula I with isoxaflutole (e.g. compound of formula I+isoxaflutole).

Mixtures of a compound of formula I with isoxaflutole and a triazine.

Mixtures of a compound of formula I with isoxaflutole and glyphosate (e.g. compound of formula I+isoxaflutole+glyphosate).

Mixtures of a compound of formula I with isoxaflutole and glufosinate (e.g. compound of formula I+isoxaflutole+glufosinate).

Mixtures of a compound of formula I with mesotrione (e.g. compound of formula I+mesotrione).

Mixtures of a compound of formula I with mesotrione and a triazine.

Mixtures of a compound of formula I with mesotrione and glyphosate (e.g. compound of formula I+mesotrione+glyphosate).

Mixtures of a compound of formula I with mesotrione and glufosinate (e.g. Compound of formula I+mesotrione+glufosinate).

Mixtures of a compound of formula I with sulcotrione (e.g. compound of formula I+sulcotrione).

Mixtures of a compound of formula I with sulcotrione and a triazine.

Mixtures of a compound of formula I with sulcotrione and glyphosate (e.g. compound of formula I+sulcotrione+glyphosate).

Mixtures of a compound of formula I with sulcotrione and glufosinate (e.g. compound of formula I+sulcotrione+glufosinate).

Mixtures of a compound of formula I with a triazolinone (e.g. compound of formula I+amicarbazone).

Mixtures of a compound of formula I with an ALS inhibitor (e.g. compound of formula I+chlorsulfuron, compound of formula I+cinosulfuron, compound of formula I+cloransulam, compound of formula I+ethametsulfuron, compound of formula I+flazasulfuron, compound of formula I+foramsulfuron, compound of formula I+flumetsulam, compound of formula I+imazamethabenz, compound of formula I+imazamox, compound of formula I+imazapic, compound of formula I+imazapyr, compound of formula I+imazethapyr, compound of formula I+iodosulfuron, compound of formula I+metsulfuron, compound of formula I+nicosulfuron, compound of formula I+oxasulfuron, compound of formula I+primisulfuron, compound of formula I+prosulfuron, compound of formula I+pyrithiobac, compound of formula I+rimsulfuron, compound of formula I+sulfosulfuron, compound of formula I+thifensulfuron, compound of formula I+triasulfuron, compound of formula I+tribenuron, compound of formula I+trifloxysulfuron, compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636)). Particularly preferred are mixtures of a compound of formula I with flazasulfuron, foramsulfuron, flumetsulam, imazapyr, imazethapyr, iodosulfuron, nicosulfuron, rimsulfuron, trifloxysulfuron or with 4-[(4,5-dihydro-3-methoxy-4-methyl-5-oxo)-1H-1,2,4-triazol-1-ylcarbonylsulfamoyl]-5-methylthiophene-3-carboxylic acid (BAY636) (i.e. compound of formula I+flazasulfuron, compound of formula I+foramsulfuron, compound of formula I+flumetsulam, compound of formula I+imazapyr, compound of formula I+imazethapyr, compound of formula I+iodosulfuron, compound of formula I+nicosulfuron, compound of formula I+rimsulfuron, compound of formula I+trifloxysulfuron, and compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636)).

Mixtures of a compound of formula I with a PPO inhibitor (e.g. compound of formula I+fomesafen, compound of formula I+flumioxazin, compound of formula I+sulfentrazone, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester). Particularly preferred are mixtures of a compound of formula I with flumioxazin, sulfentrazone or [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (i.e. compound of formula I+flumioxazin, compound of formula I+sulfentrazone, and compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy] acetic acid ethyl ester).

Mixtures of a compound of formula I with glyphosate (i.e. compound of formula I+glyphosate).

Mixtures of a compound of formula I with glufosinate (i.e. compound of formula I+glufosinate).

Mixtures of a compound of formula I with paraquat (i.e. compound of formula I+paraquat).

Mixtures of a compound of formula I with pendimethalin or trifluralin (i.e. compound of formula I+pendimethalin, compound of formula I+trifluralin). Particularly preferred are mixtures of a compound of formula I with pendimethalin (i.e. compound of formula I+pendimethalin).

Mixtures of a compound of formula I with metamitron (i.e. compound of formula I+metamitron).

Mixtures of a compound of formula I with clomazone (i.e. compound of formula I+clomazone).

Mixtures of a compound of formula I with metazachlor (i.e. compound of formula I+metazachlor).

Mixtures of a compound of formula I with clodinafop or with pinoxaden (i.e. compound of formula I+clodinafop, and compound of formula I+pinoxaden).

The compounds of formula I according to the invention can also be used in combination with safeners. Likewise, mixtures of a compound of formula I according to the invention with one or more further herbicides can also be used in combination with one or more safeners. The safeners can be cloquintocet-mexyl (CAS RN 99607-70-2) or a lithium, sodium, potassium, calcium, magnesium, aluminium, iron, ammonium, quaternary ammonium, sulfonium or phosphonium salt thereof such as those disclosed in WO 02/34048, fenchlorazol-ethyl (CAS RN 103112-35-2) and the corresponding acid (CAS RN 103112-36-3), mefenpyr-diethyl (CAS RN 135590-91-9) and the corresponding di-acid (CAS RN 135591-00-3), isoxadifen-ethyl (CAS RN 163520-33-0) and the corresponding acid (CAS RN 209866-92-2), furilazole (CAS RN 121776-33-8) and the corresponding R isomer (CAS RN 121776-57-6), benoxacor (CAS RN 98730-04-2), dichlormid (CAS RN 37764-25-3), MON4660 (CAS RN 71526-07-3), oxabetrinil (CAS RN 74782-23-3), cyometrinil (CAS RN 78370-21-5) and the corresponding (Z) isomer (CAS RN 63278-33-1), fenclorim (CAS RN 3740-92-9), N-cyclopropyl-4-(2-methoxy-benzoylsulfamoyl)-benzamide (CAS RN 221667-31-8), N-isopropyl-4-(2-methoxy-benzoylsulfamoyl)-benzamide (CAS RN 221668-34-4), naphthalic anhydride (CAS RN 81-84-5) and flurazole (CAS RN 72850-64-7).

Preferably the mixing ratio of compound of formula I to safener is from 100:1 to 1:10, especially from 20:1 to 1:1.

The mixtures can advantageously be used in the abovementioned formulations (in which case "active ingredient" relates to the respective mixture of compound of formula I with the safener).

Preferred mixtures of a compound of formula I with further herbicides and safeners include:

Mixtures of a compound of formula I with a triazine and a safener.

Mixtures of a compound of formula I with glyphosate and a safener.

Mixtures of a compound of formula I with glufosinate and a safener.

Mixtures of a compound of formula I with isoxaflutole and a safener.

Mixtures of a compound of formula I with isoxaflutole and a triazine and a safener.

Mixtures of a compound of formula I with isoxaflutole and glyphosate and a safener.

Mixtures of a compound of formula I with isoxaflutole and glufosinate and a safener.

Mixtures of a compound of formula I with mesotrione and a safener.

Mixtures of a compound of formula I with mesotrione and a triazine and a safener.

Mixtures of a compound of formula I with mesotrione and glyphosate and a safener.

Mixtures of a compound of formula I with mesotrione and glufosinate and a safener.

Mixtures of a compound of formula I with sulcotrione and a safener.

Mixtures of a compound of formula I with sulcotrione and a triazine and a safener.

Mixtures of a compound of formula I with sulcotrione and glyphosate and a safener.

Mixtures of a compound of formula I with sulcotrione and glufosinate and a safener.

The following Examples further illustrate, but do not limit, the invention.

PREPARATION EXAMPLES

Example P1

Preparation of 3-[1-(2,6-difluoro-phenyl)-2-(4-fluoro-phenyl)-ethanesulfonyl]-5,5-dimethyl-4,5-dihydroisoxazole

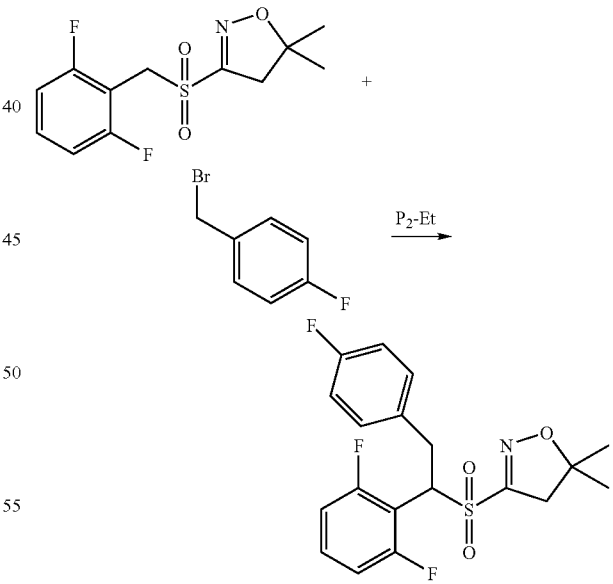

Phosphazene base 1-ethyl-2,2,4,4,4-pentakis(dimethylamino)-2-lambda$^5$-5,4-lambda$^5$-5-catenadi(phosphazene) (P$_2$-Et) (0.61 ml, 1.6 mmol) was added dropwise to a solution of 3-(2,6-difluoro-phenylmethanesulfonyl)-5,5-dimethyl-4,5-dihydroisoxazole (0.3 g, 1.04 mmol) in THF (2 ml) at room temperature. After 10 minutes 4-fluorobenzyl bromide (0.16 ml, 1.3 mmol) was added dropwise at room temperature and the mixture was stirred for 1 hour. The reaction was quenched by addition of aqueous hydrochloric acid (2M). The mixture was diluted with ethyl acetate and the two phases were separated. The organic phase was washed several times with brine, dried over magnesium sulfate and concentrated. The crude product was purified by chromatography on silica gel (eluent: ethyl acetate/hexane) to give the product (Compound No. 1.05 of Table 27) as a white solid (405 mg, 98% yield).

The same method was used with 1-bromo-prop-2-yn-3-yl and 2-bromoethyl methyl ether, as the starting material to give Compound No. 1.02 of Table 27 and Compound No. 1.03 of Table 27, respectively.

Example P2

Preparation of 3-[(2,6-difluoro-phenyl)-iodo-methanesulfonyl]-5,5-dimethyl-4,5-dihydroisoxazole

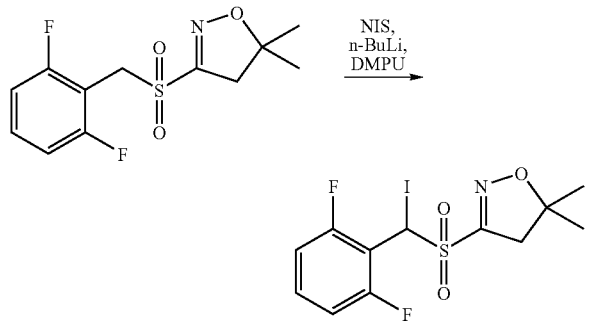

1,3-Dimethyl-3,4,5,6-tetrahydro-2(1H)-pyrimidone (DMPU) (0.10 ml, 0.83 mmol) and 3-(2,6-difluoro-phenyl-methanesulfonyl)-5,5-dimethyl-4,5-dihydro-isoxazole (0.20 g, 0.69 mmol) were dissolved under nitrogen in THF (7 ml) and cooled to −78° C. n-Butyl lithium (2.5M in hexane) (0.33 ml, 0.83 mmol) was added dropwise. After 30 min at −78° C., N-iodosuccinimide (NIS) (187 mg, 0.83 mmol) was added. The mixture was stirred for 1 hour and allowed to warm slowly to room temperature. The reaction was quenched by addition of aqueous ammonium chloride solution. Extraction was carried out several times with ethyl acetate. The combined organic phases were dried over magnesium sulfate and concentrated. The crude product was purified by chromatography on silica gel (eluent: ethyl acetate/hexane) and recrystallised from isopropyl alcohol to give the product (Compound No. 1.25 of Table 27) as a white solid (110 mg, 38% yield).

Example P3

Preparation of 3-[chloro-(2,6-difluoro-phenyl)-methanesulfonyl]-5,5-dimethyl-4,5-dihydroisoxazole

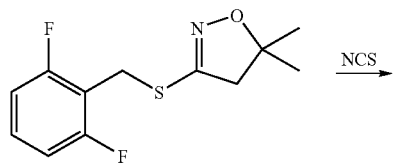

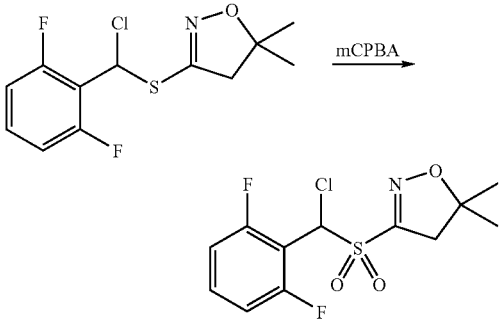

N-Chlorosuccinimide (NCS) (0.39 g, 2.93 mmol) was added to a solution of 3-(2,6-difluoro-phenylmethanesulfanyl)-5,5-dimethyl-4,5-dihydroisoxazole (0.5 g, 1.95 mmol) in dichloromethane (25 ml) at 45° C. and the mixture was stirred for 2.5 hours at 45° C. The solution was cooled to 0° C. and 3-chloroperoxybenzoic acid (mCPBA) (50-60% weight content) (1.68 g, 4.90 mmol) was added in portions. After stirring for 30 minutes at 0° C. and for 12 hours at room temperature, the reaction was quenched by addition of saturated aqueous sodium metabisulfite solution. The organic phase was washed several times with aqueous sodium hydroxide solution (2M), dried over magnesium sulfate and concentrated. Chromatographic purification on silica gel (eluent: ethyl acetate/hexane) gave the product (Compound No. 1.07 of Table 27) (158 mg) and a 1:2 mixture of 3-[chloro-(2,6-difluoro-phenyl)-methanesulfonyl]-5,5-dimethyl-4,5-dihydroisoxazole and 3-[chloro-(2,6-difluoro-phenyl)-methanesulfinyl]-5,5-dimethyl-4,5-dihydroisoxazole (364 mg). The mixture was oxidised again with mCPBA (1.0 g, 0.28 mmol) as described above. Aqueous workup and chromatographic purification on silica gel (eluent: ethyl acetate/hexane) gave more product (Compound No. 1.07 of Table 27) as a white solid (210 mg, i.e. in total 368 mg, 58% yield).

Example P4

Preparation of 4-(2,6-difluoro-phenyl)-4-(5,5-dimethyl-4,5-dihydroisoxazole-3-sulfonyl)-butyric acid ethyl ester

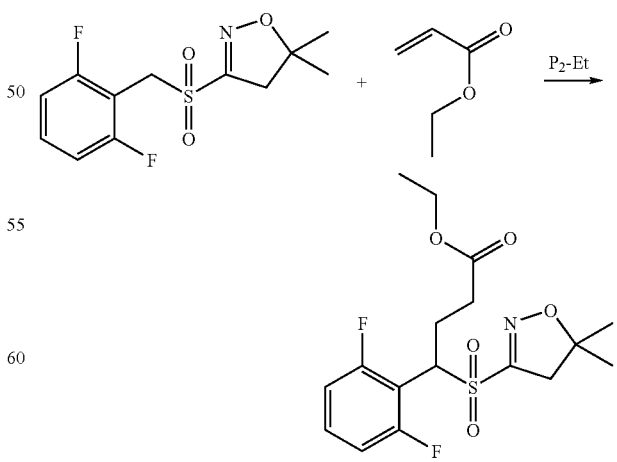

One drop of phosphazene base 1-ethyl-2,2,4,4,4-pentakis(dimethylamino)-2-lambda$^5$-5,4 lambda$^5$-5-catenadi(phosphazene) (P₂-Et) (catalytic amount, 0.1 mmol) was added to 3-(2,6-difluoro-phenylmethanesulfonyl)-5,5-dimethyl-4,5-dihydroisoxazole (300 mg, 1.04 mmol) in THF (8 ml) at −78° C. After 10 minutes ethyl acrylate (130 mg, 1.3 mmol) was added. The mixture was stirred for 3.5 hours at −78° C. and quenched by addition of aqueous hydrochloric acid (2M). Extraction was carried out several times with ethyl acetate and the organic phases were washed with brine, dried over magnesium sulfate and concentrated. The crude product was purified by chromatography on silica gel (eluent: ethyl acetate/hexane) which gave the product (Compound No. 1.08 of Table 27) as a colourless oil (375 mg, 93% yield).

The same method was used with ethyl vinyl ketone, diethyl vinyl phosphonate, N,N-dimethylacrylamide and methyl vinyl sulfone as the starting material to give Compound No. 1.09 of Table 27, Compound No. 1.10 of Table 27, Compound No. 1.11 of Table 27 and Compound No. 1.12 of Table 27, respectively.

Example P5

Preparation of N-cyclopropyl-2-(2,6-difluoro-phenyl)-2-(5,5-dimethyl-4,5-dihydroisoxazole-3-sulfonyl)-acetamide

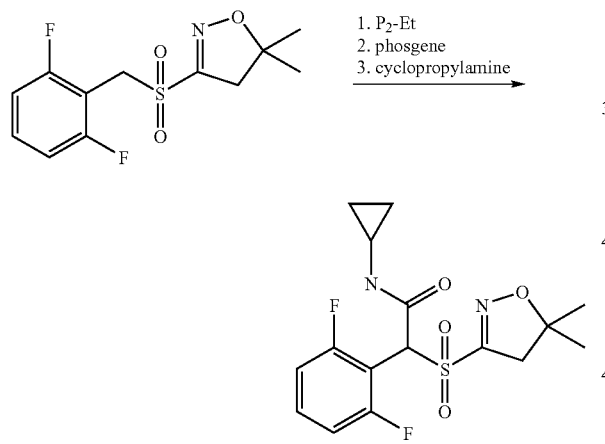

Phosphazene base 1-ethyl-2,2,4,4,4-pentakis(dimethylamino)-2-lambda⁵-5,4-lambda⁵-5-catenadi(phosphazene) (P₂-Et) (0.68 ml, 1.37 mmol) was added at 0° C. to a solution of 3-(2,6-difluoro-phenylmethanesulfonyl)-5,5-dimethyl-4,5-dihydroisoxazole (180 mg, 0.62 mmol) in THF (5 ml). Phosgene (20% by weight in toluene) (0.33 ml, 0.62 mmol) and cyclopropylamine (0.043 ml, 0.69 mmol) were added. The solution was allowed to warm slowly to room temperature and after stirring at room temperature for 2 hours was quenched by addition of aqueous hydrochloric acid (2M). The mixture was extracted with ethyl acetate, dried over magnesium sulfate and concentrated. Purification of the crude product was effected by chromatography on silica gel (eluent: ethyl acetate/hexane) which gave the product (Compound No. 1.35 of Table 27) as a white solid (460 mg, 20% yield).

The same method was used with diethylamine and 2,2-difluoroethylamine as the reagent to give Compound No. 1.36 of Table 27 and Compound No. 1.56 of Table 27, respectively.

Example P6

Preparation of 3-[1-(2,6-difluoro-phenyl)-cyclopropanesulfonyl]-5,5-dimethyl-4,5-dihydroisoxazole

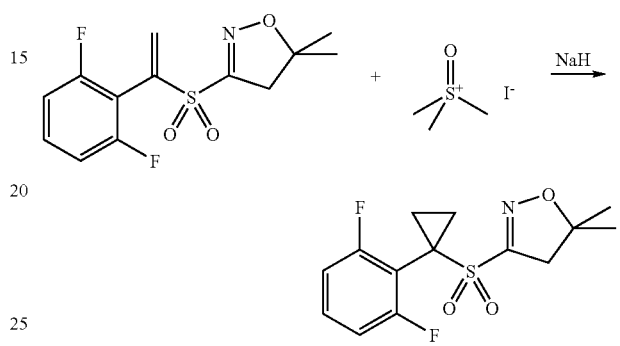

Trimethylsulfoxonium iodide (0.28 g, 1.25 mmol) was added to a suspension of sodium hydride (60% by weight in paraffin oil) (0.052 g, 1.3 mmol) in DMSO (4 ml). The mixture was stirred for 30 minutes at room temperature. A solution of 3-[1-(2,6-difluoro-phenyl)-ethenesulfonyl]-5,5-dimethyl-4,5-dihydroisoxazole (prepared according to Example P12) (80% purity) (0.3 g, 0.8 mmol) in DMSO (2 ml) was added dropwise. The mixture was stirred at room temperature for 1 hour. The reaction was quenched by addition of saturated aqueous ammonium chloride solution and the mixture was extracted several times with diethyl ether. The combined organic phases were dried over magnesium sulfate and concentrated. Purification by chromatography on silica gel (eluent: ethyl acetate/hexane) gave the product (Compound No. 1.01 in Table 27) (70 mg, 28% yield).

Example P7

Preparation of 3-[1-chloro-1-(2,6-difluoro-phenyl)-4,4-difluoro-but-3-ene-1-sulfonyl]-5,5-dimethyl-4,5-dihydroisoxazole

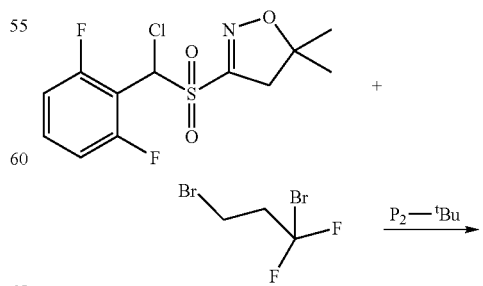

-continued

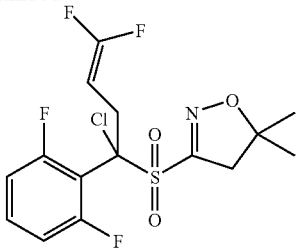

Phosphazene base 1-tert-butyl-2,2,4,4,4-pentakis(dimethylamino)-2-lambda$^5$-5,4-lambda$^5$-5-catenadi(phosphazene) (P$_2$-$^t$Bu) (2M in THF) (0.34 ml, 0.68 mmol) was added dropwise to a solution of 3-[chloro-(2,6-difluoro-phenyl)methanesulfonyl]-5,5-dimethyl-4,5-dihydroisoxazole (prepared according to Example P3) (0.1 g, 0.31 mmol) in THF (5 ml). The solution was stirred for 10 minutes at room temperature. 1,3-Dibromo-1,1-difluoropropane (0.09 ml, 0.37 mmol) was added dropwise and the mixture was stirred for 2 hours. The reaction was quenched by addition of aqueous hydrochloric acid (2M). The mixture was diluted with ethyl acetate and the two phases were separated. The organic phase was washed several times with saturated aqueous sodium chloride solution, dried over magnesium sulfate and concentrated. The crude product was purified by chromatography on silica gel (eluent: ethyl acetate/hexane) to give the product (Compound No. 1.17 of Table 27) as a white solid (58 mg, 47% yield).

The same method was used with 3-(2,6-difluoro-phenyl-methanesulfonyl)-5,5-dimethyl-4,5-dihydroisoxazole as the starting material to give Compound No. 1.04 of Table 27.

Example P8

Preparation of 3-[chloro-m-tolyl-methanesulfonyl]-5,5-dimethyl-4,5-dihydroisoxazole and 3-[dichloro-m-tolyl-methanesulfonyl]-5,5-dimethyl-4,5-dihydroisoxazole

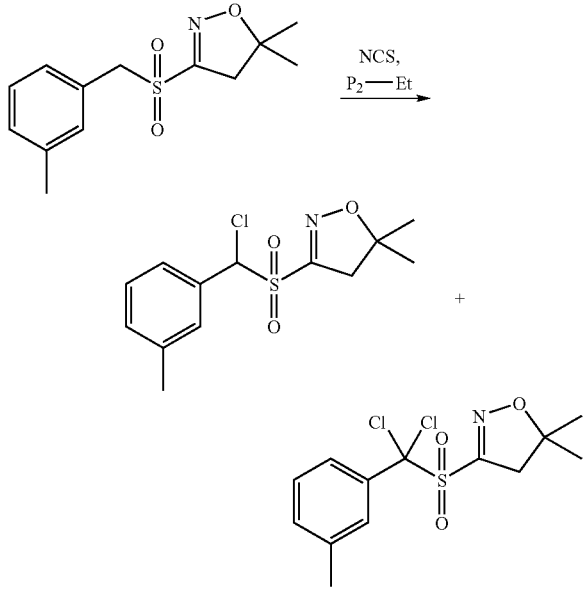

Phosphazene base 1-ethyl-2,2,4,4,4-pentakis(dimethylamino)-2-lambda$^5$-5,4-lambda$^5$-5-catenadi(phosphazene) (P$_2$-Et) (0.34 ml, 0.68 mmol) was added dropwise at 0° C. to a solution of 3-(3-methyl-phenylmethanesulfonyl)-5,5-dimethyl-4,5-dihydroisoxazole (0.2 g, 0.79 mmol) in THF (4 ml). The solution was stirred for 10 minutes at room temperature. N-chlorosuccinimide (NCS) (0.13 g, 0.95 mmol) was added and the mixture was stirred for 2 hours at room temperature. The reaction was quenched by addition of aqueous hydrochloric acid (2M). The mixture was diluted with ethyl acetate and the two phases were separated. The organic phase was washed several times with brine, dried over magnesium sulfate and concentrated. The crude product was purified by chromatography on silica gel (eluent: ethyl acetate/hexane) which gave the mono-chloro product (Compound No. 1.30 of Table 27) as a white solid (76 mg, 32% yield) and the dichloro product (Compound No. 1.31 of Table 27) as a white solid (53 mg, 20% yield).

Example P9

Preparation of 3-[dichloro-(2,6-difluoro-phenyl)-methanesulfonyl]-5,5-dimethyl-4,5-dihydroisoxazole

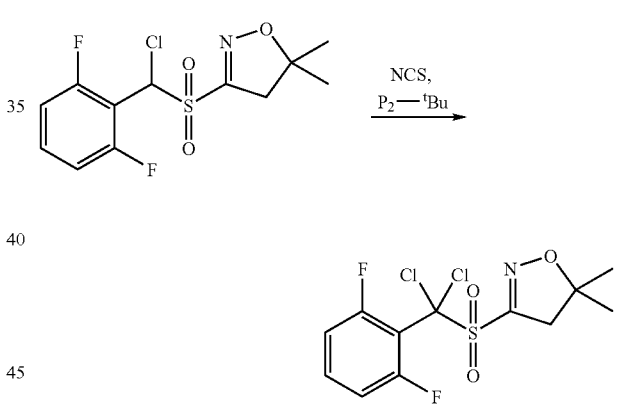

Phosphazene base 1-tert-butyl-2,2,4,4,4-pentakis(dimethylamino)-2 lambda$^5$-5,4-lambda$^5$-5-catenadi(phosphazene) (P$_2$-$^t$Bu) (2M in THF) (0.38 ml, 0.77 mmol) was added dropwise at 0° C. to a solution of 3-[chloro-(2,6-difluoro-phenyl)methanesulfonyl]-5,5-dimethyl-4,5-dihydroisoxazole (prepared according to Example P3) (0.2 g, 0.64 mmol) in THF (5 ml). The solution was stirred for 10 minutes at room temperature. N-chlorosuccinimide (NCS) (0.10 g, 0.77 mmol) was added and the mixture was stirred for 1 hour at room temperature. The reaction was quenched by addition of aqueous hydrochloric acid (2M). The mixture was diluted with ethyl acetate and the two phases were separated. The organic phase was washed several times with brine, dried over magnesium sulfate and concentrated. The crude product was recrystallised from ethanol to give the product (Compound No. 1.26 of Table 27) as a white solid (110 mg, 48% yield).

Example P10

Preparation of 3-[2,2-dichloro-1-(2,6-difluoro-phenyl)-cyclopropanesulfonyl]-5,5-dimethyl-4,5-dihydroisoxazole

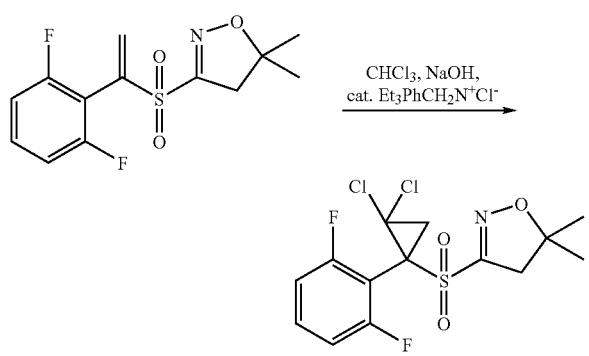

3-[1-(2,6-Difluoro-phenyl)-ethenesulfonyl]-5,5-dimethyl-4,5-dihydroisoxazole (prepared according to Example P12) (purity 80%) (0.2 g, 0.53 mmol) and a catalytic amount of triethylbenzylammonium chloride were dissolved in chloroform (1 ml). A solution of sodium hydroxide (0.64 g, 16 mmol) in water (1 ml) was added dropwise. After stirring for 1.5 hours at room temperature the mixture was diluted with water and extracted several times with chloroform. The combined organic phases were washed with water, dried over magnesium sulfate and concentrated. The crude product was purified by chromatography on silica gel (eluent: ethyl acetate/hexane) to give the product (Compound No. 1.45 of Table 27) as a light brown gum that slowly solidified (74 mg, 36% yield).

Example I1

Preparation of 1-methyl-5-(oxetan-3-yloxy)-3-trifluoromethyl-1H-pyrazole-4-carbaldehyde

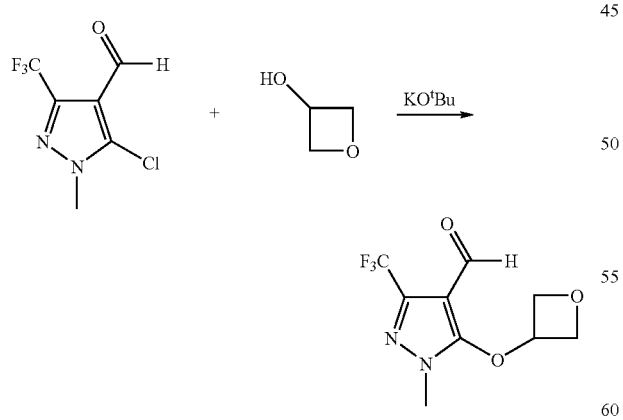

Oxetane-3-ol (6.12 g, 82.7 mmol) was added dropwise to potassium tert-butoxide (1M in THF) (69.6 ml, 69.6 mmol) at room temperature. 5-Chloro-1-methyl-3-trifluoromethyl-1H-pyrazole-4-carbaldehyde (9.86 g, 46.4 mmol) was dissolved in THF (40 ml) and added slowly to the solution. After 25 minutes the mixture was concentrated and the residue partitioned between ethyl acetate and water. The two phases were separated and the aqueous phase was extracted several times with ethyl acetate. The combined organic phases were washed with brine, dried over magnesium sulfate and concentrated to yield the product as brown oil (11.6 g) which was used in the next step without further purification.

Example I2

Preparation of [1-methyl-5-(oxetan-3-yloxy)-3-trifluoromethyl-1H-pyrazol-4-yl]-methanol

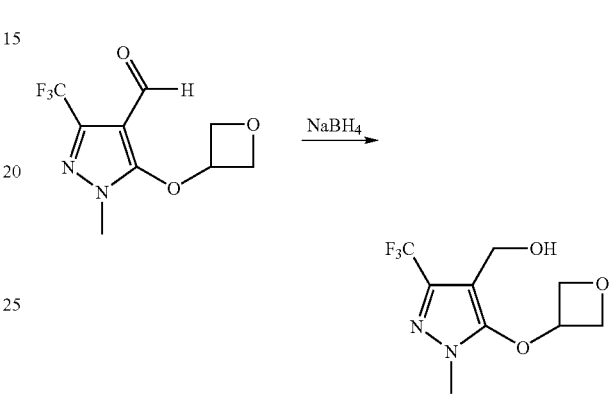

1-Methyl-5-(oxetan-3-yloxy)-3-trifluoromethyl-1H-pyrazole-4-carbaldehyde (11.6 g, 46.4 mmol) was dissolved in methanol (100 ml) and sodium borohydride (0.87 g, 23.0 mmol) was added in portions at 0° C. After stirring at 0° C. for 2 hours the mixture was concentrated and the oil was dissolved in dichloromethane (100 ml). The solution was washed with water and brine, dried over magnesium sulfate and concentrated to give the product as yellow solid (8.14 g) which was used in the next step without further purification.

Example I3

Preparation of 4-bromomethyl-1-methyl-5-(oxetan-3-yloxy)-3-trifluoromethyl-1H-pyrazole

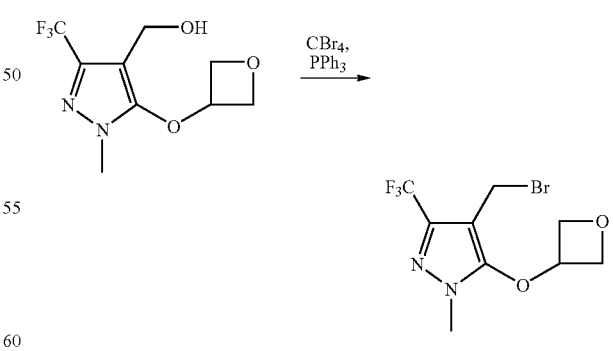

[1-Methyl-5-(oxetan-3-yloxy)-3-trifluoromethyl-1H-pyrazol-4-yl]-methanol (8.14 g, 32.3 mmol) was dissolved in dichloromethane (100 ml) and triphenyl phosphine (8.96 g, 34.2 mmol) and carbon tetrabromide (10.31 g, 31.05 mmol) were added. The solution was stirred for 2 hours and concentrated to give an orange oil. Purification by chromatography on silica gel (eluent: ethyl acetate/hexane) yielded the product as an orange oil (10.1 g) which was used in the next step without further purification.

Example I4

Preparation of 5,5-dimethyl-3-[1-methyl-5-(oxetan-3-yloxy)-3-trifluoromethyl-1H-pyrazol-4-ylmethylsulfanyl]-4,5-dihydroisoxazole

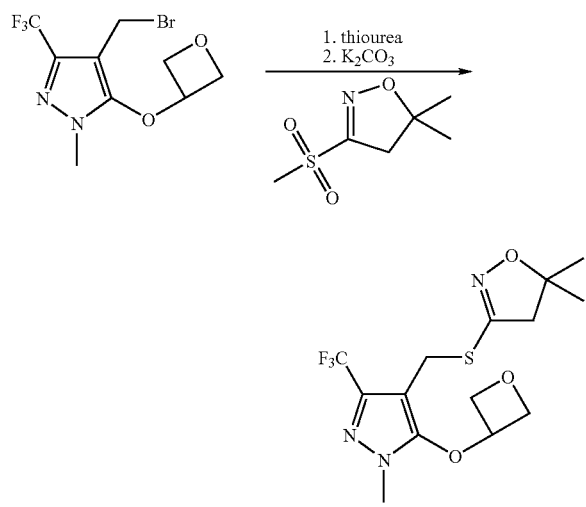

4-Bromomethyl-1-methyl-5-(oxetan-3-yloxy)-3-trifluoromethyl-1H-pyrazole (10.1 g, 32.2 mmol) and thiourea (2.7 g, 35.5 mmol) were stirred in ethanol (100 ml) at room temperature until the solids were dissolved. 3-Methanesulfonyl-5,5-dimethyl-4,5-dihydroisoxazole (6.28 g, 35.5 mmol) and potassium carbonate (4.91 g, 35.5 mmol) were added and the mixture was heated under reflux for 2 hours. The mixture was concentrated and purified by chromatography (eluent: ethyl acetate/hexane) to give the product as a white solid (4 g, 34% yield over two steps).

Example I5

Preparation of 5,5-dimethyl-3-[1-methyl-5-(oxetan-3-yloxy)-3-trifluoromethyl-1H-pyrazol-4-ylmethanesulfonyl]-4,5-dihydroisoxazole

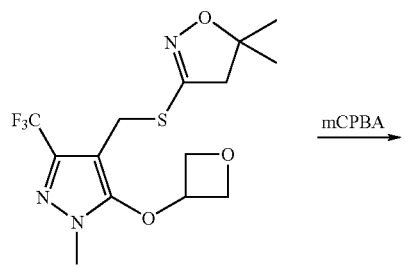

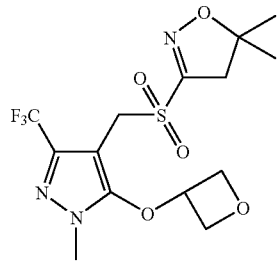

5,5-Dimethyl-3-[1-methyl-5-(oxetan-3-yloxy)-3-trifluoromethyl-1H-pyrazol-4-ylmethylsulfanyl]-4,5-dihydroisoxazole (2.71 g, 7.4 mmol) was dissolved in dichloromethane (100 ml) and 3-chloroperbenzoic acid (mCPBA) (60% by weight) (5.33 g, 18.5 mmol) was added. The solution was stored at room temperature for 18 hours and was quenched by addition of 40% aqueous sodium metabisulfite solution (20 ml). The mixture was diluted with aqueous sodium hydroxide solution (2M), the two phases were separated and the aqueous phase extracted with dichloromethane. The combined organic phases were washed with aqueous sodium hydroxide solution (1M) and brine, dried over magnesium sulfate and concentrated to yield a green oil. Purification by chromatography on silica gel (eluent: ethyl acetate/hexane) gave the product as white solid (2 g, 67% yield).

Example P11

Preparation of 3-{fluoro-[1-methyl-5-(oxetan-3-yloxy)-3-trifluoromethyl-1H-pyrazol-4-yl]-methanesulfonyl}-5,5-dimethyl-4,5-dihydroisoxazole and 3-{difluoro-[1-methyl-5-(oxetan-3-yloxy)-3-trifluoromethyl-1H-pyrazol-4-yl]-methanesulfonyl}-5,5-dimethyl-4,5-dihydroisoxazole

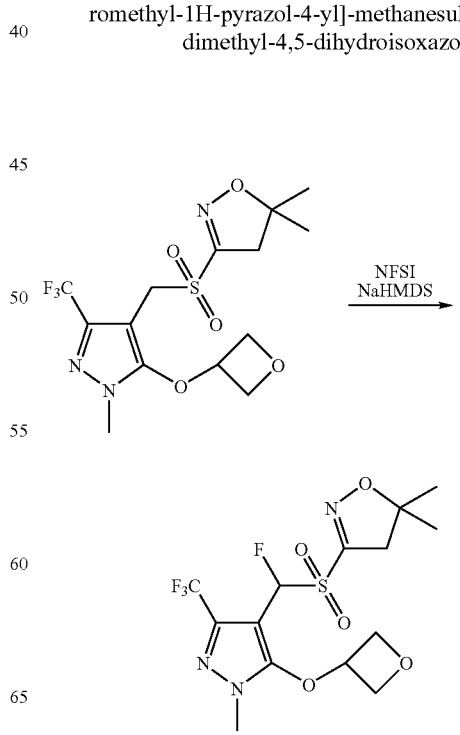

89

-continued

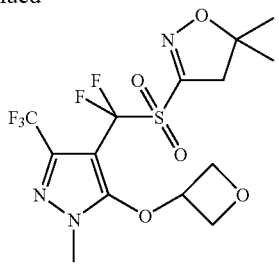

5,5-Dimethyl-3-[1-methyl-5-(oxetan-3-yloxy)-3-trifluoromethyl-1H-pyrazol-4-ylmethanesulfonyl]-4,5-dihydroisoxazole (390 mg, 1 mmol) was stirred in dry THF (8 ml) under nitrogen and sodium hexamethyldisilazide (NaHMDS) (1M in THF) (0.9 ml, 0.9 mmol) was added dropwise at −78° C. After 15 minutes N-fluorobenzenesulfonimide (NFSI) (310 mg, 1 mmol) was added. After 15 minutes more sodium hexamethyl-disilazide (NaHMDS) (1M in THF) (0.9 ml, 0.9 mmol) was added dropwise at −78° C., followed by more N-fluorobenzenesulfonimide (NFSI) (310 mg, 1 mmol). After stirring at −78° C. for 1 hour the reaction was quenched by addition of saturated aqueous ammonium chloride (0.5 ml) and the mixture was allowed to warm to room temperature. Water (2 ml) and dichloromethane (2 ml) were added, the two phases were separated and the aqueous phase was extracted three times with dichloromethane. The combined organic phases were washed with brine, dried over magnesium sulfate and concentrated. The crude product was purified by chromatography on silica gel (eluent: ethyl acetate/hexane) to give the mono-fluoro product (Compound No. 2.27 of Table 28) as a white solid (203 mg, 50% yield) and the di-fluoro product (Compound No. 2.28 of Table 28) as a colourless oil (28 mg, 7% yield).

Example P12

Preparation of 3-[1-(2,6-difluoro-phenyl)-2-methoxy-ethanesulfonyl]-5,5-dimethyl-4,5-dihydroisoxazole

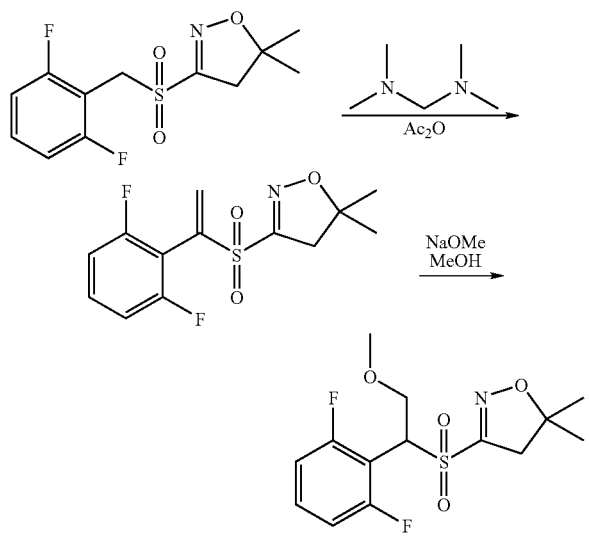

90

3-(2,6-Difluoro-phenylmethanesulfonyl)-5,5-dimethyl-4,5-dihydroisoxazole (1.0 g, 3.46 mmol) and N,N,N',N'-tetramethyldiaminomethane (1 ml, 7.34 mmol) were dissolved in DMF (7 ml) at room temperature and acetic anhydride (0.7 ml, 3.8 mmol) was added at 60° C. After stirring for 3 hours at 80° C. acetic anhydride (0.7 ml, 3.8 mmol) in DMF (2 ml) was added via syringe pump over 2.5 hours. After stirring for 3 hours at 60° C. the mixture was allowed to cool and was stirred for 10 hours at room temperature. The mixture was diluted with ethyl acetate (30 ml), washed with water (3×10 ml), dried over magnesium sulfate and concentrated. The crude product (1.02 g, 88% yield) was used without further purification. 3-[1-(2,6-Difluoro-phenyl)-ethenesulfonyl]-5,5-dimethyl-4,5-dihydroisoxazole (100 mg, 0.3 mmol) was dissolved in methanol (4 ml) under nitrogen and sodium methoxide (0.5M in methanol) (0.7 ml, 0.35 mmol) was added. After 1 hour the mixture was concentrated and the residue was purified by chromatography (eluent: ethyl acetate/hexane) to give the product (Compound No. 1.51 of Table 27) (48 mg, 48% yield).

The same method was used with pyrazole, imidazole, indazole, 4,5-dihydropyrazole and 1,2,4-triazole under neutral conditions (i.e. replacing the sodium methoxide as the starting material) to give Compound No. 1.86 of Table 27, Compound No. 1.87 of Table 27, Compound No. 1.88 of Table 27, Compound No. 1.89 of Table 27 and Compound No. 1.90 of Table 27, respectively.

Example P13

Preparation of 3-[chloro-(2,6-difluoro-phenyl)-fluoro-methanesulfonyl]-5,5-dimethyl-4,5-dihydroisoxazole

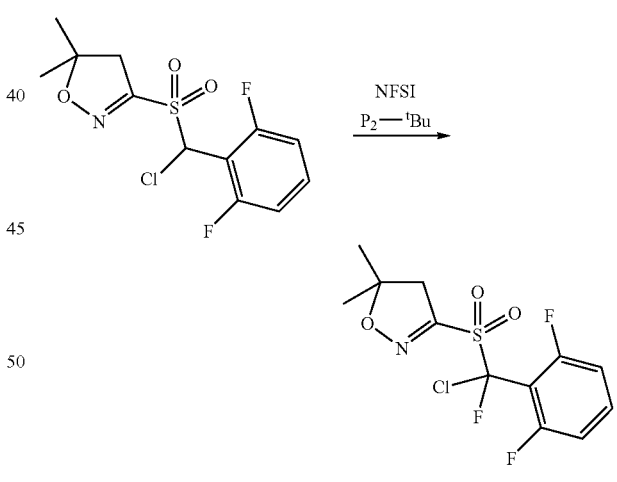

Phosphazene base 1-tert-butyl-2,2,4,4,4-pentakis(dimethylamino)-2-lambda$^5$-5,4-lambda$^5$-5-catenadi(phosphazene) (P$_2$-$^t$Bu) (2M in THF) (0.38 ml, 0.77 mmol) was added dropwise to a solution of 3-[chloro-(2,6-difluoro-phenyl)-methanesulfonyl]-5,5-dimethyl-4,5-dihydroisoxazole (0.2 g, 0.64 mmol) in THF (2 ml), and the solution was stirred for 10 minutes at room temperature. N-Fluorobenzenesulfonimide (NFSI) (0.15 g, 0.77 mmol) was added and the mixture was stirred for 1 hour. The reaction was quenched by addition of aqueous hydrochloric acid (2M). The mixture was diluted with ethyl acetate and the two phases were separated. The organic phase was washed several times with brine, dried over magnesium sulfate and concentrated. The crude product was purified by chromatography on silica gel (eluent: ethyl acetate/hexane) to give the product (Compound No. 1.21 of Table 27) as a white solid (44 mg, 98% yield).

Example P14

Preparation of 3-[fluoro-(2-trifluoromethoxy-phenyl)-methanesulfonyl]-5,5-dimethyl-4,5-dihydroisoxazole

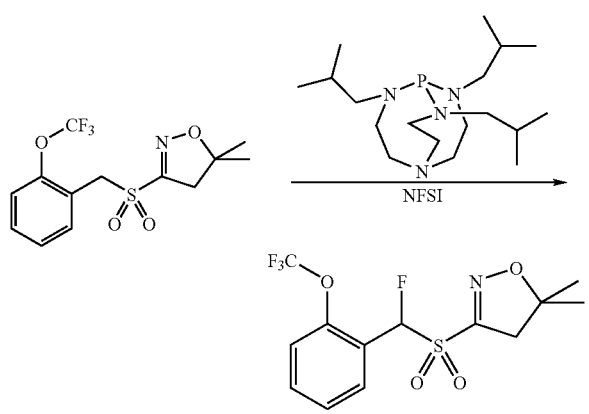

5,5-Dimethyl-3-(2-trifluoromethoxy-phenylmethanesulfonyl)-4,5-dihydroisoxazole (0.2 g, 0.59 mmol) was dissolved in acetonitrile (5 ml) and 2,8,9-triisobutyl-2,5,8,9-tetraaza-1-phosphabicyclo[3.3.3]undecane (Verkade's base) (0.44 ml, 1.24 mmol) was added dropwise at room temperature. After 5 minutes N-fluorobenzene-sulfonimide (NFSI) (393 mg, 1.24 mmol) was added in one portion. After 10 minutes the reaction was quenched by addition of water (10 ml). The mixture was acidified by addition of aqueous hydrochloric acid (2M) and extracted several times with ethyl acetate (3×10 ml). The combined organic phases were washed with saturated aqueous sodium hydrogencarbonate solution and with water, dried over magnesium sulfate and concentrated. The crude product was purified by chromatography on silica gel (eluent: ethyl acetate/hexane) to give the product (Compound No. 1.68 of Table 27) as colourless oil (145 mg, 69% yield).

Example P15

Preparation of 3-[difluoro-(5-methoxy-1-methyl-3-trifluoromethyl-1H-pyrazol-4-yl)-methanesulfonyl]-5,5-dimethyl-4,5-dihydroisoxazole

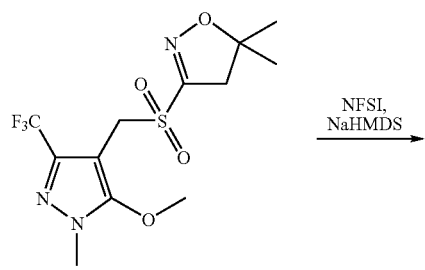

-continued

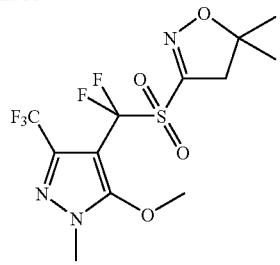

3-(5-Methoxy-1-methyl-3-trifluoromethyl-1H-pyrazol-4-ylmethanesulfonyl)-5,5-dimethyl-4,5-dihydroisoxazole (0.209 mg, 0.59 mmol) was dissolved in dry THF (4 ml) under nitrogen and sodium hexamethyldisilazide (1M in THF) (1.07 ml, 1.07 mmol) was added dropwise at −78° C. After 10 minutes N-fluorobenzenesulfonimide (NFSI) (0.185 mg, 0.59 mmol) was added. After 15 minutes more sodium hexamethyldisilazide (1M in THF) (1.07 ml, 1.07 mmol) was added, followed by more N-fluorobenzenesulfonimide (NFSI) (0.185 mg, 0.59 mmol). After stirring for 1 hour at −78° C. the reaction was quenched by addition of saturated aqueous ammonium chloride solution (0.5 ml) and the mixture was allowed to warm to room temperature. Water (2 ml) and dichloromethane (2 ml) were added, the two phases were separated and the aqueous phase was extracted three times with dichloromethane. The combined organic extracts were washed with aqueous sodium bicarbonate solution and brine, dried over magnesium sulfate and concentrated. The mixture was purified by chromatography on silica gel (eluent: ethyl acetate/hexane) and reverse phase HPLC (eluent: water/acetonitrile) to give the product (Compound No. 2.23 of Table 28) as a colourless oil (55 mg, 24% yield).

Example I6

Preparation of 3-cyclopropyl-5-methyl-isoxazole and 5-cyclopropyl-3-methyl-isoxazole

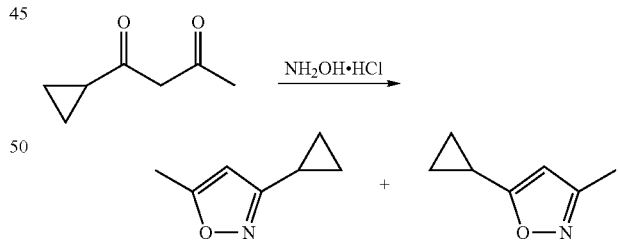

1-Cyclopropyl-butane-1,3-dione (prepared according to DE 440-4059, EP 569760) (3.5 g, 25.4 mmol), hydroxylamine hydrochloride (2.12 g, 30.5 mmol) and ethanol (1 ml) were mixed and the mixture heated in a sealed vessel in the microwave at 130° C. twice for 3 minutes. The mixture was diluted with water (50 ml) and extracted with diethyl ether (3×25 ml). The combined organic phases were dried over magnesium sulfate and concentrated. The brown oil was filtered through a plug of silica gel. The silica gel was washed with diethyl ether and the filtrate was concentrated. The mixture of crude products (5.6 g) was used without further purification.

Example I7

Preparation of 4-bromo-3-cyclopropyl-5-methyl-isoxazole and 4-bromo-5-cyclopropyl-3-methyl-isoxazole

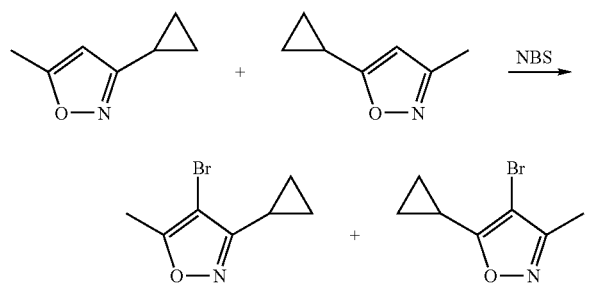

A mixture of 3-cyclopropyl-5-methyl-isoxazole and 5-cyclopropyl-3-methylisoxazole (5.6 g) was dissolved in DMF (20 ml) and N-bromosuccinimide (NBS) (8.66 g, 48.6 mmol) was added. The mixture was stirred at room temperature for 18 hours, diluted with water (50 ml) and extracted with diethyl ether (3×30 ml). The combined organic phases were dried over magnesium sulfate and concentrated. The crude mixture was purified by chromatography on silica gel (eluent: ethyl acetate/hexane) to give the mixture of products as an orange oil (3.0 g) which was used without further purification.

Example I8

Preparation of 3-cyclopropyl-4-formyl-5-methyl-isoxazole and 5-cyclopropyl-4-formyl-3-methyl-isoxazole

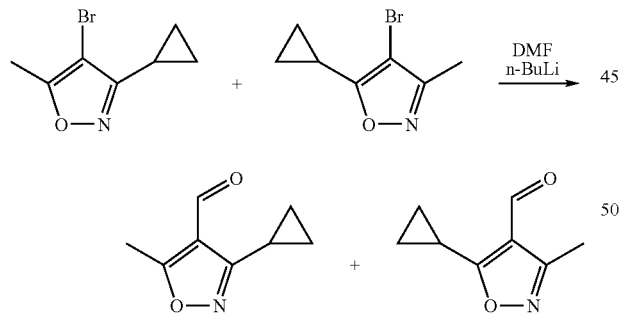

A mixture of 4-bromo-3-cyclopropyl-5-methyl-isoxazole and 4-bromo-5-cyclopropyl-3-methyl-isoxazole (3.0 g) was dissolved in diethyl ether (70 ml) under nitrogen. n-Butyl lithium (1.6M in hexane) (12.5 ml, 20 mmol) was added dropwise at −78° C., followed by the addition of DMF (1.39 ml, 18 mmol) at −78° C. The mixture was stirred at −78° C. for two hours and was allowed to warm to room temperature. The reaction was quenched by addition of water (20 ml), the two phases were separated and the aqueous phase was extracted with diethyl ether (3×50 ml). The combined organic phases were dried over magnesium sulfate and concentrated. The crude mixture was purified by chromatography on silica gel (eluent: ethyl acetate/hexane) to give the mixture of products as an orange oil (2.4 g) which was used without further purification.

Example I9

Preparation of 3-cyclopropyl-4-hydroxymethyl-5-methyl-isoxazole and 5-cyclopropyl-4-hydroxymethyl-3-methyl-isoxazole

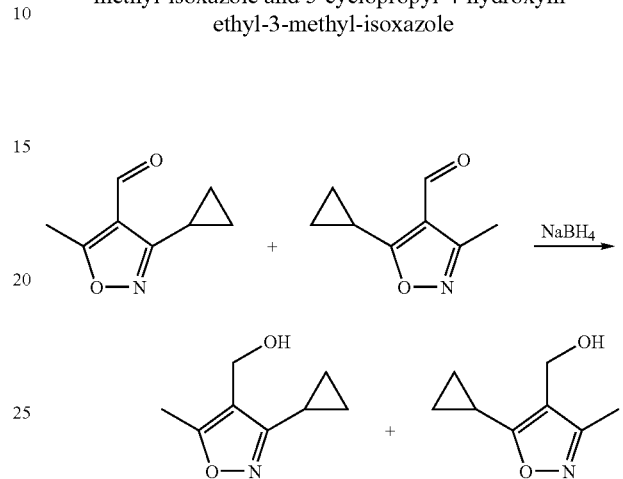

A mixture of 3-cyclopropyl-4-formyl-5-methyl-isoxazole and 5-cyclopropyl-4-formyl-3-methyl-isoxazole (2.4 g) was dissolved in methanol (20 ml) and sodium borohydride (312 mg, 8.2 mmol) was added in portions at 0° C. The mixture was allowed to warm to room temperature and was stirred at room temperature for two hours. The reaction was quenched by addition of water (20 ml) and the mixture was extracted with ethyl acetate (3×30 ml). The combined organic phases were dried over magnesium sulfate and concentrated to give the mixture of products as a colourless oil (1.95 g, 51% yield over 4 steps).

Example I10

Preparation of 4-bromomethyl-3-cyclopropyl-5-methyl-isoxazole and 4-bromomethyl-5-cyclopropyl-3-methyl-isoxazole

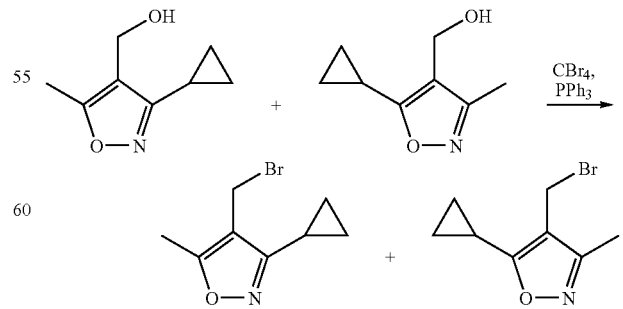

A mixture of 3-cyclopropyl-4-hydroxymethyl-5-methyl-isoxazole and 5-cyclopropyl-4-hydroxymethyl-3-methylisoxazole (1.95 g, 12.7 mmol) was dissolved in dichloromethane (20 ml) and triphenyl phosphine (4.47 g, 17 mmol) and carbon tetrabromide (4.89 g, 15 mmol) were added at 0° C. The mixture was stirred at 0° C. for 2 hours and was concentrated. The crude product was purified by chromatography on silica gel (eluent: ethyl acetate/hexane) to yield the mixture of products (706 mg, 26% yield).

Example I11

Preparation of 3-cyclopropyl-4-(5,5-dimethyl-4,5-dihydroisoxazol-3-ylsulfanylmethyl)-5-methyl-isoxazole and 5-cyclopropyl-4-(5,5-dimethyl-4,5-dihydroisoxazol-3-ylsulfanylmethyl)-3-methyl-isoxazole

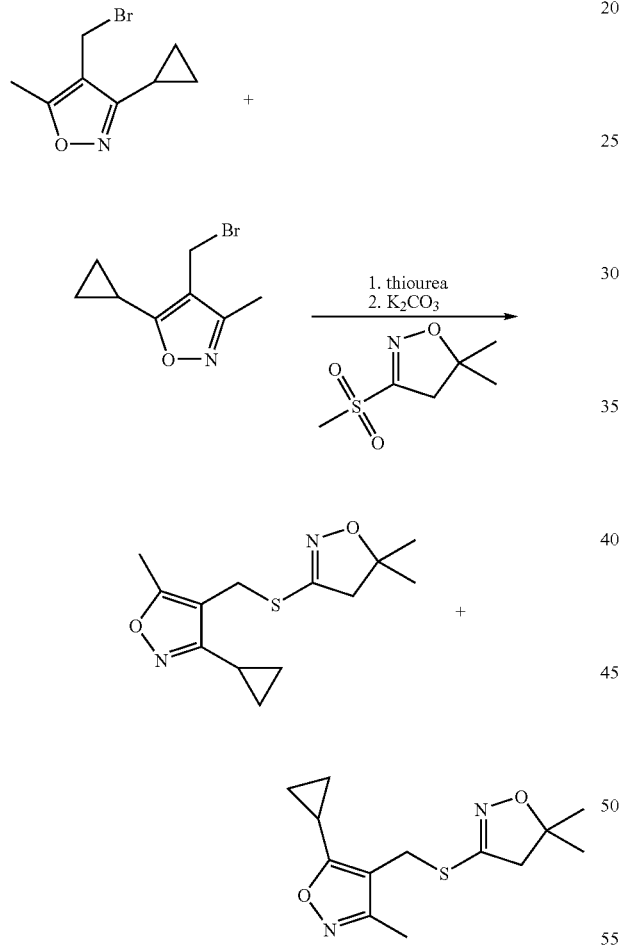

A mixture of 4-bromomethyl-3-cyclopropyl-5-methyl-isoxazole and 4-bromomethyl-5-cyclopropyl-3-methyl-isoxazole (706 mg, 3.3 mmol) were dissolved in ethanol (20 ml) and thiourea (275 mg, 3.6 mmol) was added in portions. After stirring for 1 hour at room temperature 3-methylsulfonyl-5,5-dimethyl-4,5-dihydroisoxazole (586 mg, 3.3 mmol) and potassium carbonate (454 mg, 3.3 mmol) were added and the mixture heated under reflux for 2 hours. The mixture was filtered, the crude product absorbed onto silica gel and purified by chromatography on silica gel (eluent: ethyl acetate I hexane) to give the mixture of products (930 mg, 100% yield).

Example I12

Preparation of 3-cyclopropyl-4-(5,5-dimethyl-4,5-dihydroisoxazol-3-ylsulfonylmethyl)-5-methyl-isoxazole and 5-cyclopropyl-4-(5,5-dimethyl-4,5-dihydroisoxazol-3-ylsulfonylmethyl)-3-methyl-isoxazole

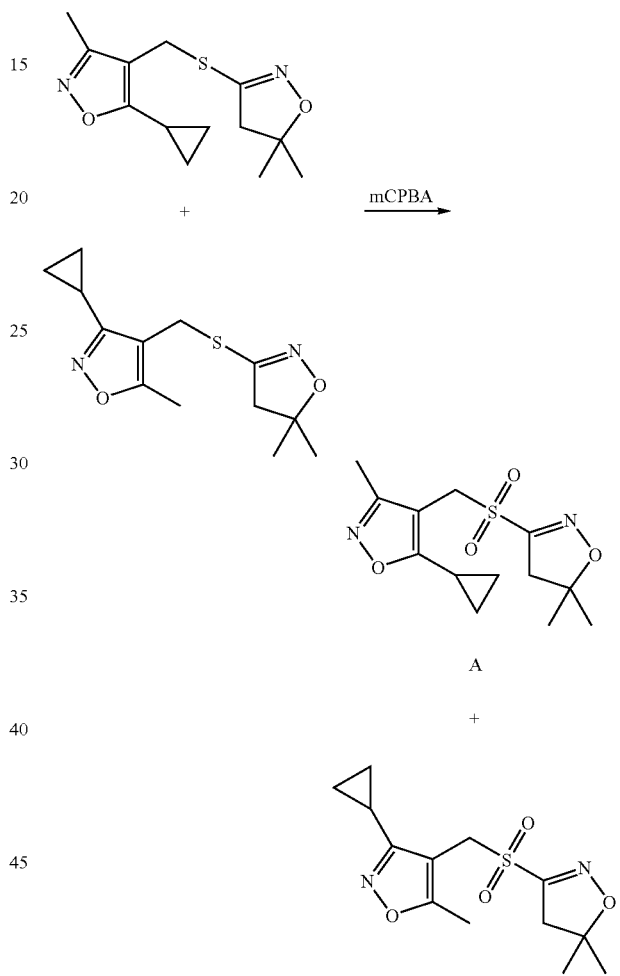

A mixture of 3-cyclopropyl-4-(5,5-dimethyl-4,5-dihydroisoxazol-3-ylsulfanylmethyl)-5-methyl-isoxazole and 5-cyclopropyl-4-(5,5-dimethyl-4,5-dihydroisoxazol-3-ylsulfanylmethyl)-3-methyl-isoxazole (930 mg, 3.5 mmol) was dissolved in dichloromethane (20 ml) and 3-chloroperoxybenzoic acid (mCPBA) (60% by weight) (2.21 g, 7.7 mmol) was added in portions. The solution was stored at room temperature for 10 hours before it was quenched by addition of 10% aqueous sodium metabisulfite solution (10 ml). The suspension was diluted with aqueous sodium hydroxide solution (IM) and extracted with dichloromethane (2×100 ml). The combined organic phases were washed with aqueous sodium hydroxide solution (1M), dried over magnesium sulfate and concentrated. The crude products were purified and separated by preparative HPLC on silica gel (eluent: hexane/dichloromethane) to give product A as a white solid (536 mg, 51% yield) and product B as a white solid (198 mg, 19% yield).

Example P16

Preparation of 4-[chloro-(5,5-dimethyl-4,5-dihydroisoxazol-3-ylsulfonyl)methyl]-4,5-cyclopropyl-3-methyl-isoxazole and 5-cyclopropyl-4-[dichloro-(5,5-dimethyl-4,5-dihydroisoxazole-3-sulfonyl)methyl]-3-methyl-isoxazole

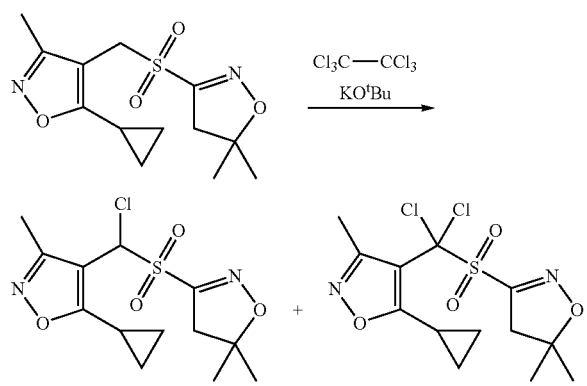

5-Cyclopropyl-4-(5,5-dimethyl-4,5-dihydroisoxazol-3-ylsulfonylmethyl)-3-methyl-isoxazole (420 mg, 1.4 mmol) was dissolved in THF (10 ml) under nitrogen. The solution was cooled to −78° C. and potassium tert-butoxide (2.2 ml, 2.2 mmol) added, followed by hexachloroethane (491 mg, 2.2 mmol). The solution was allowed to warm to room temperature, diluted with water (50 ml) and extracted with ethyl acetate (3×30 ml). The combined organic phases were dried over magnesium sulfate and concentrated. The crude products were purified and separated by chromatography on silica gel (eluent: ethyl acetate/hexane) to give the mono-chloro product (Compound No. 3.05 of Table 29) as a white solid (273 mg, 58% yield) and the di-chloro product (Compound No. 3.06 of Table 29) as a white solid (185 mg, 36% yield).

Example P17

Preparation of 4-[chloro-(5,5-dimethyl-4,5-dihydroisoxazole-3-sulfonyl)methyl]-3-cyclopropyl-5-methyl-isoxazole

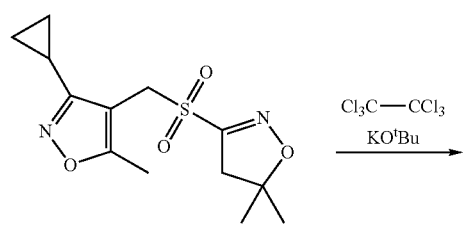

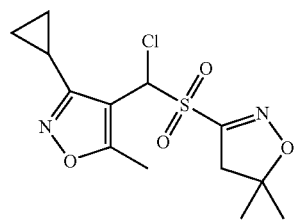

3-Cyclopropyl-4-(5,5-dimethyl-4,5-dihydroisoxazol-3-ylsulfonylmethyl)-5-methyl-isoxazole (108 mg, 0.36 mmol) was dissolved in THF (5 ml) under nitrogen. The solution was cooled to −78° C. and potassium tert-butoxide (0.4 ml, 0.4 mmol) added, followed by hexachloroethane (90 mg, 0.4 mmol). The solution was allowed to warm to room temperature, diluted with water (20 ml) and extracted with ethyl acetate (3×15 ml). The combined organic phases were dried over magnesium sulfate and concentrated. The crude product was purified by chromatography on silica gel (eluent: ethyl acetate/hexane) to give the product (Compound No. 3.07 of Table 29) as a white solid (53 mg, 44% yield).

Example I13

Preparation of 5-cyano-4-methoxycarbonyl-3-methyl-isothiazole

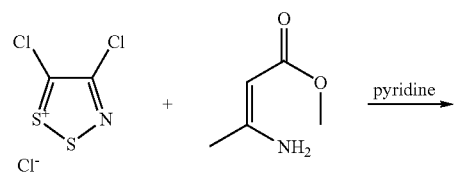

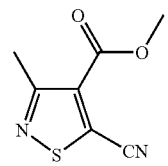

4,5-Dichloro-[1,2,3]-dithiazol-1-ylium chloride (prepared according to Chem. Ber. (1985) 118, 1632) (8.34 g, 40 mmol) was dissolved in dichloromethane (30 ml) and methyl-3-aminocrotonate (4.6 g, 40 mmol) was added dropwise at room temperature. After stirring the solution for 1 hour at room temperature pyridine (6.47 ml, 80 mmol) was added slowly. The mixture was concentrated and purified by chromatography on silica gel (eluent: ethyl acetate/hexane) to give the product as an orange solid (1.14 g, 15.6% yield). $^1$H-NMR (400 MHz, CDCl$_3$): 2.88 (3H, s, Me), 4.0 (3H, s, Me).

Example I14

Preparation of
5-cyano-4-hydroxymethyl-3-methyl-isothiazole

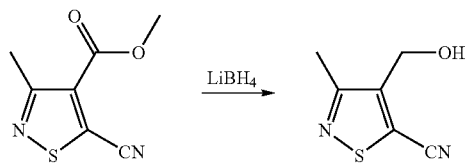

5-Cyano-4-methoxycarbonyl-3-methyl-isothiazole (1.14 g, 6.3 mmol) was dissolved in diethyl ether (20 ml) and methanol (0.38 ml, 9.4 mmol). Lithium borohydride (204 mg, 9.4 mmol) was added and the mixture was stirred at 40° C. for 2 hours. The reaction was quenched by addition of aqueous hydrochloric acid (1M) (20 ml). The two phases were separated and the aqueous phase was extracted with diethyl ether (2×20 ml). The combined organic phases were dried over magnesium sulfate and concentrated to give a crude product (1.2 g), which consisted of a 1:1 mixture of methyl ester and product. The mixture was used without further purification.

Example I15

Preparation of
4-bromomethyl-5-cyano-3-methyl-isothiazole

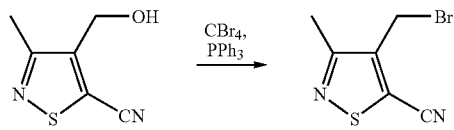

5-Cyano-4-hydroxymethyl-3-methyl-isothiazole (50% purity) (1.14 g, 3.7 mmol) was dissolved in dichloromethane (10 ml) and triphenyl phosphine (1.07 g, 4.0 mmol) and carbon tetrabromide (1.18 g, 3.6 mmol) were added at 0° C. The mixture was stirred at 0° C. for 2 hours, concentrated and the crude product was purified by chromatography on silica gel (eluent: ethyl acetate/hexane). The colourless oil (0.65 g) consisted of a 1:1 mixture of methyl ester (see Example I14) and product. The mixture was used without further purification.

Example I16

Preparation of 4-(5,5-dimethyl-4,5-dihydroisoxazol-3-ylsulfanylmethyl)-3-methyl-isothiazole-5-carbonitrile

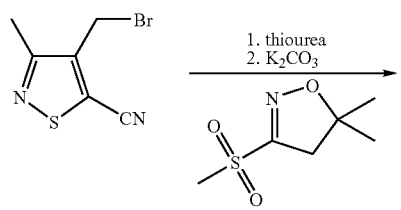

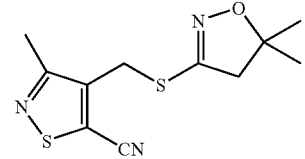

4-Bromomethyl-5-cyano-3-methyl-isothiazole (50% purity) (0.65 g, 1.5 mmol) was dissolved in ethanol (30 ml) and thiourea (242 mg, 3.2 mmol) was added. The mixture was stirred at room temperature until the solids were dissolved. 3-Methane-sulfonyl-5,5-dimethyl-4,5-dihydroisoxazole (540 mg, 3.2 mmol) and potassium carbonate (440 mg, 3.2 mmol) were added and the mixture was heated under reflux for 1 hour. The solids were removed by filtration and the filtrate was concentrated. The crude product was purified by chromatography on silica gel (eluent: ethyl acetate/hexane) to give the product (0.25 g, 62% yield). $^1$H-NMR (400 MHz, CDCl$_3$): 1.44 (6H, s, Me), 2.6 (3H, s, Me), 2.8 (2H, s, CH$_2$), 4.4 (2H, s, CH$_2$).

Example I17

Preparation of 4-(5,5-dimethyl-4,5-dihydroisoxazole-3-sulfonylmethyl)-3-methyl-isothiazole-5-carbonitrile

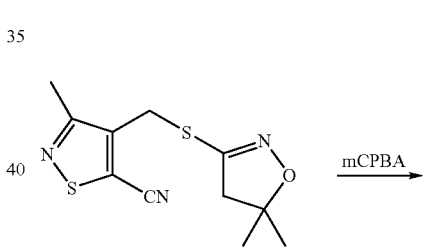

4-(5,5-Dimethyl-4,5-dihydroisoxazol-3-ylsulfanylmethyl)-3-methyl-isothiazole-5-carbonitrile (0.25 g, 1 mmol) was dissolved in dichloromethane (25 ml) and 3-chloro-peroxybenzoic acid (mCPBA) (60% by weight) (0.68 g, 2.4 mmol) was added in portions. The solution was stored at room temperature for 16 hours before it was quenched by addition of 10% aqueous sodium metabisulfite solution (20 ml). The suspension was diluted with aqueous sodium hydroxide solution (1M) and extracted with dichloromethane (2×30 ml). The combined organic phases were washed with aqueous sodium hydroxide solution (lM), dried over magnesium sulfate and concentrated. The crude product was purified by chromatography on silica (eluent: ethyl acetate/hexane) to give the product as a white solid (0.15 g, 50.1% yield).

Example P18

Preparation of 4-[(5,5-dimethyl-4,5-dihydroisoxazole-3-sulfonyl)-fluoromethyl]-3-methyl-isothiazole-5-carbonitrile and 4-[(5,5-dimethyl-4,5-dihydroisoxazole-3-sulfonyl)-difluoro-methyl]-3-methyl-isothiazole-5-carbonitrile

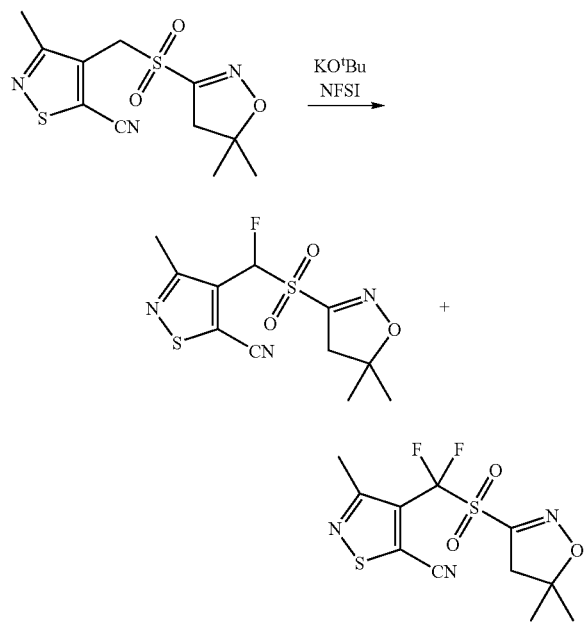

4-(5,5-Dimethyl-4,5-dihydroisoxazole-3-sulfonylmethyl)-3-methyl-isothiazole-5-carbonitrile (0.15 g, 0.57 mmol) was dissolved in THF (10 ml) under nitrogen and sodium hexamethyldisilazide (1M in THF) (1.3 ml, 1.29 mmol) was added slowly at −78° C. After 5 minutes N-fluorobenzenesulfonimide (NFSI) (0.377 g, 1.2 mmol) was added and the solution was allowed to warm to room temperature. The mixture was concentrated and the crude product was purified by chromatography on silica (eluent: ethyl acetate/hexane) to give the mono-fluoro product (Compound No. 3.01 of Table 29) as a white solid (49 mg, 25.6% yield) and the di-fluoro product (Compound No. 3.02 of Table 29) as a white solid (49 mg, 27.1% yield).

Example I18

Preparation of (3-methoxy-isoxazol-5-yl-methanol

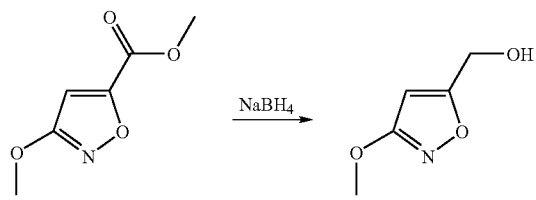

3-Methoxy-isoxazole-5-carboxylic acid methyl ester (prepared according to Eur. J. Org. Chem., 1998, 473) (1.0 g, 6.4 mmol) was dissolved in methanol (30 ml) and sodium borohydride (300 mg, 8.0 mmol) was added in portions. The mixture was stirred for 1 hour at room temperature, concentrated and the residue dissolved in dichloromethane (30 ml). The solution was washed with water, dried over magnesium sulfate and concentrated to give the product as a concentrated solution in dichloromethane. The solution was used without further purification.

Example I19

Preparation of 5-bromomethyl-3-methoxy-isoxazole

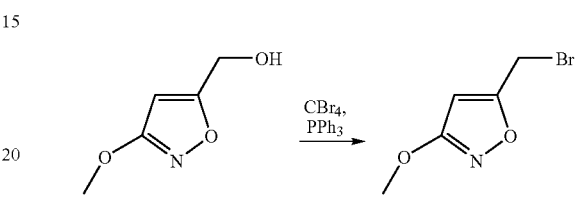

(3-Methoxy-isoxazol-5-yl)-methanol (822 mg, 6.4 mmol) was dissolved in dichloromethane (10 ml) and triphenyl phosphine (1.84 g, 7.0 mmol) and carbon tetrabromide (2 g, 6.11 mmol) were added at 0° C. The mixture was stirred for 2 hours at 0° C. and concentrated. The crude product was purified by chromatography on silica gel (eluent: ethyl acetate/hexane) to give the product as a colourless oil (1.22 g, 99% yield) which was used in the next step without further purification.

Example I20

Preparation of 5-(5,5-dimethyl-4,5-dihydroisoxazol-3-ylsulfanylmethyl)-3-methoxy-isoxazole

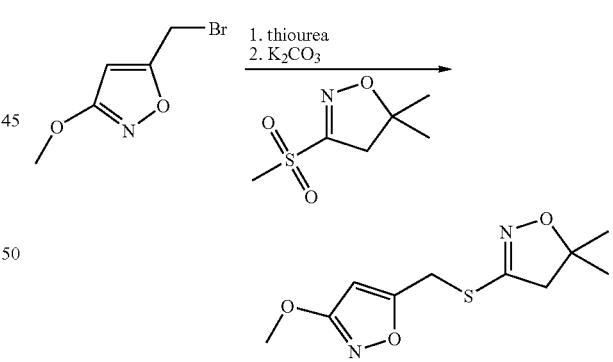

5-Bromomethyl-3-methoxy-isoxazole (1.22 g, 6.35 mmol) was dissolved in ethanol (30 ml) and thiourea (484 mg, 6.4 mmol) was added. The mixture was stirred at room temperature until the solids were dissolved. 3-Methanesulfonyl-5,5-dimethyl-4,5-dihydroisoxazole (1.08 g, 6.4 mmol) and potassium carbonate (880 mg, 6.4 mmol) were added and the mixture was heated under reflux for 1 hour. The solids were removed by filtration and the filtrate was concentrated. The crude product was purified by chromatography on silica gel (eluent: ethyl acetate/hexane) to give the product as colourless oil (0.69 g, 45% yield over 3 steps).

Example I21

Preparation of 5-(5,5-dimethyl-4,5-dihydroisoxazole-3-sulfonylmethyl)-3-methoxy-isoxazole

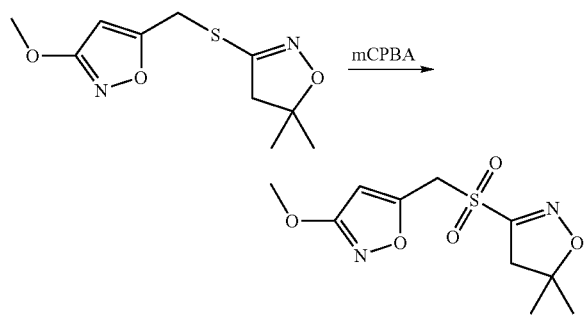

5-(5,5-Dimethyl-4,5-dihydroisoxazol-3-ylsulfanylmethyl)-3-methoxy-isoxazole (693 mg, 2.9 mmol) was dissolved in dichloromethane (10 ml) and 3-chloroperoxybenzoic acid (mCPBA) (60% by weight) (1.81 g, 6.3 mmol) was added in portions. The solution was stored at room temperature for 10 hours before it was quenched by addition of 10% aqueous sodium metabisulfite solution (10 ml). The suspension was diluted with aqueous sodium hydroxide solution (1M) and extracted with dichloromethane (2×100 ml). The combined organic phases were washed with aqueous sodium hydroxide solution (1M), dried over magnesium sulfate and concentrated. The crude product was purified by chromatography on silica gel (eluent: ethyl acetate/hexane) to give the product as a white solid (0.78 g, 99% yield).

Example P19

Preparation of 5-[(5,5-dimethyl-4,5-dihydroisoxazole-3-sulfonyl)-fluoromethyl]-3-methoxy-isoxazole and 5-[(5,5-dimethyl-4,5-dihydroisoxazole-3-sulfonyl)-difluoro-methyl]-3-methoxy-isoxazole

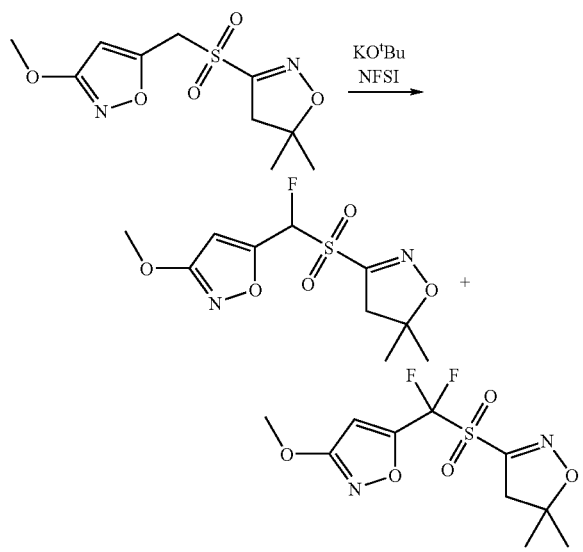

5-(5,5-Dimethyl-4,5-dihydroisoxazole-3-sulfonylmethyl)-3-methoxy-isoxazole (0.2 g, 0.73 mmol) was dissolved in THF (10 ml) under nitrogen and potassium tert-butoxide (1M in THF) (1.13 ml, 1.13 mmol) was added slowly at −78° C. N-fluoro-benzenesulfonimide (NFSI) (0.356 g, 1.13 mmol) was added and the mixture was allowed to warm to room temperature. The mixture was filtered and the filtrate was concentrated. The residue was purified by chromatography on silica (eluent: ethyl acetate/hexane) to give the mono-fluoro product (Compound No. 5.03 of Table 31) as a white solid (0.087 g, 40.8% yield) and the di-fluoro product (Compound No. 5.04 of Table 31) as a white solid (0.063 g, 27.7% yield).

Example P20

Preparation of 5-[chloro-(5,5-dimethyl-4,5-dihydroisoxazole-3-sulfonyl)-methyl]-3-methoxy-isoxazole and 5-[dichloro-(5,5-dimethyl-4,5-dihydroisoxazole-3-sulfonyl)-methyl]-3-methoxy-isoxazole

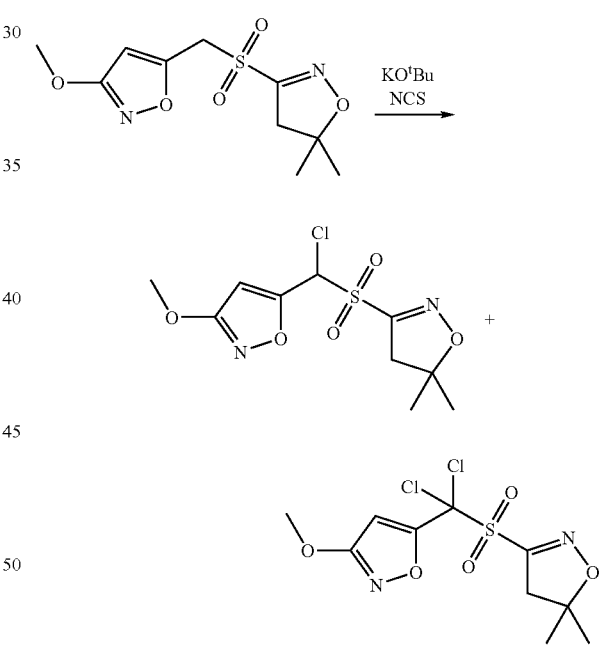

5-(5,5-Dimethyl-4,5-dihydroisoxazole-3-sulfonylmethyl)-3-methoxy-isoxazole (0.269 g, 0.98 mmol) was dissolved in THF (10 ml) under nitrogen and potassium tert-butoxide (1M in THF) (1.28 ml, 1.28 mmol) was added slowly at −78° C. N-Chloro-succinimide (NCS) (0.171 g, 1.28 mmol) was added and the mixture was allowed to warm to room temperature. The mixture was concentrated and purified by chromatography on silica (eluent: ethyl acetate/hexane) to give the mono-chloro product (Compound No. 5.01 of Table 31) as a colourless oil (90 mg, 31.1% yield) and the dichloro product (Compound No. 5.02 of Table 31) as a white solid (94 mg, 27.9% yield).

Example I22

Preparation of 1-methyl-4-trifluoromethyl-1H-pyrazole-3-carboxylic acid ethyl ester and 1-methyl-3-trifluoromethyl-1H-pyrazole-4-carboxylic acid ethyl ester

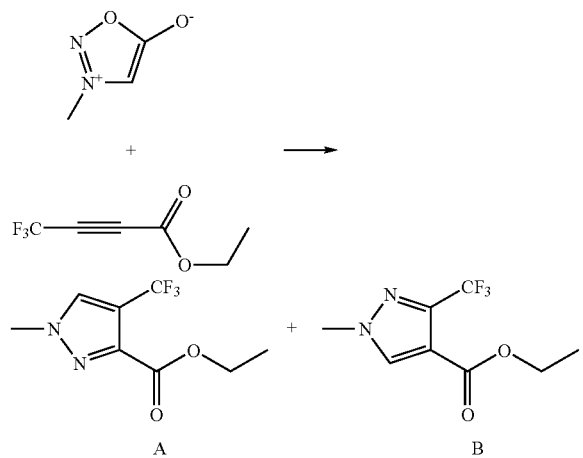

5-Hydroxy-3-methyl-[1,2,3]-oxadiazolium (3-methylsydnone) (prepared according to J. Heterocycl. Chem. (1996) 33, 719) (25.7 g, 256 mmol) was suspended in xylene (120 g) and heated to 100° C. 4,4,4-Trifluoro-but-2-ynoic acid ethyl ester (prepared according to Organic Syntheses (1992) 70, 246-255) (44.8 g, 270 mmol) was slowly added dropwise. The mixture was stirred at 100° C. for 4 hours and concentrated. Ethyl acetate (10 ml) was added to the crude oil which caused the product to crystallise. The crystalline product was washed with a 1:1 mixture of ethyl acetate and hexane (50 ml), with hexane (50 ml) and dried to give product A as white crystals (20.9 g, 36.6% yield). The mother liquor was concentrated and purified by chromatography over silica gel (eluent: ethyl acetate/cyclohexane) which gave more product A (14.3 g, 25.1% yield) and product B (10.0 g, 17.5% yield).

Example I23

Preparation of 1-methyl-4-trifluoromethyl-1H-pyrazole-3-carboxylic acid

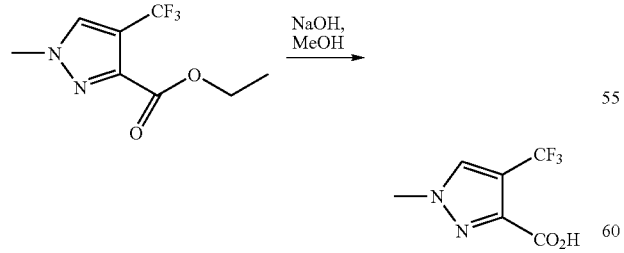

1-Methyl-4-trifluoromethyl-1H-pyrazole-3-carboxylic acid ethyl ester (20 g, 90 mmol) was dissolved in methanol (100 ml). Sodium hydroxide in methanol (1M) (95 ml, 95 mmol) was added dropwise. The mixture was stirred at room temperature for 2 hours, stored at room temperature for 16 hours and concentrated. The residue was dissolved in aqueous hydrochloric acid (2M) (55 ml) and isopropyl acetate (300 ml). The two phases were separated and the aqueous phase was extracted with more isopropyl acetate (100 ml). The combined organic extracts were dried over magnesium sulfate and concentrated. This gave the product as a white solid (17.5 g, 100% yield). M.p. 174-175° C.

Example I24

Preparation of 3-hydroxymethyl-1-methyl-4-trifluoromethyl-1H-pyrazole

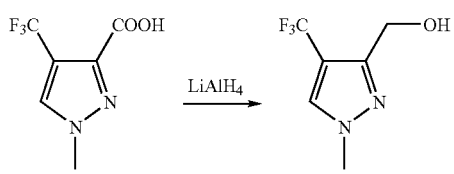

Lithium aluminium hydride (1M in THF) (11 ml, 11 mmol) was added dropwise to a solution of 1-methyl-4-trifluoromethyl-1H-pyrazole-3-carboxylic acid (1.94 g, 10 mmol) in THF (20 ml) under nitrogen. More THF (20 ml) was added to facilitate the stirring. After stirring for 5 hours at room temperature the reaction was quenched by addition of water (0.5 ml), 15% aqueous sodium hydroxide (0.5 ml), and more water (0.5 ml). Ethyl acetate (50 ml) and magnesium sulfate (25 g) were added and the mixture stored at room temperature for 18 hours. Kieselguhr (30 g) was added, the mixture filtered and the solids washed with ethyl acetate. The combined filtrate and washings were concentrated to give the product as a pale yellow oily solid (1.38 g, 77% yield). $^1$H-NMR (400 MHz, CDCl$_3$): 2.3 (1H, bs, OH), 3.91 (3H, s, Me), 4.75 (2H, s, CH$_2$), 7.62 (1H, s, CH).

Example I25

Preparation of 5,5-dimethyl-3-(1-methyl-4-trifluoromethyl-1H-pyrazol-3-ylmethylsulfanyl)-4,5-dihydroisoxazole

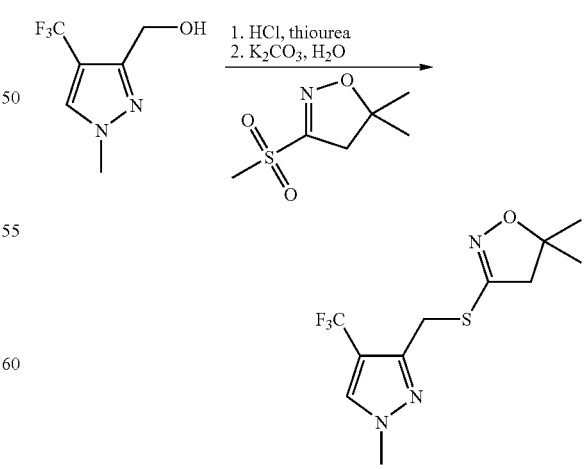

Concentrated hydrochloric acid (36% by weight) (3.0 ml, 36 mmol) was added to a solution of 3-hydroxymethyl-1- methyl-4-trifluoromethyl-1H-pyrazole (1.34 g, 7.4 mmol) and thiourea (836 mg, 11 mmol) in 1,4-dioxane (5 ml) and water (2 ml). The mixture was heated in a sealed vessel in the microwave at 130° C. for 10 minutes, cooled to room temperature and potassium carbonate (4.14 g, 30 mmol) dissolved in water (5 ml) was added. 3-Methanesulfonyl-5,5-dimethyl-4,5-dihydroisoxazole (2.12 g, 12 mmol) and 1,4-dioxane (5 ml) were added and the mixture was heated in a sealed vessel in the microwave at 150° C. for 30 minutes. More potassium carbonate (1.38 g, 10 mmol) was added and the mixture was heated in a sealed vessel in the microwave at 150° C. for 20 minutes. The mixture was cooled to room temperature, extracted with ethyl acetate (3×50 ml), the extract dried over magnesium sulfate and concentrated. The residue was purified using preparative HPLC on silica gel (eluent: dichloromethane/ethyl acetate) to give the product as a white solid (220 mg, 10% yield). $^1$H-NMR (400 MHz, CDCl$_3$): 1.42 (6H, s, Me), 2.84 (2H, s, CH$_2$), 3.89 (3H, s, Me), 4.36 (2H, s, CH$_2$), 7.60 (1H, s, CH).

Example I26

Preparation of 5,5-dimethyl-3-(1-methyl-4-trifluoromethyl-1H-pyrazol-3-ylmethanesulfonyl)-4,5-dihydroisoxazole

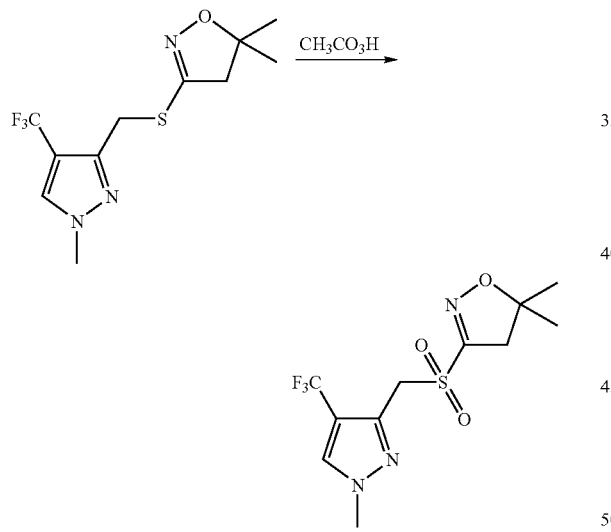

A solution of peracetic acid (40% by weight in acetic acid) (0.3 ml, 1.6 mmol) was added dropwise to a solution of 5,5-dimethyl-3-(1-methyl-4-trifluoromethyl-1H-pyrazol-3-ylmethylsulfanyl)-4,5-dihydroisoxazole (200 mg, 0.68 mmol) in dichloromethane (3 ml) at room temperature. The solution was heated under reflux for 3 hours and stored at room temperature for 17 hours. The reaction was quenched by addition of 10% aqueous sodium metabisulfite solution (1.5 ml). The two phases were separated and the aqueous phase was extracted with dichloromethane (2×3 ml). The combined organic extracts were washed with aqueous potassium carbonate solution (2M) (2 ml) and the wash extracted with dichloromethane (2×3 ml). The combined organic extracts were dried over magnesium sulfate and concentrated to give the product as a white solid (220 mg, 99% yield). M.p. 125-126° C. $^1$H-NMR (400 MHz, CDCl$_3$): 1.52 (6H, s, Me), 3.08 (2H, s, CH$_2$), 3.94 (3H, s, Me), 4.72 (2H, s, CH$_2$), 7.70 (1H, s, CH).

Example P21

Preparation of 3-[fluoro-(1-methyl-4-trifluoromethyl-1H-pyrazol-3-yl)-methanesulfonyl]-5,5-dimethyl-4,5-dihydroisoxazole and 3-[difluoro-(1-methyl-4-trifluoromethyl-1H-pyrazol-3-yl)-methanesulfonyl]-5,5-dimethyl-4,5-dihydroisoxazole

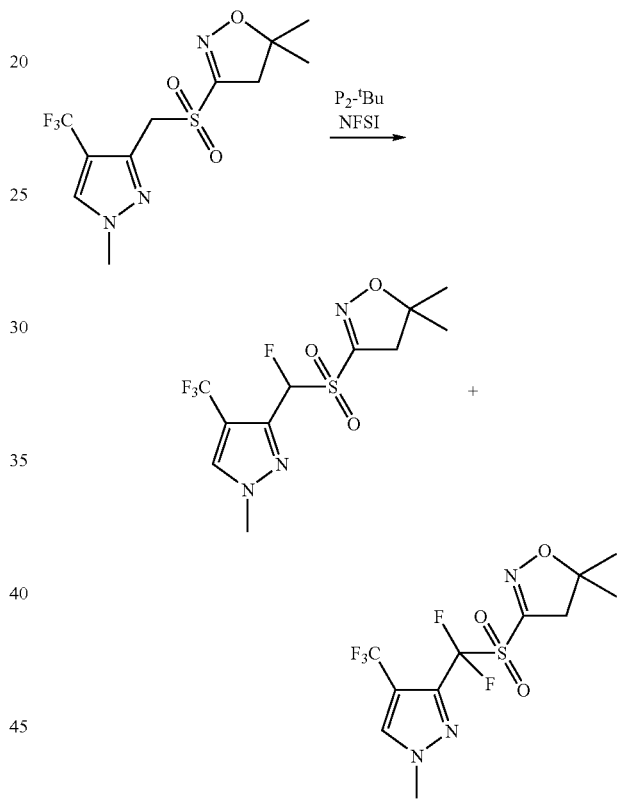

Phosphazene base 1-tert-butyl-2,2,4,4,4-pentakis(dimethylamino)-2-lambda$^5$-5,4-lambda$^5$-5-catenadi(phosphazene) (P$_2$-$^t$Bu) (2M in THF) (0.65 ml, 1.3 mmol) was added to a solution of 5,5-dimethyl-3-(1-methyl-4-trifluoromethyl-1H-pyrazol-3-ylmethane-sulfonyl)-4,5-dihydroisoxazole (200 mg, 0.61 mmol) in THF (6 ml) at room temperature. After 10 minutes N-fluorobenzenesulfonimide (NFSI) (410 mg, 1.3 mmol) was added. The mixture was stirred at room temperature for 3 hours and stored at room temperature for 17 hours. The mixture was concentrated and the residue dissolved in ethyl acetate (100 ml) and passed through silica gel. The filtrate was concentrated and the residue was purified using preparative HPLC on silica gel (eluent: dichloromethane) which gave the mono-fluoro product (Compound No. 4.04 of Table 30) as a white solid (87 mg, 41% yield) and the di-fluoro product (Compound No. 4.05 of Table 30) as a white solid (72 mg, 33% yield).

Example I27

Preparation of (1-methyl-1H-imidazol-2-yl)-methanol

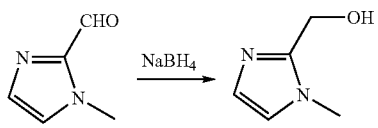

Sodium borohydride (380 mg, 10 mmol) was added to a solution of 1-methyl-1H-imidazole-2-carbaldehyde (1.1 g, 10 mmol) in ethanol (25 ml). The mixture was stirred at room temperature for 2 hours. The reaction was quenched by addition of methanol (20 ml). The mixture was partitioned between water and dichloromethane. The combined organic extracts were dried over magnesium sulfate and concentrated to give the product as a white solid (480 mg, 42% yield). $^1$H-NMR (400 MHz, CDCl$_3$): 3.73 (3H, s, Me), 4.32 (1H, bs, OH), 4.67 (2H, s, CH$_2$), 6.84 (1H, s, CH), 6.90 (1H, s, CH).

Example I28

Preparation of 5,5-dimethyl-3-(1-methyl-1H-imidazol-2-ylmethylsulfanyl)-4,5-dihydroisoxazole

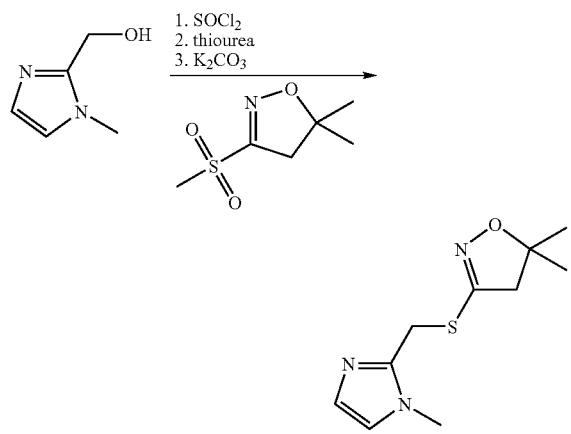

Thionyl chloride (0.909 ml, 12.5 mmol) was added dropwise to a solution of (1-methyl-1H-imidazol-2-yl)-methanol (467 mg, 4.16 mmol) in acetonitrile (30 ml). The mixture was stirred at room temperature for 3 hours and concentrated to give a yellow gum. The gum was dissolved in THF and concentrated to give a pale yellow solid. The solid was dissolved in ethanol (42 ml), thiourea (634 mg, 8.33 mmol) was added and the mixture was heated under reflux for 1 hour. The mixture was cooled slightly and 3-methanesulfonyl-5,5-dimethyl-4,5-dihydroisoxazole (740 mg, 4.18 mmol) and potassium carbonate (1.63 g, 11.8 mmol) were added to the mixture. The mixture was heated under reflux for 2 hours. The mixture was diluted with water and extracted with ethyl acetate. The combined organic extracts were concentrated. The residue was triturated with chloroform and the precipitate removed by filtration. The filtrate was concentrated to give the product as a yellow gum (829 mg, 88% yield). $^1$H-NMR (400 MHz, CDCl$_3$): 1.4 (6H, s, Me), 2.85 (2H, s, CH$_2$), 3.7 (3H, s, Me), 4.45 (2H, s, CH$_2$), 6.82 (1H, d, CH), 6.95 (1H, d, CH).

5,5-Dimethyl-3-(1-methyl-1H-imidazol-2-ylmethylsulfanyl)-4,5-dihydroisoxazole was oxidised using the method described in Example I26 and then fluorinated using the method described in Example P21 to give Compound No. 6.01 of Table 32.

Example I29

Preparation of 2-ethoxy-4-trifluoromethyl-thiazole-5-carboxylic acid ethyl ester

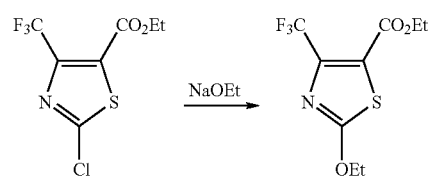

2-Chloro-4-trifluoromethyl-thiazole-5-carboxylic acid ethyl ester (259 mg, 1.0 mmol), sodium ethoxide (23% by weight in ethanol) (0.33 ml, 1.1 mmol) and ethanol (2 ml) were heated under reflux for 2 hours. The mixture was partitioned between water and ethyl acetate. The organic phase was dried over magnesium sulfate and concentrated to give the product as a yellow gum (187 mg, 70% yield). $^1$H-NMR (400 MHz, CDCl$_3$): 1.36 (3H, t, Me), 1.45 (3H, t, Me), 4.35 (2H, q, CH$_2$), 4.55 (2H, q, CH$_2$).

2-Ethoxy-4-trifluoromethyl-thiazole-5-carboxylic acid ethyl ester was reduced using the method described in Example I24, derivatised using the method described in Example I28, oxidised using the method described in Example I26 and then fluorinated using the method described in Example P21 to give Compound No. 7.01 of Table 33.

Example I30

Preparation of 3-amino-4,4,4-trifluoro-2-methyl-but-2-enoic acid ethyl ester

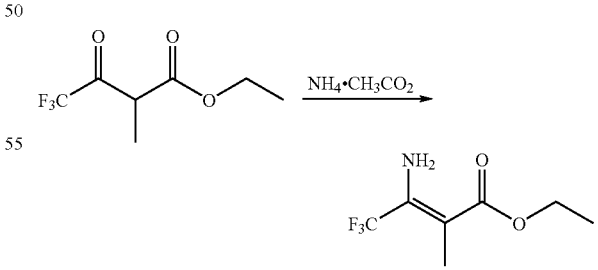

Ethyl α-methyl-4,4,4-trifluoroacetoacetate (24.5 g, 124 mmol) and ammonium acetate (28.6 g, 372 mmol) were dissolved in ethanol (50 ml) and water (2.5 ml). The solution was heated under reflux for 16 hours, allowed to cool to room temperature, diluted with water and extracted with ethyl acetate. The combined organic phases were dried over sodium sulfate and concentrated to give the product as a pale brown liquid (25.5 g, 100% yield) which was used without further purification.

Example I31

Preparation of 1,4-dimethyl-5-trifluoromethyl-1H-pyrazol-3-ol

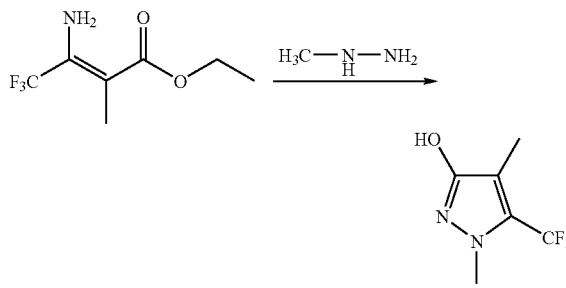

3-Amino-4,4,4-trifluoro-2-methyl-but-2-enoic acid ethyl ester (25.5 g, 124 mmol) was cooled to 0° C. and methyl hydrazine (7 ml, 132 mmol) was added dropwise. The mixture was allowed to warm to room temperature and heated to 50° C. for 20 hours. The mixture was allowed to cool to room temperature and was stirred for 16 hours. The mixture was cooled to 0° C. and saturated aqueous sodium hydrogencarbonate solution (50 ml) was added. The solid was removed by filtration and washed with cold water (0° C.) to give the product as a white solid (8.46 g, 38% yield over two steps).

Example I32

Preparation of 3-difluoromethoxy-1,4-dimethyl-5-trifluoromethyl-1H-pyrazole

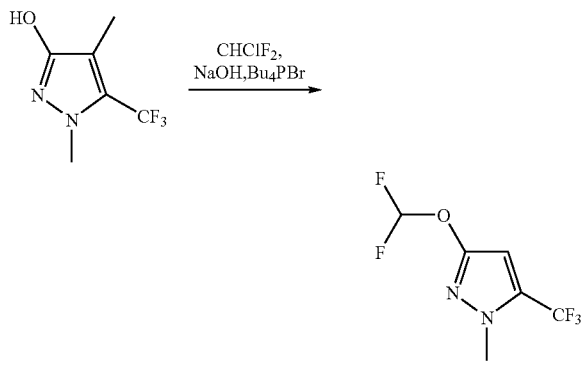

Freon gas (50 ml) was condensed into a reaction flask cooled to −78° C. and 1,4-dimethyl-5-trifluoromethyl-1H-pyrazol-3-ol (4.5 g, 25 mmol) and tetrabutylphosphonium bromide (2.8 g, 8.25 mmol) in dichloromethane (75 ml) were added. Aqueous sodium hydroxide solution (50% by weight) (75 ml) was added dropwise at −78° C. The mixture was allowed to warm to room temperature and was stirred for 3 hours. The reaction was quenched by addition of water. The two phases were separated and the aqueous phase extracted with dichloromethane. The combined organic phases were washed with water, dried over magnesium sulfate and concentrated. The crude material was purified by chromatography on silica gel (eluent: dichloromethane/hexane) to give the product as a colourless liquid (2.9 g, 50% yield). $^{19}$F-NMR (400 MHz, CDCl$_3$): −84.1 (2F, d, J=75 Hz, CF$_2$), −58.92 (3F, s, CF$_3$).

Example I33

Preparation of 4-bromomethyl-3-difluoromethoxy-1-methyl-5-trifluoromethyl-1H-pyrazole

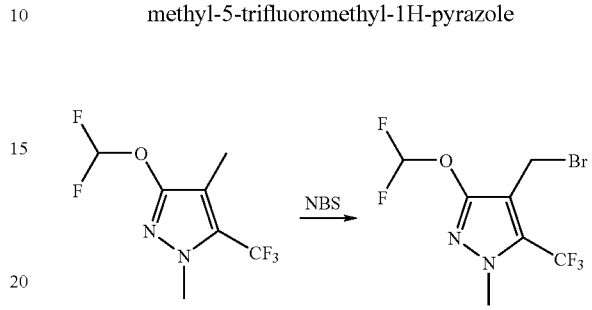

3-Difluoromethoxy-1,4-dimethyl-5-trifluoromethyl-1H-pyrazole (2.9 g, 12.6 mmol) was dissolved in carbon tetrachloride (50 ml) and N-bromosuccinimide (NBS) (2.49 g, 13.9 mmol) and AIBN (206 mg, 1.3 mmol) were added under nitrogen. The mixture was heated under reflux and illuminated with a quartz halogen sunlamp. After 30 minutes the mixture was allowed to cool to room temperature, filtered and the solids washed with dichloromethane. The combined filtrate and washings were concentrated. The crude product was purified by chromatography on silica gel (eluent: ethyl acetate/hexane) to give the product (3.3 g, 85% yield).

4-Bromomethyl-3-difluoromethoxy-1-methyl-5-trifluoromethyl-1H-pyrazole was derivatised using the method described in Example I4, oxidised using the method described in Example I21 and then fluorinated using the method described in Example P21 to give Compound No. 2.34 of Table 28.

Example I34

Preparation of 3-but-2-ynylsulfanyl-5,5-dimethyl-4,5-dihydroisoxazole

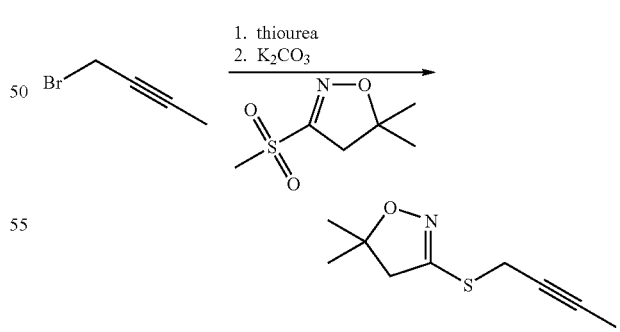

Thiourea (2.15 g, 28.21 mmol) was added to a solution of 1-bromo-2-butyne (2.47 ml, 28.21 mmol) in ethanol (69 ml) and the solution was heated under reflux for 1 hour 40 minutes. The mixture was allowed to cool to room temperature and 3-methanesulfonyl-5,5-dimethyl-4,5-dihydroisoxazole (5 g, 28.21 mmol) and potassium carbonate (4.28 g, 31.03 mmol) were added. The mixture was heated under reflux for 2 hours 35 minutes and allowed to cool to room temperature. The mixture was partitioned between water and ethyl acetate. The aqueous phase was extracted with ethyl acetate. The combined organic phases were washed with brine, dried over magnesium sulfate and concentrated. The residue was purified by chromatography on silica gel (eluent: ethyl acetate/hexane) to give the product (3.085 g, 60% yield) as a pale yellow oil. $^1$H-NMR (400 MHz, CDCl$_3$): 1.42 (6H, s, Me), 1.83 (3H, t, Me), 2.81 (2H, s, CH$_2$), 3.77 (2H, q, CH$_2$).

Example I35

Preparation of 3-bromo-5-(5,5-dimethyl-4,5-dihydroisoxazol-3-ylsulfanyl-methyl)-4-methyl-isoxazole and 3-bromo-4-(5,5-dimethyl-4,5-dihydroisoxazol-3-ylsulfanylmethyl)-5-methyl-isoxazole

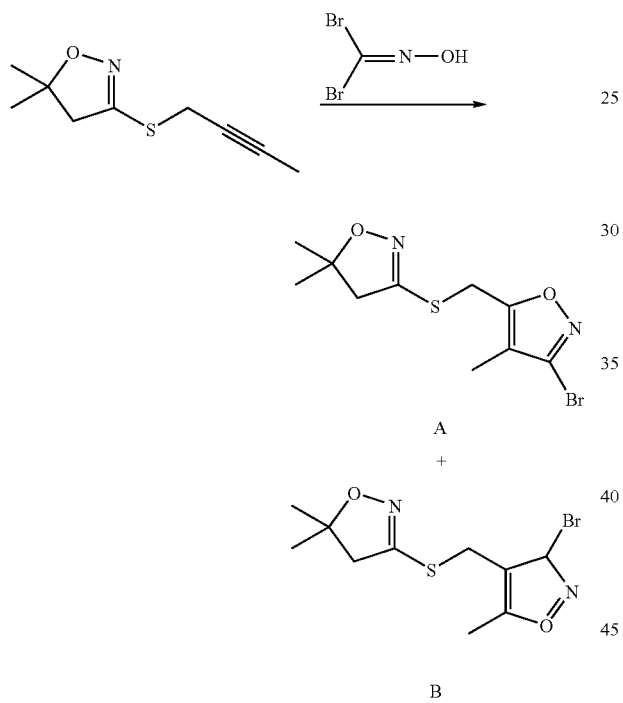

Dibromoformaldoxime (prepared according to Synlett 2002, 3071) (944 mg, 4.68 mmol) and sodium hydrogencarbonate (872 mg, 10.37 mmol) were added to a solution of 3-but-2-ynylsulfanyl-5,5-dimethyl-4,5-dihydroisoxazole (428 mg, 2.34 mmol) in ethyl acetate (4 ml) and the mixture was heated under reflux for 4 days. The mixture was allowed to cool to room temperature and was partitioned between water and ethyl acetate. The aqueous phase was extracted with ethyl acetate. The combined organic phases were washed with brine, dried over magnesium sulfate and concentrated. The residue was purified by chromatography on silica gel (eluent: ethyl acetate/hexane) to give the mixture of products (347 mg, 49% yield) as a yellow oil. A: $^1$H-NMR (400 MHz, CDCl$_3$): 1.41 (6H, s, Me), 2.51 (3H, s, Me), 2.77 (2H, s, CH$_2$); 4.01 (2H, s, CH$_2$); B: $^1$H-NMR (400 MHz, CDCl$_3$): 1.42 (6H, s, Me), 2.03 (3H, s, Me), 2.79 (2H, s, CH$_2$), 4.32 (2H, s, CH$_2$).

Example I36

Preparation of 3-bromo-5-(5,5-dimethyl-4,5-dihydroisoxazole-3-sulfonyl-methyl)-4-methyl-isoxazole and 3-bromo-4-(5,5-dimethyl-4,5-dihydroisoxazole-3-sulfonylmethyl)-5-methyl-isoxazole

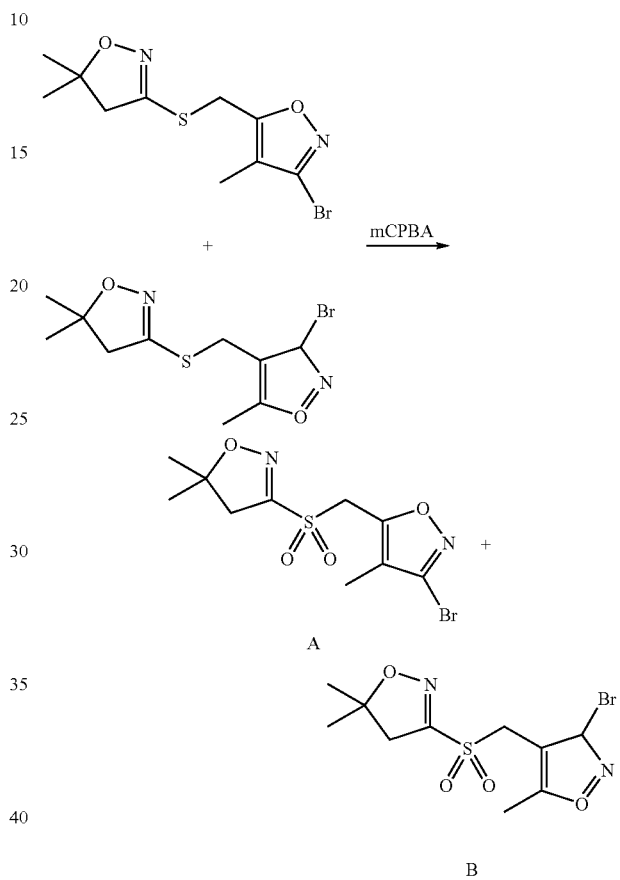

3-Chloroperoxybenzoic acid (mCPBA) (70% by weight) (774 mg, 2.24 mmol) was added to a solution of 3-bromo-5-(5,5-dimethyl-4,5-dihydroisoxazol-3-ylsulfanyl-methyl)-4-methyl-isoxazole and 3-bromo-4-(5,5-dimethyl-4,5-dihydroisoxazol-3-yl-sulfanylmethyl)-5-methyl-isoxazole (310 mg, 1.02 mmol) in dichloromethane (5 ml) at 0° C. The mixture was allowed to warm to room temperature and was stirred at room temperature for 24 hours. The reaction was quenched by addition of saturated aqueous sodium hydrogencarbonate solution. The two phases were separated and the aqueous phase was extracted with dichloromethane. The combined organic phases were washed with 20% aqueous sodium metabisulfite solution, with saturated aqueous sodium hydrogencarbonate solution, dried over magnesium sulfate and concentrated. The residue was purified by chromatography on silica gel (eluent: ethyl acetate/hexane) to give the mixture of products as a white solid. The solid was purified and separated by preparative HPLC (eluent: ethyl acetate/hexane) to give product A as a white solid (124 mg, 34% yield) and product B as a white solid (136 mg, 39% yield). A: M.p. 98.5-100.5° C. $^1$H-NMR (400 MHz, CDCl$_3$): 1.51 (6H, s, Me), 2.10 (3H, s, Me), 2.99 (2H, s, CH$_2$), 4.76

(2H, s, CH₂); B: M.p. 167-168° C. ¹H-NMR (400 MHz, CDCl₃): 1.51 (6H, s, Me), 2.58 (3H, s, Me), 3.06 (2H, s, CH₂), 4.43 (2H, s, CH₂).

Example P22

Preparation of 3-bromo-5-[(5,5-dimethyl-4,5-dihydroisoxazole-3-sulfonyl)-difluoro-methyl]-4-methyl-isoxazole

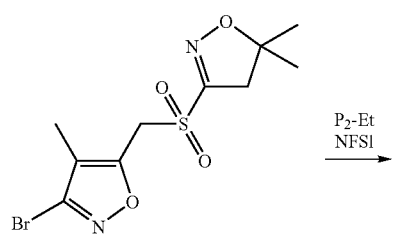

Phosphazene base 1-ethyl-2,2,4,4,4-pentakis(dimethylamino-2-lambda⁵-5,4-lambda⁵-5-catenadi(phosphazene) (P₂-Et) (0.216 ml, 0.65 mmol) was added dropwise to a solution of 3-bromo-5-(5,5-dimethyl-4,5-dihydroisoxazole-3-sulfonylmethyl)-4-methyl-isoxazole (106 mg, 0.31 mmol) in THF (3 ml) at 0° C. After 5 minutes N-fluorobenzenesulfonimide (NFSI) (205 mg, 0.65 mmol) was added. The mixture was stirred at 0° C. for 20 minutes and then allowed to warm to room temperature. The mixture was stirred at room temperature for 4 hours. The reaction was quenched by addition of aqueous hydrochloric acid (2M) and extracted twice with ethyl acetate. The combined organic phases were washed with brine, dried over magnesium sulfate and concentrated. The residue was purified by chromatography on silica gel (eluent: ethyl acetate/hexane) to give the product (Compound No. 5.06 of Table 31) as a white solid (65 mg, 56% yield).

Example I37

Preparation of 1-(2,6-difluoro-phenyl)-2,2,2-trifluoroethanol

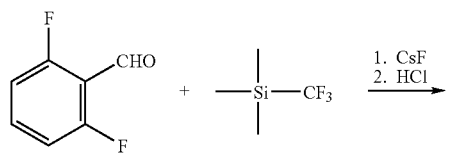

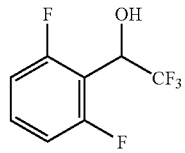

Caesium fluoride (32 mg, 2.1 mmol) was added to a mixture of 2,6-difluoro-benzaldehyde (2 ml, 18.2 mmol) and trimethyl(trifluoromethyl)silane (2 ml, 19.6 mmol) in THF (30 ml) at room temperature. The suspension was stirred at room temperature for 6 hours and stored at room temperature 18 hours. A mixture of concentrated hydrochloric acid (3 ml) in water (7 ml) was added and the solution was stirred at room temperature for 4 hours. The mixture was concentrated to give the product (3.4 g, 87% yield) which was used without further purification.

Example I38

Preparation of 2-(1-bromo-2,2,2-trifluoroethyl-13-difluorobenzene

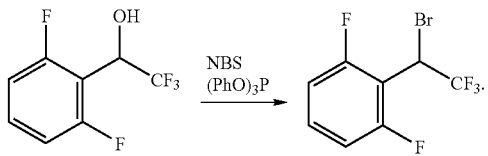 [SMILES: OC(c1c(F)cccc1F)C(F)(F)F ; Fc1cccc(F)c1C(Br)C(F)(F)F]

N-Bromosuccinimide (NBS) (500 mg, 2.9 mmol) was added to a solution of 1-(2,6-difluoro-phenyl)-2,2,2-trifluoroethanol (500 mg, 1.8 mmol) and triphenyl phosphite (0.75 ml, 2.8 mmol) in dichloromethane (5 ml) at room temperature. The mixture was stirred for 6 hours at room temperature and stored at room temperature for 48 hours. The mixture was filtered, the filtrate concentrated and the residue absorbed on to silica gel. The crude product was purified by chromatography on silica gel (eluent: ethyl acetate/hexane) to give the product as a colourless oil (240 mg, 48% yield) which was used without further purification.

Example I39

Preparation of 3-[1-(2,6-difluoro-phenyl)-2,2,2-trifluoro-ethylsulfanyl]-5,5-dimethyl-4,5-dihydroisoxazole

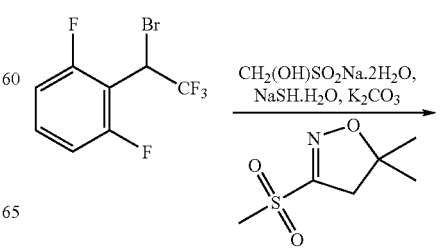

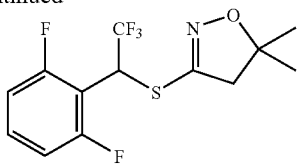

3-Methanesulfonyl-5,5-dimethyl-4,5-dihydroisoxazole (87 mg, 0.49 mmol), sodium hydrosulfide hydrate (73 mg, 0.99 mmol), sodium hydroxy methanesulfonate dihydrate (151 mg, 0.99 mmol) and potassium carbonate (136 mg, 0.99 mmol) were added to DMF (10 ml) at 0° C. and the mixture was stirred at 0° C. for 2 hours. 2-(1-Bromo-2,2,2-trifluoro-ethyl)-1,3-difluorobenzene (135 mg, 0.49 mmol) was added and the suspension was stirred at room temperature for 5 hours. The reaction was partitioned between water and ethyl acetate. The organic phase was washed with water, dried over magnesium sulfate and concentrated. The crude product was purified by chromatography on silica gel (eluent: ethyl acetate/hexane) to give the product as a white solid (55 mg, 35% yield). $^1$H-NMR (400 MHz, CDCl$_3$): 1.41 (3H, s, Me), 1.45 (3H, s, Me), 2.80 (1H, d, CH$_2$), 2.82 (1H, d, CH$_2$), 5.98 (1H, m, CH), 6.97 (2H, m, CH), 7.37 (1H, m, CH).

Example P23

Preparation of 3-[1-(2,6-difluoro-phenyl)-2,2,2-trifluoro-ethanesulfonyl]-5,5-dimethyl-4,5-dihydroisoxazole

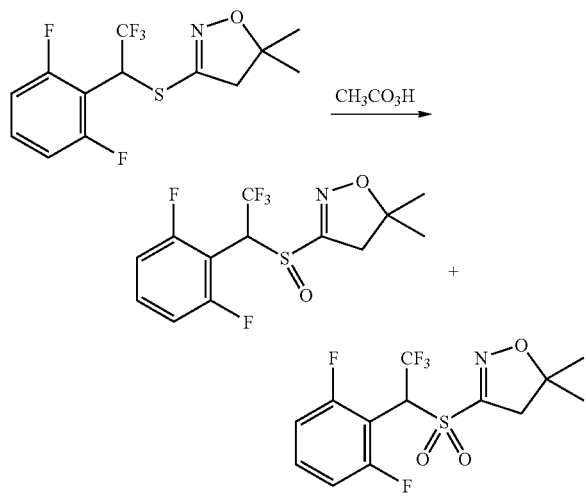

A mixture of 3-[1-(2,6-difluoro-phenyl)-2,2,2-trifluoro-ethylsulfanyl]-5,5-dimethyl-4,5-dihydroisoxazole (110 mg, 0.33 mmol) and peracetic acid (40% by weight in acetic acid) (0.2 ml, 1.05 mmol), 1,2-dichloroethane (5 ml) and dichloromethane (5 ml) was heated under reflux for 2 hours. More peracetic acid (40% by weight in acetic acid) (0.2 ml, 1.05 mmol) was added and the mixture heated under reflux for 2 hours. The mixture was allowed to cool to room temperature and was stored at room temperature for 18 hours. The mixture was poured into saturated aqueous sodium hydrogencarbonate solution and extracted with dichloromethane. The combined organic phases were washed with saturated aqueous sodium hydrogencarbonate solution, dried over magnesium sulfate and concentrated. The residue was purified by chromatography on silica gel (eluent: ethyl acetate/hexane) to give a mixture of diastereomeric sulfoxides (Compound No. 1.140 of Table 27) as a white solid (21.1 mg, 17.8% yield) and the sulfone (Compound No. 1.113 of Table 27) as a white solid (66.1 mg, 56% yield).

Example P24

Preparation of 5,5-dimethyl-3-{2,2,2-trifluoro-1-[1-methyl-5-(2,2,2-trifluoro-ethoxy)-3-trifluoromethyl-1H-pyrazol-4-yl]-ethanesulfinyl}-4,5-dihydro-isoxazole

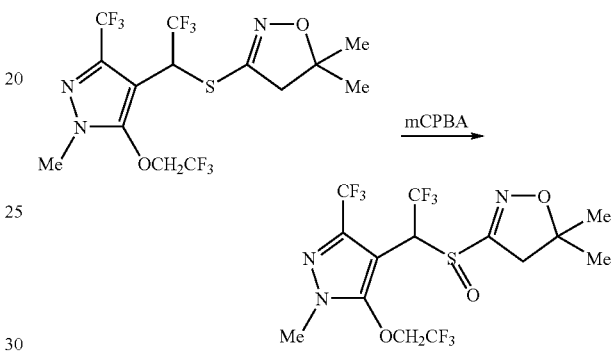

3-Chloroperoxybenzoic acid (mCPBA) (70% by weight) (305 mg, 1.24 mmol) was added in portions to a solution of 5,5-dimethyl-3-{2,2,2-trifluoro-1-[1-methyl-5-(2,2,2-trifluoro-ethoxy)-3-trifluoromethyl-1H-pyrazol-4-yl]-ethylsulfanyl}-4,5-dihydro-isoxazole (190 mg, 0.41 mmol) in dichloromethane (5 ml) at room temperature. The mixture was stirred at room temperature for 18 hours. The reaction was quenched by addition of saturated aqueous sodium metabisulfite solution, followed by addition of saturated aqueous sodium hydrogencarbonate solution. The two phases were separated and the aqueous phase was extracted with dichloromethane. The combined organic phases were washed with saturated aqueous sodium hydrogencarbonate solution, dried over magnesium sulfate and concentrated. The crude product was purified by chromatography on silica gel (eluent: hexane/dichloromethane) to give the product (Compound No. 2.35 of Table 28) as a colourless gum (105 mg, 51% yield).

Example I40

Preparation of 5,5-dimethyl-3-(1-phenyl-ethylsulfanyl)-4,5-dihydro-isoxazole

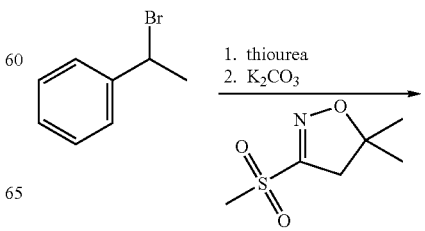

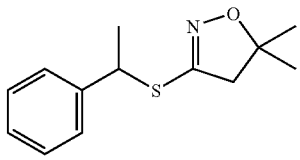

Thiourea (180 mg, 2.4 mmol) was added to a solution of 1-methyl benzyl bromide (0.3 ml, 2.2 mmol) in ethanol (10 ml) at room temperature. The mixture was heated under reflux for 5 hours. 3-Methanesulfonyl-5,5-dimethyl-4,5-dihydroisoxazole (420 mg, 2.4 mmol) and potassium carbonate (330 mg, 2.4 mmol) were added and the mixture was heated under reflux for 3 hours. The mixture was allowed to cool to room temperature, poured into water and the mixture extracted with ethyl acetate. The combined organic phases were washed with water, dried over magnesium sulfate and concentrated. The crude product was purified by chromatography on silica gel (eluent: ethyl acetate/hexane) to give the product as a white solid (210 mg, 43% yield) which was used without further purification.

Example I41

Preparation of 5,5-dimethyl-3-(1-phenyl-ethanesulfonyl)-4,5-dihydroisoxazole

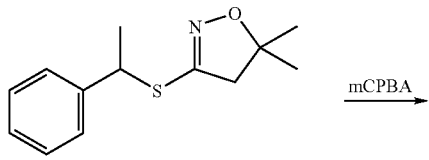

3-Chloroperoxybenzoic acid (mCPBA) (70% by weight) (615 mg, 2.5 mmol) was added in portions to a solution of 5,5-dimethyl-3-(1-phenyl-ethylsulfanyl)-4,5-dihydroisoxazole (195 mg, 0.83 mmol) in dichloromethane (15 ml) at room temperature. The suspension was stirred at room temperature for 18 hours. The reaction was quenched by addition of saturated aqueous sodium metabisulfite solution, followed by addition of saturated aqueous sodium hydrogencarbonate solution. The two phases were separated and the aqueous phase extracted with dichloromethane. The combined organic phases were dried over magnesium sulfate and concentrated. The crude product was purified by chromatography on silica gel (eluent: hexane/dichloromethane) to give the product (85-90% purity) which was used without further purification.

Example P25

Preparation of 3-(1-fluoro-1-phenyl-ethanesulfonyl)-5,5-dimethyl-4,5-dihydroisoxazole

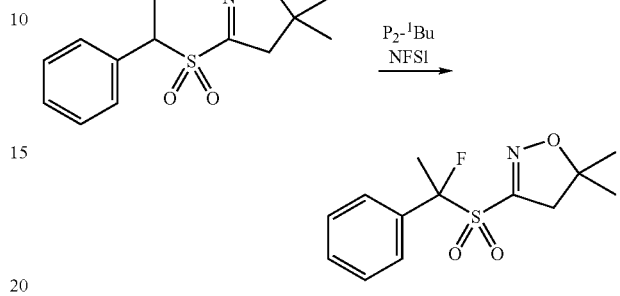

Phosphazene base 1-tert-butyl-2,2,4,4,4-pentakis(dimethylamino)-2-lambda$^5$-5,4-lambda$^5$-5-catenadi(phosphazene) (P$_2$-$^t$Bu) (2M in THF) (0.3 ml, 0.6 mmol) was added to a solution of 5,5-dimethyl-3-(1-phenyl-ethanesulfonyl)-4,5-dihydroisoxazole (150 mg, 0.56 mmol) in THF (8 ml) at room temperature. After 10 minutes N-fluorobenzene-sulfonimide (NFSI) (190 mg, 0.6 mmol) was added. The mixture was stirred at room temperature for 15 minutes. The mixture was absorbed onto silica gel and purified by chromatography on silica gel (eluent: ethyl acetate/hexane) to give the product (Compound No. 1.138 of Table 27) as a white solid (89 mg, yield 56%).

Example I42

Preparation of 3-(2,6-difluoro-benzylsulfanyl)-5 5-dimethyl-4,5-dihydroisoxazole

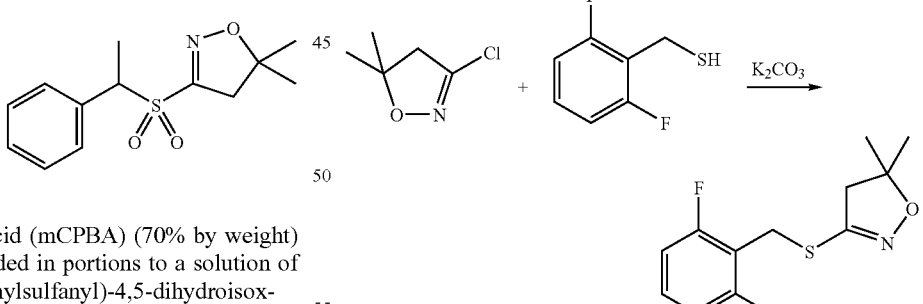

2,6-Difluorbenzylthiol (0.33 g, 2 mmol) and potassium carbonate (1.84 g, 13 mmol) were added to a solution of 3-chloro-5,5-dimethylisoxazoline (0.26 g, 2 mmol) in dry DMF (7.5 ml) under nitrogen. The mixture was stirred for 5 hours at room temperature and stored at room temperature for 1 week. The mixture was filtered and the filtrate diluted with water. The aqueous phase was extracted with ethyl acetate twice. The combined organic extracts were washed with water and brine, dried over magnesium sulfate and concentrated. The crude product was purified by chromatography on silica gel (eluent: ethyl acetate/hexane) to give the product as a white solid (0.23 g, 45% yield).

Example I43

Preparation of 3-(2,6-difluoro-benzylsulfanyl)-5,5-dimethyl-4,5-dihydroisoxazole

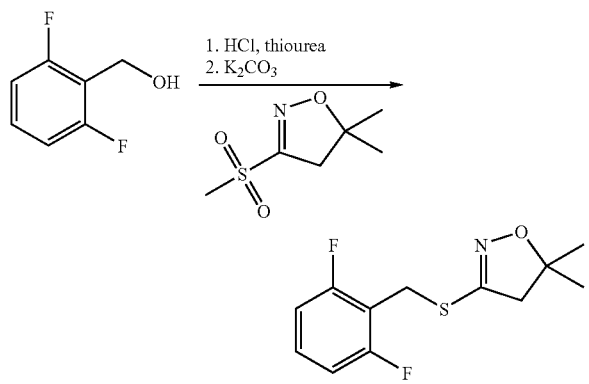

2,6-Difluorobenzyl alcohol (0.2 ml, 1.8 mmol), thiourea (165 mg, 2.2 mmol), aqueous hydrochloric acid (2M) (2.7 ml) and 1,4-dioxane (3 ml) were mixed and the mixture heated in a sealed vessel in the microwave at 140° C. for 10 minutes. Potassium carbonate (1.1 g, 8 mmol) and 3-methanesulfonyl-5,5-dimethyl-4,5-dihydroisoxazole (380 mg, 2.1 mmol) were added and the mixture was stirred in an open vessel for 10 minutes. The mixture was heated in a sealed vessel in the microwave at 150° C. for 10 minutes. The mixture was diluted with water and extracted with ethyl acetate. The organic extract was washed with water, dried over magnesium sulfate and concentrated. The crude material was purified by chromatography on silica gel (eluent: ethyl acetate/hexane) to give the product as a white solid (120 mg, 26% yield). M.p. 85-87° C. $^1$H-NMR (400 MHz, CDCl$_3$): 1.43 (6H, s, Me), 2.82 (2H, s, CH$_2$), 4.36 (2H, s, CH$_2$), 6.90 (2H, d, CH), 7.26 (1H, t, CH).

Example I44

Preparation of 3-(2-trifluoromethoxy-benzylsulfanyl)-5,5-dimethyl-4,5-dihydroisoxazole

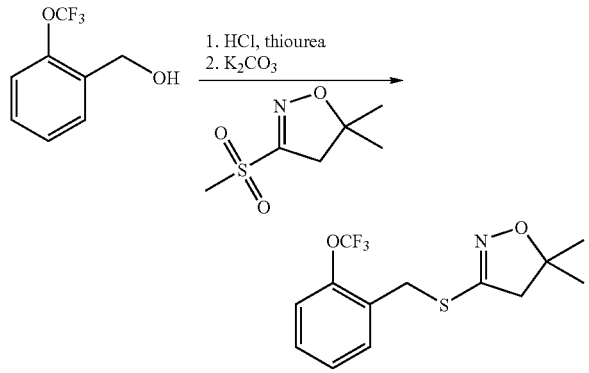

2-(Trifluoromethoxy)benzyl alcohol (200 mg, 1.04 mmol), thiourea (100 mg, 1.31 mmol), aqueous hydrochloric acid (2M) (1.6 ml) and 1,4-dioxane (3 ml) were mixed and the mixture heated in a sealed vessel in the microwave at 140° C. for 10 minutes. Potassium carbonate (620 mg, 4.5 mmol) and 3-methanesulfonyl-5,5-dimethyl-4,5-dihydroisoxazole (220 mg, 1.24 mmol) were added and the mixture was stirred in an open vessel for 10 minutes. The mixture was heated in a sealed vessel in the microwave at 150° C. for 10 minutes. The mixture was diluted with water and extracted with ethyl acetate. The organic extract was washed with water, dried over magnesium sulfate and concentrated. The crude material was purified by chromatography on silica gel (eluent: ethyl acetate/hexane) to give the product as a white solid (50 mg, 15% yield). $^1$H-NMR (400 MHz, CDCl$_3$): 1.41 (6H, s, Me), 2.78 (2H, s, CH$_2$), 4.32 (2H, s, CH$_2$), 7.2-7.4 (2H, m, CH), 7.57 (1H, m, CH).

Example I45

Preparation of 4-(5,5-dimethyl-4,5-dihydroisoxazol-3-ylsulfanylmethyl)-3,5-dimethyl-isoxazole

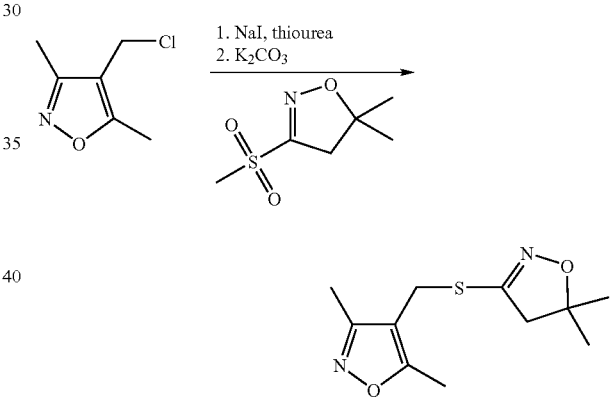

4-Chloromethyl-3,5-dimethyl-isoxazole (3.0 g, 20.6 mmol) was dissolved in ethanol (20 ml) and to it was added thiourea (1.725 g, 22.7 mmol) and sodium iodide (3.087 g, 20.6 mmol). After heating to 80° C. for 1 hour the mixture was cooled and 3-methylsulfonyl-5,5-dimethyl-4,5-dihydroisoxazole (3.676 g, 20.6 mmol), potassium carbonate (3.132 g, 22.7 mmol), ethanol (10 ml) and water (2 ml) were added and the mixture was again heated at 80° C. for 2 hours. The mixture was filtered and concentrated. The crude product was dissolved in ethyl acetate, washed with water, dried over magnesium sulfate and concentrated. The crude product was purified by chromatography over silica gel (eluent: hexane/ethyl acetate) to give the product (4.667 g, 94% yield). $^1$H NMR (400 MHz, CDCl$_3$): 1.425 (6H, s, Me), 2.3 (3H, s, Me), 2.4 (3H, s, Me), 2.8 (2H, s, CH$_2$), 4.0 (2H, s, CH$_2$).

4-(5,5-Dimethyl-4,5-dihydroisoxazol-3-ylsulfanylmethyl)-3,5-dimethyl-isoxazole was oxidised using the method described in Example I21 and then chlorinated using the method described in Example P20 to give Compound No. 3.03 of Table 29 and Compound No. 3.04 of Table 29.

Example I46

Preparation of 5-isopropylsulfanyl-1-methyl-3-trifluoromethyl-1H-pyrazole-4-carbaldehyde

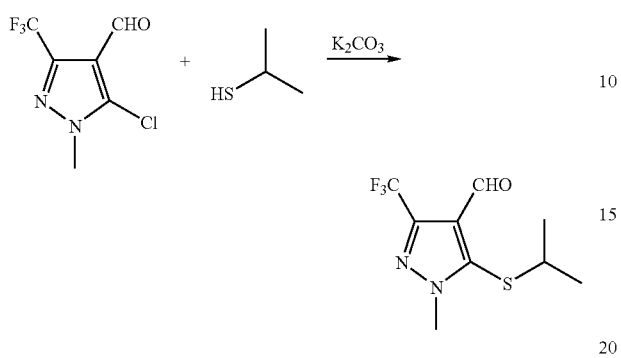

Potassium carbonate (1.68 g, 12 mmol) was suspended in DMF (50 ml) and isopropylthiol (1 ml, 11 mmol) added. The suspension was stirred at room temperature for 15 minutes before a solution of 5-chloro-1-methyl-3-trifluoromethyl-1H-pyrazole-4-carbaldehyde (2.12 g, 10 mmol) in DMF (5 ml) was added. The reaction was stirred at room temperature for 16 hours. The reaction was partitioned between aqueous ammonium chloride solution and diethyl ether and the two phases were separated. The organic phase was washed with water and brine, dried over sodium sulfate and concentrated to give the product (2.584 g, 100% yield) which was used without further purification. $^1$H NMR (400 MHz, CDCl$_3$): 1.29 (3H, s, Me), 1.31 (3H, s, Me), 3.52 (1H, heptet, CH), 4.02 (3H, s, Me), 10.03 (1H, s, CH).

Example I47

Preparation of 4-bromomethyl-5-isopropylsulfanyl-1-methyl-3-trifluoromethyl-1H-pyrazole

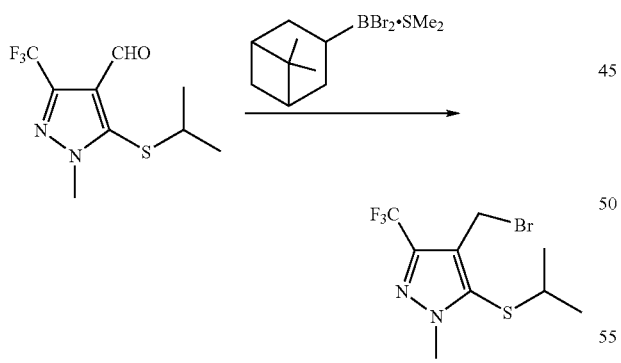

5-Isopropylsulfanyl-1-methyl-3-trifluoromethyl-1H-pyrazole-4-carbaldehyde (2.5 g, 10 mmol) was dissolved in dichloromethane (10 ml) and hexane (10 ml) and a solution of isopinocampheyl-boron dibromide dimethylsulfide complex (prepared according to J. Org. Chem. 1980 (45) 384-389) (4.49 g, 12 mmol) in dichloromethane (5 ml) was added slowly. The reaction was stirred at room temperature for 2 hours and stored at room temperature for 18 hours. The reaction was heated to reflux for 2 hours and then concentrated. The residue was partitioned between water and dichloromethane and the two phases were separated. The organic phase was dried over magnesium sulfate and concentrated. The crude product was absorbed onto silica and purified via chromatography to give the product as a mobile oil (2.5 g, 79% yield). $^1$H NMR (400 MHz, CDCl$_3$): 1.29 (3H, s, Me), 1.31 (3H, s, Me), 3.42 (1H, heptet, CH), 4.00 (3H, s, Me), 4.54 (2H, s, CH).

4-Bromomethyl-5-isopropylsulfanyl-1-methyl-3-trifluoromethyl-1H-pyrazole was derivatised using the method described in Example I4, oxidised using the method described in Example I26 and then fluorinated using the method described in Example P21 to give Compound No. 2.36 of Table 28.

Example I48

Preparation of 1,3-dimethyl-5-(2,2,2-trifluoroethoxy)-1H-pyrazole-4-carbaldehyde

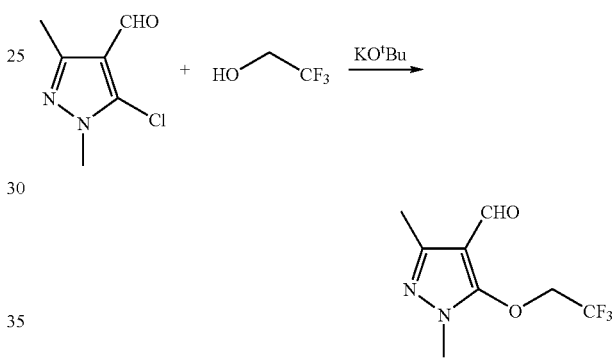

2,2,2-Trifluoroethanol (7.11 ml, 97.6 mmol) was added dropwise to potassium tert-butoxide (1M in THF) (97.6 ml, 97.6 mmol) at 0° C. A solution of 5-chloro-1,3-dimethyl-1H-pyrazole-4-carbaldehyde (10.3 g, 65.1 mmol) in THF (28 ml) was added slowly to the solution at 0° C. The solution was allowed to warm to room temperature and stirred at room temperature for 3 hours. The mixture was diluted with dichloromethane, washed with water and brine, dried over magnesium sulfate and concentrated to give the product as a yellow oil (15.82 g, 109% yield) which was used without further purification. $^1$H NMR (400 MHz, CDCl$_3$): 2.42 (s, 3H, Me), 3.65 (s, 3H, Me), 4.93 (q, 2H, CH$_2$), 9.72 (s, 1H, CH).

Example I49

Preparation of [1,3-dimethyl-5-(2,2,2-trifluoroethoxy)-1H-pyrazol-4-yl]-methanol

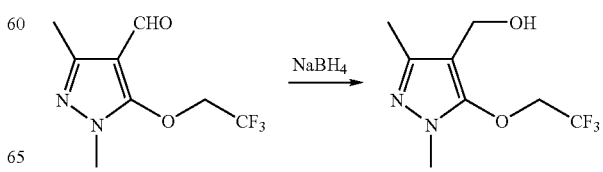

1,3-Dimethyl-5-(2,2,2-trifluoroethoxy)-1H-pyrazole-4-carbaldehyde (14.45 g, 65 mmol) was dissolved in methanol (130 ml). Sodium borohydride (1.23 g, 32.5 mmol) was added in portions at 0° C. The mixture was allowed to warm to room temperature and stirred at room temperature for 2 hours. The mixture was concentrated and the residue dissolved in dichloromethane. The solution was washed with water and brine, dried over magnesium sulfate and concentrated to give the product as a white solid (14.6 g, 100% yield) which was used without further purification. $^1$H NMR (400 MHz, CDCl$_3$): 2.20 (s, 3H, Me), 3.64 (s, 3H, Me), 4.49 (s, 2H, CH$_2$), 4.64 (q, 2H, CH$_2$).

[1,3-Dimethyl-5-(2,2,2-trifluoro-ethoxy)-1H-pyrazol-4-yl]-methanol was derivatised using the method described in Example I25, oxidised using the method described in Example I21 and then fluorinated using the method described in Example P21 to give Compound No. 2.24 of Table 28 or chlorinated using the method described in P20 to give Compound No. 2.31 of Table 28.

Example P26

Preparation of chloro-(2,6-difluorophenyl)-(5,5-dimethyl-4,5-dihydroisoxazole-3-sulfonyl)-acetic acid methyl ester

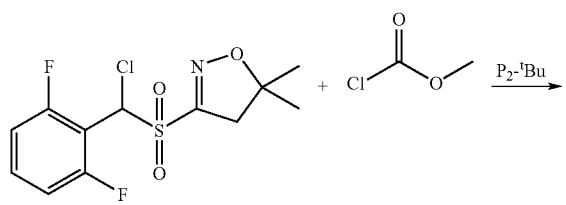

Under nitrogen 3-[chloro-(2,6-difluorophenyl)-methanesulfonyl]-5,5-dimethyl-4,5-dihydroisoxazole (200 mg, 0.62 mmol) was dissolved in dry THF (5 ml). The solution was cooled to 0° C. before 1-tert-butyl-2,2,4,4,4-pentakis(dimethylamino-2-lambda$^5$-5,4-lambda$^5$-5-catenadi(phosphazene) (P$_2$-$^t$Bu) (2M in THF) (0.37 ml, 0.74 mmol) was added followed by addition of methyl chloroformate (0.06 ml, 0.74 mmol) at 0° C. The mixture was allowed to warm to room temperature and stirred at room temperature for 2 hours. The reaction was quenched by addition of aqueous hydrochloric acid (2M) and the mixture was extracted with ethyl acetate. The combined organic extracts were dried over magnesium sulfate and concentrated. The crude product was purified by chromatography over silica gel (eluent: hexane/ethyl acetate) to give the product (Compound No. 1.14 of Table 27).

Example P27

Preparation of 3-[bromo-(2,6-difluorophenyl)-methanesulfonyl]-5,5-dimethyl-4,5-dihydroisoxazole

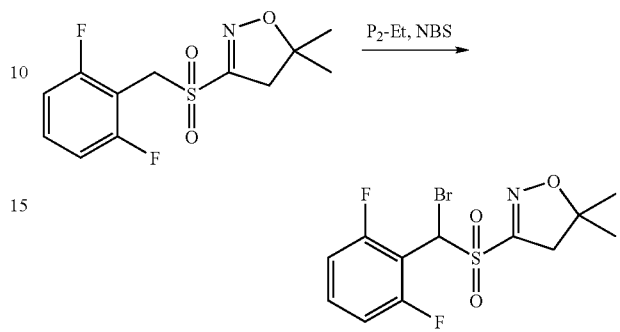

Under nitrogen 3-(2,6-difluorophenyl-methanesulfonyl)-5,5-dimethyl-4,5-dihydroisoxazole (75 mg, 0.26 mmol) was dissolved in dry THF (5 ml). The solution was cooled to 0° C. before 1-ethyl-2,2,4,4,4-pentakis(dimethylamino-2-lambda$^5$-5,4-lambda$^5$-5-catenadi(phosphazene) (P$_2$-Et) (0.1 ml, 0.3 mmol) was added followed by addition of N-bromosuccinimide (NBS) (0.05 g, 0.286 mmol) at 0° C. The mixture was allowed to warm to room temperature and stirred at room temperature for 2 hours. The reaction was quenched by addition of aqueous hydrochloric acid (2M) and the reaction mixture was extracted with ethyl acetate. The combined organic extracts were dried over magnesium sulfate and concentrated. The crude product was purified by chromatography over silica gel (eluent: hexane/ethyl acetate) to give the product (Compound No. 1.19 of Table 27) as a white solid (30 mg, 31% yield).

Example P28

Preparation of 3-[bromo-chloro-(2,6-difluorophenyl)-methanesulfonyl]-5,5-dimethyl-4,5-dihydroisoxazole

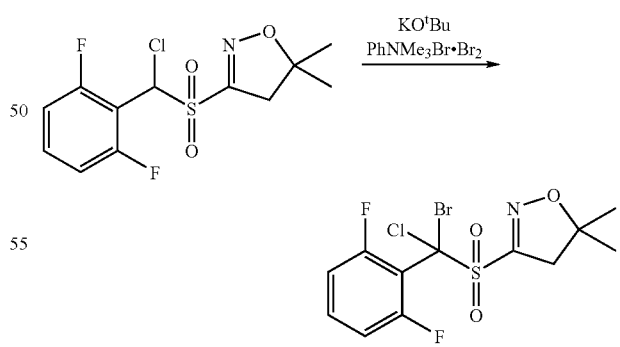

Under nitrogen 3-[chloro-(2,6-difluorophenyl)-methanesulfonyl]-5,5-dimethyl-4,5-dihydroisoxazole (6.387 g, 19.7 mmol) was dissolved in dry THF (200 ml) and the solution cooled to −78° C. Potassium tert-butoxide (1.0M in THF) (20.7 ml, 20.7 mmol) was added forming an orange solution. On addition of phenyl trimethylamino tribromide (PTT) (7.785 g, 20.7 mmol) a much paler thick precipitate formed and the mixture was allowed to warm to room temperature. The mixture was filtered through sand which was subsequently washed with ethyl acetate, the combined organic fractions were concentrated. The crude product was purified by chromatography over silica gel (eluent: hexane/ethyl acetate) to give the product (Compound No. 1.53 of Table 27) as a pale yellow solid (7.225 g, 91% yield).

Example P29

Preparation of 1-(2,6-difluorophenyl)-1-(5,5-dimethyl-4,5-dihydroisoxazole-3-sulfonyl)-propan-2-one

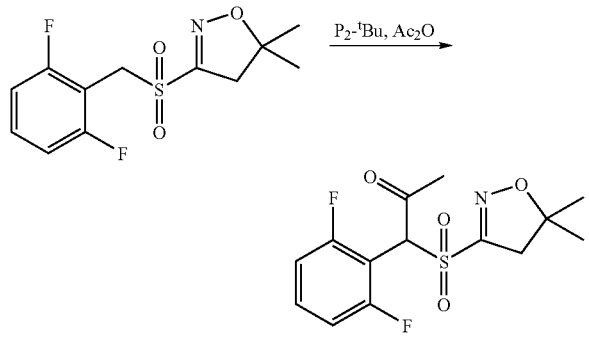

Under nitrogen 3-(2,6-difluorophenyl-methanesulfonyl)-5,5-dimethyl-4,5-dihydro-isoxazole (200 mg, 0.69 mmol) was dissolved in dry THF (5 ml). The solution was cooled to 0° C. before 1-tert-butyl-2,2,4,4,4-pentakis(dimethylamino-2-lambda$^5$-5,4-lambda$^5$-5-catenadi(phosphazene) (P$_2$-$^t$Bu) (2M in THF) (0.41 ml, 0.83 mmol) was added followed by addition of acetic anhydride (0.08 ml, 0.83 mmol) at 0° C. The mixture allowed to warm to room temperature and stirred at room temperature for 2 hours. The reaction was quenched with aqueous hydrochloric acid (2M) and the mixture was extracted with ethyl acetate. The combined organic extracts were dried over magnesium sulfate and concentrated. The crude product was purified by chromatography over silica gel (eluent: hexane/ethyl acetate) to give the product (Compound No. 1.27 of Table 27) as a white solid (57 mg, 25% yield).

The same method was used with cyclopropanecarbonyl chloride, difluoroacetyl chloride, methoxyacetyl chloride, chloroacetyl chloride as the reagent to give Compound No. 1.54 of Table 27, Compound No. 1.57 of Table 27, Compound No. 1.59 of Table 27, Compound No. 1.60 of Table 27, respectively.

Example P30

Preparation of acetic acid 1-[chloro-2,6-difluorophenyl]-(5,5-dimethyl-4,5-dihydroisoxazole-3-sulfonyl)-methyl]-vinyl ester

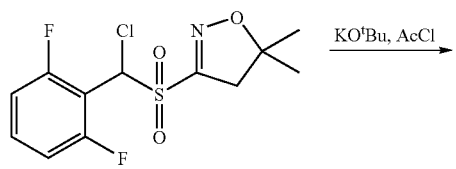

-continued

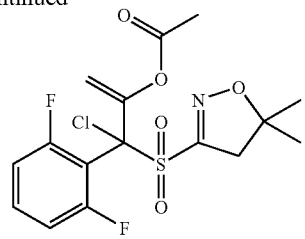

Under nitrogen 3-[chloro-(2,6-difluorophenyl)-methanesulfonyl]-5,5-dimethyl-4,5-dihydroisoxazole (250 mg, 0.77 mmol) was dissolved in dry THF (10 ml) and the solution cooled to −78° C. Potassium tert-butoxide (1.0M in THF) (0.85 ml, 0.85 mmol) was added forming a yellow solution, followed by acetyl chloride (0.06 ml, 0.85 mmol) which caused the colour to fade. The mixture was allowed to warm to room temperature. The reaction was quenched by addition of aqueous hydrochloric acid (2M) and extracted with ethyl acetate. The combined organic extracts were dried over magnesium sulfate and concentrated. The crude product was purified by chromatography over silica gel (eluent: hexane/ethyl acetate) to give the product (Compound No. 1.58 of Table 27) as a white solid (72 mg, 23% yield).

The same method was used with 3-[fluoro-(2,6-difluorophenyl)-methane-sulfonyl]-5,5-dimethyl-4,5-dihydroisoxazole as the starting material to give Compound No. 1.62 of Table 27.

Example P31

Preparation of acetic acid 2-(2,6-difluoro-phenyl)-2-(5,5-dimethyl-4,5-dihydroisoxazole-3-sulfonyl)-1-methyl-vinyl ester

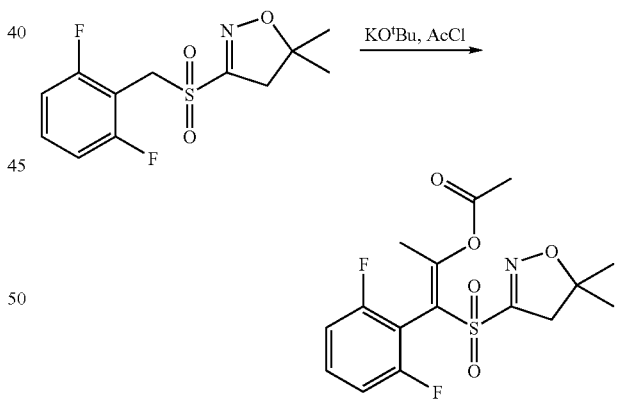

Under nitrogen 3-(2,6-difluorophenyl-methanesulfonyl)-5,5-dimethyl-4,5-dihydroisoxazole (250 mg, 0.865 mmol) was dissolved in dry THF (10 ml) and the solution cooled to −78° C. Potassium tert-butoxide (1.0M in THF) (0.95 ml, 0.95 mmol) was added forming a yellow solution, followed by acetyl chloride (0.7 ml, 0.95 mmol) which caused the colour to fade. The mixture was allowed to warm to room temperature. The reaction was quenched by addition of aqueous hydrochloric acid (2M) and extracted with ethyl acetate. The combined organic extracts were dried over magnesium sulfate and concentrated. The crude product was purified by chromatography over silica gel (eluent: hexane/ethyl acetate) to give the product (Compound No. 1.98 of Table 27) as a white solid (110 mg, 34% yield).

Example P32

Preparation of 3-[bromo-(2,6-difluorophenyl)-fluoro-methanesulfonyl]-5,5-dimethyl-4,5-dihydroisoxazole

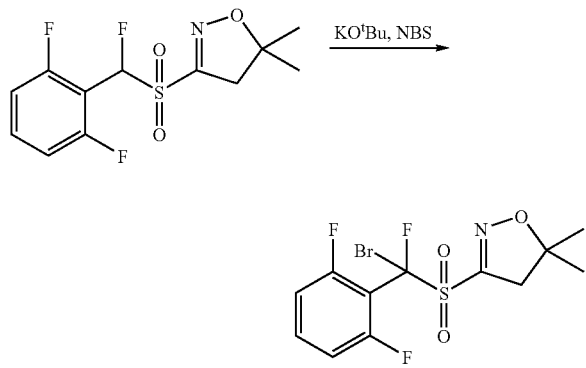

Under nitrogen 3-[fluoro-(2,6-difluorophenyl)-methanesulfonyl]-5,5-dimethyl-4,5-dihydroisoxazole (200 mg, 0.65 mmol) was dissolved in dry THF (10 ml) and the solution cooled to −78° C. Potassium tert-butoxide (10M in THF) (0.71 ml, 0.71 mmol) was added forming a yellow solution, followed by N-bromosuccinimide (NBS) (127 mg, 0.71 mmol) which caused the colour to become brown. The mixture was allowed to warm to room temperature. The reaction was quenched by addition of aqueous hydrochloric acid (2M) and extracted with ethyl acetate. The combined organic extracts were dried over magnesium sulfate and concentrated. The crude product was purified by chromatography over silica gel (eluent: hexane/ethyl acetate) and then HPLC (eluent: hexane/ethyl acetate) to give the product (Compound No. 1.63 of Table 27) as a pale yellow solid (154 mg, 62% yield).

The same method was used with N-iodosuccinimide as reagent to give Compound No. 1.61 of Table 27.

Example P33

Preparation of 3-[1-(2,6-difluoro-phenyl)-2-vinylcyclopropane-sulfonyl]-5,5-dimethyl-4,5-dihydroisoxazole

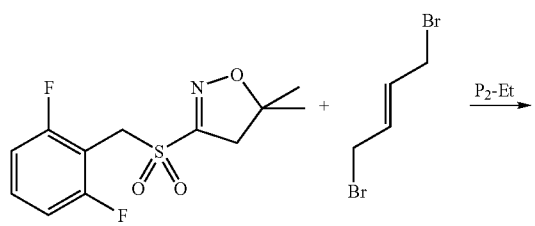

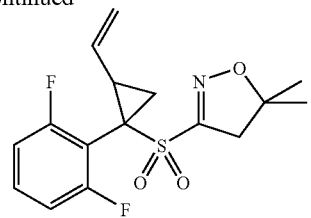

Under nitrogen, 1-ethyl-2,2,4,4,4-pentakis(dimethylamino-2-lambda⁵-5,4-lambda⁵-5-catenadi(phosphazene) (P₂-Et) (0.52 ml, 1.56 mmol) was added to a solution of 3-(2,6-difluoro-phenylmethanesulfonyl)-5,5-dimethyl-4,5-dihydroisoxazole (200 mg, 0.7 mmol) in THF (5 ml) at 0° C. After 10 minutes 1,4-dibromo-2-butene (166 mg, 0.78 mmol) was added and the mixture stirred at room temperature for 1 hour. The mixture was poured onto aqueous hydrochloric acid (2M) and extracted several times with ethyl acetate. The combined organic phases were washed with water, dried over magnesium sulfate and concentrated. The crude product was purified by chromatography over silica gel (eluent: hexane/ethyl acetate) to give the product (Compound No. 1.46 of Table 27) as a white solid (145 mg, 61% yield).

The same method was used with 1,4-dibromo-2-methyl-2-butene as reagent to give Compound No. 1.47 of Table 27.

Example P34

Preparation of 2-(2,6-difluoro-phenyl)-2-(5,5-dimethyl-4,5-dihydroisoxazole-3-sulfonyl)-acetamide

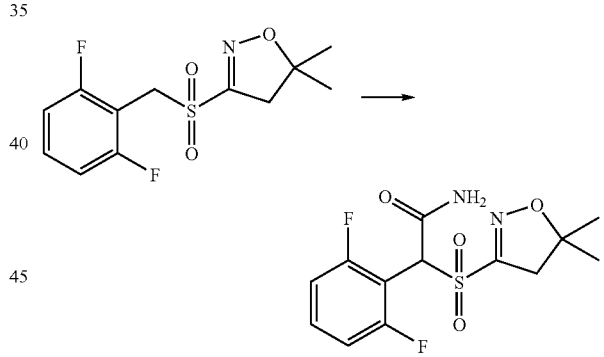

Under nitrogen 3-(2,6-difluorophenyl-methanesulfonyl)-5,5-dimethyl-4,5-dihydro-isoxazole (200 mg, 0.69 mmol) was dissolved in dry THF (5 ml). The solution was cooled to 0° C. before phosphazene base 1-tert-butyl-2,2,4,4,4-pentakis(dimethylamino)-2-lambda⁵-5,4-lambda⁵-5-catenadi (phosphazene) (P₂-ᵗBu) (2M in THF) (0.41 ml, 0.82 mmol) was added, followed by addition of trimethylsilyl isocyanate (0.11 ml, 0.83 mmol) at 0° C. The mixture was allowed to warm to room temperature and stirred at room temperature for 2 hours. The reaction was quenched by addition of aqueous hydrochloric acid (2M) and the mixture was extracted with ethyl acetate. The combined organic extracts were dried over magnesium sulfate and concentrated. The crude product was purified by chromatography over silica gel (eluent: hexane/ethyl acetate) to give the product (Compound No. 1.23 of Table 27) as a pale yellow solid (64 mg, 28% yield).

The same method was used with 4-fluorophenylisocyanate as the reagent to give Compound No. 1.22 of Table 27.

The following compounds are either commercially available or can be prepared by known literature methods and were derivatised using the method described in e.g. Example I4 or Example I45, oxidised using the method described in e.g. Example I21 or Example I26, and then fluorinated using the method described in e.g. Example P21: 8-chloromethyl-6-fluoro-4H-benzo-1,3-dioxine, 3-chloromethyl-5-methyl-isoxazole, 5-chloro-2-nitrobenzyl bromide (prepared according to J. Heterocycl. Chem. (1972), 9(1), 119-22), 2,3-difluorobenzyl bromide, 2,4-difluorobenzyl bromide, 2,5-difluorobenzyl bromide, 3,5-difluorobenzyl bromide, 2-fluoro-4-(ethoxycarbonyl)benzyl bromide (prepared according to J. Med. Chem. (1983), 26(9), 1282-93), 2-fluoro-4-(methoxycarbonyl)benzyl bromide (prepared according to J. Med. Chem. (1990), 33(9), 2437-51), 2-fluoro-6-(trifluoromethyl)benzyl bromide, 2-phenylbenzyl bromide and 2-(trifluoromethylthio)benzyl bromide.

The following compounds are either commercially available or can be prepared by known literature methods and were reduced using the methods described in e.g. Example I2, brominated using the method described in Example I3, derivatised using the method described in e.g. Example I4, oxidised using the method described in e.g. Example I21, and then fluorinated using the method described in e.g. Example P21: 2,2-difluoro-benzo-1,3-dioxole-4-carbaldehyde and 2-(methylsulfonyloxy)benzaldehyde (prepared according to J. Am. Chem. Soc. (1957), 79, 741).

The following compound is either commercially available or can be prepared by known literature methods and were reduced using the method described in e.g. Example I24, derivatised using the method described in e.g. Example I28, oxidised using the method described in e.g. Example I26 and then fluorinated using the method described in e.g. Example P21: 4-ethyl-2-methoxymethyl-thiazole-5-carboxylic acid (prepared according to EP 434620).

The following compound is either commercially available or can be prepared by known literature methods and were reduced using the method described in e.g. Example I24, derivatised using the method described in e.g. Example I25, oxidised using the method described in e.g. Example I26 and then fluorinated using the method described in e.g. Example P21: 1-methyl-3-trifluoromethyl-1H-pyrazole-4-carboxylic acid.

The following compounds are either commercially available or can be prepared by known literature methods and were reduced using the method described in e.g. Example I24, derivatised using the method described in e.g. Example I25, oxidised using the method described in e.g. Example I26 and then fluorinated using the method described in e.g. Example P21: 2-chloro-nicotinic acid ethyl ester and 2-methyl-6-trifluoromethyl-nicotinic acid ethyl ester (prepared according to WO 00/015615 and WO 01/094339).

The compounds mentioned in the following Tables can be prepared in analogous manner.

TABLE 27

Compounds of formula I.3

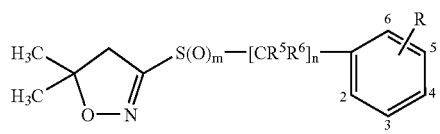

| No. | m | $R^5$ | $R^6$ | n | R | M.p. [° C.] | $^1$H-NMR (400 MHz, CDCl$_3$) |
|---|---|---|---|---|---|---|---|
| 1.01 | 2 | —CH$_2$CH$_2$— | | 1 | 2,6-F | | 1.4-1.45 (2 H, m, CH$_2$), 1.5 (6 H, s, Me), 2.08-2.1 (2 H, m, CH$_2$), 3.0 (2 H, s, CH$_2$), 6.9-7.0 (2 H, m, CH), 7.32-7.4 (1 H, m, CH). |
| 1.02 | 2 | H | —CH$_2$C≡CH | 1 | 2,6-F | 105-107 | 1.44 (3 H, s, Me), 1.48 (3 H, s, Me), 1.97 (1 H, dd, CH), 2.87 (1 H, d, CH$_2$), 3.03 (1 H, d, CH$_2$), 3.28-3.47 (2 H, m, CH$_2$), 5.17 (1 H, dd, CH), 6.98 (2 H, m, CH), 7.52 (1 H, m, CH). |
| 1.03 | 2 | H | —C$_2$H$_4$OCH$_3$ | 1 | 2,6-F | | 1.44 (3 H, s, Me), 1.48 (3 H, s, Me), 2.62 (1 H, m, CH$_2$), 2.74 (1 H, m, CH$_2$), 2.84 (1 H, d, CH$_2$), 3.03 (1 H, d, CH$_2$), 3.21-3.28 (4 H, m, CH$_2$ + Me), 3.58 (1 H, m, CH$_2$), 5.17 (1 H, dd, CH), 6.98 (2 H, m, CH), 7.49 (1 H, m, CH). |
| 1.04 | 2 | H | —CH$_2$CH=CF$_2$ | 1 | 2,6-F | 83 | 1.43 (3 H, s, Me), 1.49 (3 H, s, Me), 2.85 (1 H, d, CH$_2$), 3.30 (1 H, d, CH$_2$), 3.25 (2 H, m, CH$_2$), 4.11 (1 H, m, CH), 4.99 (1 H, dd, CH), 6.98 (2 H, m, CH), 7.40 (1 H, m, CH). $^{19}$F-NMR (400 MHz, CDCl$_3$): −87 (1F, m), −84 (2F, m). |
| 1.05 | 2 | H | —CH$_2$-4F-C$_6$H$_4$ | 1 | 2,6-F | 95 | 1.42 (3 H, s, Me), 1.49 (3 H, s, Me), 2.84 (1 H, d, CH$_2$), 3.03 (1 H, d, CH$_2$), 3.71 (2 H, m, CH$_2$), 5.28 (1 H, dd, CH), 6.89 (4 H, m, CH), 7.11 (2 H, m, CH), 7.31 (1 H, m, CH). |

TABLE 27-continued

Compounds of formula I.3

| No. | m | $R^5$ | $R^6$ | n | R | M.p. [° C.] | $^1$H-NMR (400 MHz, CDCl$_3$) |
|---|---|---|---|---|---|---|---|
| 1.06 | 2 | H | F | 1 | 2,6-F | 112 | 1.56 (3 H, s, Me), 1.57 (3 H, s, Me), 3.35 (1 H, d, CH$_2$), 3.45 (1 H, d, CH$_2$), 6.68 (0.5 H, s, CHF), 6.80 (0.5 H, s, CHF), 7.03 (2 H, m, CH), 7.51 (1 H, m, CH). $^{19}$F-NMR (400 MHz, CDCl$_3$): −182 (1F, m), −109 (2F, m). |
| 1.07 | 2 | H | Cl | 1 | 2,6-F | 128 | 1.54 (3 H, s, Me), 1.55 (3 H, s, Me), 3.35 (1 H, d, CH$_2$), 3.45 (1 H, d, CH$_2$), 6.4 (1 H, s, CH), 7.0 (2 H, m, CH), 7.5 (1 H, m, CH). |
| 1.08 | 2 | H | —C$_2$H$_4$(CO)OC$_2$H$_5$ | 1 | 2,6-F |  | 1.23 (3 H, t, Me), 1.45 (3 H, s, Me), 1.49 (3 H, s, Me), 2.32 (1 H, m, CH$_2$), 2.49 (1 H, m, CH$_2$), 2.73 (2 H, m, CH$_2$), 2.89 (1 H, d, CH$_2$), 3.06 (1 H, d, CH$_2$), 4.11 (2 H, q, OCH$_2$), 5.13 (1 H, dd, CH), 6.98 (2 H, m, CH), 7.39 (1 H, m, CH). |
| 1.09 | 2 | H | —C$_2$H$_4$COC$_2$H$_5$ | 1 | 2,6-F |  | 1.02 (3 H, t, Me), 1.46 (3 H, s, Me), 1.48 (3 H, s, Me), 2.30-2.55 (3 H, m, CH$_2$), 2.62 (2 H, m, CH$_2$), 2.72 (1 H, m, CH$_2$), 2.90 (1 H, d, CH$_2$), 3.07 (1 H, d, CH$_2$), 5.15 (1 H, dd, CH), 6.98 (2 H, m, CH), 7.38 (1 H, m, CH). |
| 1.10 | 2 | H | —C$_2$H$_4$—P(O)(OC$_2$H$_5$)$_2$ | 1 | 2,6-F |  | 1.31 (6 H, m, Me), 1.44 (3 H, s, Me), 1.49 (3 H, s, Me), 1.78 (2 H, m, CH$_2$), 2.73 (2 H, m, CH$_2$), 2.87 (1 H, d, CH$_2$), 3.03 (1 H, d, CH$_2$), 4.09 (4 H, m, OCH$_2$), 5.11 (1 H, dd, CH), 6.99 (2 H, m, CH), 7.40 (1 H, m, CH). |
| 1.11 | 2 | H | —C$_2$H$_4$CON(CH$_3$)$_2$ | 1 | 2,6-F |  | 1.46 (3 H, s, Me), 1.48 (3 H, s, Me), 2.37 (1 H, m, CH$_2$), 2.56-2.87 (3 H, m, CH$_2$), 2.91 (6 H, s, Me), 2.93 (1 H, d, CH$_2$), 3.06 (1 H, d, CH$_2$), 5.19 (1 H, dd, CH), 6.97 (2 H, m, CH), 7.37 (1 H, m, CH). |
| 1.12 | 2 | H | —C$_2$H$_4$SO$_2$CH$_3$ | 1 | 2,6-F | 146 | 1.46 (3 H, s, Me), 1.50 (3 H, s, Me), 2.85-3.20 (6 H, m, CH$_2$), 2.96 (3 H, s, Me), 5.12 (1 H, dd, CH), 7.02 (2 H, m, CH), 7.43 (1 H, m, CH). |
| 1.13 | 2 |  | =CH—N(CH$_3$)$_2$ | 1 | 2,6-F |  | 1.45 (6 H, s, Me), 2.5-3.2 (6 H, bs, Me), 3.0 (2 H, s, CH$_2$), 6.9 (2 H, m, CH), 7.35 (1 H, m, CH), 7.6 (1 H, s, CH). |
| 1.14 | 2 | —(CO)OCH$_3$ | —Cl | 1 | 2,6-F |  | 1.5 (3 H, s, Me), 1.55 (3 H, s, Me), 2.6 (3 H, m, Me), 3.15-3.25 (2 H, q, CH$_2$), 7.0 (2 H, m, CH), 7.45 (1 H, m, CH). |
| 1.15 | 2 | —CH$_3$ | Cl | 1 | 2,6-F | 109 | 1.5 (3 H, s, Me), 1.55 (3 H, s, Me), 2.6 (3 H, m, Me), 3.15 (1 H, d, CH$_2$), 3.25 (1 H, d, CH$_2$), 7.0 (2 H, m, CH), 7.43 (1 H, m, CH). |
| 1.16 | 2 | —C$_2$H$_5$ | Cl | 1 | 2,6-F | 107 | 1.2 (3 H, t, Me), 1.5 (3 H, s, Me), 1.55 (3 H, s, Me), 1.4-1.5 (1 H, m, CH$_2$), 3.2 (2 H, s, CH$_2$), 3.33-3.4 (1 H, m, CH$_2$), |

TABLE 27-continued

Compounds of formula I.3

| No. | m | R⁵ | R⁶ | n | R | M.p. [° C.] | ¹H-NMR (400 MHz, CDCl₃) |
|---|---|---|---|---|---|---|---|
| | | | | | | | 7.0 (2 H, m, CH), 7.43 (1 H, m, CH). |
| 1.17 | 2 | —CH₂CH=CF₂ | Cl | 1 | 2,6-F | 113 | 1.5 (3 H, s, Me), 1.55 (3 H, s, Me), 3.2-3.25 (3 H, m, CH₂ + CH), 4.0 (1 H, dd, CH₂), 4.2-4.3 (1 H, dt, CH₂), 7.0 (2 H, m, CH), 7.48 (1 H, m, CH). |
| 1.18 | 2 | —CH₂-4F-C₆H₄ | Cl | 1 | 2,6-F | 121 | 1.5 (3 H, s, Me), 1.55 (3 H, s, Me), 3.2 (1 H, d, CH₂), 3.3 (1 H, d, CH₂), 3.8 (1 H, m, CH₂), 4.7 (1 H, m, CH₂), 6.9-7.0 (4 H, m, CH), 7.3 (2 H, m, CH), 7.4 (1 H, m, CH). |
| 1.19 | 2 | H | Br | 1 | 2,6-F | 135 | 1.5 (3 H, s, Me), 1.55 (3 H, s, Me), 3.1 (1 H, d, CH₂), 3.2 (1 H, d, CH₂), 6.48 (1 H, s, CH), 7.0 (2 H, m, CH), 7.48 (1 H, m, CH). |
| 1.20 | 2 | F | F | 1 | 2,6-F | 124 | 1.57 (6 H, s, Me), 3.2 (2 H, s, CH₂), 7.06 (2 H, m, CH), 7.58 (1 H, m, CH). ¹⁹F-NMR (400 MHz, CDCl₃): −107 (2F, m), −96 (2F, m). |
| 1.21 | 2 | F | Cl | 1 | 2,6-F | 129 | 1.53 (3 H, s, Me), 1.57 (3 H, s, Me), 3.19 (2 H, m, CH₂), 7.03 (2 H, m, CH), 7.53 (1 H, m, CH). ¹⁹F-NMR (400 MHz, CDCl₃): −105 (1F, m), −103 (2F, m). |
| 1.22 | 2 | H | —CONH-4F-C₆H₄ | 1 | 2,6-F | | 1.49 (3 H, s, Me), 1.51 (3 H, s, Me), 3.0 (1 H, d, CH₂), 3.2 (1 H, d, CH₂), 5.88 (1 H, s, CH), 7.03 (4 H, m, CH), 7.45 (3 H, m, CH), 8.6 (1 H, s, NH). |
| 1.23 | 2 | H | —CONH₂ | 1 | 2,6-F | 175 | 1.49 (3 H, s, Me), 1.51 (3 H, s, Me), 2.95 (1 H, d, CH₂), 3.2 (1 H, d, CH₂), 5.75 (1 H, s, CH), 5.9 (1 H, bs, NH₂), 6.83 (1 H, bs, NH₂), 7.05 (2 H, m, CH), 7.5 (1 H, m, CH). |
| 1.24 | 1 | H | Cl | 1 | 2,6-F | | Diastereoisomer A: 1.55 (6 H, s, Me), 3.1 (1 H, d, CH₂), 3.3 (1 H, d, CH₂), 5.9 (1 H, s, CH), 7.0-7.05 (2 H, m, CH), 7.4-7.5 (1 H, m, CH). Diastereoisomer B: 1.3 (3 H, s, Me), 1.45 (3 H, s, Me), 2.9 (1 H, d, CH₂), 3.2 (1 H, d, CH₂), 6.03 (1 H, s, CH), 7.0-7.05 (2 H, m, CH), 7.4-7.5 (1 H, m, CH). |
| 1.25 | 2 | H | I | 1 | 2,6-F | 156 | 1.43 (3 H, s, Me), 1.5 (3 H, s, Me), 2.9 (1 H, d, CH₂), 3.2 (1 H, d, CH₂), 6.7 (1 H, s, CH), 7.0 (2 H, m, CH), 7.43 (1 H, m, CH). |
| 1.26 | 2 | Cl | Cl | 1 | 2,6-F | 126 | 1.56 (6 H, s, Me), 3.30 (2 H, s, CH₂), 7.03 (2 H, m, CH), 7.51 (1 H, m, CH). |
| 1.27 | 2 | H | —COCH₃ | 1 | 2,6-F | 116 | 1.52 (3 H, s, Me), 1.54 (3 H, s, Me), 2.28 (3 H, s, Me), 3.2 (1 H, d, CH₂), 3.4 (1 H, d, CH₂), 5.85 (1 H, s, CH), 7.1 (2 H, m, CH), 7.5 (1 H, t, CH). |
| 1.28 | 2 | H | —CH₂-4F-C₆H₄ | 1 | 3-CH₃ | 111 | 1.20 (3 H, s, Me), 1.35 (3 H, s, Me), 2.10 (1 H, d, CH₂), 2.32 (3 H, s, Me), 2.80 (1 H, d, CH₂), |

TABLE 27-continued

Compounds of formula I.3

| No. | m | R⁵ | R⁶ | n | R | M.p. [° C.] | ¹H-NMR (400 MHz, CDCl₃) |
|---|---|---|---|---|---|---|---|
| | | | | | | | 3.38 (1 H, dd, CH₂), 3.75 (1 H, dd, CH₂), 4.55 (1 H, dd, CH), 6.85 (2 H, m, CH), 6.95 (2 H, m, CH), 7.15 (3 H, m, CH), 7.25 (1 H, m, CH). |
| 1.29 | 2 | H | —CH₂—CH=CF₂ | 1 | 3-CH₃ | 94 | 1.22 (3 H, s, Me), 1.37 (3 H, s, Me), 2.15 (1 H, d, CH₂), 2.40 (3 H, s, Me), 2.75 (1 H, d, CH₂), 2.90 (1 H, m, CH₂), 3.15 (1 H, m, CH₂), 4.10 (1 H, m, CH), 4.40 (1 H, dd, CH), 7.15-7.35 (4 H, m, CH). |
| 1.30 | 2 | H | Cl | 1 | 3-CH₃ | 102 | 1.42 (3 H, s, Me), 1.50 (3 H, s, Me), 2.40 (3 H, s, Me), 2.80 (1 H, d, CH₂), 3.05 (1 H, d, CH₂), 5.95 (1 H, s, CH), 7.30-7.45 (4 H, m, CH). |
| 1.31 | 2 | Cl | Cl | 1 | 3-CH₃ | 89 | 1.50 (6 H, s, Me), 2.45 (3 H, s, Me), 2.95 (2 H, s, CH₂), 7.30-7.40 (2 H, m, CH), 7.70-7.75 (2 H, m, CH). |
| 1.32 | 2 | H | Cl | 1 | 2-F,6-Cl | 128 | 1.54 (3 H, s, Me), 1.55 (3 H, s, Me), 3.15 (1 H, d, CH₂), 3.25 (1 H, d, CH₂), 6.8 (1 H, s, CH), 7.13 (1 H, m, CH), 7.33 (1 H, d, CH), 7.4 (1 H, m, CH). |
| 1.33 | 1 | H | Cl diastereo- isomer A | 1 | 2-F,6-Cl | 100 | 1.58 (6 H, s, Me), 3.05 (1 H, d, CH₂), 3.3 (1 H, d, CH₂), 6.2 (1 H, s, CH), 7.13 (1 H, m, CH), 7.3 (1 H, d, CH), 7.4 (1 H, m, CH). |
| 1.34 | 1 | H | Cl diastereo- isomer B | 1 | 2-F,6-Cl | 100 | 1.23 (3 H, s, Me), 1.425 (3 H, s, Me), 2.9 (1 H, d, CH₂) 3.25 (1 H, d, CH₂), 6.23 (1 H, s, CH), 7.1 (1 H, m, CH), 7.3 (1 H, m, CH), 7.4 (1 H, m, CH). |
| 1.35 | 2 | H | —CONHᶜPr | 1 | 2,6-F | 150 | 0.6 (2 H, m, CH₂), 0.8 (2 H, m, CH₂), 1.5 (6 H, s, Me), 2.75-2.8 (1 H, m, CH), 3.0 & 3.2 (2 H, q, CH₂), 5.7 (1 H, s, CH), 6.8 (1 H, bs, NH), 7.0 (2 H, t, CH), 7.4-7.5 (1 H, m, CH). |
| 1.36 | 2 | H | —CON(C₂H₅)₂ | 1 | 2,6-F | 144 | 0.8 (3 H, t, Me), 1.1 (3 H, t, Me), 1.5 (6 H, s, Me), 3.0-3.05 (2 H, m, CH₂), 3.3 (1 H, m, CH₂), 3.4-3.45 (3 H, m, CH₂), 5.9 (1 H, s, CH), 7.0-7.05 (2 H, t, CH), 7.4-7.5 (1 H, m, CH). |
| 1.37 | 2 | —CH₃ | Br | 1 | 2,6-F | | 1.5 (6 H, s, Me), 2.825 (3 H, m, Me), 3.0 & 3.225 (2 H, bq, CH₂), 7.0 (2 H, m, CH), 7.45 (1 H, m, CH). |
| 1.38 | 2 | H | —CH(OH)CH₂CH₂CH₃ | 1 | 2,6-F | | 0.85 (3 H, t, Me), 1.25-1.45 (4 H, m, CH₂), 1.48 (3 H, s, Me), 1.52 (3 H, s, Me), 3.03 (1 H, d, CH₂), 3.07 (1 H, d, CH₂), 3.24 (1 H, bs, OH), 4.92 (1 H, bm, CH), 5.05 (1 H, d, CH), 7.0 (2 H, m, CH) 7.4 (1 H, m, CH). |
| 1.39 | 2 | H | —SO₂CH₂C₆H₅ | 1 | 2,6-F | | 1.50 (3 H, s, Me), 1.54 (3 H, s, Me), 3.23 (1 H, d, CH₂), 3.26 (1 H, d, CH₂), 4.5 (1 H, d, CH₂), 5.0 (1 H, d, CH₂), 6.2 (1 H, m, CH), 6.98 (1 H, m, CH), 7.05 (1 H, m, CH), 7.46 (6 H, m, CH). |

TABLE 27-continued

Compounds of formula I.3

| No. | m | R⁵ | R⁶ | n | R | M.p. [° C.] | ¹H-NMR (400 MHz, CDCl₃) |
|---|---|---|---|---|---|---|---|
| 1.40 | 2 | H | —SO₂CH₃ | 1 | 2,6-F | | 1.58 (3 H, s, Me), 1.62 (3 H, s, Me), 3.22 (1 H, d, CH₂), 3.26 (1 H, d, CH₂), 3.28 (3 H, s, Me), 6.38 (1 H, s, CH), 7.1 (2 H, m, CH), 7.55 (1 H, m, CH). |
| 1.41 | 2 | H | —CH(OH)CH₂CH₃ | 1 | 2,6-F | | 0.95 (3 H, t, Me), 1.35 (2 H, m, CH₂), 1.46 (3 H, s, Me), 1.48 (3 H, s, Me), 3.03 (1 H, d, CH₂), 3.06 (1 H, d, CH₂), 3.22 (1 H, bs, OH), 4.88 (1 H, bm, CH), 5.05 (1 H, d, CH), 7.0 (2 H, m, CH), 7.4 (1 H, m, CH). |
| 1.42 | 2 | H | —CH(OSO₂CH₃)CH₂CH₂CH₃ | 1 | 2,6-F | | 0.85 (3 H, t, Me), 1.25 (1 H, m, CH₂), 1.45 (1 H, m, CH₂), 1.49 (3 H, s, Me), 1.51 (3 H, s, Me), 1.6 (1 H, m, CH₂), 2.05 (1 H, m, CH₂), 2.98 (1 H, d, CH₂), 3.01 (1 H, d, CH₂), 3.2 (3 H, s, Me), 5.4 (1 H, d, CH), 5.8 (1 H, m, CH), 7.05 (2 H, t, CH), 7.48 (1 H, m, CH). |
| 1.43 | 2 | | =CHCH₂CH₂CH₃ | 1 | 2,6-F | | 0.92 (3 H, t, Me), 1.5 (6 H, s, Me), 1.55 (2 H, q, CH₂), 2.1 (2 H, q, CH₂), 3.0 (2 H, s, CH₂), 7.0 (2 H, t, CH), 7.4 (1 H, m, CH), 7.42 (1 H, m, CH). |
| 1.44 | 2 | F | —(CO)OCH₂CH₃ | 1 | 2-NO₂, 5-Cl | | 1.3 (3 H, t, Me), 1.53 (3 H, s, Me), 1.57 (3 H, s, Me), 3.17 (1 H, d, CH₂), 3.28 (1 H, d, CH₂), 4.32-4.42 (2 H, m, CH₂), 7.65 (1 H, dd, CH), 7.98 (1 H, d, CH), 8.2 (1 H, d, CH). |
| 1.45 | 2 | | —CCl₂CH₂— | 1 | 2,6-F | | 1.45 (3 H, s, Me), 1.50 (3 H, s, Me), 2.45 (1 H, d, CH₂), 2.95 (1 H, d, CH₂), 3.05 (1 H, d, CH₂), 3.18 (1 H, d, CH₂), 6.95-7.05 (2 H, m, CH), 7.45-7.5 (1 H, m, CH). |
| 1.46 | 2 | | —CH₂CH(CH=CH₂)— | 1 | 2,6-F | 117 | 1.50 (6 H, s, Me), 1.55 (1 H, m, CH₂), 2.30 (1 H, dd, CH), 2.90 (1 H, d, CH₂), 3.05 (1 H, d, CH₂), 3.05 (1 H, m, CH₂), 5.1 (1 H, dd, CH₂), 5.3-5.35 (2 H, m, CH₂), 6.90-7.00 (2 H, m, CH), 7.35-7.45 (1 H, m, CH). |
| 1.47 | 2 | | —CH₂CH{C(CH₃)=CH₂}— | 1 | 2,6-F | 99 | 1.48 (3 H, s, Me), 1.50 (3 H, s, Me), 1.75 (1 H, m, CH₂), 1.8 (3 H, s, Me), 2.25 (1 H, dd, CH), 2.90 (1 H, m, CH₂), 2.90 (1 H, d, CH₂), 3.05 (1 H, d, CH₂), 4.25 (1 H, s, CH₂), 4.75 (1 H, s, CH₂), 6.90-7.00 (2 H, m, CH), 7.30-7.40 (1 H, m, CH). |
| 1.48 | 2 | | —CH(NO₂)CH₂— | 1 | 2,6-F | | 1.45 (3 H, s, Me), 1.55 (3 H, s, Me), 2.30 (1 H, dd, CH₂), 3.0 (1 H, d, CH₂), 3.18 (1 H, d, CH₂), 3.3 (1 H, dd, CH₂), 4.65 (1 H, dd, CH(NO₂)), 7.0 (2 H, m, CH), 7.4-7.5 (1 H, m, CH). |
| 1.49 | 2 | | —CCl{(CO)OCH₃}CH₂— | 1 | 2,6-F | | 1.45 (3 H, s, Me), 1.50 (3 H, s, Me), 2.8 (1 H, d, CH₂), 2.95 (1 H, d, CH₂), 3.00 (1 H, d, CH₂), 3.05 (1 H, d, CH₂), 3.65 (3 H, s, Me), 6.95-7.05 (2 H, m, CH), 7.45-7.5 (1 H, m, CH). |

TABLE 27-continued

Compounds of formula I.3

| No. | m | R⁵ | R⁶ | n | R | M.p. [° C.] | ¹H-NMR (400 MHz, CDCl₃) |
|---|---|---|---|---|---|---|---|
| 1.50 | 2 | Br | Br | 1 | 2,6-F | 118 | 1.55 (6 H, s, Me), 3.35 (2 H, s, CH₂), 6.95-7.05 (2 H, m, CH), 7.45-7.55 (1 H, m, CH). |
| 1.51 | 2 | H | —CH₂OCH₃ | 1 | 2,6-F | 102 | 1.50 (6 H, s, Me), 3.05 (1 H, d, CH₂), 3.10 (1 H, d, CH₂), 3.4 (3 H, s, Me), 4.05 (1 H, dd, CH₂), 4.5 (1 H, m, CH₂), 5.2 (1 H, m, CH), 6.95-7.05 (2 H, m, CH), 7.45-7.5 (1 H, m, CH). |
| 1.52 | 2 | | —CH(COPh)CH₂— | 1 | 2,6-F | 191 | 1.45 (3 H, s, Me), 1.47 (3 H, s, Me), 2.3 (1 H, dd, CH₂), 2.45 (1 H, dd, CH₂), 2.85 (1 H, d, CH₂), 2.95 (1 H, d, CH₂), 4.15 (1 H, dd, CH), 6.7-6.8 (1 H, m, CH), 6.95-7.05 (1 H, m, CH), 7.3-7.4 (1 H, m, CH), 7.5-7.55 (2 H, m, CH), 7.6-7.65 (1 H, m, CH), 8.0-8.1 (2 H, m, CH). |
| 1.53 | 2 | Cl | Br | 1 | 2,6-F | 119 | 1.55 (3 H, s, Me), 1.57 (3 H, s, Me), 3.3 (1 H, d, CH₂), 3.35 (1 H, d, CH₂), 7.0-7.08 (2 H, m, CH), 7.45-7.55 (1 H, m, CH). |
| 1.54 | 2 | H | —COᶜPr | 1 | 2,6-F | 134 | 0.95-1.05 (2 H, m, CH₂), 1.2-1.25 (2 H, m, CH₂), 1.5 (6 H, s, Me), 1.8-1.9 (1 H, m, CH), 3.2 (1 H, d, CH₂), 3.4 (1 H, d, CH₂), 6.0 (1 H, s, CH), 7.0-7.1 (2 H, m, CH), 7.45-7.55 (1 H, m, CH). |
| 1.55 | 2 | F | —CH₃ | 1 | 2,6-F | 121 | 1.5 (3 H, s, Me), 1.55 (3 H, s, Me), 2.35 (3 H, dt, Me), 3.1 (1 H, d, CH₂), 3.22 (1 H, d, CH₂), 6.95-7.0 (2 H, m, CH), 7.4-7.5 (1 H, m, CH). |
| 1.56 | 2 | H | —CONHCH₂CHF₂ | 1 | 2,6-F | 142 | 1.5 (3 H, s, Me), 1.52 (3 H, s, Me), 3.0 (1 H, d, CH₂), 3.2 (1 H, d, CH₂), 3.6-3.8 (2 H, m, CH₂), 5.1 (1 H, bs, NH), 5.8 (1 H, s, CH), 5.9 (1 H, t, CH), 7.0-7.1 (2 H, m, CH), 7.42-7.52 (1 H, m, CH). |
| 1.57 | 2 | H | —COCHF₂ | 1 | 2,6-F | | Enol form: 1.3 (6 H, s, Me), 2.9 (2 H, s, CH₂), 5.5 (1 H, t, CHF₂), 6.8 (2 H, t, CH), 7.2 (1 H, m, CH). |
| 1.58 | 2 | Cl | —C{O(CO)CH₃}=CH₂ | 1 | 2,6-F | | 1.5 (3 H, s, Me), 1.55 (3 H, s, Me), 2.1 (3 H, s, Me), 3.2 (1 H, d, CH₂), 3.3 (1 H, d, CH₂), 5.6 (1 H, d, CH₂), 6.02 (1 H, d, CH₂), 7.0 (2 H, m, CH), 7.48 (1 H, m, CH). |
| 1.59 | 2 | H | —COCH₂OCH₃ | 1 | 2,6-F | | 1.52 (3 H, s, Me), 1.53 (3 H, s, Me), 3.28 (3 H, s, Me), 3.2 (1 H, d, CH₂), 3.35 (1 H, d, CH₂), 4.1 (2 H, s, CH₂), 6.1 (1 H, s, CH), 7.05 (2 H, t, CH), 7.5 (1 H, m, CH). |
| 1.60 | 2 | H | —COCH₂Cl | 1 | 2,6-F | | Enol form: 1.52 (6 H, s, Me), 3.14 (2 H, s, CH₂), 3.15 (1 H, bs, OH), 3.99 (2 H, s, CH₂), 6.1 6.98 (2 H, m, CH), 7.35 (1 H, m, CH). |
| 1.61 | 2 | F | I | 1 | 2,6-F | | 1.5 (3 H, s, Me), 1.52 (3 H, s, Me), 3.06 (2 H, s, CH₂), 3.16 (1 H, d, CH₂), 7.0 (2 H, m, CH), 7.5 (1 H, m, CH). |

TABLE 27-continued

Compounds of formula I.3

| No. | m | R⁵ | R⁶ | n | R | M.p. [° C.] | ¹H-NMR (400 MHz, CDCl₃) |
|---|---|---|---|---|---|---|---|
| 1.62 | 2 | F | —C{O(CO)CH₃}=CH₂ | 1 | 2,6-F | | 1.495 (3 H, s, Me), 1.505 (s, 3 H, Me), 2.14 (3 H, s, Me), 3.1 (1 H, d, CH₂), 3.2 (1 H, d, CH₂), 5.59 (1 H, m, CH₂), 5.79 (1 H, m, CH₂), 7.0 (2 H, m, CH), 7.48 (1 H, m, CH). |
| 1.63 | 2 | F | Br | 1 | 2,6-F | | 1.52 (3 H, s, Me), 1.55 (3 H, s, Me), 3.12 (1 H, d, CH₂), 3.21 (1 H, d, CH₂), 7.02 (2 H, m, CH), 7.52 (1 H, m, CH). |
| 1.64 | 2 | H | —CH₂SO₂CH₃ | 1 | 2,6-F | | 1.45 (3 H, s, Me), 1.50 (3 H, s, Me), 2.9 (1 H, d, CH₂), 2.95 (3 H, s, Me), 3.05 (1 H, d, CH₂), 4.05-4.2 (2 H, m, CH₂), 5.4-5.5 (1 H, m, CH), 7.0-7.05 (2 H, m, CH), 7.4-7.5 (1 H, m, CH). |
| 1.65 | 2 | F | F | 1 | 2-CF₃ | | 1.575 (6 H, s, Me), 3.2 (2 H, s, CH₂), 7.75 (2 H, m, CH), 7.925 (2 H, m, CH). |
| 1.66 | 2 | F | F | 1 | 2-OCHF₂ | | 1.55 (6 H, s, Me), 3.19 (2 H, s, CH₂), 6.5 (1 H, m, CH), 7.35 (1 H, d, CH), 7.4 (1 H, m, CH), 7.65 (1 H, m, CH), 7.7 (1 H, d, CH). |
| 1.67 | 2 | F | F | 1 | 2-OCF₃ | | 1.55 (6 H, s, Me), 3.2 (2 H, s, CH₂), 7.45 (2 H, m, CH), 7.7 (1 H, m, CH), 7.75 (1 H, d, CH). |
| 1.68 | 2 | H | F | 1 | 2-OCF₃ | | 1.52 (3 H, s, Me), 1.53 (3 H, s, Me), 3.1 (1 H, d, CH₂), 3.17 (1 H, d, CH₂), 6.82 (1 H, d, CH), 7.35-7.45 (2 H, m, CH), 7.55-7.62 (1 H, m, CH), 7.78 (1 H, d, CH). |
| 1.69 | 2 | F | F | 1 | 2-SOCF₃ | | 1.6 (6 H, s, Me), 3.2 (2 H, s, CH₂), 7.85 (2 H, m, CH), 7.975 (1 H, m, CH), 8.45 (1 H, d, CH). |
| 1.70 | 2 | F | F | 1 | 2-SCF₃ | | 1.6 (6 H, s, Me), 3.2 (2 H, s, CH₂), 7.85 (2 H, m, CH), 7.975 (1 H, m, CH), 8.45 (1 H, d, CH). |
| 1.71 | 2 | F | Cl | 1 | 2-CN | | 1.55 (3 H, s, Me), 1.6 (3 H, s, Me), 3.21 (1 H, d, CH₂), 3.2 (1 H, d, CH₂), 7.725 (1 H, m, CH), 7.8 (1 H, m, CH), 7.9 (1 H, d, CH), 7.965 (1 H, d, CH). |
| 1.72 | 2 | F | F | 1 | 2-CN | | 1.6 (6 H, s, Me), 3.3 (2 H, s, CH₂), 7.825 (2 H, m, CH), 7.925 (2 H, m, CH). |
| 1.73 | 2 | F | Cl | 1 | 2-F | | 1.55 (3 H, s, Me), 1.6 (3 H, s, Me), 3.1 (1 H, d, CH₂), 3.25 (1 H, d, CH₂), 7.25 (1 H, m, CH), 7.325 (1 H, m, CH), 7.6 (1 H, m, CH), 7.725 (1 H, m, CH). |
| 1.74 | 2 | F | Cl | 1 | 2-CH₃ | | 1.525 (3 H, s, Me), 1.55 (3 H, s, Me), 2.675 (3 H, d, Me), 2.925 (1 H, d, CH₂), 3.2 (1 H, d, CH₂), 7.325 (1 H, d, CH), 7.375 (1 H, m, CH), 7.475 (1 H, m, CH), 7.75 (1 H, d, CH). |
| 1.75 | 2 | F | Cl | 1 | H | | 1.525 (3 H, s, Me), 1.55 (3 H, s, Me), 2.9 (1 H, d, CH₂), 3.15 (1 H, d, CH₂), 7.55-7.65 (3 H, m, CH), 7.8 (2 H, d, CH). |

TABLE 27-continued

Compounds of formula I.3

| No. | m | R⁵ | R⁶ | n | R | M.p. [° C.] | ¹H-NMR (400 MHz, CDCl₃) |
|---|---|---|---|---|---|---|---|
| 1.76 | 2 | F | F | 1 | 3,5-OCH₃ | | 1.575 (6 H, s, Me), 3.125 (2 H, s, CH₂), 3.85 (6 H, s, Me), 6.7 (1 H, s, CH), 6.8 (2 H, s, CH). |
| 1.77 | 2 | F | F | 1 | H | | 1.525 (6 H, s, Me), 3.125 (2 H, s, CH₂), 7.55 (2 H, m, CH), 7.65 (1 H, m, CH), 7.7 (2 H, m, CH). |
| 1.78 | 2 | H | Br | 1 | 2-OCHF₂ | | 1.4 (3 H, s, Me), 1.5 (3 H, s, Me), 2.85 (1 H, d, CH₂), 3.15 (1 H, d, CH₂), 6.55 (1 H, t, CH), 6.55 (1 H, s, CH), 7.2 (1 H, d CH), 7.3-7.4 (1 H, m, CH), 7.45-7.5 (1 H, m, CH), 7.95 (1 H, d, CH). |
| 1.79 | 2 | H | Br | 1 | 2-CF₂ | | 1.42 (3 H, s, Me), 1.5 (3 H, s, Me), 2.9 (1 H, d, CH₂), 3.15 (1 H, d, CH₂), 6.45 (1 H, s, CH), 7.55-7.6 (1 H, m, CH), 7.7-7.75 (2 H, m, CH), 8.22 (1 H, d, CH). |
| 1.80 | 2 | H | Br | 1 | 2-F,6-CF₃ | | 1.55 (3 H, s, Me), 1.57 (3 H, s, Me), 3.2 (1 H, d, CH₂), 3.25 (1 H, d, CH₂), 6.7 (1 H, s, CH), 7.4-7.5 (1 H, m, CH), 7.58-7.65 (2 H, m, CH). |
| 1.81 | 2 | H | Br | 1 | H | | 1.32 (3 H, s, Me), 1.45 (3 H, s, Me), 2.5 (1 H, d, CH₂), 3.0 (1 H, d, CH₂), 6.05 (1 H, s, CH), 7.4-7.5 (3 H, m, CH), 7.6-7.65 (2 H, m, CH). |
| 1.82 | 2 | H | Br | 1 | 2-F | | 1.4 (3 H, s, Me), 1.5 (3 H, s, Me), 2.8 (1 H, d, CH₂), 3.1 (1 H, d, CH₂), 6.42 (1 H, s, CH), 7.1 (1 H, t, CH), 7.27 (1 H, m, CH), 7.4-7.5 (1 H, m, CH), 7.85 (1 H, m, CH). |
| 1.83 | 2 | H | Br | 1 | 2-CN | | 1.45 (3 H, s, Me), 1.55 (3 H, s, Me), 3.02 (1 H, d, CH₂), 3.2 (1 H, d, CH₂), 6.4 (1 H, s, CH), 7.55-7.6 (1 H, m, CH), 7.7-7.8 (2 H, m, CH), 8.1 (1 H, d, CH). |
| 1.84 | 2 | H | Br | 1 | 3,5-OCH₃ | | 1.35 (3 H, s, Me), 1.45 (3 H, s, Me), 2.5 (1 H, d, CH₂), 3.0 (1 H, d, CH₂), 3.8 (6 H, s, Me), 5.9 (1 H, s, CH), 6.5 (1 H, s, CH), 7.73 (2 H, s, CH). |
| 1.85 | 2 | H | —SCF₃ | 1 | 2,6-F | | 1.49 (3 H, s, Me), 1.52 (3 H, s, Me), 3.01 (1 H, d, CH₂), 3.18 (1 H, d, CH₂), 6.04 (1 H, s, CH), 7.04 (2 H, m, CH), 7.49 (1 H, m, CH). |
| 1.86 | 2 | H | —CH₂(1-pyrazolyl | 1 | 2,6-F | | 1.43 (3 H, s, Me), 1.47 (3 H, s, Me), 2.9 (1 H, d, CH₂), 2.95 (1 H, d, CH₂), 4.95 (1 H, dd, CH₂), 5.30 (1 H, dd, CH₂), 5.72 (1 H, dd, CH), 6.15 (1 H, t, CH), 6.95-7.0 (2 H, m, CH), 7.35-7.4 (1 H, m, CH), 7.45 (1 H, d, CH), 7.5 (1 H, d, CH). |
| 1.87 | 2 | H | —CH₂(1-imidazolyl) | 1 | 2,6-F | | 1.45 (3 H, s, Me), 1.5 (3 H, s, Me), 2.9 (1 H, d, CH₂), 3.0 (1 H, d, CH₂), 2.98 (1 H, d, CH₂), 4.90 (1 H, dd, CH₂), 5.05 (1 H, dd, CH), 5.55 (1 H, dd, CH), 6.9 (1 H, s, CH), 6.95-7.05 (2 H, m, CH), 7.35-7.45 (1 H, m, CH), 7.5 (1 H, s, CH). |

TABLE 27-continued

Compounds of formula I.3

| No. | m | R⁵ | R⁶ | n | R | M.p. [° C.] | ¹H-NMR (400 MHz, CDCl₃) |
|---|---|---|---|---|---|---|---|
| 1.88 | 2 | H | —CH₂(1-indazolyl) | 1 | 2,6-F | | 1.25 (3 H, s, Me), 1.3 (3 H, s, Me), 2.8 (1 H, d, CH₂), 2.85 (1 H, d, CH₂), 5.20 (1 H, dd, CH₂), 5.58 (1 H, dd, CH₂), 5.95 (1 H, dd, CH), 6.95-7.0 (2 H, m, CH), 7.0-7.1 (1 H, m, CH), 7.25-7.3 (1 H, m, CH), 7.30-7.40 (1 H, m, CH), 7.6-7.7 (2 H, m, CH), 8.0 (1 H, s, CH). |
| 1.89 | 2 | H | —CH₂(4,5-dihydro-pyrazol-1-yl) | 1 | 2,6-F | | 1.43 (3 H, s, Me), 1.46 (3 H, s, Me), 2.55-2.7 (2 H, m, CH₂), 2.9 (1 H, dd, CH₂), 3.05 (1 H, d, CH₂), 3.10 (1 H, d, CH₂), 3.2 (1 H, dd, CH₂), 6.83 (1 H, s, CH), 6.95-7.0 (2 H, m, CH), 7.30-7.40 (1 H, m, CH). |
| 1.90 | 2 | H | —CH₂(1,2,4-triazol-1-yl) | 1 | 2,6-F | | 1.45 (3 H, s, Me), 1.48 (3 H, s, Me), 2.90 (1 H, d, CH₂), 2.98 (1 H, d, CH₂), 5.10 (1 H, dd, CH₂), 5.33 (1 H, dd, CH₂), 5.72 (1 H, dd, CH), 6.95-7.2 (2 H, m, CH), 7.35-7.45 (1 H, m, CH), 7.9 (1 H, s, CH), 8.15 (1 H, s, CH). |
| 1.91 | 2 | H | Cl | 1 | 2-F,6-CF₃ | | 1.55 (3 H, s, Me), 1.56 (3 H, s, Me), 3.2 (1 H, d, CH₂), 3.25 (1 H, d, CH₂), 6.61 (1 H, s, CH), 7.45 (1 H, m, CH), 7.625 (2 H, m, CH). |
| 1.92 | 2 | F | F | 1 | 2-CH₃ | | 1.6 (6 H, s, Me), 2.65 (3 H, s, Me), 3.2 (2 H, s, CH₂), 7.35-7.4 (2 H, m, CH), 7.5-7.55 (1 H, m, CH), 7.65 (1 H, d, CH). |
| 1.93 | 2 | H | F | 1 | 2-CH₃ | | 1.58 (3 H, s, Me), 1.60 (3 H, s, Me), 2.55 (3 H, s, Me), 3.1 (1 H, d, CH₂), 3.2 (1 H, d, CH₂), 6.73 (1 H, d, CH), 7.32 (1 H, m, CH), 7.4 (1 H, m, CH), 7.45 (1 H, m, CH), 7.66 (1 H, d, CH). |
| 1.94 | 2 | F | F | 1 | 2-F | | 1.55 (6 H, s, Me), 3.2 (2 H, s, CH₂), 7.2-7.25 (1 H, m, CH), 7.3-7.35 (1 H, m, CH), 7.6-7.7 (2 H, m, CH). |
| 1.95 | 2 | F | Cl | 1 | 2-CF₃ | | 1.5 (3 H, s, Me), 1.58 (3 H, s, Me), 3.08 (1 H, d, CH₂), 3.18 (1 H, d, CH₂), 7.65-7.75 (2 H, d, CH), 7.9 (1 H, d, CH), 8.1 (1 H, d, CH). |
| 1.96 | 2 | F | Cl | 1 | 3,5-OCH₃ | | 1.45 (3 H, s, Me), 1.5 (3 H, s, Me), 2.8 (1 H, d, CH₂), 3.1 (1 H, d, CH₂), 3.8 (6 H, s, Me), 6.6 (1 H, s, CH), 6.82 (2 H, s, CH). |
| 1.97 | 2 | F | Cl | 1 | 2-SOCF₃ | | 1.6 (3 H, s, Me), 1.61 (3 H, s, Me), 3.16 (1 H, d, CH₂), 3.3 (1 H, d, CH₂), 7.87 (1 H, m, CH), 7.94 (1 H, m, CH), 7.95 (1 H, m, CH), 8.49 (1 H, d, CH). |
| 1.98 | 2 | H₃C-O-C(=O)-CH₃ (attached) | | 1 | 2,6-F | | 1.5 (6 H, s, Me), 2.1 (3 H, s, Me), 2.3 (3 H, s, Me), 3.05 (2 H, s, CH₂), 7.0-7.05 (2 H, m, CH), 7.4-7.5 (1 H, m, CH). |

TABLE 27-continued

Compounds of formula I.3

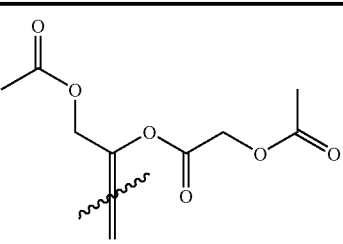

| No. | m | R⁵ | R⁶ | n | R | M.p. [° C.] | ¹H-NMR (400 MHz, CDCl₃) |
|---|---|---|---|---|---|---|---|
| 1.99 | 2 | 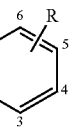 | | 1 | 2,6-F | | 1.55 (6 H, s, Me), 2.05 (3 H, s, Me), 2.2 (3 H, s, Me), 3.05 (2 H, s, CH₂), 4.7 (2 H, s, CH₂), 4.88 (2 H, s, CH₂), 7.0-7.05 (2 H, m, CH), 7.4-7.5 (1 H, m, CH). |
| 1.100 | 2 | 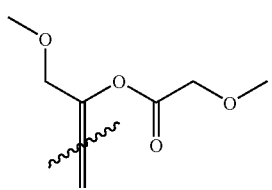 | | 1 | 2,6-F | | 1.5 (6 H, s, Me), 3.05 (2 H, s, CH₂), 3.25 (3 H, s, Me), 3.55 (3 H, s, Me), 4.15 (2 H, s, CH₂), 4.35 (2 H, s, CH₂), 7.0-7.05 (2 H, m, CH), 7.45-7.5 (1 H, m, CH). |
| 1.101 | 2 | H | Br | 1 | 2-OCH₃ | | 1.32 (3 H, s, Me), 1.43 (3 H, s, Me), 2.52 (1 H, d, CH₂), 3.04 (1 H, d, CH₂), 3.88 (3 H, s, Me), 6.73 (1 H, s, CH), 6.91 (1 H, d, CH), 7.07 (1 H, t, CH), 7.42 (1 H, m, CH), 7.85 (1 H, m, CH). |
| 1.102 | 2 | H | Br | 1 | 2,6-F,3-CH₃ | | 1.50 (3 H, s, Me), 1.53 (3 H, s, Me), 2.28 (3 H, s, Me), 3.08 (1 H, d, CH₂), 3.21 (1 H, d, CH₂), 6.47 (1 H, s, CH), 6.92 (1 H, m, CH), 7.29 (1 H, m, CH). |
| 1.103 | 2 | H | Br | 1 | 2,3-OCH₂OCH₂—, 5-F | | 1.43 (3 H, s, Me), 1.49 (3 H, s, Me), 2.83 (1 H, d, CH₂), 3.14 (1 H, d, CH₂), 4.88 (2 H, m, CH₂), 5.29 (2 H, m, CH₂), 6.55 (1 H, s, CH), 6.81 (1 H, m, CH), 7.45 (1 H, m, CH). |
| 1.104 | 2 | H | F | 1 | 2-OCH₃ | | 1.51 (3 H, s, Me), 1.53 (3 H, s, Me), 3.10 (2 H, s, CH₂), 3.90 (3 H, s, Me), 6.97 (1 H, d, CH), 6.99 (1 H, d, CH), 7.08 (1 H, t, CH), 7.49 (1 H, t, CH), 7.62 (1 H, d, CH). |
| 1.105 | 2 | H | F | 1 | 2,6-F,3-CH₃ | | 1.54 (3 H, s, Me), 1.56 (3 H, s, Me), 2.28 (3 H, s, Me), 3.21 (2 H, s, CH₂), 6.72 (1 H, d, CH), 6.93 (1 H, m, CH), 7.34 (1 H, m, CH). |
| 1.106 | 2 | H | F | 1 | 2,3-OCH₂OCH₂—, 5-F | | 1.53 (3 H, s, Me), 1.55 (3 H, s, Me), 3.14 (2 H, dd, CH₂), 4.90 (2 H, dd, CH₂), 5.29 (2 H, m, CH₂), 6.85 (1 H, d, CH), 6.87 (1 H, m, CH), 7.24 (1 H, m, CH). |
| 1.107 | 2 | F | F | 1 | 2-OCH₃ | | 1.54 (6 H, s, Me), 3.14 (2 H, s, CH₂), 3.90 (3 H, s, Me), 7.06 (2 H, m, CH), 7.56 (2 H, m, CH). |
| 1.108 | 2 | F | F | 1 | 2,6-F,3-CH₃ | | 1.56 (6 H, s, Me), 2.29 (3 H, s, Me), 3.19 (2 H, s, CH₂), 6.95 (1 H, m, CH), 7.42 (1 H, m, CH). |

TABLE 27-continued

Compounds of formula I.3

| No. | m | R⁵ | R⁶ | n | R | M.p. [° C.] | ¹H-NMR (400 MHz, CDCl₃) |
|---|---|---|---|---|---|---|---|
| 1.109 | 2 | F | F | 1 | 2,3-OCH₂OCH₂—, 5-F | | 1.55 (6 H, s, Me), 3.16 (2 H, s, CH₂), 4.93 (2 H, s, CH₂), 5.27 (2 H, s, CH₂), 6.95 (1 H, m, CH), 7.19 (1 H, m, CH). |
| 1.110 | 2 | H | F | 1 | 2-O(SO₂)CH₃ | | 1.52 (3 H, s, Me), 1.53 (3 H, s, Me), 3.09 (1 H, d, CH₂), 3.16 (1 H, d, CH₂), 3.30 (3 H, s, Me), 6.83 (1 H, d, CH), 7.46 (1 H, m, CH), 7.59 (2 H, d, CH), 7.75 (1 H, d, CH). |
| 1.111 | 2 | F | F | 1 | 2-O(SO₂)CH₃ | | 1.55 (6 H, s, Me), 3.12 (2 H, s, CH₂), 3.31 (3 H, s, Me), 7.46 (1 H, m, CH), 7.69 (2 H, m, CH), 7.72 (1 H, d, CH). |
| 1.112 | 2 | H | F | 1 | —OCH₂C≡CH | | 1.50 (3 H, s, Me), 1.52 (3 H, s, Me), 2.55 (1 H, t, CH), 3.09 (2 H, s, CH₂), 4.76 (1 H, dd, CH₂), 4.82 (1 H, dd, CH₂), 6.96 (1 H, d, CH), 7.13 (2 H, m, CH), 7.50 (1 H, t, CH), 7.63 (1 H, d, CH). |
| 1.113 | 2 | H | CF₃ | 1 | 2,6-F | | 1.52 (3 H, s, Me), 1.53 (3 H, s, Me), 3.05-3.25 (2 H, m, CH₂), 5.9-6.1 (1 H, m, CH), 6.95-7.15 (2 H, m, CH), 7.4-7.6 (1H, m, CH). |
| 1.114 | 2 | F | F | 1 | 2,5-F | 77-79 | 1.57 (6 H, s, Me), 3.19 (2 H, s, CH₂), 7.1-7.25 (1 H, m, CH), 7.3-7.45 (2 H, m, CH). |
| 1.115 | 2 | F | F | 1 | 3,5-F | 108-110 | 1.61 (6 H, s, Me), 3.21 (2 H, s, CH₂), 7.1-7.2 (1 H, m, CH), 7.25-7.4 (2 H, m, CH). |
| 1.116 | 2 | F | F | 1 | 2,3-F | 106 | 1.57 (6 H, s, Me), 3.2 (2 H, s, CH₂), 7.28 (1 H, m, CH), 7.4-7.5 (2 H, m, CH). |
| 1.117 | 2 | F | F | 1 | 2-phenyl | 89 | 1.52 (3 H, s, Me), 1.61 (3 H, s, Me), 3.03 (2 H, s, CH₂), 7.35-7.45 (6 H, m, CH), 7.58 (1 H, t, CH), 7.65 (1 H, t, CH), 7.85 (1 H, d, CH). |
| 1.118 | 2 | F | F | 1 | 2,4-F | 92 | 1.55 (6 H, s, Me), 3.2 (2 H, s, CH₂), 6.98 (1 H, t, CH), 7.06 (1 H, t, CH), 7.65 (1 H, q, CH). |
| 1.119 | 2 | F | F | 1 | 2-F, 4-CO₂CH₃ | 90-95 | 1.56 (6 H, s, Me), 3.19 (2 H, s, CH₂), 3.97 (3 H, s, Me), 7.7-7.8 (1 H, m, CH), 7.85-7.93 (1 H, m, CH), 7.95-8.05 (1 H, m, CH). |
| 1.120 | 2 | F | F | 1 | 2-F, 4-CO₂CH₂CH₃ | 99-101 | 1.41 (3 H, t, Me), 1.56 (6 H, s, Me), 3.19 (2 H, s, CH₂), 4.41 (2 H, q, CH₂), 7.72 (1 H, m, CH), 7.85 (1 H, m, CH), 7.99 (1 H, m, CH). |
| 1.121 | 2 | H | Cl | 1 | 2F, 4-CO₂CH₃ | 148-151 | 1.50 (3 H, s, Me), 1.54 (3 H, s, Me), 3.08 (1 H, d, CH₂), 3.14 (1 H, d, CH₂), 3.95 (3 H, s, Me), 6.43 (1 H, s, CH), 7.81 (1 H, m, CH), 7.89 (1 H, m, CH), 7.95 (1 H, m, CH). |
| 1.122 | 2 | H | Cl | 1 | 2F, 4-CO₂CH₂CH₃ | 112-114 | 1.41 (3 H, t, Me), 1.50 (3 H, m, Me), 1.54 (3 H, m, Me), 3.08 (1 H, m, CH₂), 3.14 (1 H, m, CH₂), 4.41 (2 H, q, CH₂), 6.43 (1 H, s, CH), 7.81 (1 H, m, CH), 7.89 (1 H, m, CH), 7.95 (1 H, m, CH). |

TABLE 27-continued

Compounds of formula I.3

| No. | m | R⁵ | R⁶ | n | R | M.p. [° C.] | ¹H-NMR (400 MHz, CDCl₃) |
|---|---|---|---|---|---|---|---|
| 1.123 | 2 | H | Cl | 1 | 3,5-F | 154-156 | 1.49 (3 H, m, Me), 1.53 (3 H, m, Me), 3.05 (1 H, m, CH₂), 3.10 (1 H, m, CH₂), 5.96 (1 H, s, CH), 6.96 (1 H, m, CH), 7.19 (2 H, m, CH). |
| 1.124 | 2 | H | Cl | 1 | 2,5-F | 132-134 | 1.50 (3 H, m, Me), 1.54 (3 H, m, Me), 3.08 (1 H, m, CH₂), 3.13 (1 H, m, CH₂), 6.37 (1 H, s, CH), 7.17 (2 H, m, CH), 7.51 (1 H, m, CH). |
| 1.125 | 2 | F | Cl | 1 | 3,5-F | 109-111 | 1.54 (6 H, m, Me), 3.07 (1 H, m, CH₂), 3.16 (1 H, m, CH₂), 7.04 (1 H, m, CH), 7.2-7.35 (2 H, m, CH). |
| 1.126 | 2 | F | Cl | 1 | 2,5-F | 103-105 | 1.50 (3 H, m, Me), 1.60 (3 H, m, Me), 3.05-3.3 (2 H, m, CH₂), 7.18 (1 H, m, CH), 7.28 (1 H, m, CH), 7.41 (1 H, m, CH). |
| 1.127 | 2 | F | Cl | 1 | 2-F, 4-CO₂CH₃ | 125-127 | 1.50-1.60 (6 H, m, Me), 3.05-3.3 (2 H, m, CH₂), 3.96 (3 H, s, Me), 7.76 (1 H, m, CH), 7.86 (1 H, m, CH), 7.96 (1 H, m, CH). |
| 1.128 | 2 | F | Cl | 1 | 2-F, 4-CO₂CH₂CO₃ | 91-93 | 1.41 (3 H, t, Me), 1.50-1.75 (6 H, m, Me), 3.05-3.3 (2 H, m, CH₂), 4.41 (2 H, q, CH₂), 7.78 (1 H, m, CH), 7.86 (1 H, m, CH), 7.94 (1 H, m, CH). |
| 1.129 | 2 | H | Cl | 1 | 2-phenyl | | 1.4 (3 H, s, Me), 1.45 (3 H, s, Me), 2.82 (1 H, d, CH₂), 3.05 (1 H, d, CH₂), 6.18 (1 H, s, CH), 7.3-7.5 (8 H, m, CH), 8.0 (1 H, m, CH). |
| 1.130 | 2 | H | Cl | 1 | 2,4-F | | 1.5 (3 H, s, Me), 1.55 (3 H, s, Me), 3.07 (1 H, d, CH₂), 3.15 (1 H, d, CH₂), 6.32 (1 H, s, CH), 6.9 (1 H, dt, CH), 7.02 (1 H, t, CH), 7.8 (1 H, q, CH). |
| 1.131 | 2 | H | Cl | 1 | 2,3-F | | 1.5 (3 H, s, Me), 1.55 (3 H, s, Me), 3.1 (1 H, d, CH₂), 3.2 (1 H, d, CH₂), 6.43 (1 H, s, CH), 7.25-7.4 (2 H, m, CH), 7.6 (1 H, t, CH). |
| 1.132 | 2 | H | Br | 1 | 2,3-F | 115-116 | 1.55 (3 H, s, Me), 1.60 (3 H, s, Me), 2.97 (1 H, d, CH₂), 3.1 (1 H, d, CH₂), 6.47 (1 H, s, CH), 7.2-7.4 (2 H, m, CH), 7.7 (1 H, t, CH). |
| 1.133 | 2 | F | Cl | 1 | 2,4-F | 102-103 | 1.52 (3 H, s, Me), 1.57 (3 H, s, Me), 3.12 (1 H, d, CH₂), 3.22 (1 H, d, CH₂), 6.95 (1 H, dt, CH), 7.05 (1 H, t, CH), 7.7 (1 H, m, CH). |
| 1.134 | 2 | H | Br | 1 | 3,5-F | 155-157 | 1.43 (3 H, s, Me), 1.51 (3 H, s, Me), 2.88 (1 H, d, CH₂), 3.10 (1 H, d, CH₂), 6.00 (s, 1 H, CH), 6.93 (1 H, m, CH), 7.1-7.3 (2 H, m, CH). |
| 1.135 | 2 | H | Br | 1 | 2,5-F | 135-138 | 1.44 (3 H, Me), 1.51 (3 H, m, Me), 2.85-3.0 (1 H, m, CH₂), 3.1-3.25 (1 H, m, CH₂), 6.93 (1 H, s, CH), 7.05-7.2 (2 H, m, CH), 7.57 (1 H, m, CH). |

TABLE 27-continued

Compounds of formula I.3

$$H_3C\text{-}C(CH_3)\text{-}CH_2\text{-}C(S(O)_m\text{-}[CR^5R^6]_n\text{-}C_6H_4\text{-}R)\text{=}N\text{-}O$$

| No. | m | $R^5$ | $R^6$ | n | R | M.p. [°C.] | $^1$H-NMR (400 MHz, CDCl$_3$) |
|---|---|---|---|---|---|---|---|
| 1.136 | 2 | H | Br | 1 | 2-F, 4-CO$_2$CH$_3$ | 162-167 | 1.44 (3 H, s, Me), 1.51 (3 H, s, Me), 2.94 (1 H, d, CH$_2$), 3.12 (1 H, d, CH$_2$), 3.95 (3 H, s, Me), 6.45 (1 H, s, CH), 7.77 (1 H, m, CH), 7.94 (2 H, m, CH). |
| 1.137 | 2 | H | Br | 1 | 2F, 4-CO$_2$CH$_2$CH$_3$ | 127-129 | 1.40 (3 H, t, Me), 1.44 (3 H, m, Me), 1.51 (3 H, m, Me), 2.95 (1 H, d, CH$_2$), 3.12 (1 H, d, CH$_2$), 4.40 (2 H, q, CH$_2$), 6.45 (1 H, s, CH), 7.77 (1 H, m, CH), 7.94 (2 H, m, CH). |
| 1.138 | 2 | Me | F | 1 | H | 91-93 | 1.37 (3 H, s, Me), 1.40 (3 H, s, Me), 2.2 (3 H, d, Me), 2.52 (2 H, d, CH$_2$), 2.92 (2 H, d, CH$_2$), 7.45-7.55 (3 H, m, CH), 7.6-7.7 (2 H, m, CH). |
| 1.139 | 1 | H | CF$_3$ | 1 | 2,6-F | | 1.50 (3 H, Me), 1.52 (3 H, s, Me), 2.90 (1 H, d, CH$_2$), 3.16 (1 H, d, CH$_2$), 3.56 (1 H, m, CH), 7.06 (2 H, m, CH), 7.48 (1 H, m, CH). |
| 1.140 | 1 | H and CF$_3$ mixture | CF$_3$ and H mixture | 1 | 2,6-F | | 1.07 (2 H, s, Me), 1.4-1.7 (4 H, m, Me), 2.7-2.9 (1 H, m, CH$_2$), 3.1-3.3 (1 H, m, CH$_2$), 5.02 (0.5 H, m, CH), 5.36 (0.5 H, m, CH), 7.02 (2 H, m, CH), 7.45 (1 H, m, CH). |
| 1.141 | 2 | H | Cl | 1 | 2-OCH$_3$ | 126-127 | 1.41 (3 H, s, Me), 1.48 (3 H, s, Me), 2.76 (1 H, d, CH$_2$), 3.08 (1 H, d, CH$_2$), 3.89 (3 H, s, Me), 6.70 (1 H, s, CH), 6.95 (1 H, d, CH), 7.08 (1 H, t, CH), 7.44 (1 H, t, CH), 7.77 (1 H, d, CH). |
| 1.142 | 2 | F | Cl | 1 | 2-OCH$_3$ | | 1.50 (3 H, s, Me), 1.51 (3 H, s, Me), 3.01 (1 H, d, CH$_2$), 3.15 (1 H, d, CH$_2$), 3.91 (3 H, s, Me), 7.05 (2 H, m, CH), 7.52 (1 H, t, CH), 7.61 (1 H, d, CH). |
| 1.143 | 2 | H | Cl | 1 | 2-OCF$_3$ | | 1.48 (3 H, s, Me), 1.53 (3 H, s, Me), 3.00 (1 H, d, CH$_2$), 3.14 (1 H, d, CH$_2$), 6.45 (1 H, s, CH), 7.35 (1 H, d, CH), 7.44 (1 H, t, CH), 7.55 (1 H, t, CH), 7.93 (1 H, d, CH). |
| 1.144 | 2 | F | Cl | 1 | 2-OCF$_3$ | | 1.52 (3 H, s, Me), 1.55 (3 H, s, Me), 3.10 (1 H, d, CH$_2$), 3.21 (1 H, d, CH$_2$), 7.43 (2 H, m, CH), 7.63 (1 H, t, CH), 7.84 (1 H, d, CH). |
| 1.145 | 2 | H | Cl | 1 | 2,6-F,3-CH$_3$ | | 1.53 (3 H, s, Me), 1.54 (3 H, s, Me), 2.28 (3 H, s, Me), 3.19 (2 H, q, CH$_2$), 6.42 (1 H, s, CH), 6.92 (1 H, t, CH), 7.31 (1 H, q, CH). |
| 1.146 | 2 | F | Cl | 1 | 2,6-F,3-CH$_3$ | 103-104 | 1.53 (3 H, s, Me), 1.55 (3 H, s, Me), 2.28 (3 H, s, Me), 3.15 (1 H, d, CH$_2$), 3.23 (1 H, d, CH$_2$), 6.93 (1 H, t, CH), 7.38 (1 H, m, CH). |
| 1.147 | 2 | H | Cl | 1 | 2,3-OCH$_2$OCH$_2$—, 5-F | 136-137 | 1.49 (3 H, s, Me), 1.52 (3 H, s, Me), 2.98 (1 H, d, CH$_2$), 3.15 (1 H, d, CH$_2$), 4.89 (2 H, s, CH$_2$), 5.30 (2 H, s, CH$_2$), 6.52 (1 H, s, CH), 6.83 (1 H, dd, CH), 7.38 (1 H, dd, CH). |
| 1.148 | 2 | Cl | F | 1 | 2,3-F | | 1.57 (6 H, s, Me), 3.12 (1 H, d, CH$_2$), 3.22 (1 H, d, CH$_2$), 7.28 |

TABLE 27-continued

Compounds of formula I.3

| No. | m | R⁵ | R⁶ | n | R | M.p. [° C.] | ¹H-NMR (400 MHz, CDCl₃) |
|-----|---|----|----|---|---|---|---|
| | | | | | | | (1 H, m, CH), 7.38-7.5 (2 H, m, CH). |
| 1.149 | 2 | Cl | F | 1 | 2-phenyl | | 1.42 (3 H, s, Me), 1.48 (3 H, s, Me), 2.88 (1 H, dd, CH₂), 3.05 (1 H, dd, CH₂) 7.20-7.45 (6 H, m, CH), 7.50 (2 H, m, CH), 7.90 (1 H, d, CH). |
| 1.150 | 2 | H | Br | 1 | 2,4-F | 86-88 | 1.45 (3 H, s, Me), 1.52 (3 H, s, Me), 2.90 (2 H, dd, CH₂), 6.38 (1 H, s, CH), 6.90 (1 H, dt, CH), 7.05 (1 H, t, CH), 7.88 (1 H, q, CH). |
| 1.151 | 2 | H | Br | 1 | 2-phenyl | 120-122 | 1.34 (3 H, s, Me), 1.43 (3 H, s, Me), 2.62 (1 H, d, CH₂), 3.00 (1 H, d, CH₂), 6.2 (1 H, s, CH), 7.3-7.5 (8 H, m, CH), 8.1 (1 H, m, CH). |
| 1.152 | 2 | F | F | 1 | 2,3-OCF₂O— | | 1.57 (6 H, s, Me), 3.2 (2 H, s, CH₂), 7.26 (1 H, m, CH), 7.4 (2 H, m, CH). |

Key:
Me = methyl;
s = singlet;
m = multiplet;
d = doublet;
dd = double doublet;
t = triplet;
q = quartet;
dt = double triplet;
bs = broad singlet;
bm = broad multiplet;
bq = broad quartet.

TABLE 28

Compounds of formula I.4

| No. | m | R⁵ | R⁶ | n | R¹⁷ | R¹⁸ | R¹⁹ | M.p. [° C.] | ¹H-NMR (400 MHz, CDCl₃) |
|-----|---|----|----|---|-----|-----|-----|---|---|
| 2.01 | 2 | F | F | 1 | CH₃ | CF₃ | —OCH₂CF₃ | 103 | 1.5 (6H, s, Me), 3.15 (2H, s, CH₂), 3.85 (3H, s, Me), 4.68 (2H, q, CH₂). |
| 2.02 | 2 | H | F | 1 | CH₃ | CF₃ | Cl | 116 | 1.55 (3H, s, Me), 1.55 (3H, s, Me), 3.15 (1H, d, CH₂), 3.2 (1H, d, CH₂), 4.0 (3H, s, Me), 6.55 (1H, d, CH). |
| 2.03 | 2 | F | F | 1 | CH₃ | CF₃ | Cl | | 1.55 (6H, s, Me), 3.2 (2H, s, CH₂), 4.0 (3H, s, Me). |
| 2.04 | 2 | H | Cl | 1 | CH₃ | CF₃ | —OCH₂CF₃ | | 1.52 (3H, s, Me), 1.53 (3H, s, Me), 3.15 (1H, d, CH₂), 3.2 (1H, d, CH₂), 3.85 (3H, s, Me), 4.7-4.82 (2H, m, CH₂), 6.2 (1H, s, CH). |

TABLE 28-continued

Compounds of formula I.4

| No. | m | R⁵ | R⁶ | n | R¹⁷ | R¹⁸ | R¹⁹ | M.p. [° C.] | ¹H-NMR (400 MHz, CDCl₃) |
|---|---|---|---|---|---|---|---|---|---|
| 2.05 | 2 | H | Cl | 1 | CH₃ | CF₃ | Cl | 98 | 1.55 (3H, s, Me), 1.56 (3H, s, Me), 3.15 (1H, d, CH₂), 3.25 (1H, d, CH₂), 3.95 (3H, s, Me), 6.2 (1H, s, CH). |
| 2.06 | 2 | H | —COCHF₂ | 1 | CH₃ | CF₃ | —OCH₂CF₃ | | 1.4 (3H, s, Me), 1.45 (3H, s, Me), 2.95 (1H, d, CH₂), 3.05 (1H, d, CH₂), 3.75 (3H, s, Me), 4.7 (2H, q, CH₂), 5.95 (1H, t, CH). |
| 2.07 | 2 | H | —CO$^c$Pr | 1 | CH₃ | CF₃ | —OCH₂CF₃ | | 1.02 (2H, m, CH₂), 1.2 (2H, m, CH₂), 1.49 (3H, s, Me), 1.51 (3H, s, Me), 1.87 (1H, m, CH), 3.14 (1H, d, CH₂), 3.31 (1H, d, CH₂), 3.87 (3H, s, Me), 4.54 (1H, m, CH₂), 4.68 (1H, m, CH₂), 5.9 (1H, s, CH). |
| 2.08 | 2 | H | —COCH₃ | 1 | CH₃ | CF₃ | —OCH₂CF₃ | | mixture of keto-enol-tautomers ratio 1:1. ketone signals: 1.45 (3H, s, Me), 1.5 (3H, s, Me), 1.9 (3H, s, Me), 3.15 (1H, d, CH₂), 3.25 (1H, d, CH₂), 3.8 (3H, s, Me), 4.5-4.75 (2H, m, CH₂), 5.7 (1H, s, CH). enol signals: 1.53 (6H, s, Me), 2.25 (3H, s, Me), 3.0 (3H, s, CH₂ + OH), 3.85 (3H, s, Me), 4.7-4.75 (2H, m, CH₂). |
| 2.09 | 2 | Br | Br | 1 | CH₃ | CF₃ | —OCH₂CF₃ | | 1.57 (6H, s, Me), 3.4 (2H, s, CH₂), 3.88 (3H, s, Me), 4.7 (2H, q, CH₂). |
| 2.10 | 2 | H | Br | 1 | CH₃ | CF₃ | —OCH₂CF₃ | | 1.5 (3H, s, Me), 1.53 (3H, s, Me), 3.1 (1H, d, CH₂), 3.18 (1H, d, CH₂), 3.83 (3H, s, Me), 4.7-4.9 (2H, m, CH₂), 6.22 (1H, s, CH). |
| 2.11 | 2 | F | F | 1 | CH₃ | CF₃ | —OCHF₂ | | 1.55 (6H, s, Me), 3.18 (2H, s, CH₂), 3.9 (3H, s, Me), 6.8 (1H, dd, CH). |
| 2.12 | 2 | F | Cl | 1 | CH₃ | CF₃ | —OCH₂CF₃ | 107-109 | 1.5 (3H, s, Me), 1.53 (3H, s, Me), 3.15 (1H, d, CH₂), 3.2 (1H, d, CH₂), 3.85 (3H, s, Me), 4.52-4.62 (1H, m, CH₂), 4.8-4.9 (1H, m, CH₂). |
| 2.13 | 2 | Cl | Cl | 1 | CH₃ | CF₃ | —OCH₂CF₃ | | 1.55 (6H, s, Me), 3.3 (2H, s, CH₂), 3.85 (3H, s, Me), 4.7 (2H, q, CH₂). |
| 2.14 | 2 | F | Cl | 1 | CH₃ | CF₃ | —OCHF₂ | | 1.5 (3H, s, Me), 1.55 (3H, s, Me), 3.15 (1H, d, CH₂), 3.2 (1H, d, CH₂), 3.9 (3H, s, Me), 6.9 (1H, t, CH). |
| 2.15 | 2 | Cl | Cl | 1 | CH₃ | CF₃ | —OCHF₂ | | 1.55 (6H, s, Me), 3.3 (2H, s, CH₂), 3.9 (3H, s, Me), 6.95 (1H, t, CH). |

TABLE 28-continued

Compounds of formula I.4

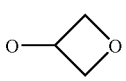

| No. | m | $R^5$ | $R^6$ | n | $R^{17}$ | $R^{18}$ | $R^{19}$ | M.p. [° C.] | $^1$H-NMR (400 MHz, CDCl$_3$) |
|---|---|---|---|---|---|---|---|---|---|
| 2.16 | 2 | H | Cl | 1 | CH$_3$ | CF$_3$ | —OCHF$_2$ | | 1.55 (6H, s, Me), 3.2 (2H, s, CH$_2$), 3.9 (3H, s, Me), 6.2 (1H, s, CH), 6.95 (1H, dd, CH). |
| 2.17 | 2 | F | F | 1 | CH$_3$ | CF$_3$ | —OCH$_2$CH$_3$ | 97-98 | 1.48 (3H, t, Me), 1.55 (6H, s, Me), 3.16 (2H, s, CH$_2$), 3.81 (3H, s, Me), 4.36 (2H, q, CH$_2$). |
| 2.18 | 2 | Cl | Cl | 1 | CH$_3$ | CF$_3$ | —OCH$_2$CH$_3$ | 98-100 | 1.50 (3H, t, Me), 1.55 (6H, s, Me) 3.28 (2H, s, CH$_2$), 3.82 (3H, s, Me), 4.32 (2H, q, CH$_2$). |
| 2.19 | 2 | H | Cl | 1 | CH$_3$ | CF$_3$ | —OCH$_2$CH$_3$ | | 1.53 (3H, t, Me), 1.55 (6H, s, Me), 3.15 (2H, dd, CH$_2$), 3.80 (3H, s, Me), 4.36 (2H, q, CH$_2$), 6.15 (1H, s, CH). |
| 2.20 | 2 | F | Cl | 1 | CH$_3$ | CF$_3$ | —OCH$_2$CH$_3$ | 94-95 | 1.50 (3H, t, Me), 1.53 (6H, s, Me), 3.17 (2H, d, CH$_2$), 3.82 (3H, s, Me), 4.29 (1H, m, CH), 4.38 (1H, m, CH). |
| 2.21 | 2 | F | F | 1 | CH$_3$ | CF$_3$ | —OCH$_2$CHF$_2$ | 82-84 | 1.56 (6H, s, Me), 3.16 (2H, s, CH$_2$), 3.85 (3H, s, Me), 4.50 (2H, dt, CH$_2$), 6.10 (1H, tt, CH). |
| 2.22 | 2 | H | F | 1 | CH$_3$ | CF$_3$ | —OCH$_2$CF$_3$ | | 1.53 (3H, s, Me), 1.54 (3H, s, Me), 3.12 (1H, d, CH$_2$), 3.18 (1H, d, CH$_2$), 3.83 (3H, s, Me), 4.5-4.6 (1H, m, CH$_2$), 4.8-4.9 (1H, m, CH$_2$), 6.6 (1H, d, CH). |
| 2.23 | 2 | F | F | 1 | CH$_3$ | CF$_3$ | —OCH$_3$ | | 1.55 (6H, s, Me), 3.16 (2H, s, CH$_2$), 3.82 (3H, s, Me), 4.11 (3H, s, Me). |
| 2.24 | 2 | H | F | 1 | CH$_3$ | CH$_3$ | —OCH$_2$CF$_3$ | | 1.54 (3H, s, Me), 1.56 (3H, s, Me), 2.31 (3H, s, Me), 3.16 (2H, dd, CH$_2$), 3.70 (3H, s, Me), 4.45-4.55 (1H, m, CH$_2$), 4.65-4.75 (1H, m, CH$_2$), 6.32 (1H, d, CH). |
| 2.25 | 2 | H | F | 1 | CH$_3$ | CF$_3$ | —OCHF$_2$ | | 1.55 (6H, s, Me) 3.15 (1H, d, CH$_2$), 3.2 (1H, d, CH$_2$), 3.9 (3H, s, Me), 6.55 (1H, d, CH), 6.8 (1H, t, CH). |
| 2.26 | 2 | H | Cl | 1 | CH$_3$ | CF$_3$ | —OCH$_3$ | | 1.52 (6H, s, Me), 3.17 (2H, dd, CH$_2$), 3.82 (3H, s, Me), 4.11 (3H, s, Me), 6.14 (1H, s, CH). |
| 2.27 | 2 | H | F | 1 | CH$_3$ | CF$_3$ | (oxetanyl) | 105-107 | 1.54 (3H, s, Me), 1.55 (3H, s, Me), 3.14 (2H, q, CH$_2$), 3.82 (3H, s, Me), 4.73-4.78 (2H, m, CH$_2$), 4.84-4.98 (2H, m, CH$_2$), 5.42-5.51 (1H, m, CH), 6.50 (1H, d, CH). |

TABLE 28-continued

Compounds of formula I.4

| No. | m | $R^5$ | $R^6$ | n | $R^{17}$ | $R^{18}$ | $R^{19}$ | M.p. [° C.] | $^1$H-NMR (400 MHz, CDCl$_3$) |
|---|---|---|---|---|---|---|---|---|---|
| 2.28 | 2 | F | F | 1 | CH$_3$ | CF$_3$ | oxetan-3-yloxy | | 1.55 (6H, s, Me), 3.14 (2H, s, CH$_2$), 3.81 (3H, s, Me), 4.82-4.88 (2H, m, CH$_2$), 4.92-4.98 (2H, m, CH$_2$), 5.36-5.44 (1H, m, CH). |
| 2.29 | 2 | H | Cl | 1 | CH$_3$ | CF$_3$ | oxetan-3-yloxy | | 1.53 (3H, s, Me), 1.54 (3H, s, Me), 3.14 (2H, s, CH$_2$), 3.78 (3H, s, Me), 4.84-4.98 (4H, m, CH$_2$), 5.40-5.46 (1H, m, CH), 6.12 (1H, s, CH). |
| 2.30 | 2 | Cl | Cl | 1 | CH$_3$ | CF$_3$ | oxetan-3-yloxy | | 1.55 (6H, s, Me), 3.26 (2H, s, CH$_2$), 3.74 (3H, s, Me), 4.95 (4H, d, CH$_2$), 5.24-5.31 (1H, m, CH). |
| 2.31 | 2 | H | Cl | 1 | CH$_3$ | CH$_3$ | —OCH$_2$CF$_3$ | | 1.53 (3H, s, Me), 1.55 (3H, s, Me), 2.36 (3H, s, Me), 3.17 (2H, q, CH$_2$), 3.70 (3H, s, Me), 4.53-4.71 (2H, m, CH$_2$), 5.93 (1H, s, CH). |
| 2.32 | 2 | \multicolumn{2}{\|c\|}{H$_3$C–C(=CH$_2$)–O–C(=O)–CH$_3$} | 1 | CH$_3$ | CF$_3$ | —OCH$_2$CF$_3$ | | 1.50 (6H, s, Me), 2.1 (3H, s, Me), 2.3 (3H, s, Me), 2.97 (1H, d, CH$_2$), 3.05 (1H, d, CH$_2$), 3.8 (3H, s, Me), 4.7 (1H, m, CH$_2$), 4.79 (1H, m, CH$_2$). |
| 2.33 | 2 | F | F | 1 | CH$_3$ | CF$_3$ | H | 102-104 | 1.55 (6H, s, Me), 3.17 (2H, s, CH$_2$), 4.03 (3H, s, Me), 7.94 (1H, s, CH). |
| 2.34 | 2 | F | F | 1 | CH$_3$ | —OCHF$_2$ | CF$_3$ | | 1.57 (6H, s, Me), 3.18 (2H, s, CH$_2$), 4.0 (3H, s, Me), 6.93 (1H, t, J = 75 Hz, CH). |
| 2.35 | 1 | H | CF$_3$ | 1 | CH$_3$ | CF$_3$ | OCH$_2$CF$_3$ | | 1.49 (6H, s, Me), 2.7-2.9 (1H, m, CH$_2$), 2.9-3.2 (1H, m, CH$_2$), 3.88 (3H, s, Me), 4.48 (1H, m, CH$_2$), 4.71 (1H, m, CH$_2$), 5.16 (1H, m, CH). |
| 2.36 | 2 | F | F | 1 | CH$_3$ | CF$_3$ | SO$_2{}^i$Pr | | 1.40 (3H, s, Me), 1.42 (3H, s, Me), 1.56 (6H, s, Me), 3.2 (2H, s, CH$_2$), 3.70 (1H, heptet, CH) 4.32 (3H, s, Me). |

Key:
Me = methyl; s = singlet; m = multiplet; d = doublet; dd = double doublet; t = triplet; tt = triplet triplet; q = quartet; dt = double triplet.

TABLE 29

Compounds of formula I.5

| No. | m | $R^5$ | $R^6$ | n | X | $R^{18}$ | $R^{19}$ | M.p. [°C.] | $^1$H-NMR (400 MHz, CDCl$_3$) |
|---|---|---|---|---|---|---|---|---|---|
| 3.01 | 2 | H | F | 1 | S | CH$_3$ | CN | | 1.58 (3H, s, Me), 1.6 (3H, s, Me), 2.7 (3H, s, Me), 3.21 (1H, d, CH$_2$), 3.29 (1H, d, CH$_2$), 6.65 (1H, d, CH). |
| 3.02 | 2 | F | F | 1 | S | CH$_3$ | CN | | 1.6 (6H, s, Me), 2.78 (3H, s, Me), 3.24 (2H, s, CH$_2$). |
| 3.03 | 2 | H | Cl | 1 | O | CH$_3$ | CH$_3$ | 137 | 1.51 (3H, s, Me), 1.55 (3H, s, Me), 2.4 (3H, s, Me), 2.57 (3H, s, Me), 3.075 (1H, d, CH$_2$), 3.2 (1H, d, CH$_2$), 5.9 (1H, s, CH). |
| 3.04 | 2 | Cl | Cl | 1 | O | CH$_3$ | CH$_3$ | 108 | 1.575 (6H, s, Me), 2.5 (3H, s, Me), 2.7 (3H, s, Me), 3.25 (2H, s, CH$_2$). |
| 3.05 | 2 | H | Cl | 1 | O | CH$_3$ | $^c$Pr | 125 | 1.175 (2H, m, CH$_2$), 1.225 (2H, m, CH$_2$), 1.5 (3H, s, Me), 1.55 (3H, s, Me), 2.23 (1H, m, CH), 2.4 (3H, s, Me), 3.025 (1H, d, CH$_2$), 3.2 (1H, d, CH$_2$), 6.0 (1H, s, CH). |
| 3.06 | 2 | Cl | Cl | 1 | O | CH$_3$ | $^c$Pr | 72 | 1.15 (2H, m, CH$_2$), 1.3 (2H, m, CH$_2$), 1.575 (6H, s, Me), 2.475 (3H, s, Me), 2.6 (1H, m, CH), 3.235 (2H, s, CH$_2$). |
| 3.07 | 2 | H | Cl | 1 | O | $^c$Pr | CH$_3$ | 159 | 1.025 (2H, m, CH$_2$), 1.075 (2H, m, CH$_2$), 1.5 (3H, s, Me), 1.55 (3H, s, Me), 1.91 (1H, m, CH), 2.58 (3H, s, Me), 3.06 (1H, d, CH$_2$), 3.2 (1H, d, CH$_2$), 6.025 (1H, s, CH). |

Key:
Me = methyl; s = singlet; m = multiplet; d = doublet.

TABLE 30

Compounds of formula I.6

| No. | m | $R^5$ | $R^6$ | n | X | $R^{18}$ | $R^{19}$ | M.p. [°C.] | $^1$H-NMR (400 MHz, CDCl$_3$) |
|---|---|---|---|---|---|---|---|---|---|
| 4.01 | 2 | F | Cl | 1 | O | H | CH$_3$ | | 1.535 (3H, s, Me), 1.54 (3H, s, Me), 2.51 (3H, s, Me), 3.11 (1H, d, CH$_2$), 3.19 (1H, d, CH$_2$), 6.4 (1H, s, CH). |
| 4.02 | 2 | H | F | 1 | O | H | CH$_3$ | 106 | 1.54 (3H, s, Me), 1.55 (3H, s, Me), 2.5 (3H, s, Me), 3.11 (1H, d, CH$_2$), 3.175 (1H, d, CH), 6.4 (1H, s, CH), 6.52 (1H, d, CH). |
| 4.03 | 2 | F | F | 1 | O | H | CH$_3$ | 91 | 1.55 (6H, s, Me), 2.55 (3H, s, Me), 3.15 (2H, s, CH$_2$), 6.4 (1H, s, CH). |
| 4.04 | 2 | H | F | 1 | N—CH$_3$ | CF$_3$ | H | 117-118 | 1.55 (3H, s, Me), 1.56 (3H, s, Me), 3.17 (1H, d, CH$_2$), 3.25 (1H, d, CH$_2$), 4.01 (3H, s, Me), 6.51 (1H, d, J = 44 Hz, CH), 7.77 (1H, s, CH). |
| 4.05 | 2 | F | F | 1 | N—CH$_3$ | CF$_3$ | H | 101—103 | 1.56 (6H, s, Me), 3.19 (2H, s, CH$_2$), 4.03 (3H, s, Me), 7.81 (1H, s, CH). |

Key:
Me = methyl; s = singlet; d = doublet.

TABLE 31

Compounds of formula I.7

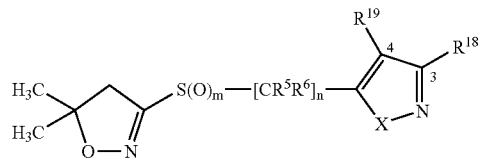

| No. | m | R⁵ | R⁶ | n | X | R¹⁸ | R¹⁹ | M.p. [° C.] | ¹H-NMR (400 MHz, CDCl₃) |
|---|---|---|---|---|---|---|---|---|---|
| 5.01 | 2 | H | Cl | 1 | O | OCH₃ | H |  | 1.53 (3H, s, Me), 1.54 (3H, s, Me), 3.06 (1H, d, CH₂), 3.13 (1H, d, CH₂), 4.0 (3H, s, Me), 6.04 (1H, s, CH), 6.39 (1H, s, CH). |
| 5.02 | 2 | Cl | Cl | 1 | O | OCH₃ | H | 118 | 1.55 (6H, s, Me), 3.11 (2H, s, CH₂), 4.01 (3H, s, Me), 6.49 (1H, s, CH). |
| 5.03 | 2 | H | F | 1 | O | OCH₃ | H | 99 | 1.545 (3H, s, Me), 1.55 (3H, s, Me), 3.1 (1H, d, CH₂), 3.175 (1H, d, CH₂), 4.02 (3H, s, Me), 6.41 (1H, d, CH), 6.43 (1H, s, CH). |
| 5.04 | 2 | F | F | 1 | O | OCH₃ | H |  | 1.57 (6H, s, Me), 3.14 (2H, s, CH₂), 4.05 (3H, s, Me), 6.55 (1H, s, CH). |
| 5.05 | 2 | F | Cl | 1 | O | OCH₃ | H |  | 1.55 (3H, s, Me), 1.56 (3H, s, Me), 3.09 (1H, d, CH₂), 3.175 (1H, d, CH₂), 4.01 (3H, s, Me), 6.49 (1H, s, CH). |
| 5.06 | 2 | F | F | 1 | O | Br | CH₃ | 70-75 | 3.14 (2H, s, CH₂), 2.23 (3H, t, J = 1.9 Hz, Me), 1.57 (6H, s, Me). |

Key:
Me = methyl; s = singlet; d = doublet.

TABLE 32

Compounds of formula I.8

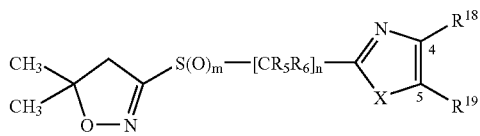

| No. | m | R⁵ | R⁶ | n | X | R¹⁸ | R¹⁹ | M.p. [° C.] | ¹H-NMR (400 MHz, CDCl₃) |
|---|---|---|---|---|---|---|---|---|---|
| 6.01 | 2 | F | F | 1 | N—CH₃ | H | H |  | 1.54 (6H, s, Me), 3.14 (2H, s, CH₂), 3.94 (3H, m, Me), 7.13 (1H, d, CH), 7.28 (1H, d, CH). |

Key:
Me = methyl; s = singlet; m = multiplet; d = doublet.

TABLE 33

Compounds of formula I.9

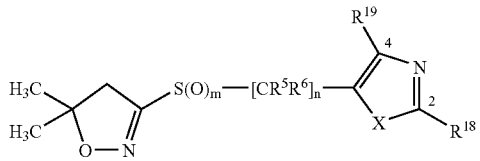

| No. | m | R⁵ | R⁶ | n | X | R¹⁸ | R¹⁹ | M.p. [° C.] | ¹H-NMR (400 MHz, CDCl₃) |
|---|---|---|---|---|---|---|---|---|---|
| 7.01 | 2 | F | F | 1 | S | CF₃ | —OC₂H₅ | 95-97 | 1.47 (3H, t, Me), 1.55 (6H, s, Me), 3.16 (2H, s, CH₂), 4.59 (2H, q, CH₂). |
| 7.02 | 2 | F | F | 1 | S | C₂H₅ | —CH₂OCH₃ |  | 1.35 (3H, t, Me), 1.60 (6H, s, Me), 2.98 (2H, q, CH₂), 3.20 (2H, s, CH₂), 3.58 (3H, s, Me), 4.77 (2H, s, CH₂). |

Key:
Me = methyl; s = singlet; t = triplet; q = quartet.

TABLE 34

Compounds of formula I.10

$$H_3C\text{-}C(CH_3)(O\text{-}N=)CH_2\text{-}C=...S(O)_m\text{-}[CR^5R^6]_n\text{-}\text{pyridyl-R}$$

| No. | m | $R^5$ | $R^6$ | n | R | M.p. [°C.] | $^1$H-NMR (400 MHz, CDCl$_3$) |
|---|---|---|---|---|---|---|---|
| 8.01 | 2 | H | Cl | 1 | 2-Cl | | 1.54 (6H, s, Me), 3.06 (1H, d, CH$_2$), 3.18 (1H, d, CH$_2$), 6.64 (1H, s, CH), 7.42 (1H, dd, CH), 8.24 (1H, dd, CH), 8.52 (1H, dd, CH). |
| 8.02 | 2 | H | F | 1 | 2-Cl | | 1.56 (3H, s, Me), 1.57 (3H, s, Me), 3.16 (1H, d, CH$_2$), 3.20 (1H, d, CH$_2$), 6.98 (1H, s, CH), 7.43 (1H, dd, CH), 8.08 (1H, dd, CH), 8.57 (1H, dd, CH). |
| 8.03 | 2 | Cl | F | 1 | 2-Cl | | 1.54 (3H, s, Me), 1.57 (3H, s, Me), 3.15 (1H, d, CH$_2$), 3.25 (1H, d, CH$_2$), 7.43 (1H, dd, CH), 8.20 (1H, dd, CH), 8.58 (1H, dd, CH). |
| 8.04 | 2 | F | F | 1 | 2-Cl | | 1.58 (6H, s, Me), 3.21 (2H, s, CH$_2$), 7.46 (1H, dd, CH), 8.07 (1H, dd, CH), 8.64 (1H, dd, CH). |
| 8.05 | 2 | H | F | 1 | 2-Me, 6-CF$_3$ | | 1.56 (3H, s, Me), 1.58 (3H, s, Me), 2.82 (3H, s, Me), 3.15 (1H, d, CH$_2$), 3.22 (1H, d, CH$_2$), 6.78 (1H, d, CH), 7.68 (1H, d, CH), 8.10 (1H, d, CH). |
| 8.06 | 2 | H | Cl | 1 | 2-Me, 6-CF$_3$ | | 1.52 (3H, s, Me), 1.57 (3H, s, Me), 2.82 (3H, s, Me), 3.12 (1H, d, CH$_2$), 3.20 (1H, d, CH$_2$), 6.40 (1H, s, CH), 7.67 (1H, d, CH), 8.26 (1H, d, CH). |
| 8.07 | 2 | F | F | 1 | 2-Me, 6-CF$_3$ | | 1.59 (6H, s, Me), 2.92 (3H, t, Me), 3.21 (2H, s, CH$_2$), 7.68 (1H, d, CH), 8.10 (1H, d, CH). |
| 8.08 | 2 | Cl | F | 1 | 2-Me, 6-CF$_3$ | | 1.57 (3H, s, Me), 1.58 (3H, s, Me), 2.93 (3H, d, Me), 3.15 (1H, d, CH$_2$), 3.26 (1H, d, CH$_2$), 7.67 (1H, d, CH), 8.21 (1H, d, CH). |

Key:
Me = methyl; s = singlet; d = doublet; dd = double doublet.

BIOLOGICAL EXAMPLES

Example B1

Herbicidal Action

Monocotyledonous and dicotyledonous test plants were sown in seed trays in standard soil. Immediately after sowing (pre-emergence) or after 8 to 9 days cultivation (post-emergence), the test compounds were applied by spraying in the form of an aqueous solution derived from the formulation of the technical active ingredient in 0.6 ml acetone and 45 ml formulation solution containing 10.6% Emulsogen EL (CAS RN 61791-12-6), 42.2% N-methylpyrrolidone, 42.2% dipropylene glycol monomethyl ether (CAS RN 34590-94-8) and 0.2% X-77 (CAS RN 11097-66-8). The test plants were then grown in a greenhouse under optimum conditions. After a test duration of 3 weeks (post-emergence) or 4 weeks (pre-emergence), the test was evaluated (10=total damage to plant, 0=no damage to plant).

TABLE B1a

Application post-emergence

| Comp. No. | [g/ha] | Setaria | Panicum | Digitaria | Sida | Abutilon | Amaranthus |
|---|---|---|---|---|---|---|---|
| 1.02 | 250 | 7 | 10 | 6 | 5 | 0 | 9 |
| 1.03 | 250 | — | 9 | 6 | 5 | 0 | 9 |
| 1.07 | 250 | 7 | 7 | 5 | 2 | 5 | 3 |
| 1.14 | 250 | 3 | 0 | 3 | 3 | 4 | — |
| 1.19 | 250 | 5 | 5 | 6 | 2 | 6 | 5 |
| 1.20 | 250 | 6 | 0 | 6 | 5 | 7 | 3 |
| 1.21 | 250 | 7 | 9 | 7 | 5 | 7 | — |
| 1.24 | 250 | 6 | 6 | 6 | — | — | — |
| 1.25 | 250 | 3 | 3 | 4 | 4 | 5 | — |
| 1.26 | 250 | 5 | 3 | 4 | — | 4 | — |
| 1.27 | 250 | 3 | 5 | 2 | 4 | 4 | — |
| 1.31 | 250 | 0 | 7 | 1 | 7 | 3 | — |
| 1.34 | 250 | 6 | 8 | 5 | 3 | 3 | 5 |
| 1.53 | 250 | 7 | 7 | 7 | 2 | 5 | 7 |
| 1.55 | 250 | 7 | 5 | 6 | 3 | 5 | 3 |
| 1.61 | 250 | 6 | 4 | 7 | 3 | 3 | 0 |
| 1.62 | 250 | 6 | 8 | 7 | 5 | 4 | 2 |
| 1.63 | 250 | 7 | 7 | 7 | 4 | 4 | 3 |
| 1.65 | 250 | 5 | 7 | 8 | 2 | 2 | 0 |
| 1.66 | 250 | 7 | 5 | 8 | 5 | 8 | 5 |
| 1.67 | 250 | 5 | 3 | — | 4 | 4 | 3 |
| 1.69 | 250 | 7 | 5 | 8 | 5 | 4 | 3 |
| 1.70 | 250 | 7 | 5 | 8 | 5 | 5 | 2 |
| 1.71 | 250 | 3 | 0 | 8 | 2 | 0 | 5 |
| 1.72 | 250 | 8 | 7 | 7 | 0 | 3 | 8 |
| 1.74 | 250 | 3 | 5 | 8 | 3 | 0 | 0 |

TABLE B1a-continued

Application post-emergence

| Comp. No. | [g/ha] | Setaria | Panicum | Digitaria | Sida | Abutilon | Amaranthus |
|---|---|---|---|---|---|---|---|
| 1.75 | 250 | 5 | 5 | 8 | 4 | 5 | 3 |
| 1.76 | 250 | 5 | 5 | — | 5 | 5 | 3 |
| 1.77 | 250 | 6 | 5 | 8 | 3 | 5 | 0 |
| 1.80 | 250 | 7 | 5 | 8 | 5 | 4 | 0 |
| 1.83 | 250 | 7 | 7 | 9 | 3 | 5 | 5 |
| 1.92 | 250 | 7 | 5 | 8 | 7 | 5 | 3 |
| 1.93 | 250 | 3 | 8 | 7 | 2 | 3 | 7 |
| 1.94 | 250 | 8 | 7 | 8 | 0 | 5 | 7 |
| 1.95 | 250 | 3 | 7 | 8 | 2 | 0 | 0 |
| 1.96 | 250 | 3 | 5 | 8 | 2 | 5 | 0 |
| 1.97 | 250 | 7 | 5 | 8 | 0 | 4 | 5 |
| 1.102 | 250 | 4 | 5 | 8 | 2 | 0 | 0 |
| 1.104 | 250 | 7 | 7 | 8 | 2 | 3 | 0 |
| 1.105 | 250 | 4 | 5 | 8 | 7 | 2 | 5 |
| 1.107 | 250 | 5 | 7 | 8 | 5 | 4 | 0 |
| 1.108 | 250 | 5 | 5 | 8 | 8 | 7 | 8 |
| 1.109 | 250 | 3 | 5 | 6 | 2 | 6 | 5 |
| 1.113 | 250 | 7 | 3 | 8 | 4 | 2 | 0 |
| 1.114 | 250 | 8 | 3 | 8 | 2 | 3 | 3 |
| 1.115 | 250 | 7 | 8 | 8 | 0 | 2 | 5 |
| 1.116 | 250 | 7 | 7 | 8 | 0 | 5 | 5 |
| 1.117 | 250 | 6 | 5 | 7 | 6 | 4 | 7 |
| 1.118 | 250 | 7 | 5 | 8 | 3 | 5 | 3 |
| 1.119 | 250 | 7 | 7 | 3 | 4 | 3 | 5 |
| 1.120 | 250 | 4 | 3 | 8 | 0 | 7 | 0 |
| 1.125 | 250 | 5 | 7 | 8 | 3 | 0 | 0 |
| 1.126 | 250 | 5 | 5 | 8 | 5 | 3 | 0 |
| 1.128 | 250 | 3 | 7 | 4 | 0 | 2 | 5 |
| 1.132 | 250 | 5 | 8 | 8 | 0 | 3 | 3 |
| 1.133 | 250 | 5 | 7 | 8 | 4 | 0 | 5 |
| 1.142 | 250 | 5 | 7 | 8 | 3 | 0 | 0 |
| 1.143 | 250 | 6 | 7 | 7 | 2 | 3 | 7 |
| 1.144 | 250 | 7 | 7 | 8 | 5 | 3 | 3 |
| 1.146 | 250 | 6 | 5 | 8 | 2 | 5 | 3 |
| 1.147 | 250 | 0 | 8 | 7 | 0 | 2 | 3 |
| 1.148 | 250 | 8 | 8 | 8 | 2 | 0 | 7 |
| 1.149 | 250 | 3 | 5 | 5 | 5 | 4 | 4 |
| 2.01 | 250 | 5 | 5 | 7 | 6 | 8 | 5 |
| 2.03 | 250 | 7 | 7 | 7 | 6 | 7 | 0 |
| 2.04 | 250 | 6 | 8 | 4 | 6 | 7 | 4 |
| 2.05 | 250 | 0 | 7 | 3 | 3 | 4 | 0 |
| 2.09 | 250 | 7 | 8 | 8 | 2 | 7 | 7 |
| 2.10 | 250 | 5 | 7 | 6 | 4 | 6 | 8 |
| 2.11 | 250 | 7 | 7 | 7 | 7 | 7 | 5 |
| 2.12 | 250 | 7 | 7 | 6 | 6 | 6 | 0 |
| 2.13 | 250 | 8 | 7 | 5 | 7 | 6 | 7 |
| 2.14 | 250 | 4 | 7 | 7 | 7 | 7 | 8 |
| 2.15 | 250 | 4 | 2 | 6 | 4 | 4 | 0 |
| 2.16 | 250 | 8 | 0 | 4 | 7 | 7 | 8 |
| 8.01 | 250 | 0 | 3 | 0 | 3 | 3 | 0 |
| 8.02 | 250 | 3 | 3 | 6 | 3 | 2 | 0 |
| 8.03 | 250 | 4 | 6 | 7 | 0 | 4 | 0 |
| 8.04 | 250 | 2 | 3 | 50 | 0 | 3 | 50 |

TABLE B1b

Application pre-emergence

| Comp. No. | [g/ha] | Setaria | Panicum | Digitaria | Sida | Amaranthus |
|---|---|---|---|---|---|---|
| 1.01 | 250 | 8 | 8 | 7 | 0 | 2 |
| 1.02 | 250 | 3 | 6 | — | 0 | — |
| 1.04 | 250 | 2 | 5 | 7 | 0 | 0 |
| 1.06 | 250 | 9 | 10 | 5 | 7 | 10 |
| 1.07 | 250 | 10 | 10 | 10 | 7 | 8 |
| 1.14 | 250 | 9 | 9 | 9 | 6 | 8 |
| 1.15 | 250 | 8 | 10 | 9 | 0 | 10 |
| 1.16 | 250 | 4 | 5 | 4 | 0 | 0 |
| 1.19 | 250 | 10 | 10 | 10 | 6 | 10 |
| 1.20 | 250 | 10 | 10 | 10 | 9 | 10 |
| 1.21 | 250 | 10 | 10 | 10 | 9 | 10 |
| 1.23 | 250 | 7 | 10 | 4 | 0 | 7 |
| 1.24 | 250 | 7 | 10 | 8 | 4 | 8 |
| 1.25 | 250 | 10 | 10 | 10 | 3 | 10 |
| 1.26 | 250 | 10 | 10 | 9 | 4 | 10 |
| 1.27 | 250 | 5 | 9 | 4 | 2 | 7 |
| 1.29 | 250 | 7 | 7 | 3 | 0 | 2 |
| 1.30 | 250 | 9 | 10 | 9 | 2 | 0 |
| 1.31 | 250 | 7 | 9 | 9 | 0 | 0 |
| 1.33 | 250 | 7 | 10 | 8 | 0 | 0 |
| 1.34 | 250 | 10 | 10 | 9 | 7 | 9 |
| 1.37 | 250 | 9 | 9 | 9 | 5 | 0 |
| 1.39 | 250 | 3 | 7 | 7 | 0 | 3 |
| 1.46 | 250 | 3 | 5 | 6 | 0 | 3 |

TABLE B1b-continued

Application pre-emergence

| Comp. No. | [g/ha] | Setaria | Panicum | Digitaria | Sida | Amaranthus |
|---|---|---|---|---|---|---|
| 1.50 | 250 | 10 | 10 | 9 | 7 | 10 |
| 1.51 | 250 | 8 | 9 | 9 | 0 | 8 |
| 1.53 | 250 | 10 | 10 | 10 | 5 | 9 |
| 1.54 | 250 | 8 | 8 | 8 | 0 | 0 |
| 1.55 | 250 | 10 | 10 | 10 | 5 | 9 |
| 1.57 | 250 | 8 | 10 | 8 | 6 | 9 |
| 1.58 | 250 | 7 | 9 | 8 | 3 | 5 |
| 1.60 | 250 | 9 | 10 | 9 | 0 | 7 |
| 1.61 | 250 | 10 | 10 | 10 | 7 | 10 |
| 1.62 | 250 | 10 | 10 | 9 | 8 | 10 |
| 1.63 | 250 | 10 | 10 | 10 | 8 | 10 |
| 1.65 | 250 | 10 | 10 | 10 | 8 | 10 |
| 1.66 | 250 | 10 | 10 | 10 | 9 | 10 |
| 1.67 | 250 | 10 | 10 | 10 | 9 | 10 |
| 1.69 | 250 | 10 | 10 | 10 | 4 | 5 |
| 1.70 | 250 | 10 | 10 | 10 | 8 | 10 |
| 1.71 | 250 | 9 | 10 | 9 | 5 | 10 |
| 1.72 | 250 | 10 | 10 | 10 | 6 | 10 |
| 1.73 | 250 | 10 | 10 | 10 | 8 | 10 |
| 1.74 | 250 | 9 | 10 | 9 | 7 | 5 |
| 1.75 | 250 | 10 | 10 | 10 | 7 | 10 |
| 1.76 | 250 | 8 | 10 | 9 | 3 | 9 |
| 1.77 | 250 | 10 | 10 | 10 | 7 | 10 |
| 1.78 | 250 | 10 | 10 | 10 | 2 | 10 |
| 1.79 | 250 | 10 | 10 | 10 | 6 | 8 |
| 1.80 | 250 | 10 | 10 | 10 | 9 | 10 |
| 1.81 | 250 | 5 | 8 | 6 | 0 | 9 |
| 1.82 | 250 | 9 | 10 | 9 | 0 | 10 |
| 1.83 | 250 | 9 | 10 | 9 | 0 | 9 |
| 1.84 | 250 | 9 | 10 | 9 | 0 | 10 |
| 1.87 | 250 | 7 | 5 | 7 | 0 | 3 |
| 1.90 | 250 | 0 | 0 | 4 | 5 | 4 |
| 1.91 | 250 | 9 | — | 10 | 10 | 3 |
| 1.92 | 250 | 10 | 10 | 10 | 8 | 10 |
| 1.93 | 250 | 10 | 10 | 10 | 6 | 8 |
| 1.94 | 250 | 10 | 10 | 10 | 8 | 10 |
| 1.95 | 250 | 10 | 10 | 10 | 7 | 7 |
| 1.96 | 250 | 10 | 10 | 10 | 4 | 9 |
| 1.97 | 250 | 9 | 10 | 10 | 0 | 8 |
| 1.98 | 250 | 9 | 9 | 8 | 4 | 7 |
| 1.101 | 250 | 8 | 8 | 8 | 0 | 9 |
| 1.102 | 250 | 9 | 10 | 10 | 2 | 8 |
| 1.103 | 250 | 5 | 9 | 9 | 0 | 3 |
| 1.104 | 250 | 8 | 10 | 9 | 3 | 0 |
| 1.105 | 250 | 10 | 10 | 8 | 7 | 10 |
| 1.106 | 250 | 6 | 8 | 7 | 0 | 3 |
| 1.107 | 250 | 10 | 9 | 7 | 0 | 9 |
| 1.108 | 250 | 10 | 10 | 10 | 9 | 10 |
| 1.109 | 250 | 9 | 10 | 10 | 0 | 10 |
| 1.113 | 250 | 10 | 10 | 9 | 0 | 8 |
| 1.114 | 250 | 10 | 10 | 10 | 9 | 10 |
| 1.115 | 250 | 10 | 10 | 10 | 8 | 10 |
| 1.116 | 250 | 10 | 10 | 10 | 7 | 10 |
| 1.117 | 250 | 8 | 10 | 10 | 4 | 9 |
| 1.118 | 250 | 10 | 10 | 10 | 8 | 10 |
| 1.120 | 250 | 0 | 8 | 6 | 5 | 8 |
| 1.125 | 250 | 10 | 10 | 10 | 7 | 10 |
| 1.126 | 250 | 10 | 10 | 10 | 8 | 10 |
| 1.132 | 250 | 10 | 10 | 10 | 4 | 10 |
| 1.133 | 250 | 10 | 10 | 10 | 6 | 10 |
| 1.134 | 250 | 9 | 10 | 10 | 0 | 5 |
| 1.135 | 250 | 9 | 10 | 10 | 0 | 7 |
| 1.139 | 250 | 7 | 0 | 8 | 0 | 0 |
| 1.141 | 250 | 9 | 9 | 9 | 0 | 5 |
| 1.143 | 250 | 10 | 10 | 10 | 7 | 7 |
| 1.144 | 250 | 10 | 10 | 10 | 8 | 10 |
| 1.145 | 250 | 10 | 10 | 10 | 7 | 10 |
| 1.146 | 250 | 10 | 10 | 10 | 5 | 8 |
| 1.147 | 250 | 9 | 10 | 10 | 0 | 5 |
| 1.148 | 250 | 10 | 10 | 10 | 6 | 10 |
| 1.150 | 250 | 9 | 10 | 10 | 0 | 6 |
| 1.151 | 250 | 7 | 8 | 0 | 4 | 5 |
| 2.01 | 250 | 10 | 10 | 10 | 9 | 10 |
| 2.03 | 250 | 10 | 10 | 10 | 8 | 10 |
| 2.04 | 250 | 10 | 10 | 10 | 8 | 10 |
| 2.05 | 250 | 10 | 10 | 9 | 8 | 5 |
| 2.06 | 250 | 7 | 8 | 8 | 3 | 7 |
| 2.08 | 250 | — | 9 | 2 | 2 | 4 |
| 2.09 | 250 | 10 | 10 | 10 | 8 | 10 |
| 2.10 | 250 | 10 | 10 | 10 | 8 | 10 |
| 2.11 | 250 | 10 | 10 | 10 | 9 | 10 |
| 2.12 | 250 | 10 | 10 | 10 | 8 | 10 |
| 2.13 | 250 | 10 | 10 | 10 | 7 | 10 |
| 2.14 | 250 | 10 | 10 | 10 | 9 | 10 |
| 2.15 | 250 | 10 | 10 | 10 | 8 | 10 |
| 2.16 | 250 | 10 | 10 | 10 | 7 | 10 |
| 2.17 | 250 | 8 | 8 | 8 | 5 | 10 |
| 2.21 | 250 | 10 | 10 | 10 | 8 | 10 |
| 2.23 | 250 | 9 | 8 | 7 | 3 | 8 |
| 2.24 | 250 | 10 | — | 10 | 5 | 10 |
| 2.32 | 250 | 4 | 7 | 4 | 0 | 7 |
| 2.35 | 250 | 5 | 9 | 10 | 0 | 10 |
| 3.01 | 250 | 7 | 10 | 8 | 0 | 7 |
| 3.02 | 250 | 10 | 10 | 10 | 0 | 7 |
| 3.03 | 250 | 10 | 10 | 9 | 0 | 7 |
| 3.04 | 250 | 9 | 10 | 9 | 0 | 3 |
| 3.07 | 250 | 8 | — | 9 | 2 | 4 |
| 4.01 | 250 | 8 | 8 | 8 | 8 | 8 |
| 4.02 | 250 | 7 | 10 | 8 | 0 | 10 |
| 4.03 | 250 | 10 | — | 10 | 7 | 9 |
| 5.01 | 250 | 8 | — | 8 | 2 | 0 |
| 5.03 | 250 | 9 | — | — | 2 | 10 |
| 8.01 | 250 | 5 | 8 | 8 | 0 | 5 |
| 8.02 | 250 | 8 | 10 | 9 | 0 | 7 |
| 8.03 | 250 | 8 | 10 | 10 | 6 | 8 |
| 8.04 | 250 | 10 | 10 | 10 | 3 | 10 |

Example B2

Herbicidal Action

Monocotyledonous and dicotyledonous test plants were sown in sterilised standard soil in seed trays each having 96 cells. After one day (pre-emergence) or after 8 to 9 days cultivation (post-emergence) under controlled conditions in a climatic chamber (cultivation at 17/23° C.; 13 hours light; 50-60% humidity; after application at 19/24° C.), the plants were treated with an aqueous spray solution of 1000 mg/l of the active ingredient used (rate of application: 500 g/l; incl. 10% DMSO as solvent). The plants were grown on in the climatic chamber until the test was evaluated (10 total damage to plant, 0=no damage to plant) after 9 or 13 days.

TABLE B2a

Application post-emergence

| Comp. No. | [g/ha] | Agrostis | Poa | Setaria | Amaranthus |
|---|---|---|---|---|---|
| 1.06 | 1000 | 8 | 8 | 7 | 8 |
| 1.07 | 1000 | 8 | 8 | 7 | 7 |
| 1.32 | 1000 | 8 | 8 | 6 | 6 |
| 1.34 | 1000 | 8 | 8 | 8 | 5 |

TABLE B2b

Application pre-emergence

| Comp. No. | [g/ha] | Digitaria | Agrostis | Poa | Setaria |
|---|---|---|---|---|---|
| 1.01 | 1000 | 9 | 10 | 10 | 9 |
| 1.02 | 1000 | 9 | 8 | 5 | 9 |
| 1.06 | 1000 | 10 | 10 | 10 | 10 |
| 1.07 | 1000 | 10 | 10 | 10 | 10 |
| 1.08 | 1000 | 8 | 7 | 9 | 3 |
| 1.14 | 1000 | 9 | 10 | 10 | 10 |
| 1.15 | 1000 | 9 | 2 | 10 | 9 |
| 1.19 | 1000 | 9 | 10 | 10 | 9 |
| 1.20 | 1000 | 10 | 10 | 10 | 10 |
| 1.21 | 1000 | 10 | 10 | 10 | 9 |
| 1.23 | 1000 | 8 | 10 | 10 | 8 |
| 1.24 | 1000 | 10 | 10 | 10 | 9 |
| 1.25 | 1000 | 9 | 10 | 10 | 8 |
| 1.26 | 1000 | 10 | 10 | 10 | 9 |
| 1.27 | 1000 | 9 | 10 | 9 | 9 |
| 1.29 | 1000 | 9 | 10 | 8 | 4 |
| 1.30 | 1000 | 10 | 10 | 10 | 10 |
| 1.31 | 1000 | 9 | 9 | 9 | 10 |
| 1.37 | 1000 | 9 | 10 | 10 | 9 |
| 1.39 | 1000 | 5 | 10 | 10 | 3 |
| 1.45 | 1000 | 8 | 7 | 10 | 6 |
| 1.48 | 1000 | 9 | 10 | 10 | 8 |
| 1.59 | 1000 | 8 | 9 | 10 | 9 |
| 1.100 | 1000 | 7 | 5 | 9 | 3 |
| 2.02 | 1000 | 9 | 10 | 10 | 10 |

Example E1

Pre-Emergent Safening Test on Maize

The test plants were sown in seed trays under greenhouse conditions. A standard earth was used as the culture substrate. In a pre-emergent stage, the herbicides were applied both by themselves and in a mixture with safeners to the soil surface. The application was carried out with an aqueous suspension of the test substances, prepared from a 25% wettable powder (Example F3, b according to WO 97/34485) or from a suspension concentrate (Example F8 according to WO 97/34485), to achieve a field equivalent of 200 l/ha. The tests were evaluated after 14 days (100%=plants completely dead; 0%=no phytotoxic action on the plants).

TABLE E1

Safener action on pre-emergent use on maize (Marista)

| Comp. 1.07 WP 25% AW/W | | Comp. 1.07 WP 25% AW/W + Benoxacor WP 25% AW/W | | Comp. 1.07 WP 25% AW/W + Dichlormid EC 250 GA/L | | Comp. 1.07 WP 25% AW/W + Furilazole WP 5% AW/W | |
|---|---|---|---|---|---|---|---|
| 400 | 200 [g/ha] | 400 | 200 [g/ha] | 400 | 200 [g/ha] | 400 | 200 [g/ha] |
|  |  | 100 | 50 [g/ha] | 100 | 50 [g/ha] | 100 | 50 [g/ha] |
| 27.5 | 20 [%] | 5 | 0 [%] | 0 | 0 [%] | 0 | 0 [%] |

| Comp. 2.04 WP 25% AW/W | | Comp. 2.04 WP 25% AW/W + Benoxacor WP 25% AW/W | | Comp. 2.04 WP 25% AW/W + Dichlormid EC 250 GA/L | | Comp. 2.04 WP 25% AW/W + Furilazole WP 5% AW/W | |
|---|---|---|---|---|---|---|---|
| 200 | 100 [g/ha] | 200 | 100 [g/ha] | 200 | 100 [g/ha] | 200 | 100 [g/ha] |
|  |  | 50 | 25 [g/ha] | 50 | 25 [g/ha] | 50 | 25 [g/ha] |
| 15 | 10 [%] | 2.5 | 0 [%] | 5 | 5 [%] | 0 | 0 [%] |

TABLE E2

Safener action on pre-emergent use on maize (Lorenzo)

| Comp. 1.07 WP 25% AW/W | | Comp. 1.07 WP 25% AW/W + Benoxacor WP 25% AW/W | | Comp. 1.07 WP 25% AW/W + Dichlormid EC 250 GA/L | | Comp. 1.07 WP 25% AW/W + Furilazole WP 5% AW/W | |
|---|---|---|---|---|---|---|---|
| 400 | 200 [g/ha] | 400 | 200 [g/ha] | 400 | 200 [g/ha] | 400 | 200 [g/ha] |
|  |  | 100 | 50 [g/ha] | 100 | 50 [g/ha] | 100 | 50 [g/ha] |
| 30 | 2.5 [%] | 0 | 0 [%] | 2.5 | 0 [%] | 0 | 0 [%] |

| Comp. 2.04 WP 25% AW/W | | Comp. 2.04 WP 25% AW/W + Benoxacor WP 25% AW/W | | Comp. 2.04 WP 25% AW/W + Dichlormid EC 250 GA/L | | Comp. 2.04 WP 25% AW/W + Furilazole WP 5% AW/W | |
|---|---|---|---|---|---|---|---|
| 200 | 100 [g/ha] | 200 | 100 [g/ha] | 200 | 100 [g/ha] | 200 | 100 [g/ha] |
|  |  | 50 | 25 [g/ha] | 50 | 25 [g/ha] | 50 | 25 [g/ha] |
| 17.5 | 2.5 [%] | 0 | 0 [%] | 7.5 | 0 [%] | 2.5 | 0 [%] |

The test substances showed good results. The same results were obtained when the compounds of the formula I were formulated in accordance with the other Examples of WO 97/34485.

Example F1

Post-Emergent Safening Test on Maize

The test plants were sown in containers under glasshouse conditions. A standard earth was used as the culture substrate. In a maize growth stage of one leaf (GS 11), the herbicides were applied both by themselves and in a mixture with safeners to the soil and leaf surface. The application was carried out with an aqueous suspension of the test substances, prepared from a 25% wettable powder (Example F3,b according to WO 97/34485) or a suspension concentrate (Example F8 according to WO 97/34485), to achieve a field equivalent of 200 l/ha. The tests were evaluated after 28 days (100%=plants completely dead; 0%=no phytotoxic action on the plants).

TABLE F1

Safener action on post-emergent use on maize (Marista 11f)

| Comp. 2.10 WP 25% AW/W | | | Comp. 2.10 WP 25% AW/W | | | Benoxacor WP 25% AW/W | | |
|---|---|---|---|---|---|---|---|---|
| 150 | 75 | 37.5 | [g/ha] | 150 | 75 | 37.5 | [g/ha] |
| 75 | 50 | 20 | [%] | 37.5 | 19 | 9.5 | [g/ha] |
| | | | | 10 | 0 | 0 | [%] |

What is claimed is:
1. A compound of formula

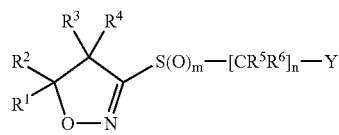

(I)

wherein
R$^1$ and R$^2$ are each independently of the other hydrogen, C$_1$-C$_{10}$alkyl, C$_1$-C$_{10}$haloalkyl, C$_3$-C$_8$cycloalkyl or C$_3$-C$_8$cycloalkyl-C$_1$-C$_3$alkyl,
R$^3$ and R$^4$ are each independently of the other hydrogen, C$_1$-C$_{10}$alkyl, C$_1$-C$_{10}$haloalkyl, C$_3$-C$_8$cycloalkyl-C$_1$-C$_{10}$alkyl, C$_1$-C$_6$alkoxy-C$_1$-C$_{10}$alkyl or C$_3$-C$_8$cycloalkyl,
R$^5$ and R$^6$ are each independently of the other, C$_1$-C$_6$haloalkyl, C$_1$-C$_6$-hydroxyalkyl, pyrazolyl-CH$_2$—, 4,5-dihydropyrazolyl-CH$_2$—, triazolyl-CH$_2$—, imidazolyl-CH$_2$—, indazolyl-CH$_2$—, C$_2$-C$_6$alkenyl, C$_2$-C$_6$alkynyl, C$_2$-C$_6$haloalkenyl, C$_1$-C$_6$alkylcarbonyloxy-C$_2$-C$_6$alkenyl, C$_1$-C$_6$alkylcarbonyl, C$_1$-C$_6$haloalkylcarbonyl, C$_3$-C$_6$cycloalkylcarbonyl, C$_1$-C$_6$alkoxy-C$_1$-C$_6$alkylcarbonyl, or
R$^5$ and R$^6$ are each independently of the other halogen, C$_1$-C$_6$alkylcarbonyl-C$_1$-C$_2$alkyl, C$_1$-C$_6$alkoxycarbonyl-C$_1$-C$_2$alkyl, C$_1$-C$_6$alkylaminocarbonyl-C$_1$-C$_2$alkyl, di-C$_1$-C$_6$alkylamino-carbonyl- C$_1$-C$_2$alkyl, C$_1$-C$_6$alkoxy-C$_1$-C$_2$alkyl, C$_1$-C$_2$alkyl-P(O)(OC$_1$-C$_6$alkyl)$_2$, or R$_5$ and R$_6$ are each independently of the other C$_1$-C$_6$alkylthio, C$_1$-C$_6$haloalkylthio, C$_1$-C$_6$alkylsulfonyl, C$_1$-C$_6$haloalkylsulfonyl, C$_1$-C$_6$alkylsulfonyl-C$_1$-C$_6$alkyl, C$_1$-C$_6$alkylsulfonyloxy-C$_1$-C$_6$alkyl, benzylsulfonyl or benzylsulfonyl substituted by one to three halogen, or
R$^5$ and R$^6$ are each independently of the other benzyl or benzyl substituted by one to three halogen, or
R$^5$ and R$^6$ are each independently of the other -CONR$^7$R$^8$ wherein R$^7$ and R$^8$ are each independently of the other hydrogen, C$_1$-C$_6$alkyl, C$_3$-C$_6$cycloalkyl, C$_1$-C$_6$haloalkyl, phenyl or phenyl substituted by C$_1$-C$_6$haloalkyl, nitro, cyano or by halogen,
R$^6$ may additionally be hydrogen, cyano, C$_1$-C$_6$alkyl or C$_1$-C$_6$alkoxycarbonyl, or
R$^5$ and R$^6$ together with the carbon atom to which they are bonded form a 3- to 10-membered ring, which is optionally substituted by one to four substituents independently selected from C$_1$-C$_6$alkyl, C$_1$-C$_6$alkoxycarbonyl, C$_1$-C$_6$alkenyl, halogen, nitro, phenylcarbonyl or
R$^5$ and R$^6$ together with the carbon atom to which they are bonded form a group of the formula C=CR$^{10}$R$^{11}$ wherein R$^{10}$ and R$^{11}$ are independently selected from hydrogen, C$_1$-C$_6$alkyl, —NH(C$_1$-C$_6$alkyl), —N(C$_1$-C$_6$alkyl)$_2$, C$_1$-C$_6$alkoxy-C$_1$-C$_2$alkyl, C$_1$-C$_6$alkylcarbonyloxy, C$_1$-C$_6$alkylcarbonyloxy-C$_1$-C$_2$alkyl, C$_1$-C$_6$alkoxy-C$_1$-C$_2$alkylcarbonyl-oxy or C$_1$-C$_6$alkylcarbonyloxy-C$_1$-C$_2$alkylcarbonyloxy;
m is 0, 1 or 2;
n is 1, 2 or 3;
Y is phenyl, naphthyl or tetrahydronaphthyl, which is optionally substituted by one to three substituents independently selected from C$_1$-C$_6$alkyl, C$_1$-C$_6$haloalkyl, C$_1$-C$_6$alkoxycarbonyl, nitro, cyano, halogen, C$_1$-C$_6$alkylthio, C$_1$-C$_6$haloalkylthio, C$_1$-C$_6$haloalkylsulfinyl, C$_1$-C$_6$haloalkylsulfonyl, C$_1$-C$_6$alkylsulfinyl, C$_1$-C$_6$alkylsulfonyl, C$_1$-C$_6$alkoxy, C$_1$-C$_6$haloalkoxy, C$_2$-C$_6$alkenyloxy, C$_2$-C$_6$alkynyloxy, C$_1$-C$_6$alkylsulfonyloxy, C$_1$-C$_6$ haloalkylsulfonyloxy, phenyl or phenyl substituted by
C$_1$C$_6$haloalkyl, nitro, cyano or by halogen,
Y is a 5- to 10-membered heterocycle containing one to three nitrogen, oxygen or sulfur atoms, which is optionally substituted by one to three substituents independently selected from C$_1$-C$_6$alkyl, C$_3$-C$_6$cycloalkyl, C$_1$-C$_6$haloalkyl, C$_1$-C$_6$alkoxy-C$_1$-C$_6$alkyl, cyano, halogen, C$_1$-C$_6$alkylsulfonyl, C$_1$-C$_6$haloalkylsulfonyl, C$_1$-C$_6$alkoxy, C$_3$-C$_6$cycloalkyloxy wherein one of the CH$_2$ groups is optionally replaced by an oxygen atom, or C$_1$-C$_6$haloalkoxy,
and to N-oxides, salts and optical isomers of compounds of formula I.

2. A process for the preparation of a compound of formula I wherein R$^1$, R$^2$, R$^3$, R$^4$, R$^5$, R$^6$ and Y are as defined in claim 1, m is 2, and n is 1, wherein a compound of formula Ia

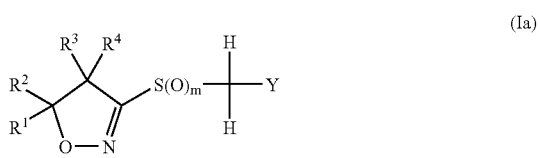

(Ia)

wherein R$^1$, R$^2$, R$^3$, R$^4$, and Y are as defined in claim 1, and m is 2, is reacted in an inert solvent in the presence of a base in a single step or stepwise in succession with compounds of formula R⁵—X and/or R⁶—X, wherein R⁵ and R⁶ are as defined in claim 1, and X is a leaving group.

3. A process according to claim 2 wherein R⁵ and/or R⁶ are halogen.

4. A process for the preparation of a compound of formula I wherein R¹, R², R³, R⁴, R⁵ and Y are as defined in claim 1, R⁶ is $C_1$-$C_{10}$alkyl or halogen, m is 2, and n is 1, wherein a compound of formula Ib

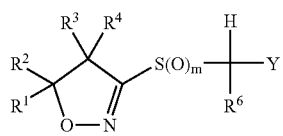

wherein R¹, R², R³, R⁴, and Y are as defined in claim 1, R⁶ is $C_1$-$C_{10}$alkyl or halogen, and m is 2, is reacted in an inert solvent in the presence of a base with a compound of formula R⁵-X, wherein R⁵ is as defined in claim 1, and X is a leaving group.

5. A process according to claim 4 wherein R⁵ is halogen.

6. A process for the preparation of a compound of formula I wherein R¹, R², R3, R4 and Y are as defined in claim 1, R⁵ and R⁶ together with the carbon atom to which they are bonded form a cyclopropyl ring which is optionally substituted by one to four substituents independently selected from $C_1$-$C_6$alkyl, $C_1$-$C_6$alkoxycarbonyl, $C_1$-$C_6$alkylcarbonyl, nitro or phenylcarbonyl, m is 2, and n is 1, wherein a compound of formula VII

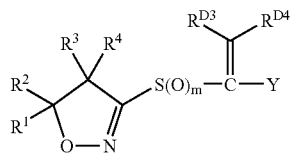

wherein R¹, R², R³, R" and Y are as defined in claim 1, m is 2, and $R^{D3}$ and $R^{D4}$ are hydrogen or $C_1$-$C_6$alkyl, is reacted with tri($C_1$-$C_6$alkyl)sulfonium halide or tri($C_1$-$C_6$alkyl)sulfoxonium halide, or with a compound of the formula

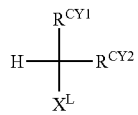

wherein $R^{CY1}$ and $R^{CY2}$ are halogen, $C_1$-$C_6$alkoxycarbonyl, $C_1$-$C_6$alkylcarbonyl, phenylcarbonyl or nitro, $R^{CY}$ additionally can be hydrogen, and $X^L$ is a leaving group in an inert solvent in the presence of a base.

7. A process for the preparation of a compound of formula I wherein R¹, R², R³, R⁴, R⁶ and Y are as defined in claim 1, R⁵ is chlorine, bromine or iodine, m is 1 or 2, and n is 1, wherein a compound of formula Ic

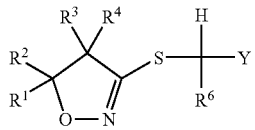

wherein R¹, R², R³, R⁴, R⁶ and Y are as defined in claim 1, is reacted in an inert solvent in succession with an N-halosuccinimide and an oxidising agent.

8. A herbicidal composition which comprises a herbicidally effective amount of a compound of formula I according to claim 1 in addition to formulation adjuvants.

9. A method of controlling grasses and weeds in crops of useful plants, which comprises applying a herbicidally effective amount of a compound of formula I, or of a composition comprising such a compound, to the plants or to the locus thereof.

10. A composition according to claim 8, which comprises a further herbicide in addition to the compound of formula I.

11. A composition according to claim 8, which comprises a safener in addition to the compound of formula I.

12. A compound of formula I according to claim 1 wherein R¹ and R² are both $C_1$-$C_{10}$alkyl.

13. A compound of formula I according to claim 12 wherein R¹ and R² are both methyl.

14. A compound of formula I according to claim 1 wherein R³ and R⁴ are both hydrogen.

15. A compound of formula I according to claim 1 wherein m is 1 or 2.

16. A compound of formula I according to claim 1 wherein R⁵ and R⁶ are each independently of the other fluoro, chloro, bromo, iodo, acetyl, 1-acetyloxy-ethen-1-yl, benzylsulfonyl, carbamoyl, chloroacetyl, N-cyclopropyl-carbamoyl, cyclopropylcarbonyl, N,N-diethyl-carbamoyl, 2-diethylphosphonato-eth-1-yl, difluoroacetyl, N-(2,2-difluoroethyl)-carbamoyl, 1,1-difluoroprop-1-en-3-yl, 4,5-dihydropyrazol-1-ylmethyl, 2-(N,N-dimethyl-carbamoyl)-eth-1-yl, 2-ethoxycarbonyl-eth-1-yl, 4-fluoroanilinocarbonyl, 4-fluorobenzyl, 1-hydroxy-but-1-yl, 1-hydroxy-prop-1-yl, imidazol-1-ylmethyl, indazol-1-ylmethyl, methoxyacetyl, 2-methoxy-eth-1-yl, methoxymethyl, methylsulfonyl, 2-methylsulfonyl-eth-1-yl, methylsulfonylmethyl, 1-methylsulfonyloxy-but-1-yl, propargyl, 2-propionoyl-eth-1-yl, pyrazol-l-ylmethyl, 1,2,4-triazol-1-ylmethyl, trifluoromethyl, or trifluoromethylthio, R⁶ is additionally hydrogen, ethoxycarbonyl, ethyl, methoxycarbonyl or methyl, or R⁵ and R⁶ together with the carbon they are bonded to form 1-chloro-1-methoxycarbonyl-cyclopropyl, cyclopropyl, 1,1-dichlorocyclopropyl, nitro-cyclopropyl, phenylcarbonyl-cyclopropyl, propen-2-yl-cyclopropyl, or vinyl-cyclopropyl, or R⁵ and R⁶ together with the carbon they are bonded to form 3-acetyloxy-2-acetyloxyacetyloxy-propylidene, 2-acetyloxy-propylidene, butylidene, N,N-dimethylaminoethylidene, or 3-methoxy-2-methoxyacetyloxy-propylidene.

17. A compound of formula I according to claim 1 wherein R⁵ and R⁶ are both halogen.

18. A compound of formula I according to claim 17 wherein R⁵ and R⁶ are both fluorine.

19. A compound according to claim 1 wherein m is 2.

20. A compound of formula I according to claim 1 wherein n is 1.

21. A compound of formula I according to claim 1 wherein Y is phenyl which is optionally substituted by one to three substituents independently selected from fluoro, chloro, cyano, difluoromethoxy, ethoxycarbonyl, methoxy, methoxycarbonyl, methyl, methylsulfonyloxy, nitro, phenyl, propargyloxy, trifluoromethoxy, trifluoromethyl, trifluoromethylthio or trifluoromethylsulfinyl.

22. A herbicidal composition which comprises a herbicidally effective amount of a compound of according to claim 13 in addition to formulation adjuvants.

* * * * *